US007166283B2

(12) United States Patent
Tsuji et al.

(10) Patent No.: US 7,166,283 B2
(45) Date of Patent: Jan. 23, 2007

(54) METHODS OF TREATING AN INFLAMMATORY DISORDER AND PROHIBITING PROLIFERATION, CYTOKINE PRODUCTION, AND SIGNAL TRANSDUCTION WITH ANTIBODY AGAINST COSTIMULATORY SIGNAL TRANSDUCTION MOLECULE AILIM

(75) Inventors: Takashi Tsuji, Nagareyama (JP); Katsunari Tezuka, Yokohama (JP); Nobuaki Hori, Yokohama (JP)

(73) Assignee: Japan Tobacco Inc., Tokyo (JP)

( * ) Notice: Subject to any disclaimer, the term of this patent is extended or adjusted under 35 U.S.C. 154(b) by 419 days.

(21) Appl. No.: 10/625,105

(22) Filed: Jul. 22, 2003

(65) Prior Publication Data

US 2004/0180052 A1  Sep. 16, 2004

Related U.S. Application Data

(62) Division of application No. 09/859,053, filed on May 16, 2001, now Pat. No. 6,803,039.

(30) Foreign Application Priority Data

May 18, 2000 (JP) .............................. 2000-147116
Mar. 30, 2001 (JP) ................................ 2001-99508

(51) Int. Cl.
*A61K 39/395* (2006.01)
*C07K 16/00* (2006.01)

(52) U.S. Cl. ............................... 424/144.1; 424/130.1; 424/133.1; 424/134.1; 424/141.1; 424/142.1; 424/154.1; 530/387.1; 530/388.1; 530/388.15; 530/388.2; 530/388.22; 530/388.7; 530/388.75

(58) Field of Classification Search ..................... None
See application file for complete search history.

(56) References Cited

U.S. PATENT DOCUMENTS

| | | | |
|---|---|---|---|
| 5,484,892 A | 1/1996 | Tedder et al. | |
| 5,506,126 A | 4/1996 | Seed et al. | |
| 5,521,288 A | 5/1996 | Linsley et al. | |
| 5,747,461 A | 5/1998 | Markov | |
| 5,770,197 A | 6/1998 | Linsley et al. | |
| 5,914,112 A | 6/1999 | Bednar et al. | |
| 6,075,181 A | 6/2000 | Kucherlapati et al. | |
| 6,451,305 B1 | 9/2002 | Boussiotis et al. | |
| 6,531,505 B1 | 3/2003 | Xu et al. | |
| 2002/0115831 A1 | 8/2002 | Tamatani et al. | |
| 2002/0156242 A1 | 10/2002 | Tamatani et al. | |
| 2002/0164697 A1 | 11/2002 | Coyle et al. | |
| 2002/0177191 A1 | 11/2002 | Kroczek | |
| 2002/0182667 A1 | 12/2002 | Kroczek | |

FOREIGN PATENT DOCUMENTS

| | | |
|---|---|---|
| AU | 13320/99 | 4/1999 |
| CA | 2293666 | 12/1998 |
| DE | 19821060 | 4/1999 |
| EP | 0984023 A1 | 3/2000 |
| EP | 1 125 585 A1 | 8/2001 |
| JP | 5-72204 | 3/1993 |
| JP | 11-228442 | 8/1999 |
| JP | 2000-154151 | 6/2000 |
| WO | WO 89/06138 | 7/1989 |
| WO | WO 94/11499 | 5/1994 |
| WO | WO 95/33770 | 12/1995 |
| WO | WO 97/26912 | 7/1997 |
| WO | WO 98/11909 | 3/1998 |
| WO | WO 98/19706 | 5/1998 |
| WO | WO 98/37415 | 8/1998 |
| WO | WO 98/38216 | 9/1998 |
| WO | WO 98/45331 | 10/1998 |
| WO | WO 99/15553 | 4/1999 |
| WO | WO 00/19988 | 4/2000 |
| WO | WO 00/46240 | 8/2000 |
| WO | WO 00/67788 | 11/2000 |
| WO | WO 01/08700 | 2/2001 |
| WO | WO 01/12658 | 2/2001 |
| WO | WO 01/15732 | 3/2001 |
| WO | WO 01/18022 | 3/2001 |
| WO | WO 01/21796 | 3/2001 |
| WO | WO 01/32675 | 5/2001 |
| WO | WO 01/64704 | 9/2001 |
| WO | WO 01/87981 | 11/2001 |
| WO | WO 02/44364 | 6/2002 |
| WO | WO 02/70010 | 9/2002 |
| WO | WO 02/76504 | 10/2002 |

OTHER PUBLICATIONS

Blazar et al., J. Immunol., 1996, 157: 3250-3259.*

(Continued)

*Primary Examiner*—Phillip Gambel
*Assistant Examiner*—Ilia Ouspenski
(74) *Attorney, Agent, or Firm*—Fish & Richardson P.C.

(57) ABSTRACT

Immunization of human antibody-producing transgenic mice, which have been created using genetic engineering techniques, with AILIM molecule as an antigen resulted in various human monoclonal antibodies capable of binding to AILIM and capable of controlling a variety of biological reactions (for example, cell proliferation, cytokine production, immune cytolysis, cell death, induction of ADCC, etc.) associated with AILIM-mediated costimulatory signal (secondary signal) transduction. Furthermore, it has been revealed that the human monoclonal antibody is effective to treat and prevent various diseases associated with AILIM-mediated costimulatory signal transduction, being capable of inhibiting the onset and/or advancement of the diseases.

102 Claims, 78 Drawing Sheets

OTHER PUBLICATIONS

Perrin et al., J. Neuroimmunol, 1996, 157: 31-39.*
Rudikoff et al., Proc. Natl. Acad. Sci. USA, 1982, 79: 1979-1983.*
Panka et al., Proc. Natl. Acad. Sci. USA, 1988, 85: 3080-3084.*
Chaouat et al., J. Immunol., 1995, vol. 154, pp. 4261-4268.*
Aicher et al., "Characterization of Human Inducible Costimulator Ligand Expression and Function," J. Immunol., 164(9):4689-4696 (2000).
Bajorath, "A molecular model of inducible costimulator protein and three-dimensional analysis of its relation to the CD28 family of T cell-specific costimulatory receptors," J. Mol. Model 5:169-176 (1999).
Beier et al., "Induction, binding specificity and function of human ICOS," Eur. J. Immunol., 30(12):3707-3717 (2000).
Brodie et al., "LICOS, a primordial costimulatory ligand?," Curr. Biol., 10(6):333-336 (2000).
Buonfiglio et al., "Characterization of a novel human surface molecule selectively expressed by mature thymocytes, activated T cells and subsets of T cell lymphomas," Eur. J. Immunol., 29(9)2863-2874 (1999).
Buonfiglio et al., "The T cell activation molecule H4 and the CD28-like molecule ICOS are identical," Eur. J. Immunol. 30(12):3463-3467 (2000).
Cameron "Recent advances in transgenic technology" Molecular Biotechnology 7:253-65 (1997).
Chambers, "The expanding world of co-stimulation: the two-signal model revisited," Trends in Immunology, 22(4):217-223 (2001).
Cocks et al., "A novel receptor involved in T-cell activation," NATURE, 376:260-263 (1995).
Coyle et al., "The CD28-Related Molecule ICOS Is Required for Effective T Cell-Dependent Immune Responses," IMMUNITY 13(1):95-105 (2000).
Dong et al., "Cutting Edge: Critical Role of Inducible Costimulator in Germinal Center Reactions," J. Immunol., 166(6):3659-3662 (2001).
Dong, "ICOS co-stimulatory receptor is essential for T-cell activation and function," NATURE 409(6816):97-101 (2001).
Gonzalo et al., "Cutting Edge: The Related Molecules CD28 and Inducible Costimulator Deliver Both Unique and Complementary Signals Required for Optimal T Cell Activation," J. Immunol., 166(1):1-5 (2001).
Guo et al., "Stimulatory Effects of B7-Related Protein-1 on Cellular and Humoral Immune Responses in Mice," J. Immunol., 166(9):5578-5584 (2001).
Hanzawa et al., "Characteristics of a TTH1 antibody which blocks an unknown adhesion phenomenon," Proceedings of the Japanese Society for Immunology, vol. 24, Abstract NO. W17-13 (1994) [Original Japanese and English Language Translation].
Heyeck et al., "Developmental regulation of a murine T-cell-specific tyrosine kinase gene, Tsk," Proc. Natl. Acad. Sci. USA, 90:669-673 (1993).
Houdebine "Production of pharmaceutical proteins from transgenic animals" J. Biotechnol. 34:269-87 (1994).
Hutloff et al., "ICOS is an inducible T-cell co-stimulator structurally and functionally related to CD28," Nature, 397(6716):263-266 (1999).
Ishikawa et al., "Prediction of the Coding Sequences of Unidentified Human Genes. X. The Complete Sequences of 100 New cDNA Clones for Brain Which Can Code for Large Proteins in vitro," DNA Research, 5:169-176 (1998).
Kappel et al. "Regulating gene expression in transgenic animals" Current Opinion in Biotechnology 3:548-53 (1992).
Kopf et al., "Inducible Costimulator Protein (ICOS) Controls T Helper Cell Subset Polarization after Virus and Parasite Infection," J. Exp. Med., 192(1):53-61 (2000).
Kuchroo et al., "B7-1 and B7-2 costimulatory molecules activate differentially the Th1/Th2 developmental pathways: Application to autoimmune disease therapy," Cell, 80:707-718 (1995).
Ling et al., "Cutting Edge: Identification of GL50, a Novel B7-Like Protein That Functionally Binds to ICOS Receptor," J. Immunol., 164(4):1653-1657 (2000).

Mages et al., "Molecular cloning and characterization of murine ICOS and identification of B7h as ICOS ligand," Eur. J. Immunol., 30(4):1040-1047 (2000).
Marguet et al., "cDNA Cloning for Mouse Thymocyte-activating Molecule," The Journal of Biological Chemistry, 267(4):2200-2208 (1992).
McAdam et al. (2000) "Mouse inducible costimulatory (ICOS) molecule expression is increased by CD28 costimulation and regulates development of Th2 cells," FASEB Journal, 14(6):A1169.
McAdam, "ICOS is critical for CD40-mediated antibody class switching," NATURE 409(6816):102-105 (2001).
McAdam, "Mouse Inducible Costimulatory Molecule (ICOS) Expression Is Enhanced by CD28 Costimulation and Regulates Differentiation of $CD4^+$ T Cells," J. Immunol., 165(9):5035-5040 (2000).
Mueller, "T cells: A proliferation of costimulatory molecules," Curr. Biol. 10(6):R227-R230 (2000).
Mullins et al. "Expression of the DBA/2J Ren-2 gene int he adrenal gland of transgenic mice"Embo J., 8:4065-72 (1989).
Mullins et al. "Fulminant hypertension in transgenic rats harbouring the mouse Ren-2 gene" NATURE, 344:541-44 (1990).
Mullins et al. "Transgenesis in nonmurine species" Hypertension 22:630-33 (1993).
Niemann "Transgenic farm animals get off the ground" Transgenic Research, 7:73-75 (1998).
Nojima et al., "The 4F9 antigen is a member of the tetra spans transmembrane protein family and functions as an accessory molecule in T cell activation and adhesion," Cellular Immunology, 152:249-260 (1993).
Overbeek "Factors affecting transgenic animal production," Transgenic Animal Technology, A Laboratory Handbook 96-98 (1994).
Özkaynak et al., "Importance of ICOS-B7RP-1 constimulation in acute and chronic allograft rejection," Nature Immunology 2(7):591-596 (2001).
Tezuka et. al., Poster, Kyoto International Conference Hall, Takaragaike Sakyo-ku, Kyoto, JAPAN (Nov. 30, 1994) [Original Japanese and English Language Translation].
Redoglia et al., "Characterization of H4: a mouse T lymphocyte activation molecule functionally associated with the CD3/T cell receptor," Eur. J. Immunol., 26(11):2781-2789 (1996).
Riley et al., "ICOS Costimulation Requires IL-2 and Can Be Presented by CTLA-4 Engagement," J. Immunol., 166(8):4933-4948 (2001).
Robert et al., "Antibody Cross-Linking of the Thymocyte-Specific Cell Surface Molecule CTX Causes Abnormal Mitosis and Multinucleation of Tumor Cells," Experimental Cell Research, 235:227-237 (1997).
Sato et al. (2000) "Up-regulation of inducible co-stimulator (ICOS) expression and its regulation of cytokine production in inflammatory bowel disease," Gastroenterology, 118(4):A662.
Sharpe, "Analysis of lymphocyte costimulation in vivo using transgenic and 'knockout' mice," Current Opinion in Immunology, 7:389-395 (1995).
Sigmund "Are studies in genetically altered mice out of control?" Arterioscler. Thromb. Vasc. Biol., 20:1425-29 (2000).
Swallow et al., "B7h, a Novel Costimulatory Homolog of B7.1 and B7.2, Is Induced by TNFα," IMMUNITY, 11(4):423-432 (1999).
Tafuri et al., "ICOS is essential for effective T-helper-cell responses," NATURE 409(6816):105-109 (2001).
Tai et al., "A role for CD9 molecules in T cell activation," J. Exp. Med., 184:753-758 (1996).
Tamatani et al., "AILIM/ICOS: a novel lymphocyte adhesion molecule," International Immunology, 12(1):51-55 (2000).
Tamatani et al., "Characteristics of an antibody which induces an ICAM-1-LFA-1-independent adhesion pathway," Proceedings of the Japanese Society for Immunology, vol. 23, Abstract No. H-160 (1993) [Original Japanese and English Language Translation].
Tezuka et al., "Genetic cloning of a lymphocyte surface signal transduction molecule which induces an unknown adhesion phenomenon," Proceedings of the Japanese Society for Immunology, vol. 24, Abstract No. W17-14 (1994) [Original Japanese and English Language Translation].

Tezuka et al., "Identification and Characterization of Rat AILIM/ICOS, a Novel T-Cell Costimulatory Molecule, Related to the CD28/CTLA4 Family," Biochem. Biophys. Res. Commun., 276(1):335-345 (2000).

Wall "Transgenic livestock: progress and prospects for the future" THERIOGENOLOGY 45:57-68 (1996).

Wang et al., "Costimulation of T cells by B7-H2, a B7-like molecule that binds ICOS," BLOOD, 96(8):2808-2813 (2000).

Yoshinaga et al., "Characterization of a new human B7-related protein: B7RP-1 is the ligand to the co-stimulatory protein ICOS," International Immunology, 12(10):1439-1447 (2000).

Yoshinaga et al., "T-cell co-stimulation through B7RP-1 and ICOS," NATURE, 402(6763):827-832 (1999).

Abbas, "T-cell stimulation: an abundance of B7s," Nat Med. 5(12):1345-6 (1999).

Bensimon et al., "Human lupus anti-DNA autoantibodies undergo essentially primary V kappa gene rearrangements," EMBO J. 13(13):2951-62 (1994).

Campbell et al., "Separable effector T cell populations specialized for B cell help or tissue inflammation,"Nat Immunol. 2(9):876-81 (2001).

Chapoval et al., "B7-H3: a costimulatory molecule for T cell activation and IFN-gamma production," Nat Immunol. 2(3):269-74 (2001).

Dong et al., "B7-HI, a third member of the B7 family, co-stimulates T-cell proliferation and interleukin-10 secretion," Nat. Med. 5(12):1365-9 (1999).

Eljaschewitsch et al., "Identification of a novel activation antigen on human CD4+ T cells," IMMUNOBIOL., 194(1-3):27 (1995).

Goding, "Monoclonal Antibodies: Principles and Practice," 2nd Edition, Academic Press, Orlando, Florida, Chapter 8, pp. 281-293 (1986).

Goni et al., "Structural and idiotypic characterization of the L chains of human IgM autoantibodies with different specificities," J. Immunol. 142(9):3158-63 (1989).

Gonzalo et al., "ICOS is critical for T Helper cell-mediated lung mucosal inflammatory responses,"Nat Immunol. 2(7):597-604 (2001).

Harlow and Lane, "Antibodies: A Laboratory Manual," Cold Spring Harbor Laboratory, p. 285 (1988).

Hutloff et al., "Identification and initial characterization of a novel T cell-specific cell surface activation antigen," IMMUNOBIOL., 197(2-4):172 (1997).

Ihara et al., "Association studies of CTLA-4, CD28, and ICOS gene polymorphisms with type 1 diabetes in the Japanese population," IMMUNOGENETICS 53(6):447-54 (2001).

Iiyama et al., "The role of inducible co-stimulator (ICOS)/B7-related protein-1 (B7RP-1) interaction in the functional development of Peyer's patches," Immunology Letters Uncorrected Proof available online Apr. 11, 2003, http://www.sciencedirect.com/science/journal/01652478.

Lamhemedi-Cherradi et al., "Further mapping of the Idd5.1 locus for autoimmune diabetes in NOD mice," DIABETES 50(12):2874-8 (2001).

Ling et al., "Assembly and annotation of human chromosome 2q33 sequence containing the CD28, CTLA4, and ICOS gene cluster: analysis by computational, comparative, and microarray approaches," GENOMICS 78(3):155-68 (2001).

Ling et al., "Differential expression of inducible costimulator-ligand splice variants: lymphoid regulation of mouse GL50-B and human GL50 molecules," J Immunol. 166(12):7300-8 (2001).

Linsley, "T cell activation: you can't get good help," Nat Immunol. 2(2):139-40 (2001).

Liu et al. "B7H costimulates clonal expansion of, and cognate destruction of tumor cells by, CD8(+) T lymphocytes in vivo," J Exp Med. 194(9):1339-48 (2001).

Lucia et al., "Expression of the novel T cell activation molecule hpH4 in HIV-infected patients: Correlation with disease status", AIDS Research and Human Retroviruses 16(6):549-557 (2000).

Mackay et al., "Follicular homing T helper (Th) cells and the Th1/Th2 paradigm," J Exp Med. 192(11):F31-4 (2000).

Nurieva et al., "Inducible costimulator is essential for collagen-induced arthritis," J. Clin. Invest. 111(5):701-06 (2003).

Ogawa et al., "Opposing effects of anti-activation-inducible lymphocyte-immunomodulatory molecule/inducible costimulator antibody on the development of acute versus chronic graft-versus-host disease," J Immunol. 167(10):5741-8 (2001).

O'Neill, "Co-stimulating allergy," Trends Immunol. 22(4):183 (2001).

Pech et al., "A large section of the gene locus encoding human immunoglobulin variable regions of the kappa type is duplicated," J. Mol Biol. 183(3):291-9 (1985).

Pound, "A new T-helper cell subset?" Trends Immunol. 22(4):182-3 (2001).

Richter et al., "Tumor necrosis factor-αregulates the epxression of inducible costimulator receptor ligand on CD34+ progenitor cells during differentiation into antigen presenting cells, " J. of Biological Chem. 276(49):45686-45693 (2001).

Rottman et al., "The costimulatory molecule ICOS plays an important role in the immunopathogenesis of EAE," Nat Immunol. 2(7):605-11 (2001).

Sakamoto et al., "AILIM/ICOS: its expression and functional analysis with monoclonal antibodies," Hybridoma and Hybridomics, 20(5):293-303 (2001).

Schwartz, "Immunology. It takes more than two to tango," NATURE 409(6816):31-2 (2001).

Sperling et al., "ICOS costimulation: It's not just for TH2 cells anymore," Nat Immunol. 2(7):573-4 (2001).

Sperling, "ICOS costimulation: is it the key to selective immunotherapy?," Clin Immunol. 100(3):261-2 (2001).

Sporici et al., "ICOS ligand costimulation is required for T-cell encephalitogenicity," Clin Immunol. 100(3:277-88 (2001).

Sporici et al., "Costimulation of memory T-cells by ICOS: a potential therapeutic target for autoimmunity?", Clin Immunol. 100(3):263-9 (2001).

Tamura et al. "B7-H1 costimulation preferentially enhances CD28-independent T-helper cell function," BLOOD 97(6):1809-16 (2001).

Tesciuba et al., "Inducible costimulator regulates Th2-mediated inflammation, but not Th2 differentiation, in a model of allergic airway disease," J Immunol. 167(4):1996-2003 (2001).

Tomlinson et al., "The repertoire of human germline VH sequences reveals about fifty groups of VH segments with different hypervariable loops," J. Mol. Biol. 227(3):776-98 (1992).

Wallin et al., "Enhancement of CD8+ T cell responses by ICOS/B7h costimulation," J Immunol. 167(1):132-9 (2001).

* cited by examiner

Coated amount of B7hIgFc

— □ — 0 ng/well-B7hIgFc
— ◇ — 25 ng/well-B7hIgFc
— ○ — 50 ng/well-B7hIgFc
— △ — 100 ng/well-B7hIgFc
— ⊞ — 200 ng/well-B7hIgFc
— ◆ — 400 ng/well-B7hIgFc
— ⊕ — 800 ng/well-B7hIgFc
— ▽ — 1600 ng/well-B7hIgFc

```
                          SEQUENCE LISTING

<160> NUMBER OF SEQ ID NOS: 43

<210> SEQ ID NO 1
<211> LENGTH: 45
<212> TYPE: DNA
<213> ORGANISM: Artificial Sequence
<220> FEATURE:
<223> OTHER INFORMATION: Artificially synthesized primer sequence,
      NotI-T
<220> FEATURE:
<221> NAME/KEY: primer_bind
<222> LOCATION: (1)...(45)

<400> SEQUENCE: 1
aactggaagc ttcagcggcc gcagagattt tttttttttt ttttt              45

<210> SEQ ID NO 2
<211> LENGTH: 20
<212> TYPE: DNA
<213> ORGANISM: Artificial Sequence
<220> FEATURE:
<223> OTHER INFORMATION: Artificially synthesized linker sequence, 20adp

<400> SEQUENCE: 2
cgtggtgtca tggcactgcg                                          20

<210> SEQ ID NO 3
<211> LENGTH: 24
<212> TYPE: DNA
<213> ORGANISM: Artificial Sequence
```

-continued

```
<220> FEATURE:
<223> OTHER INFORMATION: Artificially synthesized linker sequence, 24adp

<400> SEQUENCE: 3
aattcgcagt gccatgacac cacg                                          24

<210> SEQ ID NO 4
<211> LENGTH: 23
<212> TYPE: DNA
<213> ORGANISM: Artificial Sequence
<220> FEATURE:
<223> OTHER INFORMATION: Artificially synthesized primer sequence, HIGLC
<220> FEATURE:
<221> NAME/KEY: primer_bind
<222> LOCATION: (1)...(23)

<400> SEQUENCE: 4
gtctgctttg ctcagcgtca ggg                                           23

<210> SEQ ID NO 5
<211> LENGTH: 21
<212> TYPE: DNA
<213> ORGANISM: Artificial Sequence
<220> FEATURE:
<223> OTHER INFORMATION: Artificially synthesized primer sequence, NHCc2
<220> FEATURE:
<221> NAME/KEY: primer_bind
<222> LOCATION: (1)...(21)

<400> SEQUENCE: 5
caccggttcg gggaagtagt c                                             21

<210> SEQ ID NO 6
<211> LENGTH: 21
<212> TYPE: DNA
<213> ORGANISM: Artificial Sequence
<220> FEATURE:
<223> OTHER INFORMATION: Artificially synthesized primer sequence,
      ExcellE
<220> FEATURE:
<221> NAME/KEY: primer_bind
<222> LOCATION: (1)...(21)

<400> SEQUENCE: 6
ggtgacacta tagaatacag g                                             21

<210> SEQ ID NO 7
<211> LENGTH: 25
<212> TYPE: DNA
<213> ORGANISM: Artificial Sequence
<220> FEATURE:
<223> OTHER INFORMATION: Artificially synthesized primer sequence, ck117
<220> FEATURE:
<221> NAME/KEY: primer_bind
<222> LOCATION: (1)...(25)

<400> SEQUENCE: 7
gcaggcacac aacagaggca gttcc                                         25

<210> SEQ ID NO 8
<211> LENGTH: 20
<212> TYPE: DNA
<213> ORGANISM: Artificial Sequence
<220> FEATURE:
<223> OTHER INFORMATION: Artificially synthesized primer sequence, M13R
<220> FEATURE:
<221> NAME/KEY: primer_bind
<222> LOCATION: (1)...(20)
```

```
<400> SEQUENCE: 8
cacaggaaac agctatgacc                                              20

<210> SEQ ID NO 9
<211> LENGTH: 21
<212> TYPE: DNA
<213> ORGANISM: Artificial Sequence
<220> FEATURE:
<223> OTHER INFORMATION: Artificially synthesized primer sequence, 136H
<220> FEATURE:
<221> NAME/KEY: primer_bind
<222> LOCATION: (1)...(21)

<400> SEQUENCE: 9
cctggacaag ggcttgagtg g                                            21

<210> SEQ ID NO 10
<211> LENGTH: 21
<212> TYPE: DNA
<213> ORGANISM: Artificial Sequence
<220> FEATURE:
<223> OTHER INFORMATION: Artificially synthesized primer sequence,
      138/9H
<220> FEATURE:
<221> NAME/KEY: primer_bind
<222> LOCATION: (1)...(21)

<400> SEQUENCE: 10
acaggaaaag gtctggagtg g                                            21

<210> SEQ ID NO 11
<211> LENGTH: 21
<212> TYPE: DNA
<213> ORGANISM: Artificial Sequence
<220> FEATURE:
<223> OTHER INFORMATION: Artificially synthesized primer sequence,
      AILIMHC1
<220> FEATURE:
<221> NAME/KEY: primer_bind
<222> LOCATION: (1)...(21)

<400> SEQUENCE: 11
acagtaatac acggccgtgt c                                            21

<210> SEQ ID NO 12
<211> LENGTH: 21
<212> TYPE: DNA
<213> ORGANISM: Artificial Sequence
<220> FEATURE:
<223> OTHER INFORMATION: Artificially synthesized primer sequence, HCc1
<220> FEATURE:
<221> NAME/KEY: primer_bind
<222> LOCATION: (1)...(21)

<400> SEQUENCE: 12
gactacttcc ccgaaccggt g                                            21

<210> SEQ ID NO 13
<211> LENGTH: 22
<212> TYPE: DNA
<213> ORGANISM: Artificial Sequence
<220> FEATURE:
<223> OTHER INFORMATION: Artificially synthesized primer sequence, HCc7
<220> FEATURE:
<221> NAME/KEY: primer_bind
<222> LOCATION: (1)...(22)

<400> SEQUENCE: 13
```

```
gtggcaggac cgtcagtctt cc                                            22
```

<210> SEQ ID NO 14
<211> LENGTH: 24
<212> TYPE: DNA
<213> ORGANISM: Artificial Sequence
<220> FEATURE:
<223> OTHER INFORMATION: Artificially synthesized primer sequence, HCc8
<220> FEATURE:
<221> NAME/KEY: primer_bind
<222> LOCATION: (1)...(24)

<400> SEQUENCE: 14

```
aagaggaaga ctgacggtcc tgcc                                          24
```

<210> SEQ ID NO 15
<211> LENGTH: 23
<212> TYPE: DNA
<213> ORGANISM: Artificial Sequence
<220> FEATURE:
<223> OTHER INFORMATION: Artificially synthesized primer sequence, HCc3
<220> FEATURE:
<221> NAME/KEY: primer_bind
<222> LOCATION: (1)...(23)

<400> SEQUENCE: 15

```
ccgttgtgca ccaggactgg ctg                                           23
```

<210> SEQ ID NO 16
<211> LENGTH: 23
<212> TYPE: DNA
<213> ORGANISM: Artificial Sequence
<220> FEATURE:
<223> OTHER INFORMATION: Artificially synthesized primer sequence, HCc4
<220> FEATURE:
<221> NAME/KEY: primer_bind
<222> LOCATION: (1)...(23)

<400> SEQUENCE: 16

```
tgcacttgta ctccttgccg ttc                                           23
```

<210> SEQ ID NO 17
<211> LENGTH: 23
<212> TYPE: DNA
<213> ORGANISM: Artificial Sequence
<220> FEATURE:
<223> OTHER INFORMATION: Artificially synthesized primer sequence, HCc6
<220> FEATURE:
<221> NAME/KEY: primer_bind
<222> LOCATION: (1)...(23)

<400> SEQUENCE: 17

```
cagccggaga acaactacaa gac                                           23
```

<210> SEQ ID NO 18
<211> LENGTH: 22
<212> TYPE: DNA
<213> ORGANISM: Artificial Sequence
<220> FEATURE:
<223> OTHER INFORMATION: Artificially synthesized primer sequence, HIGHC
<220> FEATURE:
<221> NAME/KEY: primer_bind
<222> LOCATION: (1)...(22)

<400> SEQUENCE: 18

```
tcttgtagtt gttctccggc tg                                            22
```

<210> SEQ ID NO 19

```
<211> LENGTH: 22
<212> TYPE: DNA
<213> ORGANISM: Artificial Sequence
<220> FEATURE:
<223> OTHER INFORMATION: Artificially synthesized primer sequence, HCc9
<220> FEATURE:
<221> NAME/KEY: primer_bind
<222> LOCATION: (1)...(22)

<400> SEQUENCE: 19
tacttcccag gcacccagca tg                                              22

<210> SEQ ID NO 20
<211> LENGTH: 23
<212> TYPE: DNA
<213> ORGANISM: Artificial Sequence
<220> FEATURE:
<223> OTHER INFORMATION: Artificially synthesized primer sequence, HCc5
<220> FEATURE:
<221> NAME/KEY: primer_bind
<222> LOCATION: (1)...(23)

<400> SEQUENCE: 20
atgctgggtg cctgggaagt atg                                             23

<210> SEQ ID NO 21
<211> LENGTH: 21
<212> TYPE: DNA
<213> ORGANISM: Artificial Sequence
<220> FEATURE:
<223> OTHER INFORMATION: Artificially synthesized primer sequence, polyA
<220> FEATURE:
<221> NAME/KEY: primer_bind
<222> LOCATION: (1)...(21)

<400> SEQUENCE: 21
tcaaactatc ggccttgctg g                                               21

<210> SEQ ID NO 22
<211> LENGTH: 21
<212> TYPE: DNA
<213> ORGANISM: Artificial Sequence
<220> FEATURE:
<223> OTHER INFORMATION: Artificially synthesized primer sequence,
      AILIMLC1
<220> FEATURE:
<221> NAME/KEY: primer_bind
<222> LOCATION: (1)...(21)

<400> SEQUENCE: 22
tagcctggta tcagcagaaa c                                               21

<210> SEQ ID NO 23
<211> LENGTH: 21
<212> TYPE: DNA
<213> ORGANISM: Artificial Sequence
<220> FEATURE:
<223> OTHER INFORMATION: Artificially synthesized primer sequence,
      AILIMLC2
<220> FEATURE:
<221> NAME/KEY: primer_bind
<222> LOCATION: (1)...(21)

<400> SEQUENCE: 23
gtttctgctg ataccaggct a                                               21

<210> SEQ ID NO 24
<211> LENGTH: 22
<212> TYPE: DNA
```

```
<213> ORGANISM: Artificial Sequence
<220> FEATURE:
<223> OTHER INFORMATION: Artificially synthesized primer sequence, LCc1
<220> FEATURE:
<221> NAME/KEY: primer_bind
<222> LOCATION: (1)...(22)

<400> SEQUENCE: 24
gcaccatctg tcttcatctt cc                                              22

<210> SEQ ID NO 25
<211> LENGTH: 21
<212> TYPE: DNA
<213> ORGANISM: Artificial Sequence
<220> FEATURE:
<223> OTHER INFORMATION: Artificially synthesized primer sequence, LCc2
<220> FEATURE:
<221> NAME/KEY: primer_bind
<222> LOCATION: (1)...(21)

<400> SEQUENCE: 25
caaagagctt caacagggga g                                               21

<210> SEQ ID NO 26
<211> LENGTH: 20
<212> TYPE: DNA
<213> ORGANISM: Artificial Sequence
<220> FEATURE:
<223> OTHER INFORMATION: Artificially synthesized primer sequence, HIK
<220> FEATURE:
<221> NAME/KEY: primer_bind
<222> LOCATION: (1)...(20)

<400> SEQUENCE: 26
aggctggaac tgaggagcag                                                 20

<210> SEQ ID NO 27
<211> LENGTH: 1616
<212> TYPE: DNA
<213> ORGANISM: Homo sapiens
<220> FEATURE:
<221> NAME/KEY: 5'UTR
<222> LOCATION: (1)...(68)
<220> FEATURE:
<221> NAME/KEY: CDS
<222> LOCATION: (69)...(1478)
<220> FEATURE:
<221> NAME/KEY: 3'UTR
<222> LOCATION: (1482)...(1616)
<220> FEATURE:
<221> NAME/KEY: sig_peptide
<222> LOCATION: (69)...(125)

<400> SEQUENCE: 27
gaattcgcag tgccatgaca ccacgcatct gtcctctaga gaatcccctg agagctccgt     60 tcctcacc atg gac tgg acc tgg agg atc ctc ttc ttg gtg gca gca gcc    110
         Met Asp Trp Thr Trp Arg Ile Leu Phe Leu Val Ala Ala Ala
             -15                 -10 aca gga gcc cac tcc cag gtg cag ctg gtg cag tct ggg gct gag gtg    158
Thr Gly Ala His Ser Gln Val Gln Leu Val Gln Ser Gly Ala Glu Val
 -5              1               5                  10 aag aag cct ggg gcc tca gtg aag gtc tcc tgc aag gct tct gga tac    206
Lys Lys Pro Gly Ala Ser Val Lys Val Ser Cys Lys Ala Ser Gly Tyr
            15                  20                  25 acc ttc acc ggc tac tat atg cac tgg gtg cga cag gcc cct gga caa    254
Thr Phe Thr Gly Tyr Tyr Met His Trp Val Arg Gln Ala Pro Gly Gln
         30                  35                  40
```

```
ggg ctt gag tgg atg gga tgg atc aac cct cac agt ggt ggc aca aac    302
Gly Leu Glu Trp Met Gly Trp Ile Asn Pro His Ser Gly Gly Thr Asn
         45                  50                  55 tat gca cag aag ttt cag ggc agg gtc acc atg acc agg gac acg tcc    350
Tyr Ala Gln Lys Phe Gln Gly Arg Val Thr Met Thr Arg Asp Thr Ser
 60                  65                  70                  75 atc agc aca gcc tac atg gag ctg agc agg ctg aga tcc gac gac acg    398
Ile Ser Thr Ala Tyr Met Glu Leu Ser Arg Leu Arg Ser Asp Asp Thr
                 80                  85                  90 gcc gtg tat tac tgt gcg agg acg tat tac tat gat agt agt ggt tat    446
Ala Val Tyr Tyr Cys Ala Arg Thr Tyr Tyr Tyr Asp Ser Ser Gly Tyr
             95                 100                 105 tac cat gat gct ttt gat atc tgg ggc caa ggg aca atg gtc acc gtc    494
Tyr His Asp Ala Phe Asp Ile Trp Gly Gln Gly Thr Met Val Thr Val
        110                 115                 120 tct tca gcc tcc acc aag ggc cca tcg gtc ttc ccc ctg gcg ccc tgc    542
Ser Ser Ala Ser Thr Lys Gly Pro Ser Val Phe Pro Leu Ala Pro Cys
125                 130                 135 tcc agg agc acc tcc gag agc aca gcg gcc ctg ggc tgc ctg gtc aag    590
Ser Arg Ser Thr Ser Glu Ser Thr Ala Ala Leu Gly Cys Leu Val Lys
140                 145                 150                 155 gac tac ttc ccc gaa ccg gtg acg gtg tcg tgg aac tca ggc gct ctg    638
Asp Tyr Phe Pro Glu Pro Val Thr Val Ser Trp Asn Ser Gly Ala Leu
                160                 165                 170 acc agc ggc gtg cac acc ttc cca gct gtc cta cag tcc tca gga ctc    686
Thr Ser Gly Val His Thr Phe Pro Ala Val Leu Gln Ser Ser Gly Leu
            175                 180                 185 tac tcc ctc agc agc gtg gtg acc gtg ccc tcc agc aac ttc ggc acc    734
Tyr Ser Leu Ser Ser Val Val Thr Val Pro Ser Ser Asn Phe Gly Thr
        190                 195                 200 cag acc tac acc tgc aac gta gat cac aag ccc agc aac acc aag gtg    782
Gln Thr Tyr Thr Cys Asn Val Asp His Lys Pro Ser Asn Thr Lys Val
    205                 210                 215 gac aag aca gtt gag cgc aaa tgt tgt gtc gag tgc cca ccg tgc cca    830
Asp Lys Thr Val Glu Arg Lys Cys Cys Val Glu Cys Pro Pro Cys Pro
220                 225                 230                 235 gca cca cct gtg gca gga ccg tca gtc ttc ctc ttc ccc cca aaa ccc    878
Ala Pro Pro Val Ala Gly Pro Ser Val Phe Leu Phe Pro Pro Lys Pro
                240                 245                 250 aag gac acc ctc atg atc tcc cgg acc cct gag gtc acg tgc gtg gtg    926
Lys Asp Thr Leu Met Ile Ser Arg Thr Pro Glu Val Thr Cys Val Val
            255                 260                 265 gtg gac gtg agc cac gaa gac ccc gag gtc cag ttc aac tgg tac gtg    974
Val Asp Val Ser His Glu Asp Pro Glu Val Gln Phe Asn Trp Tyr Val
        270                 275                 280 gac ggc gtg gag gtg cat aat gcc aag aca aag cca cgg gag gag cag    1022
Asp Gly Val Glu Val His Asn Ala Lys Thr Lys Pro Arg Glu Glu Gln
    285                 290                 295 ttc aac agc acg ttc cgt gtg gtc agc gtc ctc acc gtt gtg cac cag    1070
Phe Asn Ser Thr Phe Arg Val Val Ser Val Leu Thr Val Val His Gln
300                 305                 310                 315 gac tgg ctg aac ggc aag gag tac aag tgc aag gtc tcc aac aaa ggc    1118
Asp Trp Leu Asn Gly Lys Glu Tyr Lys Cys Lys Val Ser Asn Lys Gly
                320                 325                 330 ctc cca gcc ccc atc gag aaa acc atc tcc aaa acc aaa ggg cag ccc    1166
Leu Pro Ala Pro Ile Glu Lys Thr Ile Ser Lys Thr Lys Gly Gln Pro
            335                 340                 345 cga gaa cca cag gtg tac acc ctg ccc cca tcc cgg gag gag atg acc    1214
Arg Glu Pro Gln Val Tyr Thr Leu Pro Pro Ser Arg Glu Glu Met Thr
        350                 355                 360
```

-continued

```
aag aac cag gtc agc ctg acc tgc ctg gtc aaa ggc ttc tac ccc agc      1262
Lys Asn Gln Val Ser Leu Thr Cys Leu Val Lys Gly Phe Tyr Pro Ser
365                 370                 375 gac atc gcc gtg gag tgg gag agc aat ggg cag ccg gag aac aac tac      1310
Asp Ile Ala Val Glu Trp Glu Ser Asn Gly Gln Pro Glu Asn Asn Tyr
380                 385                 390                 395 aag acc aca cct ccc atg ctg gac tcc gac ggc tcc ttc ttc ctc tac      1358
Lys Thr Thr Pro Pro Met Leu Asp Ser Asp Gly Ser Phe Phe Leu Tyr
            400                 405                 410 agc aag ctc acc gtg gac aag agc agg tgg cag cag ggg aac gtc ttc      1406
Ser Lys Leu Thr Val Asp Lys Ser Arg Trp Gln Gln Gly Asn Val Phe
        415                 420                 425 tca tgc tcc gtg atg cat gag gct ctg cac aac cac tac acg cag aag      1454
Ser Cys Ser Val Met His Glu Ala Leu His Asn His Tyr Thr Gln Lys
    430                 435                 440 agc ctc tcc ctg tct ccg ggt aaa tgagtgccac ggccggcaag ccccgctcc      1508
Ser Leu Ser Leu Ser Pro Gly Lys
445                 450 ccaggctctc ggggtcgcgt gaggatgctt ggcacgtacc ccgtgtacat acttcccagg    1568
cacccagcat ggaaataaag cacccagcgc tgccctggaa aaaaaaaa                 1616
```

<210> SEQ ID NO 28
<211> LENGTH: 470
<212> TYPE: PRT
<213> ORGANISM: Homo sapiens

<400> SEQUENCE: 28

```
Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro His Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Thr Tyr Tyr Asp Ser Ser Gly Tyr His
        115                 120                 125

Asp Ala Phe Asp Ile Trp Gly Gln Gly Thr Met Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220
```

-continued

```
Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465             470

<210> SEQ ID NO 29
<211> LENGTH: 974
<212> TYPE: DNA
<213> ORGANISM: Homo sapiens
<220> FEATURE:
<221> NAME/KEY: 5'UTR
<222> LOCATION: (1)...(38)
<220> FEATURE:
<221> NAME/KEY: CDS
<222> LOCATION: (39)...(746)
<220> FEATURE:
<221> NAME/KEY: 3'UTR
<222> LOCATION: (750)...(974)
<220> FEATURE:
<221> NAME/KEY: sig_peptide
<222> LOCATION: (39)...(104)

<400> SEQUENCE: 29
gaattcgcag tgccatgaca ccacggtcag gacacagc atg gac atg agg gtc ccc     56
                                         Met Asp Met Arg Val Pro
                                                 -20 gct cag ctc ctg ggg ctc ctg ctg ctc tgg ttc cca ggt tcc aga tgc    104
Ala Gln Leu Leu Gly Leu Leu Leu Leu Trp Phe Pro Gly Ser Arg Cys
    -15                 -10                  -5 gac atc cag atg acc cag tct cca tct tcc gtg tct gca tct gta gga    152
Asp Ile Gln Met Thr Gln Ser Pro Ser Ser Val Ser Ala Ser Val Gly
  1               5                  10                  15
```

```
gac aga gtc acc atc act tgt cgg gcg agt cag ggt att agc agg ttg        200
Asp Arg Val Thr Ile Thr Cys Arg Ala Ser Gln Gly Ile Ser Arg Leu
             20                  25                  30 tta gcc tgg tat cag cag aaa cca ggg aaa gcc cct aaa ctc ctg atc        248
Leu Ala Trp Tyr Gln Gln Lys Pro Gly Lys Ala Pro Lys Leu Leu Ile
         35                  40                  45 tat gtt gca tcc agt ttg caa agt ggg gtc cca tca agg ttc agc ggc        296
Tyr Val Ala Ser Ser Leu Gln Ser Gly Val Pro Ser Arg Phe Ser Gly
     50                  55                  60 agt gga tct ggg aca gat ttc act ctc acc atc agc agc ctg cag cct        344
Ser Gly Ser Gly Thr Asp Phe Thr Leu Thr Ile Ser Ser Leu Gln Pro
 65                  70                  75                  80 gaa gat ttt gca act tac tat tgt caa cag gct aac agt ttc ccg tgg        392
Glu Asp Phe Ala Thr Tyr Tyr Cys Gln Gln Ala Asn Ser Phe Pro Trp
                 85                  90                  95 acg ttc ggc caa ggg acc aag gtg gaa atc aaa cga act gtg gct gca        440
Thr Phe Gly Gln Gly Thr Lys Val Glu Ile Lys Arg Thr Val Ala Ala
            100                 105                 110 cca tct gtc ttc atc ttc ccg cca tct gat gag cag ttg aaa tct gga        488
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc        536
Thr Ala Ser Val Val Cys Leu Leu Asn Asn Phe Tyr Pro Arg Glu Ala
130                 135                 140 aaa gta cag tgg aag gtg gat aac gcc ctc caa tcg ggt aac tcc cag        584
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc        632
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac        680
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc        728
Ala Cys Glu Val Thr His Gln Gly Leu Ser Ser Pro Val Thr Lys Ser
        195                 200                 205 ttc aac agg gga gag tgt tagagggaga agtgccccca cctgctcctc               776
Phe Asn Arg Gly Glu Cys
    210 agttccagcc tgaccccctc ccatcctttg gcctctgacc cttttccac agggaccta        836 cccctattgc ggtcctccag ctcatctttc acctcacccc cctcctcctc cttggcttta     896 attatgctaa tgttggagga gaatgaataa ataaagtgaa tctttgcaaa aaaaaaaaa      956 aaaaatctct gcggccgc                                                    974

<210> SEQ ID NO 30
<211> LENGTH: 236
<212> TYPE: PRT
<213> ORGANISM: Homo sapiens

<400> SEQUENCE: 30

Met Asp Met Arg Val Pro Ala Gln Leu Leu Gly Leu Leu Leu Leu Trp
  1               5                  10                  15

Phe Pro Gly Ser Arg Cys Asp Ile Gln Met Thr Gln Ser Pro Ser Ser
             20                  25                  30

Val Ser Ala Ser Val Gly Asp Arg Val Thr Ile Thr Cys Arg Ala Ser
         35                  40                  45

Gln Gly Ile Ser Arg Leu Leu Ala Trp Tyr Gln Gln Lys Pro Gly Lys
```

```
                  50                    55                    60
Ala Pro Lys Leu Leu Ile Tyr Val Ala Ser Ser Leu Gln Ser Gly Val
 65                  70                    75                    80

Pro Ser Arg Phe Ser Gly Ser Gly Ser Gly Thr Asp Phe Thr Leu Thr
                     85                    90                    95

Ile Ser Ser Leu Gln Pro Glu Asp Phe Ala Thr Tyr Tyr Cys Gln Gln
                100                   105                   110

Ala Asn Ser Phe Pro Trp Thr Phe Gly Gln Gly Thr Lys Val Glu Ile
                115                   120                   125

Lys Arg Thr Val Ala Ala Pro Ser Val Phe Ile Phe Pro Pro Ser Asp
130                   135                   140

Glu Gln Leu Lys Ser Gly Thr Ala Ser Val Val Cys Leu Leu Asn Asn
145                   150                   155                   160

Phe Tyr Pro Arg Glu Ala Lys Val Gln Trp Lys Val Asp Asn Ala Leu
                165                   170                   175

Gln Ser Gly Asn Ser Gln Glu Ser Val Thr Glu Gln Asp Ser Lys Asp
                180                   185                   190

Ser Thr Tyr Ser Leu Ser Ser Thr Leu Thr Leu Ser Lys Ala Asp Tyr
                195                   200                   205

Glu Lys His Lys Val Tyr Ala Cys Glu Val Thr His Gln Gly Leu Ser
     210                   215                   220

Ser Pro Val Thr Lys Ser Phe Asn Arg Gly Glu Cys
225                   230                   235

<210> SEQ ID NO 31
<211> LENGTH: 1708
<212> TYPE: DNA
<213> ORGANISM: Homo sapiens
<220> FEATURE:
<221> NAME/KEY: 5'UTR
<222> LOCATION: (1)...(93)
<220> FEATURE:
<221> NAME/KEY: CDS
<222> LOCATION: (94)...(1503)
<220> FEATURE:
<221> NAME/KEY: 3'UTR
<222> LOCATION: (1507)...(1708)
<220> FEATURE:
<221> NAME/KEY: sig_peptide
<222> LOCATION: (94)...(150)
<220> FEATURE:
<221> NAME/KEY: misc_feature
<222> LOCATION: (1)...(1708)
<223> OTHER INFORMATION: n = A,T,C or G

<400> SEQUENCE: 31
gaattcgcag taccatgaca ccacgggagc cccagccttg ggattcccaa gtgtttgtaa      60
tcagtgatca ggactgagca cacaggactc acc atg gag ttg ggg ctg agc tgg     114
                                  Met Glu Leu Gly Leu Ser Trp
                                                           -15 gtt ttc ctt gtt gct ata tta gaa ggt gtc cag tgt gag gtg cag ctg     162
Val Phe Leu Val Ala Ile Leu Glu Gly Val Gln Cys Glu Val Gln Leu
         -10                  -5                   1 gtg gag tct ggg gga ggc ttg gta cag cct ggg ggg tcc ctg aga ctc     210
Val Glu Ser Gly Gly Gly Leu Val Gln Pro Gly Gly Ser Leu Arg Leu
  5                   10                   15                   20 tcc tgt gca gcc tct gga ttc acc ttc agt agc tac gac atg cac tgg     258
Ser Cys Ala Ala Ser Gly Phe Thr Phe Ser Ser Tyr Asp Met His Trp
                     25                   30                   35 gtc cgc caa gct aca gga aaa ggt ctg gag tgg gtc tca gct att ggt     306
Val Arg Gln Ala Thr Gly Lys Gly Leu Glu Trp Val Ser Ala Ile Gly
             40                   45                   50
```

-continued

| | |
|---|---|
| act gct ggt gac aca tac tat cca ggc tcc gtg aag ggc cga ttc acc<br>Thr Ala Gly Asp Thr Tyr Tyr Pro Gly Ser Val Lys Gly Arg Phe Thr<br>        55                  60                  65 | 354 |
| atc tcc aga gaa aat gcc aag aac tcc ttg tat ctt caa atg aac agc<br>Ile Ser Arg Glu Asn Ala Lys Asn Ser Leu Tyr Leu Gln Met Asn Ser<br>    70                  75                  80 | 402 |
| ctg aga gcc ggg gac acg gct gtg tat tac tgt gta aga gat aat agg<br>Leu Arg Ala Gly Asp Thr Ala Val Tyr Tyr Cys Val Arg Asp Asn Arg<br>85                  90                  95                 100 | 450 |
| aag gtg acc cac gag cac tac tac tac ggt atg gac gtc tgg ggc<br>Lys Val Thr His Glu His Tyr Tyr Tyr Gly Met Asp Val Trp Gly<br>                105                 110                 115 | 498 |
| caa ggg acc acg gtc acc gtc tcc tca gcc tcc acc aag ggc cca tcg<br>Gln Gly Thr Thr Val Thr Val Ser Ser Ala Ser Thr Lys Gly Pro Ser<br>            120                 125                 130 | 546 |
| gtc ttc ccc ctg gcg ccc tgc tcc agg agc acc tcc gag agc aca gcg<br>Val Phe Pro Leu Ala Pro Cys Ser Arg Ser Thr Ser Glu Ser Thr Ala<br>        135                 140                 145 | 594 |
| gcc ctg ggc tgc ctg gtc aag gac tac ttc ccc gaa ccg gtg acg gtg<br>Ala Leu Gly Cys Leu Val Lys Asp Tyr Phe Pro Glu Pro Val Thr Val<br>    150                 155                 160 | 642 |
| tcg tgg aac tca ggc gct ctg acc agc ggc gtg cac acc ttc cca gct<br>Ser Trp Asn Ser Gly Ala Leu Thr Ser Gly Val His Thr Phe Pro Ala<br>165                 170                 175                 180 | 690 |
| gtc cta cag tcc tca gga ctc tac tcc ctc agc agc gtg gtg acc gtg<br>Val Leu Gln Ser Ser Gly Leu Tyr Ser Leu Ser Ser Val Val Thr Val<br>                185                 190                 195 | 738 |
| ccc tcc agc aac ttc ggc acc cag acc tac acc tgc aac gta gat cac<br>Pro Ser Ser Asn Phe Gly Thr Gln Thr Tyr Thr Cys Asn Val Asp His<br>            200                 205                 210 | 786 |
| aag ccc agc aac acc aag gtg gac aag aca gtt gag cgc aaa tgt tgt<br>Lys Pro Ser Asn Thr Lys Val Asp Lys Thr Val Glu Arg Lys Cys Cys<br>        215                 220                 225 | 834 |
| gtc gag tgc cca ccg tgc cca gca cca cct gtg gca gga ccg tca gtc<br>Val Glu Cys Pro Pro Cys Pro Ala Pro Pro Val Ala Gly Pro Ser Val<br>    230                 235                 240 | 882 |
| ttc ctc ttc ccc cca aaa ccc aag gac acc ctc atg atc tcc cgg acc<br>Phe Leu Phe Pro Pro Lys Pro Lys Asp Thr Leu Met Ile Ser Arg Thr<br>245                 250                 255                 260 | 930 |
| cct gag gtc acg tgc gtg gtg gtg gac gtg agc cac gaa gac ccc gag<br>Pro Glu Val Thr Cys Val Val Val Asp Val Ser His Glu Asp Pro Glu<br>                265                 270                 275 | 978 |
| gtc cag ttc aac tgg tac gtg gac ggc gtg gag gtg cat aat gcc aag<br>Val Gln Phe Asn Trp Tyr Val Asp Gly Val Glu Val His Asn Ala Lys<br>            280                 285                 290 | 1026 |
| aca aag cca cgg gag gag cag ttc aac agc acg ttc cgt gtg gtc agc<br>Thr Lys Pro Arg Glu Glu Gln Phe Asn Ser Thr Phe Arg Val Val Ser<br>        295                 300                 305 | 1074 |
| gtc ctc acc gtt gtg cac cag gac tgg ctg aac ggc aag gag tac aag<br>Val Leu Thr Val Val His Gln Asp Trp Leu Asn Gly Lys Glu Tyr Lys<br>    310                 315                 320 | 1122 |
| tgc aag gtc tcc aac aaa ggc ctc cca gcc ccc atc gag aaa acc atc<br>Cys Lys Val Ser Asn Lys Gly Leu Pro Ala Pro Ile Glu Lys Thr Ile<br>325                 330                 335                 340 | 1170 |
| tcc aaa acc aaa ggg cag ccc cga gaa cca cag gtg tac acc ctg ccc<br>Ser Lys Thr Lys Gly Gln Pro Arg Glu Pro Gln Val Tyr Thr Leu Pro<br>                345                 350                 355 | 1218 |
| cca tcc cgg gag gag atg acc aag aac cag gtc agc ctg acc tgc ctg<br>Pro Ser Arg Glu Glu Met Thr Lys Asn Gln Val Ser Leu Thr Cys Leu | 1266 |

|  |  |
|---|---|
| gtc aaa ggc ttc tac ccc agc gac atc gcc gtg gag tgg gag agc aat<br>Val Lys Gly Phe Tyr Pro Ser Asp Ile Ala Val Glu Trp Glu Ser Asn<br>      375                    380                    385 | 1314 |
| ggg cag ccg gag aac aac tac aag acc aca cct ccc atg ctg gac tcc<br>Gly Gln Pro Glu Asn Asn Tyr Lys Thr Thr Pro Pro Met Leu Asp Ser<br>390                    395                    400 | 1362 |
| gac ggc tcc ttc ttc ctc tac agc aag ctc acc gtg gac aag agc agg<br>Asp Gly Ser Phe Phe Leu Tyr Ser Lys Leu Thr Val Asp Lys Ser Arg<br>405                    410                    415                    420 | 1410 |
| tgg cag cag ggg aac gtc ttc tca tgc tcc gtg atg cat gag gct ctg<br>Trp Gln Gln Gly Asn Val Phe Ser Cys Ser Val Met His Glu Ala Leu<br>                    425                    430                    435 | 1458 |
| cac aac cac tac acg cag aag agc ctc tcc ctg tct ccg ggt aaa<br>His Asn His Tyr Thr Gln Lys Ser Leu Ser Leu Ser Pro Gly Lys<br>              440                    445                    450 | 1503 |
| tgagtgccac ggccggcaag ccccgctcc ccaggctctc ggggtcgcgt gaggatgctt | 1563 |
| ggcacgtacc ccgtgtacat acttcccagg cacccagcat ggaaataaag cacccagcgc | 1623 |
| tgccctgggc ccctgcnaaa aaaaaaaaaa aaaaaaaaaa aaaaaaaaaa aaaaaaaaaa | 1683 |
| aaaaaaaaaa aatctctgcg gccgc | 1708 |

<210> SEQ ID NO 32
<211> LENGTH: 470
<212> TYPE: PRT
<213> ORGANISM: Homo sapiens

<400> SEQUENCE: 32

Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Ser Leu Arg Leu Ser Cys Ala Ala Ser Gly Phe Thr Phe
        35                  40                  45

Ser Ser Tyr Asp Met His Trp Val Arg Gln Ala Thr Gly Lys Gly Leu
    50                  55                  60

Glu Trp Val Ser Ala Ile Gly Thr Ala Gly Asp Thr Tyr Tyr Pro Gly
65                  70                  75                  80

Ser Val Lys Gly Arg Phe Thr Ile Ser Arg Glu Asn Ala Lys Asn Ser
                85                  90                  95

Leu Tyr Leu Gln Met Asn Ser Leu Arg Ala Gly Asp Thr Ala Val Tyr
            100                 105                 110

Tyr Cys Val Arg Asp Asn Arg Lys Val Thr His Glu His Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

```
Tyr Thr Cys Asn Val Asp His Lys Pro Ser Asn Thr Lys Val Asp Lys
225                 230                 235                 240

Thr Val Glu Arg Lys Cys Val Glu Cys Pro Pro Cys Pro Ala Pro
            245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 33
<211> LENGTH: 948
<212> TYPE: DNA
<213> ORGANISM: Homo sapiens
<220> FEATURE:
<221> NAME/KEY: 5'UTR
<222> LOCATION: (1)...(27)
<220> FEATURE:
<221> NAME/KEY: CDS
<222> LOCATION: (28)...(735)
<220> FEATURE:
<221> NAME/KEY: 3'UTR
<222> LOCATION: (739)...(948)
<220> FEATURE:
<221> NAME/KEY: sig_peptide
<222> LOCATION: (28)...(87)
<220> FEATURE:
<221> NAME/KEY: misc_feature
<222> LOCATION: (1)...(948)
<223> OTHER INFORMATION: n = A,T,C or G

<400> SEQUENCE: 33
gaattcgcag tgccatgaca ccacgcc atg gaa acc cca gcg cag ctt ctc ttc    54
                               Met Glu Thr Pro Ala Gln Leu Leu Phe
                                -20                 -15 ctc ctg cta ctc tgg ctc cca gat acc acc gga gaa att gtg ttg acg   102
Leu Leu Leu Leu Trp Leu Pro Asp Thr Thr Gly Glu Ile Val Leu Thr
```

|      |      |      |      |      |      |      |      |      |      |      |      |      |      |      |      |     |
|------|------|------|------|------|------|------|------|------|------|------|------|------|------|------|------|-----|
|      | -10  |      |      |      | -5   |      |      |      | 1    |      |      |      | 5    |      |      |     |
| cag  | tct  | cca  | ggc  | acc  | ctg  | tct  | ttg  | tct  | cca  | ggg  | gaa  | aga  | gcc  | acc  | ctc  | 150 |
| Gln  | Ser  | Pro  | Gly  | Thr  | Leu  | Ser  | Leu  | Ser  | Pro  | Gly  | Glu  | Arg  | Ala  | Thr  | Leu  |     |
|      |      |      |      | 10   |      |      |      |      | 15   |      |      |      | 20   |      |      |     |
| tcc  | tgc  | agg  | gcc  | agt  | cag  | aat  | att  | aga  | agc  | agc  | tac  | tta  | gcc  | tgg  | tac  | 198 |
| Ser  | Cys  | Arg  | Ala  | Ser  | Gln  | Asn  | Ile  | Arg  | Ser  | Ser  | Tyr  | Leu  | Ala  | Trp  | Tyr  |     |
|      |      | 25   |      |      |      |      | 30   |      |      |      |      | 35   |      |      |      |     |
| cag  | cag  | aaa  | cct  | ggc  | cag  | gct  | ccc  | ggg  | ctc  | ctc  | atc  | tat  | ggt  | gca  | tcc  | 246 |
| Gln  | Gln  | Lys  | Pro  | Gly  | Gln  | Ala  | Pro  | Gly  | Leu  | Leu  | Ile  | Tyr  | Gly  | Ala  | Ser  |     |
|      |      |      | 40   |      |      |      |      | 45   |      |      |      |      | 50   |      |      |     |
| agc  | agg  | gcc  | act  | ggc  | atc  | cca  | gac  | agg  | ttc  | agt  | ggc  | agt  | ggg  | tct  | ggg  | 294 |
| Ser  | Arg  | Ala  | Thr  | Gly  | Ile  | Pro  | Asp  | Arg  | Phe  | Ser  | Gly  | Ser  | Gly  | Ser  | Gly  |     |
|      | 55   |      |      |      |      | 60   |      |      |      |      | 65   |      |      |      |      |     |
| aca  | gac  | ttc  | act  | ctc  | acc  | atc  | agc  | aga  | ctg  | gag  | cct  | gaa  | gat  | ttt  | gca  | 342 |
| Thr  | Asp  | Phe  | Thr  | Leu  | Thr  | Ile  | Ser  | Arg  | Leu  | Glu  | Pro  | Glu  | Asp  | Phe  | Ala  |     |
| 70   |      |      |      |      | 75   |      |      |      |      | 80   |      |      |      |      | 85   |     |
| gtg  | tat  | tac  | tgt  | cag  | cag  | ttt  | ggt  | agc  | tca  | cct  | atg  | tgc  | agt  | ttt  | ggc  | 390 |
| Val  | Tyr  | Tyr  | Cys  | Gln  | Gln  | Phe  | Gly  | Ser  | Ser  | Pro  | Met  | Cys  | Ser  | Phe  | Gly  |     |
|      |      |      |      | 90   |      |      |      |      | 95   |      |      |      |      | 100  |      |     |
| cag  | ggg  | acc  | aag  | ctg  | gag  | atc  | aaa  | cga  | act  | gtg  | gct  | gca  | cca  | tct  | gtc  | 438 |
| Gln  | Gly  | Thr  | Lys  | Leu  | Glu  | Ile  | Lys  | Arg  | Thr  | Val  | Ala  | Ala  | Pro  | Ser  | Val  |     |
|      |      |      | 105  |      |      |      |      | 110  |      |      |      |      | 115  |      |      |     |
| ttc  | atc  | ttc  | ccg  | cca  | tct  | gat  | gag  | cag  | ttg  | aaa  | tct  | gga  | act  | gcc  | tct  | 486 |
| Phe  | Ile  | Phe  | Pro  | Pro  | Ser  | Asp  | Glu  | Gln  | Leu  | Lys  | Ser  | Gly  | Thr  | Ala  | Ser  |     |
|      || 120  |      |      |      |      | 125  |      |      |      |      | 130  |      |      |      |     |
| gtt  | gtg  | tgc  | ctg  | ctg  | aat  | aac  | ttc  | tat  | ccc  | aga  | gag  | gcc  | aaa  | gta  | cag  | 534 |
| Val  | Val  | Cys  | Leu  | Leu  | Asn  | Asn  | Phe  | Tyr  | Pro  | Arg  | Glu  | Ala  | Lys  | Val  | Gln  |     |
| 135  |      |      |      |      | 140  |      |      |      |      | 145  |      |      |      |      |      |     |
| tgg  | aag  | gtg  | gat  | aac  | gcc  | ctc  | caa  | tcg  | ggt  | aac  | tcc  | cag  | gag  | agt  | gtc  | 582 |
| Trp  | Lys  | Val  | Asp  | Asn  | Ala  | Leu  | Gln  | Ser  | Gly  | Asn  | Ser  | Gln  | Glu  | Ser  | Val  |     |
| 150  |      |      |      | 155  |      |      |      |      | 160  |      |      |      |      | 165  |      |     |
| aca  | gag  | cag  | gac  | agc  | aag  | gac  | agc  | acc  | tac  | agc  | ctc  | agc  | agc  | acc  | ctg  | 630 |
| Thr  | Glu  | Gln  | Asp  | Ser  | Lys  | Asp  | Ser  | Thr  | Tyr  | Ser  | Leu  | Ser  | Ser  | Thr  | Leu  |     |
|      |      |      | 170  |      |      |      |      | 175  |      |      |      |      | 180  |      |      |     |
| acg  | ctg  | agc  | aaa  | gca  | gac  | tac  | gag  | aaa  | cac  | aaa  | gtc  | tac  | gcc  | tgc  | gaa  | 678 |
| Thr  | Leu  | Ser  | Lys  | Ala  | Asp  | Tyr  | Glu  | Lys  | His  | Lys  | Val  | Tyr  | Ala  | Cys  | Glu  |     |
|      |      | 185  |      |      |      |      | 190  |      |      |      |      | 195  |      |      |      |     |
| gtc  | acc  | cat  | cag  | ggc  | ctg  | agc  | tcg  | ccc  | gtc  | aca  | aag  | agc  | ttc  | aac  | agg  | 726 |
| Val  | Thr  | His  | Gln  | Gly  | Leu  | Ser  | Ser  | Pro  | Val  | Thr  | Lys  | Ser  | Phe  | Asn  | Arg  |     |
|      |      | 200  |      |      |      |      | 205  |      |      |      |      | 210  |      |      |      |     |

| gga gag tgt tagagggaga antgccccca cctgctcctc agttccagcc | 775 |
| Gly Glu Cys | |
| 215 | |

| tgacccctc ccatcctttg gcctctgacc ctttttccac aggggaccta cccctattgc | 835 |
| ggtcctccag ctcatctttc acctcacccc cctcctcctc cttggcttta attatgctaa | 895 |
| tgttggagga gaatgaataa ataaagtgaa tctttgcacc tgtgaaaaaa aaa | 948 |

<210> SEQ ID NO 34
<211> LENGTH: 236
<212> TYPE: PRT
<213> ORGANISM: Homo sapiens

<400> SEQUENCE: 34

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Asn

-continued

```
                35                  40                  45
Ile Arg Ser Ser Tyr Leu Ala Trp Tyr Gln Gln Lys Pro Gly Gln Ala
 50                  55                  60

Pro Gly Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Tyr Cys Gln Gln Phe
            100                 105                 110

Gly Ser Ser Pro Met Cys Ser Phe Gly Gln Gly Thr Lys Leu Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 35
<211> LENGTH: 1673
<212> TYPE: DNA
<213> ORGANISM: Homo sapiens
<220> FEATURE:
<221> NAME/KEY: 5'UTR
<222> LOCATION: (1)...(95)
<220> FEATURE:
<221> NAME/KEY: CDS
<222> LOCATION: (96)...(1505)
<220> FEATURE:
<221> NAME/KEY: 3'UTR
<222> LOCATION: (1509)...(1673)
<220> FEATURE:
<221> NAME/KEY: sig_peptide
<222> LOCATION: (96)...(152)

<400> SEQUENCE: 35
gaattcgcag tgccatgaca ccacggtgga gccccagcct tgggattccc aagtgtttgt    60
attcagtgat caggactgaa cacacaggac tcacc atg gag ttg ggg ctg agc     113
                                      Met Glu Leu Gly Leu Ser
                                                          -15 tgg gtt ttc ctt gtt gct ata tta gaa ggt gtc cag tgt gag gtg cag    161
Trp Val Phe Leu Val Ala Ile Leu Glu Gly Val Gln Cys Glu Val Gln
        -10                 -5                   1 ctg gtg gag tct ggg gga ggc ttg gta cag cct ggg ggg tcc ctg aga    209
Leu Val Glu Ser Gly Gly Gly Leu Val Gln Pro Gly Gly Ser Leu Arg
  5                  10                  15 ctc tcc tgt gca gcc tct gga ttc acc ttc agt agc tac gac atg cac    257
Leu Ser Cys Ala Ala Ser Gly Phe Thr Phe Ser Ser Tyr Asp Met His
 20                  25                  30                  35 tgg gtc cgc caa gct aca gga aaa ggt ctg gag tgg gtc tca gct att    305
Trp Val Arg Gln Ala Thr Gly Lys Gly Leu Glu Trp Val Ser Ala Ile
                 40                  45                  50
```

```
ggt act gct ggt gac aca tac tat cca ggc tcc gtg aag ggc cga ttc      353
Gly Thr Ala Gly Asp Thr Tyr Tyr Pro Gly Ser Val Lys Gly Arg Phe
            55                  60                  65 acc atc tcc aga gaa aat gcc aag aac tcc ttg tat ctt caa atg aac      401
Thr Ile Ser Arg Glu Asn Ala Lys Asn Ser Leu Tyr Leu Gln Met Asn
        70                  75                  80 agc ctg aga gcc ggg gac acg gct gtg tat tac tgt gta aga gat aag      449
Ser Leu Arg Ala Gly Asp Thr Ala Val Tyr Tyr Cys Val Arg Asp Lys
    85                  90                  95 agg acg gtg acc cac gag cac tac tac tac ggt atg gac gtc tgg          497
Arg Thr Val Thr His Glu His Tyr Tyr Tyr Gly Met Asp Val Trp
100                 105                 110                 115 ggc caa ggg acc acg gtc acc gtc tcc tca gcc tcc acc aag ggc cca      545
Gly Gln Gly Thr Thr Val Thr Val Ser Ser Ala Ser Thr Lys Gly Pro
            120                 125                 130 tcg gtc ttc ccc ctg gcg ccc tgc tcc agg agc acc tcc gag agc aca      593
Ser Val Phe Pro Leu Ala Pro Cys Ser Arg Ser Thr Ser Glu Ser Thr
        135                 140                 145 gcg gcc ctg ggc tgc ctg gtc aag gac tac ttc ccc gaa ccg gtg acc      641
Ala Ala Leu Gly Cys Leu Val Lys Asp Tyr Phe Pro Glu Pro Val Thr
    150                 155                 160 gtg tcg tgg aac tca ggc gct ctg acc agc ggc gtg cac acc ttc cca      689
Val Ser Trp Asn Ser Gly Ala Leu Thr Ser Gly Val His Thr Phe Pro
165                 170                 175 gct gtc cta cag tcc tca gga ctc tac tcc ctc agc agc gtg gtg acc      737
Ala Val Leu Gln Ser Ser Gly Leu Tyr Ser Leu Ser Ser Val Val Thr
180                 185                 190                 195 gtg ccc tcc agc aac ttc ggc acc cag acc tac acc tgc aac gta gat      785
Val Pro Ser Ser Asn Phe Gly Thr Gln Thr Tyr Thr Cys Asn Val Asp
            200                 205                 210 cac aag ccc agc aac acc aag gtg gac aag aca gtt gag cgc aaa tgt      833
His Lys Pro Ser Asn Thr Lys Val Asp Lys Thr Val Glu Arg Lys Cys
        215                 220                 225 tgt gtc gag tgc cca ccg tgc cca gca cca cct gtg gca gga ccg tca      881
Cys Val Glu Cys Pro Pro Cys Pro Ala Pro Pro Val Ala Gly Pro Ser
    230                 235                 240 gtc ttc ctc ttc ccc cca aaa ccc aag gac acc ctc atg atc tcc cgg      929
Val Phe Leu Phe Pro Pro Lys Pro Lys Asp Thr Leu Met Ile Ser Arg
245                 250                 255 acc cct gag gtc acg tgc gtg gtg gtg gac gtg agc cac gaa gac ccc      977
Thr Pro Glu Val Thr Cys Val Val Val Asp Val Ser His Glu Asp Pro
260                 265                 270                 275 gag gtc cag ttc aac tgg tac gtg gac ggc gtg gag gtg cat aat gcc      1025
Glu Val Gln Phe Asn Trp Tyr Val Asp Gly Val Glu Val His Asn Ala
            280                 285                 290 aag aca aag cca cgg gag gag cag ttc aac agc acg ttc cgt gtg gtc      1073
Lys Thr Lys Pro Arg Glu Glu Gln Phe Asn Ser Thr Phe Arg Val Val
        295                 300                 305 agc gtc ctc acc gtt gtg cac cag gac tgg ctg aac ggc aag gag tac      1121
Ser Val Leu Thr Val Val His Gln Asp Trp Leu Asn Gly Lys Glu Tyr
    310                 315                 320 aag tgc aag gtc tcc aac aaa ggc ctc cca gcc ccc atc gag aaa acc      1169
Lys Cys Lys Val Ser Asn Lys Gly Leu Pro Ala Pro Ile Glu Lys Thr
325                 330                 335 atc tcc aaa acc aaa ggg cag ccc cga gaa cca cag gtg tac acc ctg      1217
Ile Ser Lys Thr Lys Gly Gln Pro Arg Glu Pro Gln Val Tyr Thr Leu
340                 345                 350                 355 ccc cca tcc cgg gag gag atg acc aag aac cag gtc agc ctg acc tgc      1265
Pro Pro Ser Arg Glu Glu Met Thr Lys Asn Gln Val Ser Leu Thr Cys
```

-continued

```
                360                 365                 370
ctg gtc aaa ggc ttc tac ccc agc gac atc gcc gtg gag tgg gag agc     1313
Leu Val Lys Gly Phe Tyr Pro Ser Asp Ile Ala Val Glu Trp Glu Ser
            375                 380                 385 aat ggg cag ccg gag aac aac tac aag acc aca cct ccc atg ctg gac     1361
Asn Gly Gln Pro Glu Asn Asn Tyr Lys Thr Thr Pro Pro Met Leu Asp
        390                 395                 400 tcc gac ggc tcc ttc ttc ctc tac agc aag ctc acc gtg gac aag agc     1409
Ser Asp Gly Ser Phe Phe Leu Tyr Ser Lys Leu Thr Val Asp Lys Ser
    405                 410                 415 agg tgg cag cag ggg aac gtc ttc tca tgc tcc gtg atg cat gag gct     1457
Arg Trp Gln Gln Gly Asn Val Phe Ser Cys Ser Val Met His Glu Ala
420                 425                 430                 435 ctg cac aac cac tac acg cag aag agc ctc tcc ctg tct ccg ggt aaa     1505
Leu His Asn His Tyr Thr Gln Lys Ser Leu Ser Leu Ser Pro Gly Lys
                440                 445                 450 tgagtgccac ggccggcaag cccccgctcc ccaggctctc ggggtcgcgt gaggatgctt   1565
ggcacgtacc ccgtgtacat acttcccagg cacccagcat ggaaataaag cacccagcgc   1625
tgccctgggc ccctgcgaaa aaaaaaaaaa aaaaatctct gcggccgc                1673

<210> SEQ ID NO 36
<211> LENGTH: 470
<212> TYPE: PRT
<213> ORGANISM: Homo sapiens

<400> SEQUENCE: 36

Met Glu Leu Gly Leu Ser Trp Val Phe Leu Val Ala Ile Leu Glu Gly
 1               5                  10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Asp Met His Trp Val Arg Gln Ala Thr Gly Lys Gly Leu
    50                  55                  60

Glu Trp Val Ser Ala Ile Gly Thr Ala Gly Asp Thr Tyr Tyr Pro Gly
65                  70                  75                  80

Ser Val Lys Gly Arg Phe Thr Ile Ser Arg Glu Asn Ala Lys Asn Ser
                85                  90                  95

Leu Tyr Leu Gln Met Asn Ser Leu Arg Ala Gly Asp Thr Ala Val Tyr
            100                 105                 110

Tyr Cys Val Arg Asp Lys Arg Thr Val Thr His Glu His Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
```

```
                225                 230                 235                 240
Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 37
<211> LENGTH: 970
<212> TYPE: DNA
<213> ORGANISM: Homo sapiens
<220> FEATURE:
<221> NAME/KEY: 5'UTR
<222> LOCATION: (1)...(32)
<220> FEATURE:
<221> NAME/KEY: CDS
<222> LOCATION: (33)...(740)
<220> FEATURE:
<221> NAME/KEY: 3'UTR
<222> LOCATION: (744)...(970)
<220> FEATURE:
<221> NAME/KEY: sig_peptide
<222> LOCATION: (33)...(92)

<400> SEQUENCE: 37
gaattcgcag tgccatgaca ccacggggaa cc atg gaa acc cca gcg cag ctt        53
                                    Met Glu Thr Pro Ala Gln Leu
                                    -20                 -15 ctc ttc ctc ctg cta ctc tgg ctc cca gat acc acc gga gaa att gtg      101
Leu Phe Leu Leu Leu Leu Trp Leu Pro Asp Thr Thr Gly Glu Ile Val
        -10                 -5                  1 ttg acg cag tct cca ggc acc ctg tct ttg tct cca ggg gaa aga gcc      149
Leu Thr Gln Ser Pro Gly Thr Leu Ser Leu Ser Pro Gly Glu Arg Ala
    5                   10                  15
```

-continued

| | |
|---|---|
| acc ctc tcc tgc agg gcc agt cag agt att agc agc agc tcc tta gcc<br>Thr Leu Ser Cys Arg Ala Ser Gln Ser Ile Ser Ser Ser Leu Ala<br>20               25               30               35 | 197 |
| tgg tac cag cag aaa cct ggc cag gct ccc ggg ctc ctc atc ttt ggt<br>Trp Tyr Gln Gln Lys Pro Gly Gln Ala Pro Gly Leu Leu Ile Phe Gly<br>               40               45               50 | 245 |
| gca tcc agc agg gcc act ggc atc cca gac agg ttc agt ggc agt ggg<br>Ala Ser Ser Arg Ala Thr Gly Ile Pro Asp Arg Phe Ser Gly Ser Gly<br>          55               60               65 | 293 |
| tct ggg aca gac ttc act ctc acc atc agc aga ctg gag cct gaa gat<br>Ser Gly Thr Asp Phe Thr Leu Thr Ile Ser Arg Leu Glu Pro Glu Asp<br>    70               75               80 | 341 |
| ttt gca gtg tat tac tgt cag cag ttt ggt agc tca cct atg tgc agt<br>Phe Ala Val Tyr Tyr Cys Gln Gln Phe Gly Ser Ser Pro Met Cys Ser<br>85               90               95 | 389 |
| ttt ggc cag ggg acc aag ctg gag atc aaa cga act gtg gct gca cca<br>Phe Gly Gln Gly Thr Lys Leu Glu Ile Lys Arg Thr Val Ala Ala Pro<br>100              105            110            115 | 437 |
| tct gtc ttc atc ttc ccg cca tct gat gag cag ttg aaa tct gga act<br>Ser Val Phe Ile Phe Pro Pro Ser Asp Glu Gln Leu Lys Ser Gly Thr<br>              120                 125            130 | 485 |
| gcc tct gtt gtg tgc ctg ctg aat aac ttc tat ccc aga gag gcc aaa<br>Ala Ser Val Val Cys Leu Leu Asn Asn Phe Tyr Pro Arg Glu Ala Lys<br>          135               140              145 | 533 |
| gta cag tgg aag gtg gat aac gcc ctc caa tcg ggt aac tcc cag gag<br>Val Gln Trp Lys Val Asp Asn Ala Leu Gln Ser Gly Asn Ser Gln Glu<br>150              155            160 | 581 |
| agt gtc aca gag cag gac agc aag gac agc acc tac agc ctc agc agc<br>Ser Val Thr Glu Gln Asp Ser Lys Asp Ser Thr Tyr Ser Leu Ser Ser<br>    165               170               175 | 629 |
| acc ctg acg ctg agc aaa gca gac tac gag aaa cac aaa gtc tac gcc<br>Thr Leu Thr Leu Ser Lys Ala Asp Tyr Glu Lys His Lys Val Tyr Ala<br>180              185            190            195 | 677 |
| tgc gaa gtc acc cat cag ggc ctg agc tcg ccc gtc aca aag agc ttc<br>Cys Glu Val Thr His Gln Gly Leu Ser Ser Pro Val Thr Lys Ser Phe<br>              200               205            210 | 725 |
| aac agg gga gag tgt tagagggaga agtgccccca cctgctcctc agttccagcc<br>Asn Arg Gly Glu Cys<br>          215 | 780 |
| tgaccccctc ccatcctttg gcctctgacc ctttttccac aggggaccta ccctattgc | 840 |
| ggtcctccag ctcatctttc acctcacccc cctcctcctc cttggcttta attatgctaa | 900 |
| tgttggagga gaatgaataa ataaagtgaa tctttgcaaa aaaaaaaaaa aaaaaaatct | 960 |
| ctgcggccgc | 970 |

<210> SEQ ID NO 38
<211> LENGTH: 236
<212> TYPE: PRT
<213> ORGANISM: Homo sapiens

<400> SEQUENCE: 38

Met Glu Thr Pro Ala Gln Leu Leu Phe Leu Leu Leu Leu Trp Leu Pro
1               5                    10                 15

Asp Thr Thr Gly Glu Ile Val Leu Thr Gln Ser Pro Gly Thr Leu Ser
               20                    25                    30

Leu Ser Pro Gly Glu Arg Ala Thr Leu Ser Cys Arg Ala Ser Gln Ser
          35                    40                    45

Ile Ser Ser Ser Ser Leu Ala Trp Tyr Gln Gln Lys Pro Gly Gln Ala
50                    55                    60

```
Pro Gly Leu Leu Ile Phe Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Tyr Cys Gln Gln Phe
            100                 105                 110

Gly Ser Ser Pro Met Cys Ser Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235
```

```
<210> SEQ ID NO 39
<211> LENGTH: 35
<212> TYPE: DNA
<213> ORGANISM: Artificial Sequence
<220> FEATURE:
<223> OTHER INFORMATION: Artificially synthesized primer sequence
<220> FEATURE:
<221> NAME/KEY: primer_bind
<222> LOCATION: (1)...(35)

<400> SEQUENCE: 39
gaggtctccg ccctcgagat gcggctgggc agtcc                        35

<210> SEQ ID NO 40
<211> LENGTH: 33
<212> TYPE: DNA
<213> ORGANISM: Artificial Sequence
<220> FEATURE:
<223> OTHER INFORMATION: Artificially synthesized primer sequence
<220> FEATURE:
<221> NAME/KEY: primer_bind
<222> LOCATION: (1)...(33)

<400> SEQUENCE: 40
cacaggacag ccagggatc ccacgtggcc gcg                           33

<210> SEQ ID NO 41
<211> LENGTH: 6
<212> TYPE: PRT
<213> ORGANISM: Homo sapiens

<400> SEQUENCE: 41

Met Tyr Pro Pro Pro Tyr
 1                   5

<210> SEQ ID NO 42
<211> LENGTH: 4
<212> TYPE: PRT
```

```
-continued

<213> ORGANISM: Homo sapiens

<400> SEQUENCE: 42

Tyr Met Asn Met
1

<210> SEQ ID NO 43
<211> LENGTH: 4
<212> TYPE: PRT
<213> ORGANISM: Homo sapiens

<400> SEQUENCE: 43

Tyr Val Lys Met
1
```

US 7,166,283 B2

METHODS OF TREATING AN INFLAMMATORY DISORDER AND PROHIBITING PROLIFERATION, CYTOKINE PRODUCTION, AND SIGNAL TRANSDUCTION WITH ANTIBODY AGAINST COSTIMULATORY SIGNAL TRANSDUCTION MOLECULE AILIM

This application is a divisional of U.S. patent application Ser. No. 09/859,053, filed May 16, 2001, which now U.S. Pat. No. 6,803,039 claims priority from Japanese Application No. 2000-147116, filed May 18, 2000, and Japanese Application No. 2001-99598, Filed Mar. 30, 2001. The prior applications are incorporated herein by reference in their entirety.

FIELD OF THE INVENTION

The present invention relates to human antibodies which bind to AILIM (activation inducible lymphocyte immunomodulatory molecule, also referred to as ICOS (inducible co-stimulator); human monoclonal antibodies which bind to AILIM or a portion thereof; DNA encoding said human monoclonal antibody or a portion thereof, or a portion of said DNA; cells (including genetic recombinant cells) producing said human monoclonal antibody or a portion thereof; human monoclonal antibody or a portion thereof produced by said genetic recombinant cells; pharmaceutical composition comprising said human monoclonal antibody or a portion thereof; pharmaceutical composition comprising antibody to AILIM for treating disorders related to the delayed allergy; method for identifying, quantitating or assaying substances that bind to AILIM or AILIM ligand; and kit used for said method.

BACKGROUND OF THE INVENTION

A living body of mammals has immune response systems that excludes pathogenic microorganisms (viruses, bacteria, parasites, etc.) or foreign bodies (both are called "antigen" in the following) that have invaded the living body. One of them is called natural immune response system, another acquired immune response system. The former is an exclusion mechanism comprising phagocytosis by phagocytes (polymorphonuclear leukocytes, monocytes, macrophages, etc.), attack by natural killer (NK) cells, and non-specific recognition such as opsonization of antigen by complements. The latter, acquired immune response system, is an exclusion mechanism by lymphocytes (mainly, T cells and B cells) that acquired the specificity to the antigen (namely, activated lymphocytes). B cells that acquired antigen specificity attack the antigen existing outside of the cells through production of antibodies specific to the antigen. T cells that acquired antigen specificity (namely, activated T cells) are classified into helper T cells and cytotoxic T cells (cytotoxic lymphocyte, CTL). The helper T cells regulate a differentiation of B cells and a production of antibodies, and destroy the antigen cooperating with phagocytes. The latter, CTLs attack virus-infected cells and so on by themselves (Experimental Medicine: SUPPLEMENT, "Bio Science Term Library, Immunity", Yodosha, pp.14–17 (1995)).

This acquisition of antigen specificity by T cells (namely, activation of T cells) is initiated through recognition by T cells the antigen presented by antigen-presenting cells (APC) such as macrophage, B cells, or dendritic cells. Antigen-presenting cells process the antigens so incorporated and present these processed antigens through binding them to major histocompatibility complex (MHC). T cells receive primary signal for activation of the cells (or acquisition of specificity) by recognizing the processed antigens presented by antigen-presenting cells through a complex between T cell receptor (TcR) and CD3 antigen existing on the surface of the cell membrane (TcR/CD3 complex).

However, the TcR/CD3 complex-mediated primary signal alone cannot activate T cells sufficiently and leads to unresponsiveness or clonal anergy, so that the cells can not react with any stimulation received thereafter. The autocrine of interleukin 2 (IL-2) is necessary for T cells to be activated, to be differentiated into antigen specific T cell clones, and to be proliferated. In clonal anergy, T cells are inactivated due to no production of IL-2 and such and no cell division. Namely, the activation of T cells accompanied by production of cytokines such as IL-2 requires the secondary signal following the first signal through TcR/CD3 complex. This secondary signal is called costimulatory signal.

T cells receive this secondary signal and transmit it into the cells by interacting (cell adhesion) with molecules other than MHC on antigen-presenting cells through molecules other than TcR/CD3 complex on the T cell surface. This secondary signal avoids cell anergy (clonal anergy) and activates the cells.

Although some part of the mechanism of the secondary signal transmission between antigen-presenting cells and lymphocytes such as T cells have not yet been elucidated in detail, studies so far have revealed that an important factor for the secondary signal transmission is the interaction of CD28 (also named Tp44, T44, or 9.3 antigen), which is a cell surface molecule expressed mainly on T cells and thymus cells, with CD80 (also named B7-1, B7, BB1, or B7/BB1), which is a cell surface molecule expressed on antigen-presenting cells (macrophages, monocytes, dendritic cells, etc.) and with CD86 (also named B7-2 or B70), which is also a cell surface molecule on antigen-presenting cells (namely, cell adhesion through the binding between these molecules). Moreover, it has been experimentally elucidated that the interaction of Cytolytic T lymphocyte associated antigen 4 (CTLA-4), whose expression is thought to be enhanced depending on the secondary signal, with the CD80 (B7-1) and CD86 (B7-2) (namely, cell adhesion through the binding between these molecules) also plays an important role in the regulation of T cell activation by the secondary signal. In other words, the regulation of T cell activation by the transmission of the secondary signal involves at least the interaction between CD28 and CD80/CD86, the enhancement of CTLA-4 expression, which is thought to depend on the interaction, and the interaction between CTLA-4 and CD80/CD86.

CD28 is known to be a costimulator molecule transmitting the secondary signal (costimulatory signal) required for the activation of T cells and for the avoidance of anergy. The secondary signal transmitted by binding this molecule to costimulator molecules, CD80 (B7-1) and CD86 (B7-2), on antigen-presenting cells (cell adhesion through the binding between these molecules), stabilizes mRNA of Th1-type cytokines and consequently promotes production by T cells of a large amount of Th1-type cytokines such as IL-2, IFNγ, and TNFα. The expression of CTLA-4 is induced by the primary signal transmitted through TcR/CD3, and the expression is also enhanced by the secondary signal transmitted by the binding between CD28 and CD80. It is being revealed that CTLA-4 receives these signals to work to inhibit T cell function, which is contrary to the activation of T cells by the secondary signal transmitted by CD28.

Human CD28 and CTLA-4 are type I glycoproteins whose molecular weights are 44 kD and 41 to 43 kD, respectively. Both have an immunoglobulin-like domain, belong to the immunoglobulin superfamily, and have both function as a cell adhesion molecule and function as a signal transmission molecule.

Human CD28 forms a homodimer with a disulfide bond while CTLA-4 exists as a monomer. Both CD28 and CTLA-4 genes are located at "2q33" on human chromosome and "1C" on mouse chromosome, and are composed of four (4) exons. Human CD28 and CTLA-4 are composed of 220 and 223 amino acids, respectively, including the leader sequences, and amino acid homology between them is 20 to 30%.

The ligands for CD28 and CTLA-4 are CD80 (B7-1) and CD86 (B7-2) in human and mice. CTLA-4 has about 20 times as high affinity to both ligands as CD28. It has been elucidated that the amino acid sequence structures "MYPPPY (Met-Tyr-Pro-Pro-Pro-Tyr; SEQ ID NO:41)" conserved through animal species is important for the binding of CD28 and CTLA-4 to CD80 (B7-1). It has also been reported that, when CD28 is stimulated, PI3 kinase (phosphoinositide 3 kinase, PI3K) associates with the phosphorylated tyrosine residue in a partial sequence "YMNM (Tyr-Met-Asn-Met: SEQ ID NO:42)" of CD28 and that CD28 plays an important role in intracellular signal transmission through this "YxxM" structure. Furthermore, it has been reported that CTLA-4 also has a sequence represented by "YxxM," namely "YVKM (Tyr-Val-Lys-Met; SEQ ID NO:43)" in its cytoplasmic region and that, after being stimulated, SYP associates with this sequence.

CD28 is expressed specifically in thymocytes and peripheral blood T cells, and CTLA-4 is expressed specifically in activated T cells (Cell Engineering: SUPPLEMENT, "Handbook of Adhesion Molecule", Shujunsha, pp.93–102 (1994); ibid. pp.120–136; Experimental Medicine: SUPPLEMENT, "BIO SCIENCE Term Library, Immunity", Yodosha, pp.94–98 (1995); Experimental Medicine: SUPPLEMENT, "BIO SCIENCE Term Library, Intracellular Signal Transduction", Yodosha, pp.58–59 (1997); Nihon Rinsho, Vol. 55, No.6, pp.215–220 (1997)).

In the regulation of T cell function (the activation and the inhibition of function of T cells), the importance of interactions among multiple molecules such as costimulator molecules (CD28, CD80 (B7-1), CD86 (B7-2), etc.) and CTLA-4, which cooperates with them, has thus been recognized, and this has been drawn attention to the relationship between these molecules and diseases, and the treatment of diseases by regulating the function of these molecules.

As described above, although a living body activates its acquired immune response system against antigens that are foreign bodies to the living body (self), it also has immunological tolerance so as to show no immune response against its own component (autoantigen). If immunological tolerance breaks down by some reason, immune response to the autoantigen occurs, autoantigen-reactive T cells are induced by the same mechanism as mentioned above to fall into abnormal state of immunity, and various autoimmune diseases are caused.

In other words, since non-stimulated antigen presenting cells (APC) in normal tissues do not express costimulatory molecules when the immune system of a living body is normal, T cells are in the unresponsiveness state to maintain immunological tolerance even if autoantigen-reactive T cells, which reacts with autoantigen, exist. It has been suggested that in abnormal state of immunity, more autoantigen-reactive T cells are activated due to abnormal excess and continuous expression of costimulatory molecules to thereby cause autoimmune diseases.

From such viewpoints recently, many attempts to treat various autoimmune diseases by modulating the transmission of costimulatory signals, for example, the above-mentioned signal transmission between CD28/CTLA-4 and CD80/CD86, are proposed.

The results of such attempts have not yet clarified in detail the mechanism of the T cell activation by interaction between costimulatory molecules and the related molecules. Other unknown molecules may be involved in this mechanism.

Recently, there has been identified a novel co-stimulatory molecule like the above-described "CD28" and "CTLA-4", which is thought to carry out the transduction of a second signal (co-stimulatory signal) essential for the activation of lymphocytes such as T cells, and functional regulation coupled with said signal of activated lymphocytes such as activated T cells. This molecule has been designated as AILIM (activation inducible lymphocyte immunomodulatory molecule) (in humans, mice and rats: Int. Immunol., Vol. 12, No. 1, p.51–55, 2000), also referred to as ICOS (inducible co-stimulator) (in humans: Nature, Vol. 397, No.6716, p.263–266, 1999)).

On the other hand, novel molecules celled B7h, B7RP-1, GL50 or LICOS which are ligands (AILIM ligands) interacting with this costimulatory transmission molecule AILIM (ICOS) have been identified very recently (Nature. Vol.402, No.6763, pp.827–832, 1999; Nature Medicine, Vol.5, No.12, pp.1365–1369, 1999; J. Immunology, Vol.164, pp.1653–1657, 2000; Curr. Biol., Vol.10, No.6, pp.333–336, 2000).

The identification of these two kinds of novel molecules, namely AILIM (ICOS) and B7RP-1 (B7h, GL50, LICOS), as the signal transduction pathway for the costimulatory signal essential for the above activation of lymphocytes such as T cells, and the control of the function of activated T cells, revealed that there is the novel third pathway by the interaction between AILIM (ICOS) and B7RP-1 (B7h, GL50, LICOS), besides the known first and second signal pathways which are already known transduction pathway between CD28 and CD80 (B7-1)/CD86 (B7-2), and that between CTLA4 and CD80 (B7-1)/CD86 (B7-2).

Studies on the biological functions of these novel molecules, the function control of lymphocytes, such as T cells, through this third costimulatory signal transduction by the molecules, and the relationship between the novel signal transduction and diseases are in progress (J. Immunol., 166(1), pp.1, 2001; J. Immunol., 165(9), pp.5035, 2000; Biochem. Biophys. Res. Commun., 276(1), pp.335, 2000; Immunity, 13(1), pp.95, 2000; J. Exp. Med., 192(1), pp.53, 2000; Eur. J. Immunol., 30(4), pp.1040, 2000; WO 01/15732).

SUMMARY OF THE INVENTION

Specifically, an objective of the present invention is to reveal biological functions of the novel molecule AILIM, considered, like "CD28" and "CTLA-4", as a molecule which transmits the secondary signal (costimulatory signal) essential for the activation of lymphocytes, such as T cells, and which controls the functions of activated lymphocytes, such as activated T cells, by working with the signal; to reveal relationships between the expression of AILIM and diseases; and to provide a method and a pharmaceutical which inhibit the development of the various diseases dependent on the expression pattern of AILIM or which treat the diseases by controlling the biological functions of the AILIM using the medical and pharmaceutical methods (for example, a drug such as a monoclonal antibody and a low molecular compound).

To achieve the above-described purposes, the present inventors have actively pursued studies on human antibodies (particularly human monoclonal antibodies) against mammalian AILIMs (particularly human AILIM), and as a result, by immunizing transgenic mice prepared using genetic recombination techniques so as to produce human antibodies with AILIM (specifically cell membrane fraction of cells expressing human AILIM), succeeded first in the world in preparing a variety of monoclonal antibodies which bind to human AILIM, particularly those which bind to human AILIM that regulate signal transduction mediated by human AILIM.

Since antibodies (particularly monoclonal antibodies) of this invention are derived from humans, they do not induce any severe immune rejection due to the immunogenicity against humans, HAMA (human anti-mouse antigenicity), in the host at all, which has been a big problem (side effect) in therapy using antibody pharmaceuticals comprising antibodies derived from non-human mammals such as mice, and thus dramatically enhancing the value of antibody as medicine.

Therefore, human antibodies (particularly human monoclonal antibodies) which bind to mammalian AILIMs (particularly human AILIM) of this invention and pharmaceutical compositions comprising said human antibodies (particularly human monoclonal antibodies) are useful as drugs to control, with no induction of immune rejection due to HAMA in the host, various physiological reactions related to the transduction of co-stimulatory signal to AILIM-expressing cells mediated by AILIM (for example, proliferation of AILIM-expressing cells, cytokine production by AILIM-expressing cells, immune cytolysis or apoptosis of AILIM-expressing cells, and activity to induce antibody-dependent cytotoxicity to AILIM-expressing cells, and so on), and/or are also useful as drugs to suppress and prevent development of symptoms and/or progress of various disorders related to the signal transduction mediated by said AILIM, and as medicine to treat or prevent said disorder.

Specifically, pharmaceutical compositions according to this invention are able to control (suppress or stimulate) proliferation of AILIM-expressing cells or production of cytokine (for example, interferon g or interleukin 4, etc.) by AILIM-expressing cells, thereby enabling suppression of various pathological conditions and treatment or prevention of various disorders caused by diverse physiological phenomena related to signal transduction mediated by AILIM.

Use of pharmaceutical compositions according to this invention enables suppression, prevention and/or treatment of, for example, various disorders (for example, rheumatoid arthritis, multiple sclerosis, autoimmune thyroiditis, allergic contact-type dermatitis, chronic inflammatory dermatosis such as lichen planus, systemic lupus erythematosus, insulin-dependent diabetes mellitus, psoriasis, etc.) classified into autoimmune or allergic disorders (particularly autoimmune disease and delayed allergy caused by cellular immunity); arthropathia (for example, rheumatoid arthritis (RA) and osteoarthritis (OA)), inflammation (e.g., hepatitis); graft versus host reaction (GVH reaction); graft versus host disease (GVHD); immune rejection accompanying transplantation (homoplasty or heteroplasty) of a tissue (tissues such as skin, cornea, bone, etc.) or organ (liver, heart, lung, kidney, pancreas, etc.); immune response triggered by a foreign antigen or autoantigen (for example, production of antibodies against said antigen, cell proliferation, production of cytokines); and disorders possibly caused by the abnormal intestinal immunity (specifically inflammatory intestinal disorders (particularly clone disease and ulcerative colitis) and alimentary allergy).

Furthermore, in the field of suppression/treatment of immune rejection accompanying transplantation of above-described tissues and organs, it is possible to augment the suppressive effect on transplant rejection of known immunosuppressant by using the pharmaceutical composition of this invention together with said drugs which have been utilized for suppression of immune rejection in such a transplantation treatment.

Moreover, the pharmaceutical composition of the present invention can be applied for treating or preventing, any inflammatory diseases to which various steroids are indicated as antiphlogistic.

The pharmaceutical composition of the present invention can be applied to inflammatory disease for example, inflammation accompanying various arthritis (for example, rheumatoid arthritis, osteoarthritis), pneumonia, hepatitis (including viral hepatitis), inflammation accompanying infectious diseases, inflammatory bowel diseases, intestinal enteritis, nephritis (inflammation accompanying glomerular nephritis, nephrofibrosis), gastritis, angiitis, pancreatitis, peritonitis, bronchitis, myocarditis, cerebritis, inflammation in postischemic reperfusion injury (myocardial ischemic reperfusion injury), inflammation attributed to immune rejection after transplantation of tissue and organ, burn, various skin inflammation (psoriasis, allergic contact-type dermatitis, lichen planus which is chronic inflammatory skin disease), inflammation in multiple organ failure, inflammation after operation of PTCA or PTCR, and inflammation accompanying arteriosclerosis, and autoimmune thyroiditis.

In addition, by using a method for identifying substances that bind to AILIM or AILIM ligand, which is one of the present inventions, it becomes possible to screen to select pharmaceuticals (chemical synthetic compounds or antibodies) with potential activity to treat various disorders by binding to AILIM or AILIM ligands to regulate signal transduction mediated by interaction of them.

Specifically, the present invention is the invention described from the following (1) to (108).

(1) A human antibody which binds to AILIM.

(2) The human antibody of (1), wherein said AILIM is derived from human.

(3) A human monoclonal antibody which binds to AILIM or a portion thereof.

(4) The human monoclonal antibody or a portion thereof of (3), wherein said AILIM is derived from human.

(5) The human monoclonal antibody or a portion thereof of (3) or (4), wherein said human monoclonal antibody has an activity to inhibit a signal transduction into a cell mediated by AILIM.

(6) The human monoclonal antibody or a portion thereof of (5), wherein said activity to inhibit a signal transduction is (a) or (b) of the followings:

(a) activity to inhibit proliferation of AILIM-expressing cells, or (b) activity to inhibit cytokine production from AILIM-expressing cells.

(7) The human monoclonal antibody or a portion thereof of (6), wherein said cytokine is one of the cytokines produced by Th1-type or Th2-type T cell.

(8) The human monoclonal antibody or a portion thereof of (7), wherein said cytokine is interferon y or interleukin 4.

(9) The human monoclonal antibody or a portion thereof of (5), wherein said human monoclonal antibody has an activity to prevent mixed lymphocyte reaction.

(10) The human monoclonal antibody or a portion thereof of (3) or (4), wherein said human monoclonal antibody has an activity to induce signal transduction into a cell mediated by AILIM.

(11) The human monoclonal antibody or a portion thereof of (10), wherein said activity to induce signal transduction is (a) or (b) of the followings:

(a) activity to induce proliferation of AILIM-expressing cells, or (b) activity to induce cytokine production from AILIM-expressing cells.

(12) The human monoclonal antibody or a portion thereof of (11), wherein said cytokine is one of the cytokines produced by Th1-type or Th2-type T cell.

(13) The human monoclonal antibody or a portion thereof of (12), wherein said cytokine is interferon γ or interleukin 4.

(14) The human monoclonal antibody or a portion thereof of (3) or (4), wherein said human monoclonal antibody has an activity to induce antibody-dependent cytotoxicity to AILIM-expressing cells, and/or immune cytolysis or apoptosis of AILIM-expressing cells.

(15) The human monoclonal antibody or a portion thereof of (3) or (4), wherein the binding rate constant (ka) between said monoclonal antibody and AILIM is $1.0 \times 10^3$ (1/M.Sec) or more.

(16) The human monoclonal antibody or a portion thereof of (15), wherein said binding rate constant (ka) is $1.0 \times 10^4$ (1/M.Sec) or more.

(17) The human monoclonal antibody or a portion thereof of (16), wherein said binding rate constant (ka) is $1.0 \times 10^5$ (1/M.Sec) or more.

(18) The human monoclonal antibody or a portion thereof of (3) or (4), wherein the dissociation rate constant (kd) between said monoclonal antibody and AILIM is $1.0 \times 10^{-3}$ (1/Sec) or less.

(19) The human monoclonal antibody or a portion thereof of (18), wherein said dissociation rate constant (kd) is $1.0 \times 10^{-4}$ (1/Sec) or less.

(20) The human monoclonal antibody or a portion thereof of (19), wherein said dissociation rate constant (kd) is $1.0 \times 10^{-5}$ (1/Sec) or less.

(21) The human monoclonal antibody or a portion thereof of (3) or (4), wherein the dissociation constant (Kd) between said monoclonal antibody and AILIM is $1.0 \times 10^{-6}$ (M) or less.

(22) The human monoclonal antibody or a portion thereof of (21), wherein said dissociation constant (Kd) is $1.0 \times 10^{-7}$ (M) or less.

(23) The human monoclonal antibody or a portion thereof of (22), wherein said dissociation constant (Kd) is $1.0 \times 10^{-8}$ (M) or less.

(24) The human monoclonal antibody or a portion thereof of (23), wherein said dissociation constant (Kd) is $1.0 \times 10^{-9}$ (M) or less.

(25) The human monoclonal antibody or a portion thereof of (4), wherein a V region DNA encoding a heavy chain variable region of said human monoclonal antibody is derived from either the human immunoglobulin heavy chain V gene segment 1-02 or 3-13.

(26) The human monoclonal antibody or a portion thereof of (4), wherein a V region DNA encoding a light chain variable region of said human monoclonal antibody is derived from either the human immunoglobulin light chain V gene segment L5 or A27.

(27) The human monoclonal antibody or a portion thereof of (25) or (26), wherein a V region DNA encoding a heavy chain variable region of said human monoclonal antibody is derived from either the human immunoglobulin heavy chain V gene segment 1-02 or 3-13, and wherein a V region DNA encoding a light chain variable region of said human monoclonal antibody is derived from either the human immunoglobulin light chain V gene segment L5 or A27.

(28) The human monoclonal antibody or a portion thereof of (27), wherein the V region DNA encoding a heavy chain variable region of said human monoclonal antibody is derived from the human immunoglobulin heavy chain V gene segment 1-02, and the V region DNA encoding a light chain variable region of said human monoclonal antibody is derived from the human immunoglobulin light chain V gene segment L5.

(29) The human monoclonal antibody or a portion thereof of (27), wherein the V region DNA encoding a heavy chain variable region of said human monoclonal antibody is derived from the human immunoglobulin heavy chain V gene segment 3-13, and the V region DNA encoding a light chain variable region of said human monoclonal antibody is derived from the human immunoglobulin light chain V gene segment A27.

(30) The human monoclonal antibody or a portion thereof of (4), wherein a heavy chain variable region of said human monoclonal antibody has an amino acid sequence defined in any of the following (a) through (f):

(a) amino acid sequence comprising amino acids from position 20 through 117 of SEQ ID NO:28, (b) amino acid sequence comprising amino acids from position 20 through 117 of SEQ ID NO:28 in which one or more amino acid residues are deleted or substituted, or to which one or more amino acid residues are inserted or added.

(c) amino acid sequence comprising amino acids from position 20 through 116 of SEQ ID NO:32, (d) amino acid sequence comprising amino acids from position 20 through 116 of SEQ ID NO:32 in which one or more amino acid residues are deleted or substituted, or to which one or more amino acid residues are inserted or added.

(e) amino acid sequence comprising amino acids from position 20 through 116 of SEQ ID NO:36, or (f) amino acid sequence comprising amino acids from position 20 through 116 of SEQ ID NO:36, in which one or more amino acid residues are deleted or substituted, or to which one or more amino acid residues are inserted or added.

(31) The human monoclonal antibody or a portion thereof of (4), wherein a heavy chain polypeptide of said human monoclonal antibody has an amino acid sequence defined in any of the following (a) through (f):

(a) amino acid sequence comprising amino acids from position 20 through 470 of SEQ ID NO:28, (b) amino acid sequence comprising amino acids from position 20 through 470 of SEQ ID NO:28 in which one or more amino acid residues are deleted or substituted, or to which one or more amino acid residues are inserted or added.

(c) amino acid sequence comprising amino acids from position 20 through 470 of SEQ ID NO:32, (d) amino acid sequence comprising amino acids from position 20 through 470 of SEQ ID NO:32 in which one or more amino acid residues are deleted or substituted, or to which one or more amino acid residues are inserted or added.

(e) amino acid sequence comprising amino acids from position 20 through 470 of SEQ ID NO:36, or (f) amino acid sequence comprising amino acids from position 20 through 470 of SEQ ID NO:36 in which one or more amino acid residues are deleted or substituted, or to which one or more amino acid residues are inserted or added.

(32) The human monoclonal antibody or a portion thereof of (4), wherein a light chain variable region of said human monoclonal antibody has an amino acid sequence defined in any of the following (a) through (f):

(a) amino acid sequence comprising amino acids from position 23 through 116 of SEQ ID NO:30, (b) amino acid sequence comprising amino acids from position 23 through 116 of SEQ ID NO:30 in which one or more amino acid residues are deleted or substituted, or to which one or more amino acid residues are inserted or added.

(c) amino acid sequence comprising amino acids from position 21 through 116 of SEQ ID NO:34, (d) amino acid sequence comprising amino acids from position 21 through 116 of SEQ ID NO:34 in which one or more amino acid residues are deleted or substituted, or to which one or more amino acid residues are inserted or added.

(e) amino acid sequence comprising amino acids from position 21 through 116 of SEQ ID NO:38, or (f) amino acid sequence comprising amino acids from position 21 through 116 of SEQ ID NO:38 in which one or more amino acid residues are deleted or substituted, or to which one or more amino acid residues are inserted or added.

(33) The human monoclonal antibody or a portion thereof of (4), wherein a light chain polypeptide of said human monoclonal antibody has an amino acid sequence defined in any of the following (a) through (f):

(a) amino acid sequence comprising amino acids from position 23 through 236 of SEQ ID NO:30, (b) amino acid sequence comprising amino acids from position 23 through 236 of SEQ ID NO:30 in which one or more amino acid residues are deleted or substituted, or to which one or more amino acid residues are inserted or added.

(c) amino acid sequence comprising amino acids from position 21 through 236 of SEQ ID NO:34, (d) amino acid sequence comprising amino acids from position 21 through 236 of SEQ ID NO:34 in which one or more amino acid residues are deleted or substituted, or to which one or more amino acid residues are inserted or added.

(e) amino acid sequence comprising amino acids from position 21 through 236 of SEQ ID NO:38, or (f) amino acid sequence comprising amino acids from position 21 through 236 of SEQ ID NO:38 in which one or more amino acid residues are deleted or substituted, or to which one or more amino acid residues are inserted or added.

(34) The human monoclonal antibody or a portion thereof of (4), wherein said human monoclonal antibody has the following characteristics (a) and (b):

(a) a heavy chain variable region has an amino acid sequence comprising the amino acid sequence from amino acid 20 through 117 according to SEQ ID NO:28, and (b) a light chain variable region has an amino acid sequence comprising the amino acid sequence from amino acid 23 through 116 according to SEQ ID NO:30.

(35) The human monoclonal antibody or a portion thereof of (4), wherein said human monoclonal antibody has the following characteristics (a) and (b):

(a) a heavy chain polypeptide has an amino acid sequence from amino acid 20 through 470 according to SEQ ID NO:28, and (b) a light chain polypeptide has an amino acid sequence from amino acid 23 through 236 according to SEQ ID NO:30.

(36) The human monoclonal antibody or a portion thereof of (4), wherein said human monoclonal antibody has the following characteristics (a) and (b):

(a) a heavy chain variable region has an amino acid sequence comprising the amino acid sequence from amino acid 20 through 116 according to SEQ ID NO:32, and (b) a light chain variable region has an amino acid sequence comprising the amino acid sequence from amino acid 21 through 116 according to SEQ ID NO:34.

(37) The human monoclonal antibody or a portion thereof of (4), wherein said human monoclonal antibody has the following characteristics (a) and (b):

(a) a heavy chain polypeptide has an amino acid sequence comprising the amino acid sequence from amino acid 20 through 470 according to SEQ ID NO:32, and (b) a light chain polypeptide has an amino acid sequence comprising the amino acid sequence from amino acid 21 through 236 according to SEQ ID NO:34.

(38) The human monoclonal antibody or a portion thereof of (4), wherein said human monoclonal antibody has the following characteristics (a) and (b):

(a) a heavy chain variable region has an amino acid sequence comprising the amino acid sequence from amino acid 20 through 116 according to SEQ ID NO:36, and (b) a light chain variable region has an amino acid sequence comprising the amino acid sequence from amino acid 21 through 116 according to SEQ ID NO:38.

(39) The human monoclonal antibody or a portion thereof of (4), wherein said human monoclonal antibody has the following characteristics (a) and (b):

(a) a heavy chain polypeptide has an amino acid sequence comprising the amino acid sequence from amino acid 20 through 470 according to SEQ ID NO:36, and (b) a light chain polypeptide has an amino acid sequence comprising the amino acid sequence from amino acid 21 through 236 according to SEQ ID NO:38.

(40) The human monoclonal antibody or a portion thereof of any one of (3) through (29), wherein said human monoclonal antibody is a monoclonal antibody derived from a transgenic non-human mammal capable of producing human antibodies.

(41) The human monoclonal antibody or a portion thereof of (40), wherein said human monoclonal antibody is obtained by immunizing transgenic non-human mammal capable of producing human antibody with AILIM-expressing cells, membrane fractions derived from said cells, whole molecules constituting AILIM or a portion thereof, or genes encoding AILIM or a portion thereof.

(42) The human monoclonal antibody or a portion thereof of (40) or (41), wherein said transgenic non-human mammal is a transgenic mouse.

(43) A DNA or a portion thereof encoding a polypeptide selected from the group consisting of (a) through (f) below:

(a) a polypeptide comprising the amino acid sequence from amino acid 20 through 117 according to SEQ ID NO:28, (b) a polypeptide comprising the amino acid sequence from amino acid 23 through 116 according to SEQ ID NO:30, (c) a polypeptide comprising the amino acid sequence from amino acid 20 through 116 according to SEQ ID NO:32, (d) a polypeptide comprising the amino acid sequence from amino acid 21 through 116 according to SEQ ID NO:34, (e) a polypeptide comprising the amino acid sequence from amino acid 20 through 116 according to SEQ ID NO:36, and (f) a polypeptide comprising the amino acid sequence from amino acid 21 through 116 according to SEQ ID NO:38.

(44) A DNA or a portion thereof encoding a polypeptide selected from the group consisting of (a) through (f) below:

(a) a polypeptide comprising the amino acid sequence from amino acids 20 through 470 according to SEQ ID NO:28, (b) a polypeptide comprising the amino acid sequence from amino acids 23 through 236 according to SEQ ID NO:30, (c) a polypeptide comprising the amino acid sequence from amino acid 20 through 470 according to SEQ ID NO:32, (d) a polypeptide comprising the amino acid sequence from amino acids 21 through 236 according to SEQ ID NO:34, (e) a polypeptide comprising the amino acid sequence from amino acids 20 through 470 according to SEQ ID NO:36, and (f) a polypeptide comprising the amino acid sequence from amino acids 21 through 236 according to SEQ ID NO:38.

(45) A DNA or a portion thereof selected from the group consisting of (a) through (f) below:

(a) a DNA comprising the nucleotide sequence from nucleotides 126 through 419 according to SEQ ID NO:27, (b) a DNA comprising the nucleotide sequence from nucleotides 105 through 386 according to SEQ ID NO:29, (c) a DNA comprising the nucleotide sequence from nucleotides 151 through 441 according to SEQ ID NO:31, (d) a DNA comprising the nucleotide sequence from nucleotides 88 through 375 according to SEQ ID NO:33, (e) a DNA comprising the nucleotide sequence from nucleotides 153 through 443 according to SEQ ID NO:35, and (f) a DNA comprising the nucleotide sequence from nucleotides 93 through 380 according to SEQ ID NO:37.

(46) A DNA or a portion thereof selected from a group consisting of (a) through (f) below:

(a) a DNA comprising the nucleotide sequence from nucleotides 69 through 1481 according to SEQ ID NO:27, (b) a DNA comprising the nucleotide sequence from nucleotides 39 through 749 according to SEQ ID NO:29, (c) a DNA comprising the nucleotide sequence from nucleotides 94 through 1506 defined in SEQ ID NO:31, (d) a DNA comprising the nucleotide sequence from nucleotides 28 through 738 according to SEQ ID NO:33, (e) a DNA comprising the nucleotide sequence from nucleotides 96 through 1508 according to SEQ ID NO:35, and (f) a DNA comprising the nucleotide sequence from nucleotides 33 through 743 according to SEQ ID NO:37.

(47) A vector comprising the DNA of any one of (43) through (46).

(48) The vector of (47) comprising a DNA according to any of the following (a) through (c):

(a) a DNA comprising the nucleotide sequence from nucleotides 126 through 419 according to SEQ ID NO:27, (b) a DNA comprising the nucleotide sequence from nucleotides 151 through 441 according to SEQ ID NO:31, or (c) a DNA comprising the nucleotide sequence from nucleotides 153 through 443 according to SEQ ID NO:35.

(49) The vector of (47) comprising a DNA according to any of the following (a) through (c):

(a) a DNA comprising the nucleotide sequence from nucleotides 69 through 1481 according to SEQ ID NO:27, (b) a DNA comprising the nucleotide sequence from nucleotides 94 through 1506 according to SEQ ID NO:31, or (c) a DNA comprising the nucleotide sequence from nucleotides 96 through 1508 according to SEQ ID NO:35.

(50) The vector of (47) comprising a DNA according to any of the following (a) through (c):

(a) a DNA comprising the nucleotide sequence from nucleotides 105 through 386 according to SEQ ID NO:29, (b) a DNA comprising the nucleotide sequence from nucleotides 88 through 375 according to SEQ ID NO:33, or (c) a DNA comprising the nucleotide sequence from nucleotides 93 through 380 according to SEQ ID NO:37.

(51) The vector of (47) comprising a DNA according to any of the following (a) through (c):

(a) a DNA comprising the nucleotide sequence from nucleotides 39 through 749 according to SEQ ID NO:29, (b) a DNA comprising the nucleotide sequence from nucleotides 28 through 738 according to SEQ ID NO:33, or (c) a DNA comprising the nucleotide sequence from nucleotides 33 through 743 according to SEQ ID NO:37.

(52) The vector of (47) comprising a DNA according to the following (a) and (b):

(a) a DNA comprising the nucleotide sequence from nucleotides 126 through 419 according to SEQ ID NO:27, and (b) a DNA comprising the nucleotide sequence from nucleotides 105 through 386 according to SEQ ID NO:29.

(53) The vector of (47) comprising a DNA according to the following (a) and (b):

(a) a DNA comprising the nucleotide sequence from nucleotides 69 through 1481 according to SEQ ID NO:27, and (b) a DNA comprising the nucleotide sequence from nucleotides 39 through 749 according to SEQ ID NO:29.

(54) The vector of (47) comprising a DNA according to the following (a) and (b):

(a) a DNA comprising the nucleotide sequence from nucleotides 151 through 441 according to SEQ ID NO:31, and (b) a DNA comprising the nucleotide sequence from nucleotides 88 through 375 according to SEQ ID NO:33.

(55) The vector of (47) comprising a DNA according to the following (a) and (b):

(a) a DNA comprising the nucleotide sequence from nucleotides 94 through 1506 according to SEQ ID NO:31, and (b) a DNA comprising the nucleotide sequence from nucleotides 28 through 738 according to SEQ ID NO:33.

(56) The vector of (47) comprising a DNA according to the following (a) and (b):

(a) a DNA comprising the nucleotide sequence from nucleotides 153 through 443 according to SEQ ID NO:35, and (b) a DNA comprising the nucleotide sequence from nucleotides 93 through 380 according to SEQ ID NO:37.

(57) The vector of (47) comprising a DNA according to the following (a) and (b):

(a) a DNA comprising the nucleotide sequence from nucleotides 96 through 1508 according to SEQ ID NO:35, and (b) a DNA comprising the nucleotide sequence from nucleotides 33 through 743 according to SEQ ID NO:37.

(58) A cell producing a human monoclonal antibody of any one of (3) through (42).

(59) The cell of (58), wherein said cell is a fused cell obtained by fusing B cell, derived from a mammal capable of producing said human monoclonal antibody, and myeloma cell derived from a mammal.

(60) A genetic recombinant host transformed by transferring a DNA described below in (a) or a vector comprising said DNA, a DNA described below in (b) or a vector comprising said DNA, or both DNAs described below in (a) and (b) or a vector comprising both of said DNAs:

(a) a DNA encoding a heavy chain polypeptide or a portion thereof of a monoclonal antibody which binds to human AILIM; or (b) a DNA encoding a light chain polypeptide or a portion thereof of a monoclonal antibody which binds to human AILIM.

(61) The genetic recombinant host of (60), wherein said monoclonal antibody is a human monoclonal antibody.

(62) The genetic recombinant host of (60) or (61), wherein said host is a mammalian cell.

(63) The genetic recombinant host of (60) or (61), wherein said host is a mammalian fertilized egg.

(64) The genetic recombinant host of any one of (60) through (63), wherein said heavy chain polypeptide is one of the heavy chain polypeptides selected from the group consisting of the following (a) through (c):

(a) a heavy chain polypeptide comprising the amino acid sequence from amino acids 20 through 117 according to SEQ ID NO:28, (b) a heavy chain polypeptide comprising the amino acid sequence from amino acids 20 through 116 according to SEQ ID NO:32, and (c) a heavy chain polypeptide comprising the amino acid sequence from amino acids 20 through 116 according to SEQ ID NO:36.

(65) The genetic recombinant host of any one of (60) through (63), wherein said heavy chain polypeptide is one of the heavy chain polypeptide selected from the group consisting of the following (a) through (c):

(a) a heavy chain polypeptide comprising the amino acid sequence from amino acids 20 through 470 according to SEQ ID NO:28, (b) a heavy chain polypeptide comprising the amino acid sequence from amino acids 20 through 470 according to SEQ ID NO:32, and (c) a heavy chain polypeptide comprising the amino acid sequence from amino acids 20 through 470 according to SEQ ID NO:36.

(66) The genetic recombinant host of any one of (60) through (63), wherein said light chain polypeptide is one of the light chain polypeptide selected from the group consisting of the following (a) through (c):

(a) a heavy chain polypeptide comprising the amino acid sequence from amino acids 23 through 116 according to SEQ ID NO:30, (b) a heavy chain polypeptide comprising the amino acid sequence from amino acids 21 through 116 according to SEQ ID NO:34, and (c) a heavy chain polypeptide comprising the amino acid sequence from amino acids 21 through 116 according to SEQ ID NO:38.

(67) The genetic recombinant host of any one of (60) through (63), wherein said light chain polypeptide is one of the light chain polypeptide selected from the group consisting of the following (a) through (c):

(a) a light chain polypeptide comprising the amino acid sequence from amino acids 23 through 236 according to SEQ ID NO:30, (b) a light chain polypeptide comprising the amino acid sequence from amino acids 21 through 236 according to SEQ ID NO:34, and (c) a light chain polypeptide comprising the amino acid sequence from amino acids 21 through 236 according to SEQ ID NO:38.

(68) The genetic recombinant host of any one of (60) through (63), wherein said heavy chain and light chain polypeptides are those defined below in (a) and (b), respectively:

(a) a heavy chain polypeptide comprising the amino acid sequence from amino acids 20 through 117 according to SEQ ID NO:28, and (b) a light chain polypeptide comprising the amino acid sequence from amino acids 23 through 116 according to SEQ ID NO:30.

(69) The genetic recombinant host of any one of (60) through (63), wherein said heavy chain and light chain polypeptides are those defined below in (a) and (b), respectively:

(a) a heavy chain polypeptide comprising the amino acid sequence from amino acids 20 through 470 according to SEQ ID NO:28, and (b) a light chain polypeptide comprising the amino acid sequence from amino acids 23 through 236 according to SEQ ID NO:30.

(70) The genetic recombinant host of any one of (60) through (63), wherein said heavy chain and light chain polypeptides are those defined below in (a) and (b), respectively:

(a) a heavy chain polypeptide comprising the amino acid sequence from amino acids 20 through 116 according to SEQ ID NO:32, and (b) a light chain polypeptide comprising the amino acid sequence from amino acids 21 through 116 according to SEQ ID NO:34.

(71) The genetic recombinant host of any one of (60) through (63), wherein said heavy chain and light chain polypeptides are those defined below in (a) and (b), respectively:

(a) a heavy chain polypeptide comprising the amino acid sequence from amino acids 20 through 470 according to SEQ ID NO:32, and (b) a light chain polypeptide comprising the amino acid sequence from amino acids 21 through 236 according to SEQ ID NO:34.

(72) The genetic recombinant host of any one of (60) through (63), wherein said heavy chain and light chain polypeptides are those defined below in (a) and (b), respectively:

(a) a heavy chain polypeptide comprising the amino acid sequence from amino acids 20 through 116 according to SEQ ID NO:36, and (b) a light chain polypeptide comprising the amino acid sequence from amino acids 21 through 116 according to SEQ ID NO:38.

(73) The genetic recombinant host of any one of (60) through (63), wherein said heavy chain and light chain polypeptides are those defined below in (a) and (b), respectively:

(a) a heavy chain polypeptide comprising the amino acid sequence from amino acids 20 through 470 according to SEQ ID NO:36, and (b) a light chain polypeptide comprising the amino acid sequence from amino acids 21 through 236 according to SEQ ID NO:38.

(74) The genetic recombinant host of any one of (60) through (63), wherein the DNA encoding said heavy chain polypeptide is a DNA defined in any of following (a) through (c):

(a) a DNA comprising the nucleotide sequence from nucleotides 126 through 419 according to SEQ ID NO:27, (b) a DNA comprising the nucleotide sequence from nucleotides 151 through 441 according to SEQ ID NO:31, and (c) a DNA comprising the nucleotide sequence from nucleotides 153 through 443 according to SEQ ID NO:35.

(75) The genetic recombinant host of any one of (60) through (63), wherein the DNA encoding said heavy chain polypeptide is a DNA defined in any of following (a) through (c):

(a) a DNA comprising the nucleotide sequence from nucleotides 69 through 1481 according to SEQ ID NO:27, (b) a DNA comprising the nucleotide sequence from nucleotides 94 through 1506 according to SEQ ID NO:31, and (c) a DNA comprising the nucleotide sequence from nucleotides 96 through 1508 according to SEQ ID NO:35.

(76) The genetic recombinant host of any one of (60) through (63), wherein the DNA encoding said light chain polypeptide is a DNA defined in any of following (a) through (c):

(a) a DNA comprising the nucleotide sequence from nucleotides 105 through 386 according to SEQ ID NO:29, (b) a DNA comprising the nucleotide sequence from nucleotides 88 through 375 according to SEQ ID NO:33, and (c) a DNA comprising the nucleotide sequence from nucleotides 93 through 380 according to SEQ ID NO:37.

(77) The genetic recombinant host of any one of (60) through (63), wherein the DNA encoding said light chain polypeptide is a DNA as defined in any of following (a) through (c):

(a) a DNA comprising the nucleotide sequence from nucleotides 39 through 749 according to SEQ ID NO:29, (b) a DNA comprising the nucleotide sequence from nucleotides 28 through 738 according to SEQ ID NO:33, and (c) a DNA comprising the nucleotide sequence from nucleotides 33 through 743 according to SEQ ID NO:37.

(78) The genetic recombinant host of any one of (60) through (63), wherein the DNA encoding said heavy chain polypeptide is a DNA described below in (a), and the DNA encoding said light chain polypeptide is a DNA as described below in (b):

(a) a DNA comprising the nucleotide sequence from nucleotides 126 through 419 according to SEQ ID NO:27, and (b) a DNA comprising the nucleotide sequence from nucleotides 105 through 386 according to SEQ ID NO:29.

(79) The genetic recombinant host of any one of (60) through (63), wherein the DNA encoding said heavy chain polypeptide is the DNA described below in (a), and the DNA encoding said light chain polypeptide is the DNA described below in (b):

(a) a DNA comprising the nucleotide sequence from nucleotides 69 through 1481 according to SEQ ID NO:27, and (b) a DNA comprising the nucleotide sequence from nucleotides 39 through 749 according to SEQ ID NO:29.

(80) The genetic recombinant host of any one of (60) through (63), wherein the DNA encoding said heavy chain polypeptide is the DNA described below in (a), and the DNA encoding said light chain polypeptide is the DNA described below in (b):

(a) a DNA comprising the nucleotide sequence from nucleotides 151 through 441 according to SEQ ID NO:31, and (b) a DNA comprising the nucleotide sequence from nucleotides 88 through 375 V SEQ ID NO:33.

(81) The genetic recombinant host of any one of (60) through (63), wherein the DNA encoding said heavy chain polypeptide is the DNA described below in (a), and the DNA encoding said light chain polypeptide is the DNA described below in (b):

(a) a DNA comprising the nucleotide sequence from nucleotides 94 through 1506 according to SEQ ID NO:31, and (b) a DNA comprising the nucleotide sequence from nucleotides 28 through 738 according to SEQ ID NO:33.

(82) The genetic recombinant host of any one of (60) through (63), wherein the DNA encoding said heavy chain polypeptide is the DNA described below in (a), and the DNA encoding said light chain polypeptide is the DNA described below in (b):

(a) a DNA comprising the nucleotide sequence from nucleotides 153 through 443 according to SEQ ID NO:35, and (b) a DNA comprising the nucleotide sequence from nucleotides 93 through 380 according to SEQ ID NO:37.

(83) The genetic recombinant host of any one of (60) through (63), wherein the DNA encoding said heavy chain polypeptide is the DNA described below in (a), and the DNA encoding said light chain polypeptide is the DNA described below in (b):

(a) a DNA comprising the nucleotide sequence from nucleotides 96 through 1508 according to SEQ ID NO:35, and (b) a DNA comprising the nucleotide sequence from nucleotides 33 through 743 according to SEQ ID NO:37.

(84) A human monoclonal antibody or a portion thereof produced by a genetic recombinant host (provided excluding the case where said host is a fertilized egg) of any one of (60) through (62), or of any one of (64) through (83).

(85) A pharmaceutical composition comprising the human antibody of (1) or (2), and a pharmaceutically acceptable carrier.

(86) A pharmaceutical composition comprising the human monoclonal antibody or a portion thereof of any one of (3) to (42), and a pharmaceutically acceptable carrier.

(87) A pharmaceutical composition comprising a human monoclonal antibody or a portion thereof of (84), and a pharmaceutically acceptable carrier.

(88) The pharmaceutical composition of any one of (85) through (87), wherein said pharmaceutical composition is used to inhibit signal transduction into the cell mediated by AILIM.

(89) The pharmaceutical composition of any one of (85) through (87), wherein said pharmaceutical composition is used to prevent proliferation of AILIM-expressing cells.

(90) The pharmaceutical composition of any one of (85) through (87), wherein said pharmaceutical composition is used to prevent production of a cytokine from AILIM-expressing cells.

(91) The pharmaceutical composition of any one of (85) through (87), wherein said pharmaceutical composition is used to induce signal transduction into a cell mediated by AILIM.

(92) The pharmaceutical composition of any one of (85) through (87), wherein said pharmaceutical composition is used to induce proliferation of AILIM-expressing cells.

(93) The pharmaceutical composition of any one of (85) through (87), wherein said pharmaceutical composition is used to induce production of a cytokine from AILIM-expressing cells.

(94) The pharmaceutical composition of any one of (85) through (87), wherein said pharmaceutical composition is used to induce antibody-dependent cytotoxicity against AILIM-expressing cells, and/or immune cytolysis or apoptosis of AILIM-expressing cells.

(95) A pharmaceutical composition for preventing, treating, or prophylaxis of delayed type allergy, comprising a substance having an activity in modulating signal transduction mediated by AILIM, and a pharmaceutically acceptable carrier.

(96) The pharmaceutical composition of (95), wherein the substance is a protein substance.

(97) The pharmaceutical composition of (96), wherein the protein substance is selected from the group consisting of:
 a) an antibody which binds to AILIM or a portion thereof,
 b) a polypeptide comprising the whole or a portion of an extracellular region of AILIM;
 c) a fusion polypeptide comprising the whole or a portion of an extracellular region of AILIM, and the whole or a portion of a constant region of immunoglobulin heavy chain; and
 d) a polypeptide which binds to AILIM.

(98) The pharmaceutical composition of (97), wherein said antibody that binds to AILIM is the human antibody of (1) or (2).

(99) The pharmaceutical composition of (97), wherein said antibody that binds to AILIM is the human monoclonal antibody of any one of (3) through (42).

(100) The pharmaceutical composition of (97), wherein said antibody against AILIM is the human monoclonal antibody of (84).

(101) The pharmaceutical composition of (95), wherein the substance is a non-protein substance.

(102) The pharmaceutical composition of (101), wherein the non-protein substance is DNA, RNA, or a chemically synthesized compound.

(103) A method for identifying substances that bind to AILIM or AILIM ligand comprising the following processes:
 (a) preparing an insoluble carrier on which the entire extracellular region of AILIM or a portion thereof is immobilized;
 (b) preparing a polypeptide comprising the whole extracellular region of AILIM ligand or a portion thereof labeled with a labeling material that emit a detectable signal;
 (c) reacting the insoluble carrier in process (a) with the polypeptide in process (b);
 (d) reacting the insoluble carrier of process (a), the polypeptide of process (b) and said substance to each other in any arbitrary orders;
 (e) detecting the signal emitted from said labeling material contained in the complex produced in process (c), and the signal emitted from said labeling material contained in the complex produced in process (d), respectively; and
 (f) comparing the magnitude of each of signals detected in process (e).

(104) A method for identifying substances that bind to AILIM or AILIM ligand comprising the following processes:
 (a) preparing an insoluble carrier on which the entire extracellular region of AILIM ligand or a portion thereof is immobilized;
 (b) preparing a polypeptide comprising the whole extracellular region of AILIM or a portion thereof labeled with a labeling material that emit a detectable signal;
 (c) reacting the insoluble carrier in process (a) with the polypeptide in process (b);
 (d) reacting the insoluble carrier of process (a), the polypeptide of process (b) and said substance to each other in any arbitrary orders;
 (e) detecting the signal emitted from said labeling material contained in the complex produced in process (c), and the signal emitted from said labeling material contained in the complex produced in process (d), respectively; and
 (f) comparing the magnitude of each of signals detected in process (e).

(105) The method of (103) or (104), wherein said polypeptide comprising the whole extracellular region of AILIM or a portion thereof is a fusion polypeptide comprising a polypeptide, comprising the whole extracellular region of AILIM or a portion thereof, and the whole constant region of immunoglobulin heavy chain or a portion thereof.

(106) The method of (103) or (104), wherein said polypeptide comprising the whole extracellular region of AILIM ligand or a portion thereof is a fusion polypeptide comprising a polypeptide, comprising the whole extracellular region of AILIM ligand or a portion thereof, and the whole constant region of immunoglobulin heavy chain or a portion thereof.

(107) The method of any one of (103) through (106), wherein said AILIM is a human AILIM.

(108) The method of any one of (103) through (107), wherein said AILIM ligand is a human AILIM ligand.

Panels (a) to (l) show respective results of the assays indicated below.

Figure 1A:
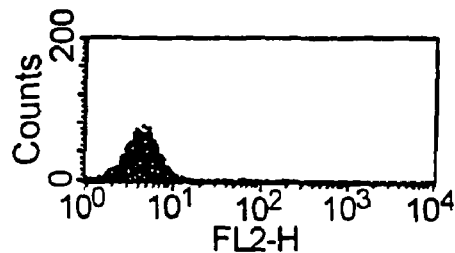
FIGS. 1A–1L show respective reactivities of anti-human IgG antibody, anti-human Igκ antibody and anti-human IgFc antibody to the human anti-human AILIM monoclonal antibody, analyzed by cell ELISA using a flow cytometer.

FIG. 1A shows the result of an assay in which biotin-labeled anti-human IgG antibody as a secondary antibody was added in the absence of primary antibody into the microplate where wild-type HPB-ALL cells had been plated.

Figure 1B:
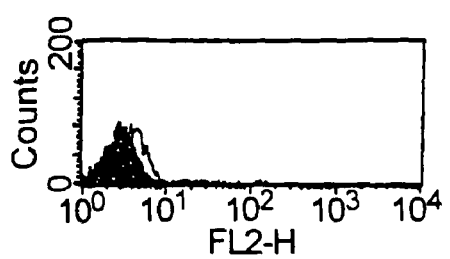

FIG. 1B shows the result of an assay in which biotin-labeled anti-human Igκ antibody as a secondary antibody was added in the absence of primary antibody into the microplate where wild-type HPB-ALL cells had been plated.

Figure 1C:
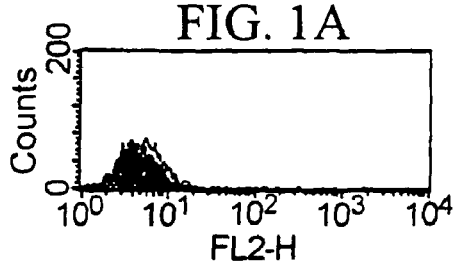

FIG. 1C shows the result of an assay in which biotin-labeled anti-human IgFc antibody as a secondary antibody was added in the absence of primary antibody into the microplate where wild-type HPB-ALL cells had been plated.

Figure 1D:
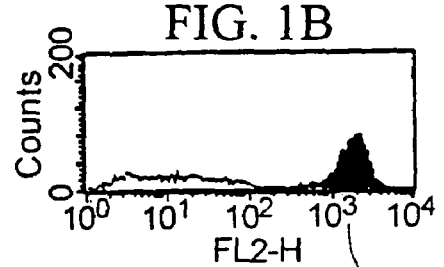

FIG. 1D shows the result of an assay in which human anti-human AILIM monoclonal antibody JMab-136 was used as a primary antibody and biotin-labeled anti-human IgG antibody was used as a secondary antibody.

Figure 1E:
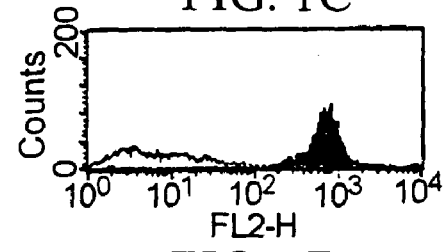

FIG. 1E shows the result of an assay in which human anti-human AILIM monoclonal antibody JMab-136 was used as a primary antibody and biotin-labeled anti-human Igκ antibody was used as a secondary antibody.

Figure 1F:
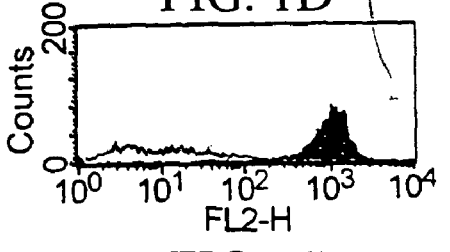

FIG. 1F shows the result of an assay in which human anti-human AILIM monoclonal antibody JMab-136 was used as a primary antibody and biotin-labeled anti-human IgFc antibody was used as a secondary antibody.

Figure 1G:
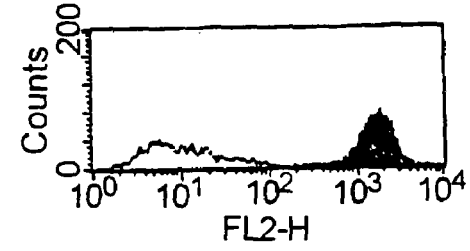

FIG. 1G shows the result of an assay in which human anti-human AILIM monoclonal antibody JMab-138 was used as a primary antibody and biotin-labeled anti-human IgG antibody was used as a secondary antibody.

Figure 1H:
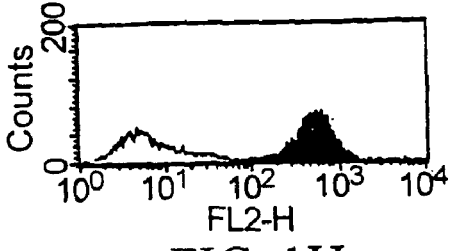

FIG. 1H shows the result of an assay in which human anti-human AILIM monoclonal antibody JMab-138 was used as a primary antibody and biotin-labeled anti-human Igκ antibody was used as a secondary antibody.

Figure 1I:
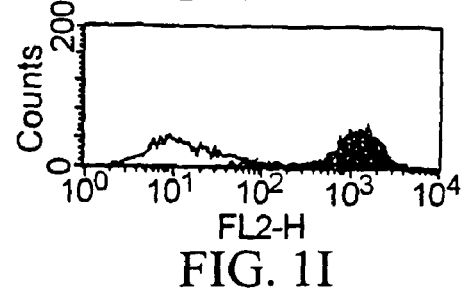

FIG. 1I shows the result of an assay in which human anti-human AILIM monoclonal antibody JMab-138 was used as a primary antibody and biotin-labeled anti-human IgFc antibody was used as a secondary antibody.

Figure 1J:
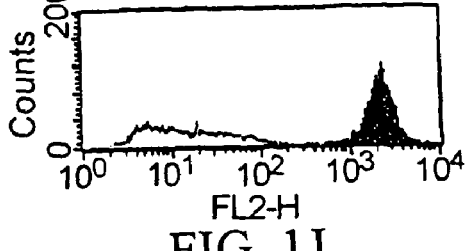

FIG. 1J shows the result of an assay in which human anti-human AILIM monoclonal antibody JMab-139 was used as a primary antibody and biotin-labeled anti-human IgG antibody was used as a secondary antibody.

Figure 1K:
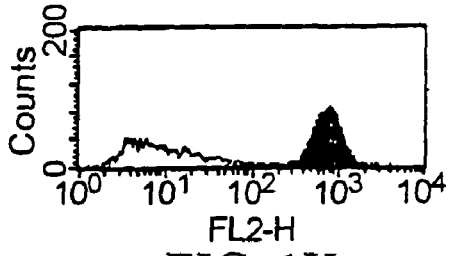

FIG. 1K shows the result of an assay in which human anti-human AILIM monoclonal antibody JMab-139 was used as a primary antibody and biotin-labeled anti-human Igκ antibody was used as a secondary antibody.

Figure 1L:
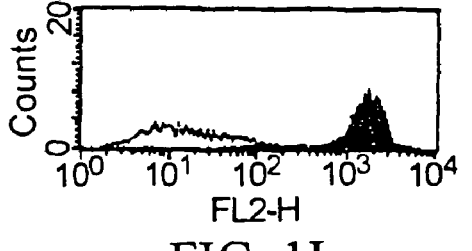

FIG. 1L shows the result of an assay in which human anti-human AILIM monoclonal antibody JMab-139 was used as a primary antibody and biotin-labeled anti-human IgFc antibody was used as a secondary antibody.

The curve with open symbols in each panel corresponds to the result of assay in which human anti-KLH monoclonal antibody was used as the control antibody.

Figure 2:
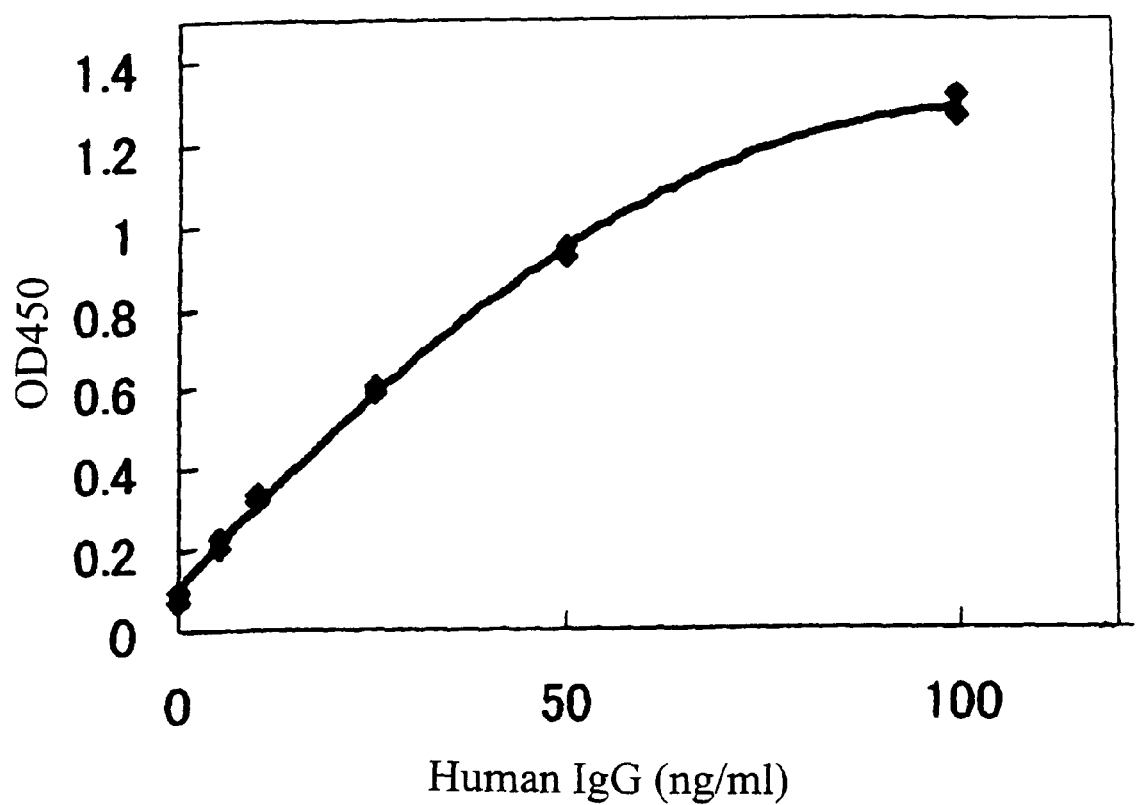

FIG. 2 shows a calibration curve with respect to human IgG monoclonal antibody (standard material) assayed by sandwich ELISA using anti-human IgG antibody.

The vertical axis indicates fluorescence intensity, and the horizontal axis indicates the concentration of the standard material.

Figure 3:
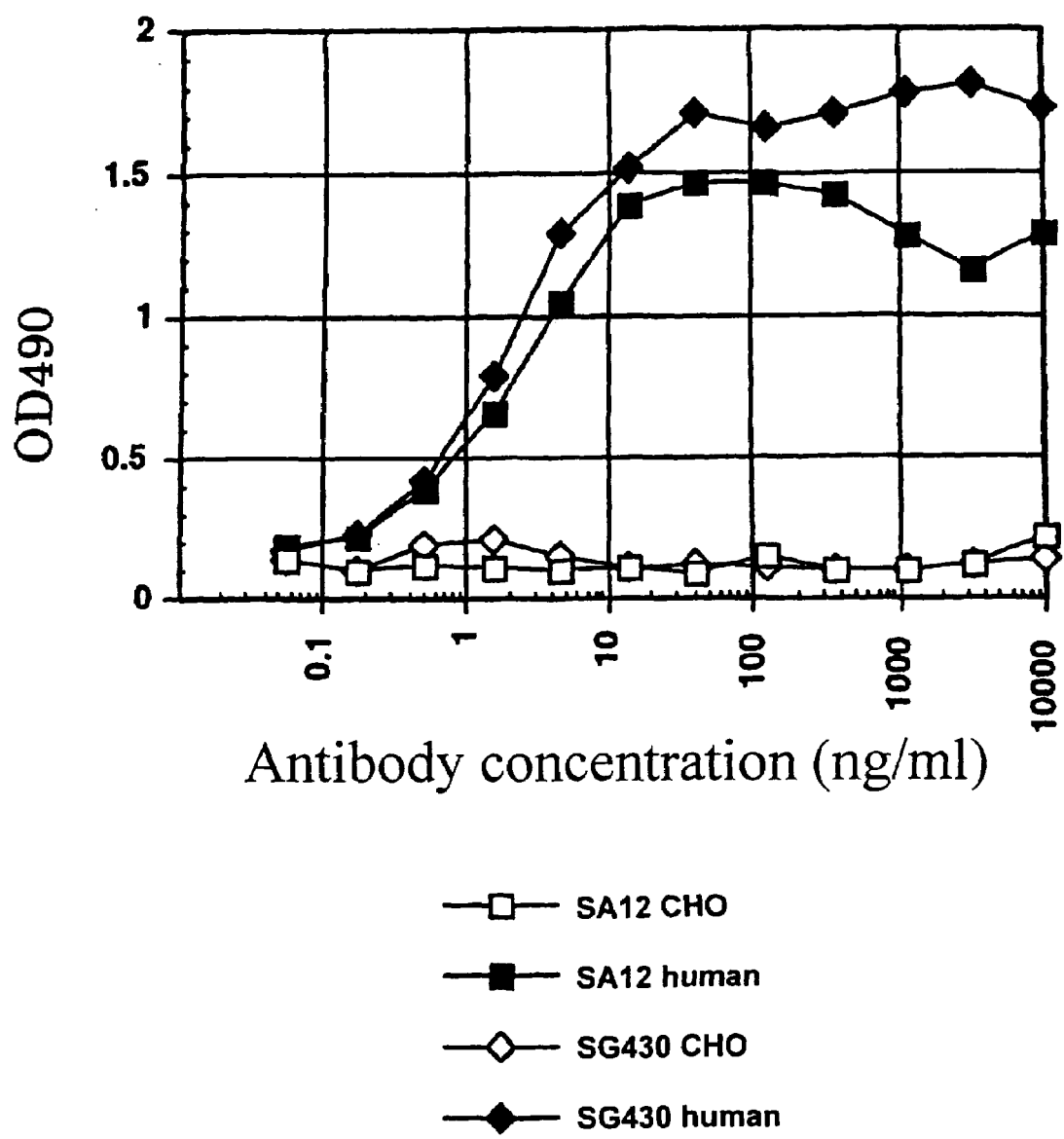

FIG. 3 shows binding activities of various mouse anti-human AILIM monoclonal antibodies to human AILIM-overexpressing recombinant CHO cells or wild-type CHO cells.

The vertical axis indicates fluorescence intensity as an index of binding activity to the recombinant cells, and the horizontal axis indicates the concentration of the antibody added.

The term "CHO" in the figure indicates the result of a binding assay to the wild-type CHO cell, and "human" indicates the result of a binding assay to the human AILIM-overexpressing recombinant CHO cell.

Figure 4:
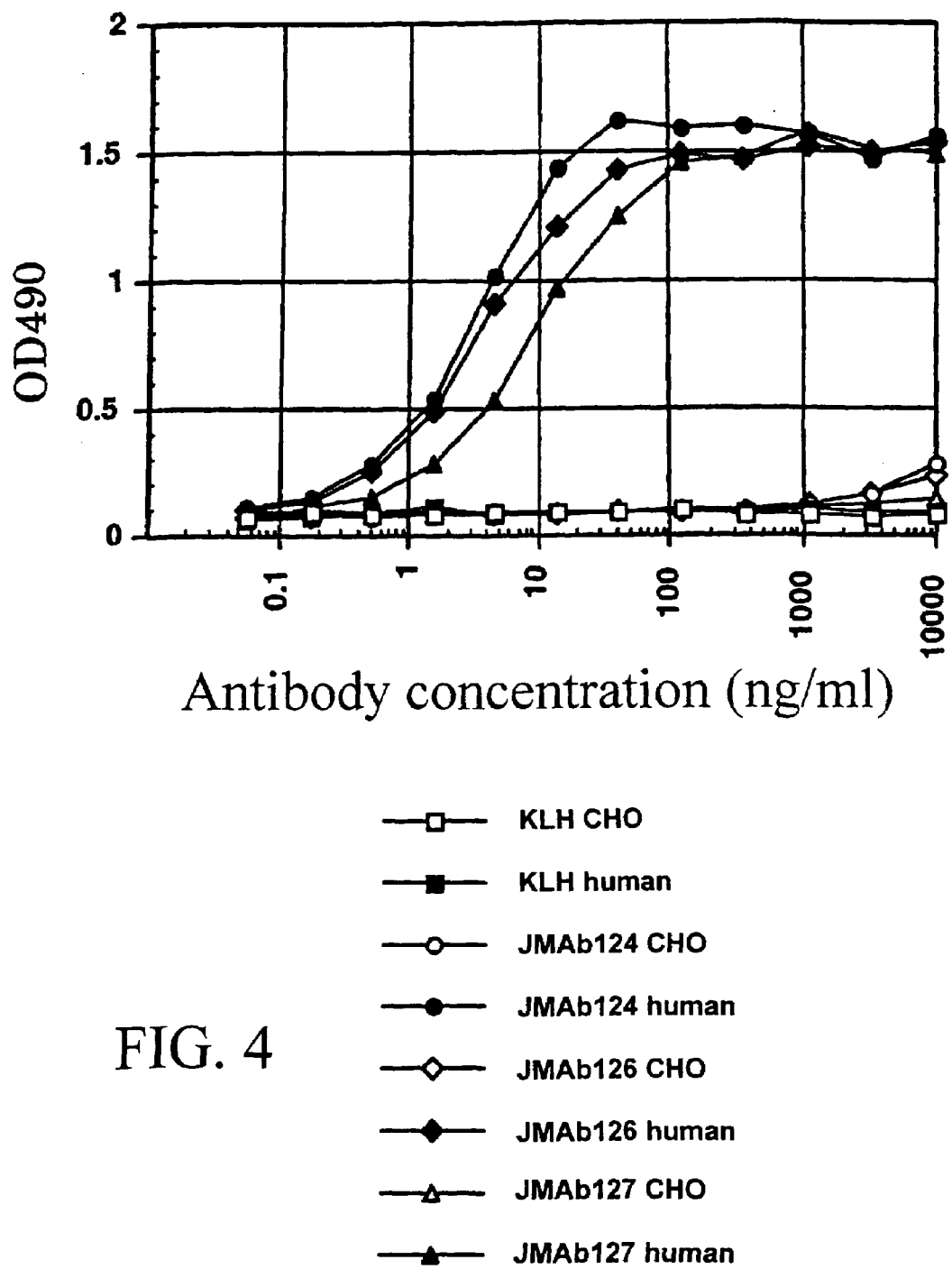

FIG. 4 shows binding activities of various human anti-human AILIM monoclonal antibodies or human anti-KLH monoclonal antibodies as a negative control to human AILIM-overexpressing recombinant CHO cells or wild-type CHO cells.

The vertical axis indicates fluorescence intensity as an index of binding activity to the recombinant cells, and the horizontal axis indicates the concentration of the antibody added.

The term "CHO" in the figure indicates the result of a binding assay to the wild-type CHO cell, and "human" indicates the result of a binding assay to the human AILIM-overexpressing recombinant CHO cell.

Figure 5:
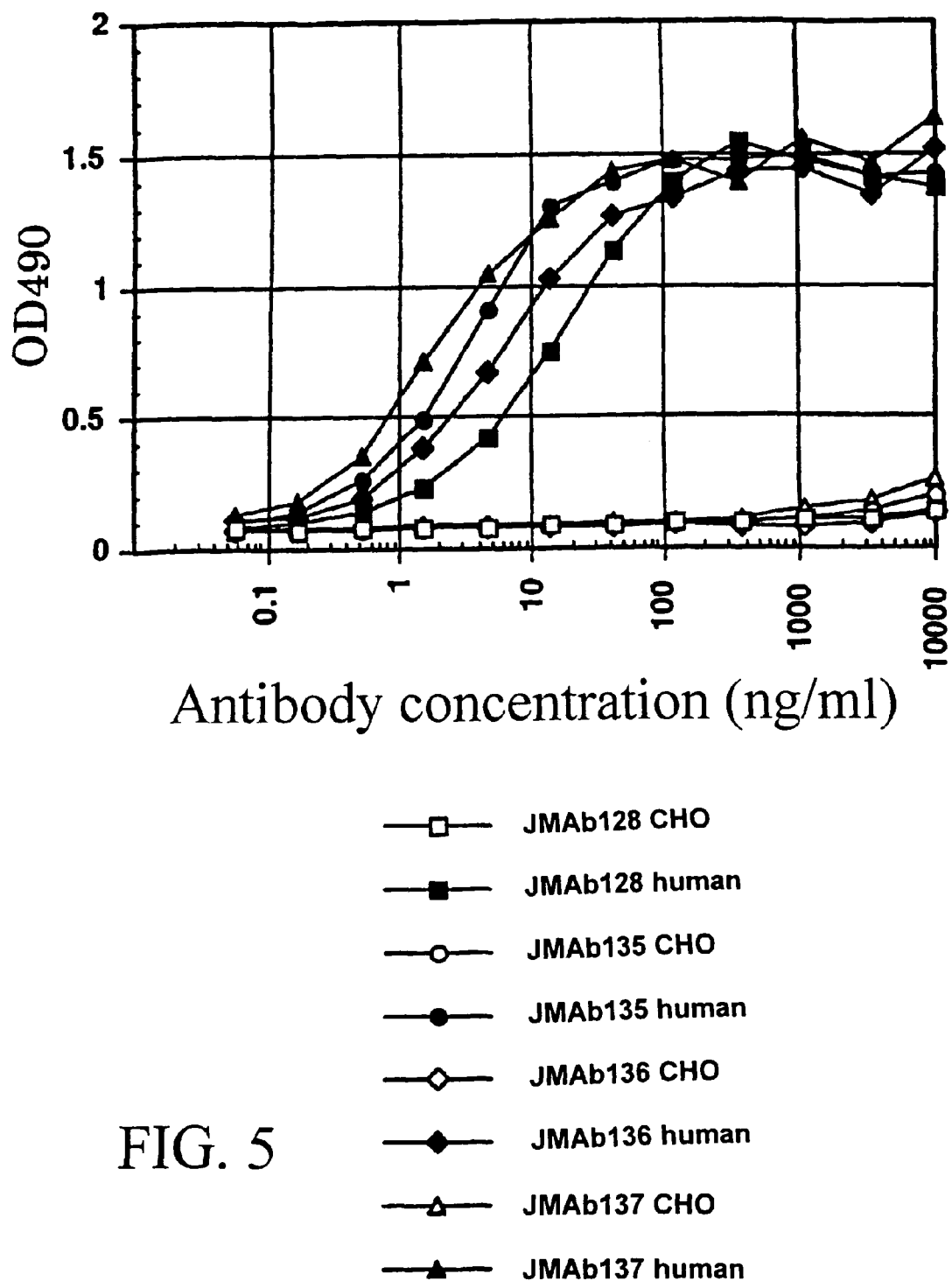

FIG. 5 shows binding activities of various human anti-human AILIM monoclonal antibodies to human AILIM-overexpressing recombinant CHO cells or wild-type CHO cells.

The vertical axis indicates fluorescence intensity as an index of binding activity to the recombinant cells, and the horizontal axis indicates the concentration of the antibody added.

The term "CHO" in the figure indicates the result of a binding assay to the wild-type CHO cell, and "human" indicates the result of a binding assay to the human AILIM-overexpressing recombinant CHO cell.

Figure 6:
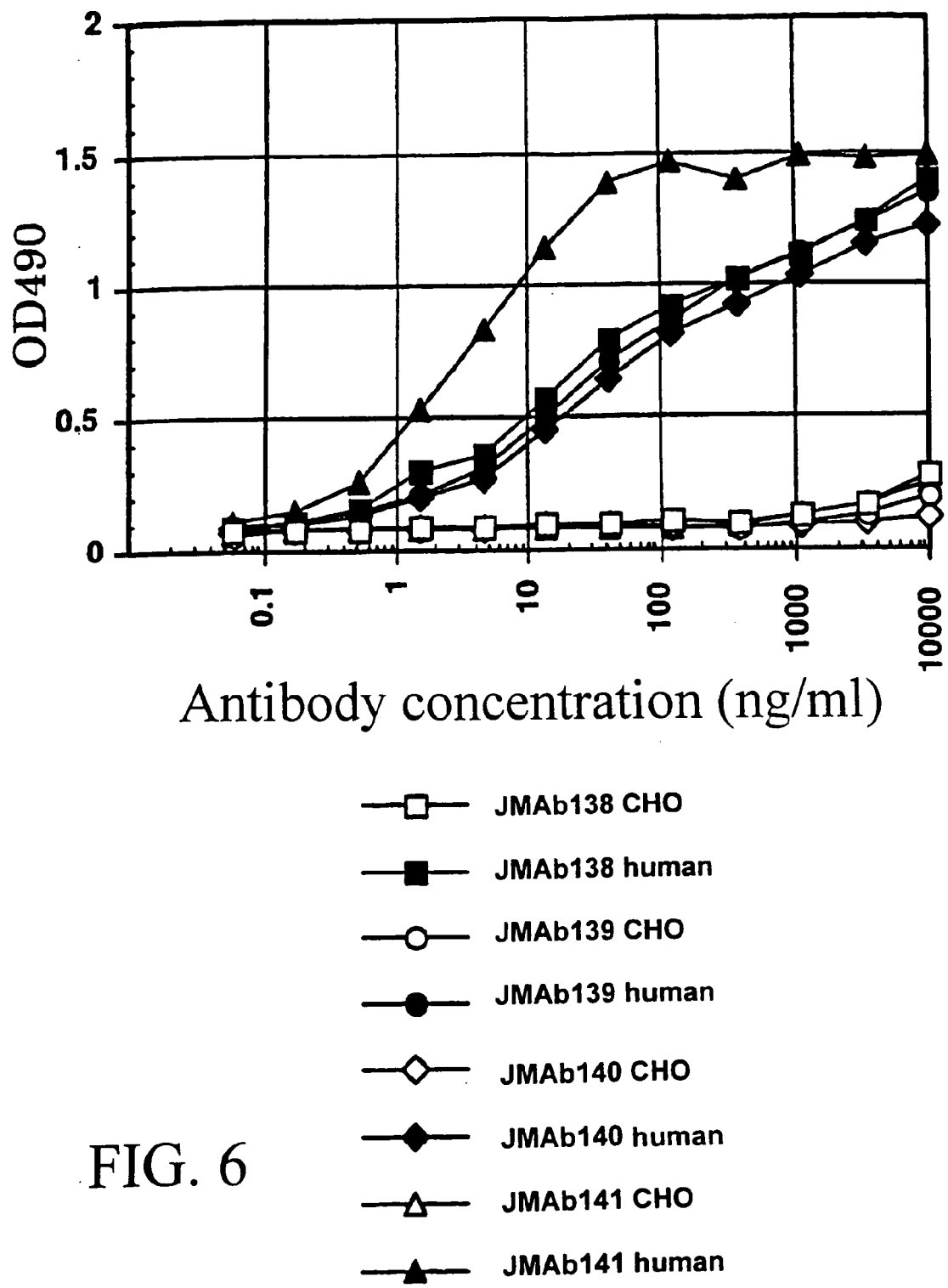

FIG. 6 shows binding activities of various human anti-human AILIM monoclonal antibodies to human AILIM-overexpressing recombinant CHO cells or wild-type CHO cells.

The vertical axis indicates fluorescence intensity as an index of binding activity to the recombinant cells, and the horizontal axis indicates the concentration of the antibody added.

The term "CHO" in the figure indicates the result of a binding assay to the wild-type CHO cell, and "human" indicates the result of a binding assay to the human AILIM-overexpressing recombinant CHO cell.

Figure 7:
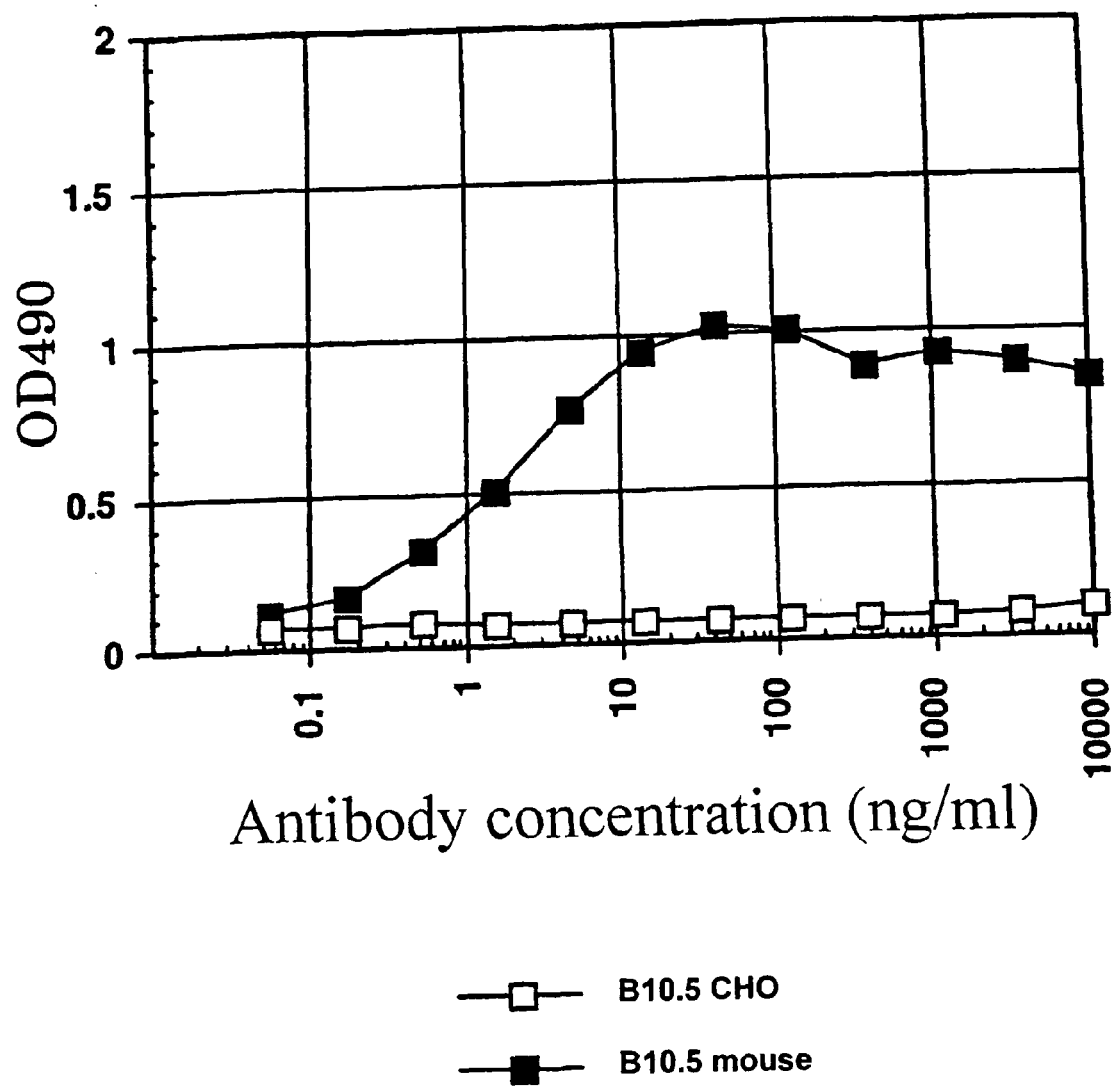

FIG. 7 shows binding activities of rat anti-human AILIM monoclonal antibodies to mouse AILIM-overexpressing recombinant CHO cells or wild-type CHO cells.

The vertical axis indicates fluorescence intensity as an index of binding activity to the recombinant cells, and the horizontal axis indicates the concentration of the antibody added.

The term "CHO" in the figure indicates the result of a binding assay to the wild-type CHO cell, and "mouse" indicates the result of a binding assay to the mouse AILIM-overexpressing recombinant CHO cell.

Figure 8:
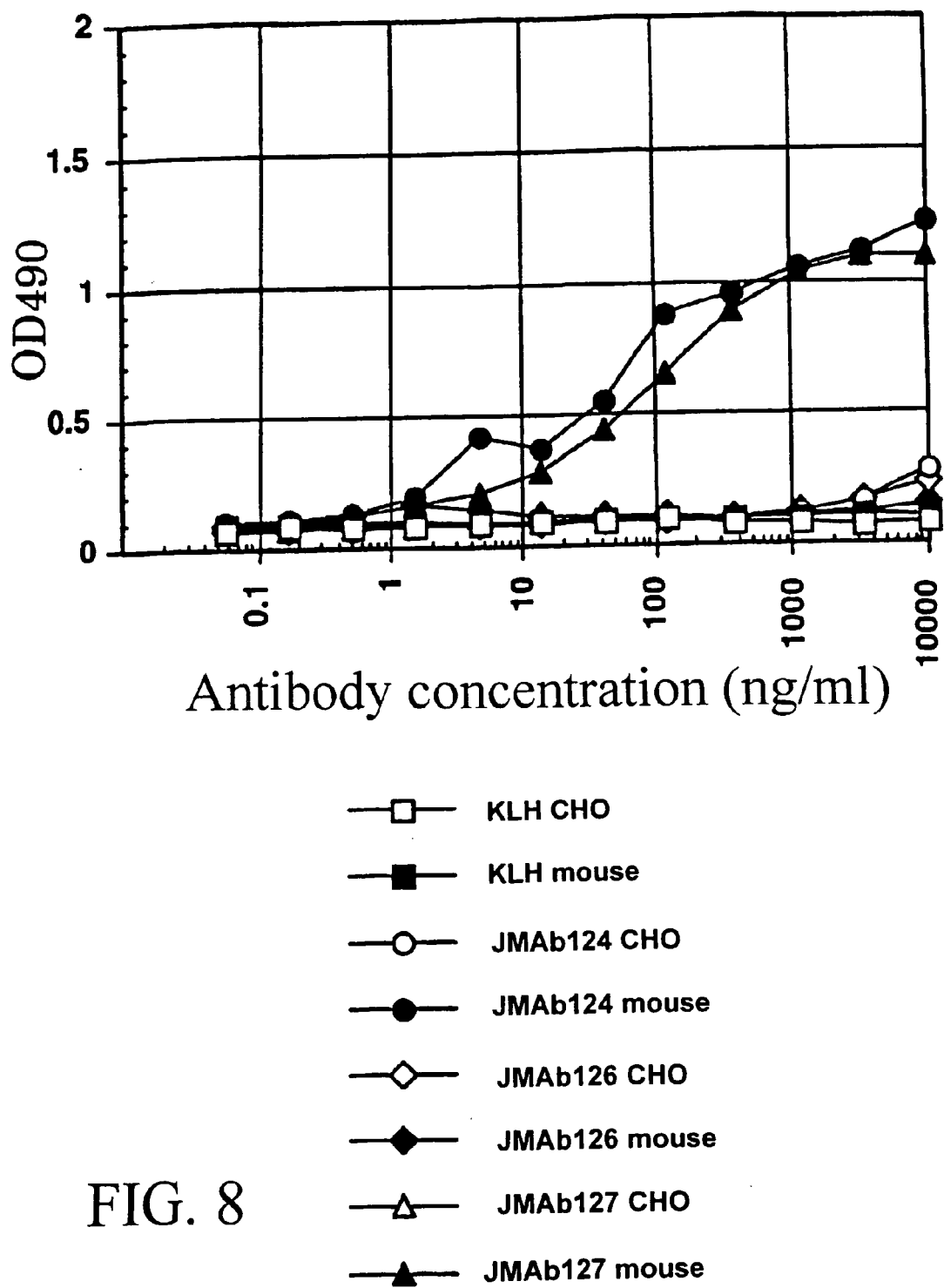

FIG. 8 shows binding activities of various human anti-human AILIM monoclonal antibodies or human anti-KLH monoclonal antibodies as a negative control to mouse AILIM-overexpressing recombinant CHO cells or wild-type CHO cells.

The vertical axis indicates fluorescence intensity as an index of binding activity to the recombinant cells, and the horizontal axis indicates the concentration of the antibody added.

The term "CHO" in the figure indicates the result of a binding assay to the wild-type CHO cell, and "mouse" indicates the result of a binding assay to the mouse AILIM-overexpressing recombinant CHO cell.

Figure 9:
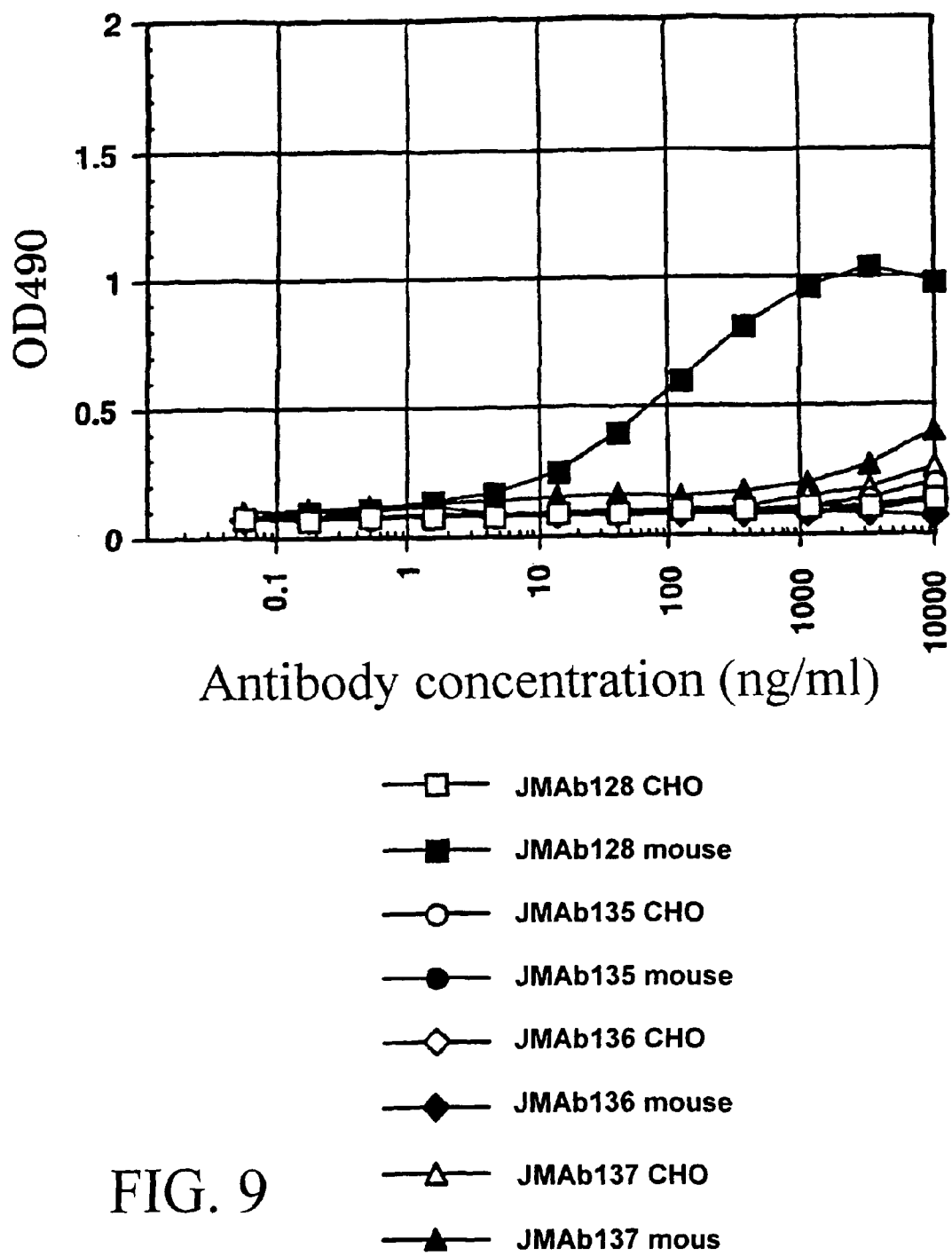

FIG. 9 shows binding activities of various human anti-human AILIM monoclonal antibodies to mouse AILIM-overexpressing recombinant CHO cells or wild-type CHO cells.

The vertical axis indicates fluorescence intensity as an index of binding activity to the recombinant cells, and the horizontal axis indicates the concentration of the antibody added.

The term "CHO" in the figure indicates the result of a binding assay to the wild-type CHO cell, and "mouse" indicates the result of a binding assay to the mouse AILIM-overexpressing recombinant CHO cell.

Figure 10:
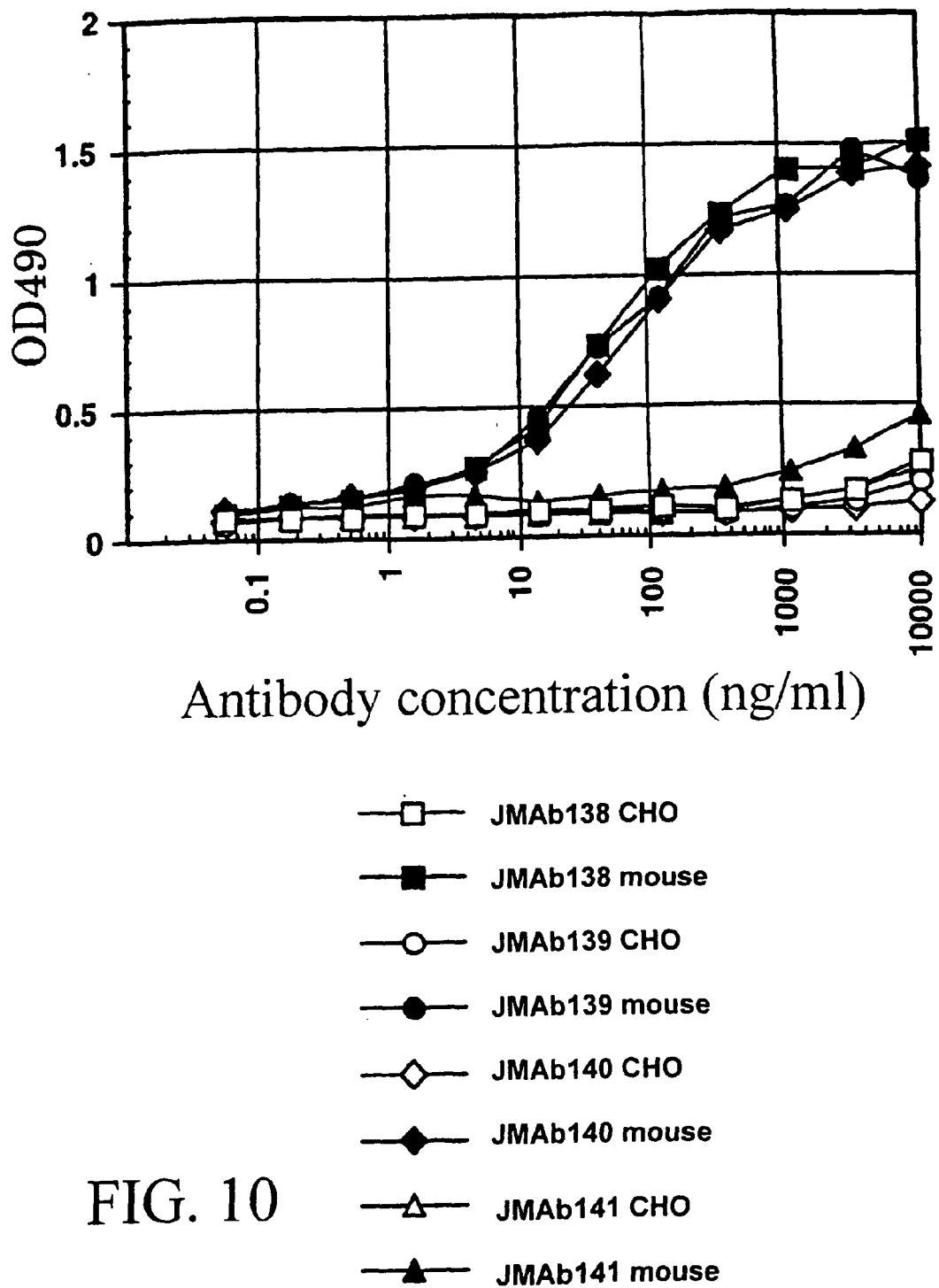

FIG. 10 shows binding activities of various human anti-human AILIM monoclonal antibodies to mouse AILIM-overexpressing recombinant CHO cells or wild-type CHO cells.

The vertical axis indicates fluorescence intensity as an index of binding activity to the recombinant cells, and the horizontal axis indicates the concentration of the antibody added.

The term "CHO" in the figure indicates the result of a binding assay to the wild-type CHO cell, and "mouse" indicates the result of binding assay to the mouse AILIM-overexpressing recombinant CHO cell.

Figure 11:
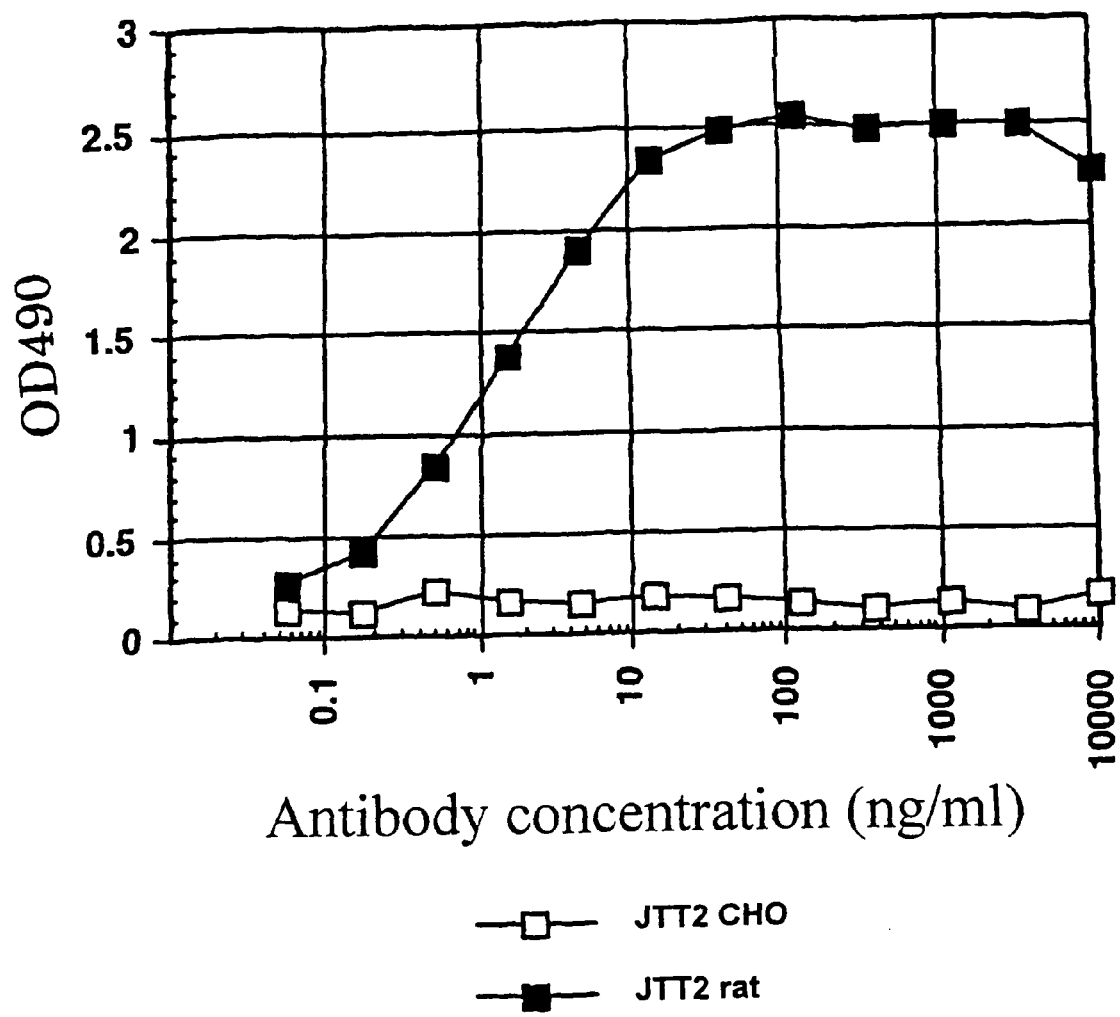

FIG. 11 shows binding activities of various mouse anti-rat AILIM monoclonal antibodies to rat AILIM-overexpressing recombinant CHO cells or wild-type CHO cells.

The vertical axis indicates fluorescence intensity as an index of binding activity to the recombinant cells, and the horizontal axis indicates the concentration of the antibody added.

The term "CHO" in the figure indicates the result of a binding assay to the wild-type CHO cell, and "rat" indicates the result of a binding assay to the rat AILIM-overexpressing recombinant CHO cell.

Figure 12:
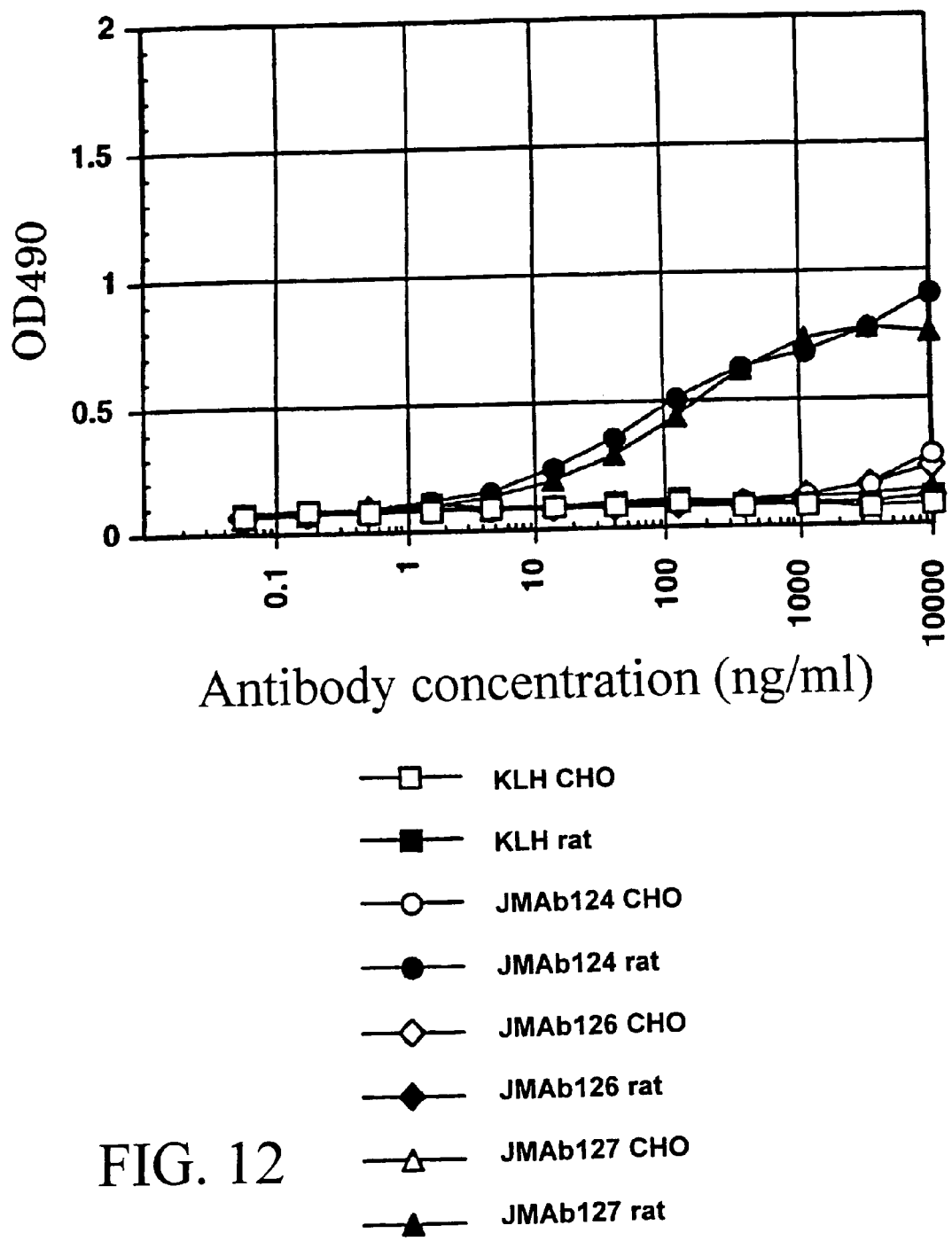

FIG. 12 shows binding activities of various human anti-human AILIM monoclonal antibodies or human anti-KLH monoclonal antibodies as a negative control to rat AILIM-overexpressing recombinant CHO cells or wild-type CHO cells.

The vertical axis indicates fluorescence intensity as an index of binding activity to the recombinant cells, and the horizontal axis indicates the concentration of the antibody added.

The term "CHO" in the figure indicates the result of a binding assay to the wild-type CHO cell, and "rat" indicates the result of a binding assay to the rat AILIM-overexpressing recombinant CHO cell.

Figure 13:
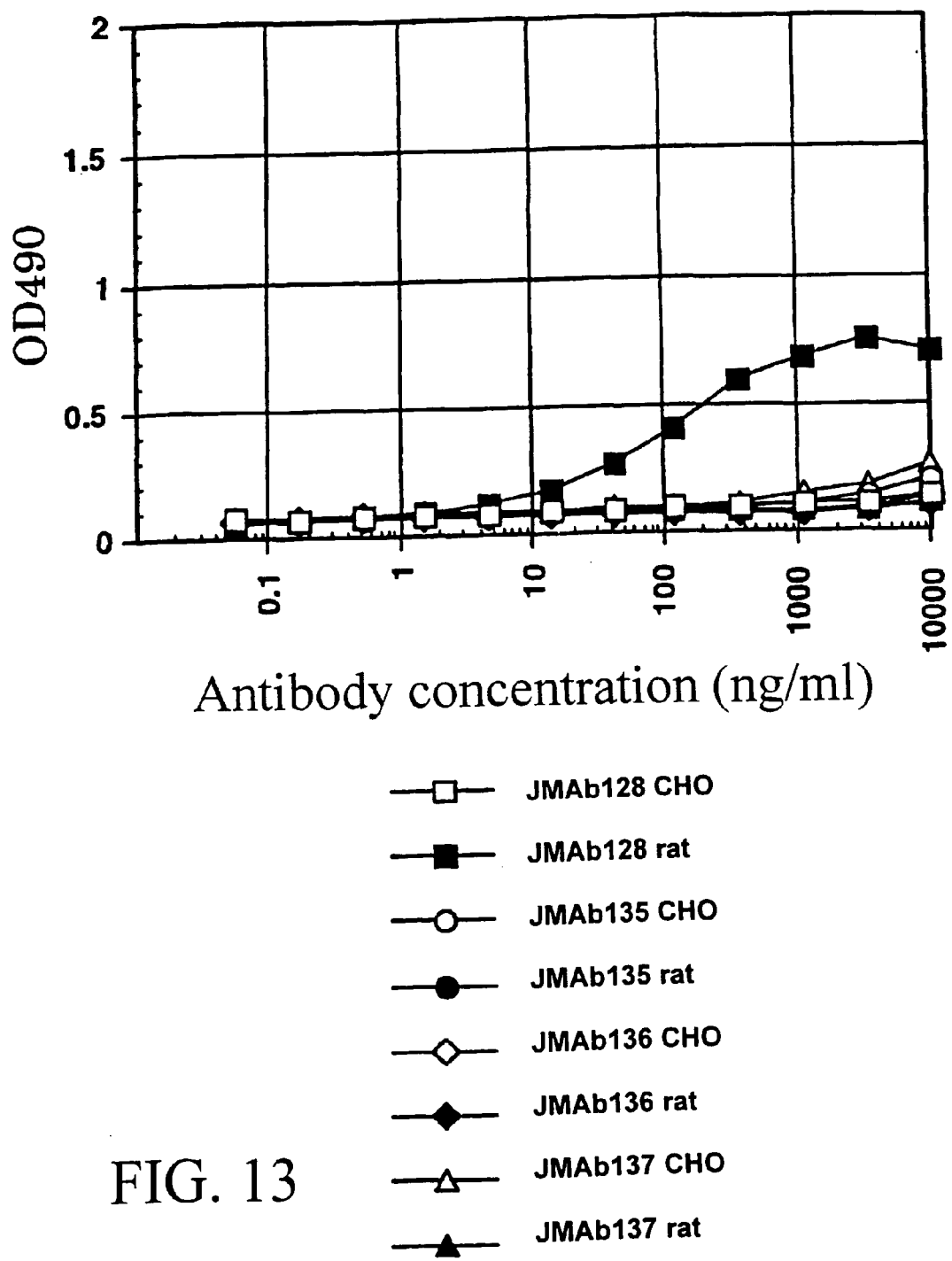

FIG. 13 shows binding activities of various human anti-human AILIM monoclonal antibodies to rat AILIM-overexpressing recombinant CHO cells or wild-type CHO cells.

The vertical axis indicates fluorescence intensity as an index of binding activity to the recombinant cells, and the horizontal axis indicates the concentration of the antibody added.

The term "CHO" in the figure indicates the result of a binding assay to the wild-type CHO cell, and "rat" indicates the result of a binding assay to the rat AILIM-overexpressing recombinant CHO cell.

Figure 14:
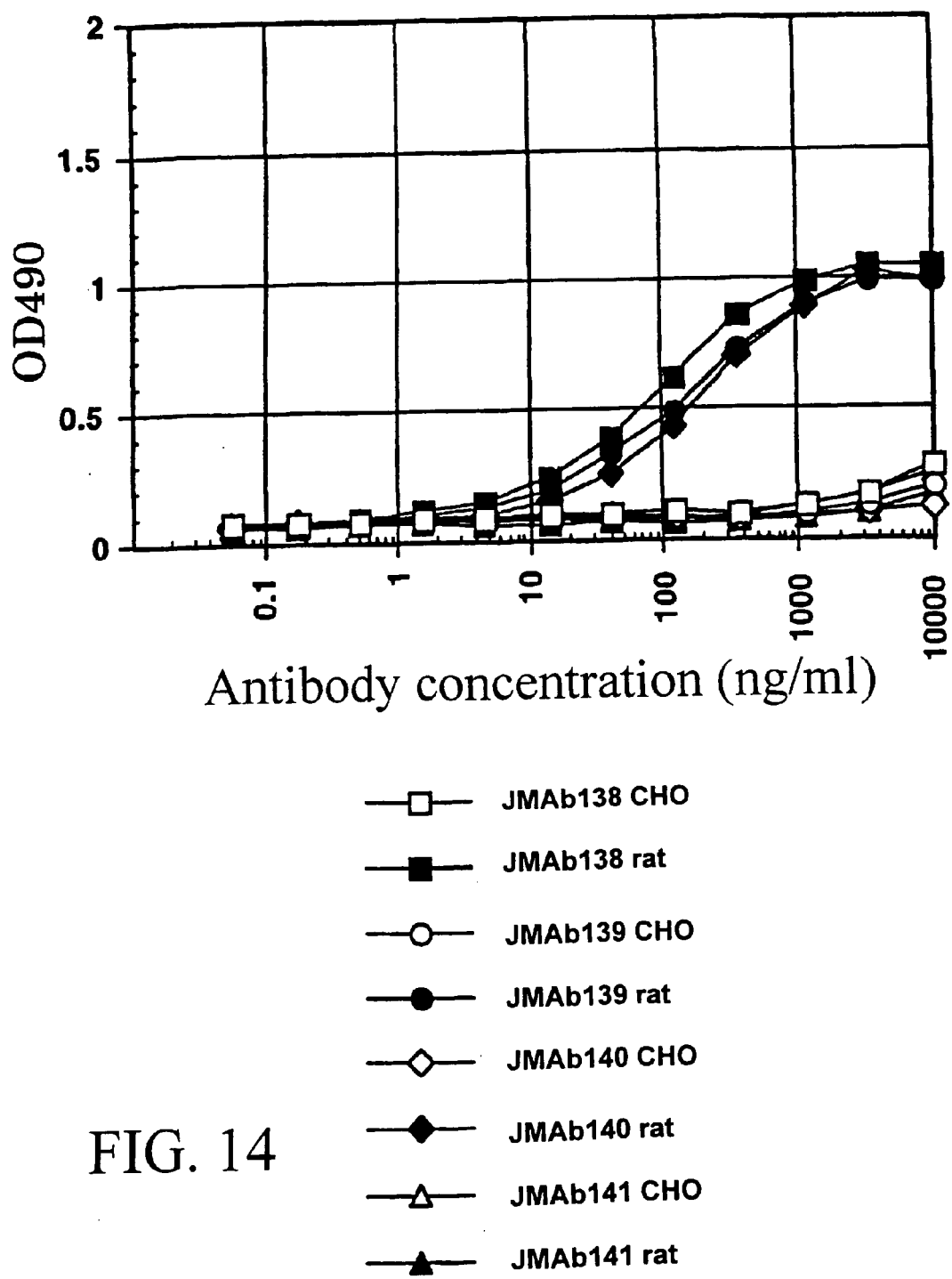

FIG. 14 shows binding activities of various human anti-human AILIM monoclonal antibodies to rat AILIM-overexpressing recombinant CHO cells or wild-type CHO cells.

The vertical axis indicates fluorescence intensity as an index of binding activity to the recombinant cells, and the horizontal axis indicates the concentration of the antibody added.

The term "CHO" in the figure indicates the result of a binding assay to the wild-type CHO cell, and "rat" indicates the result of a binding assay to the rat AILIM-overexpressing recombinant CHO cell.

Figure 15:
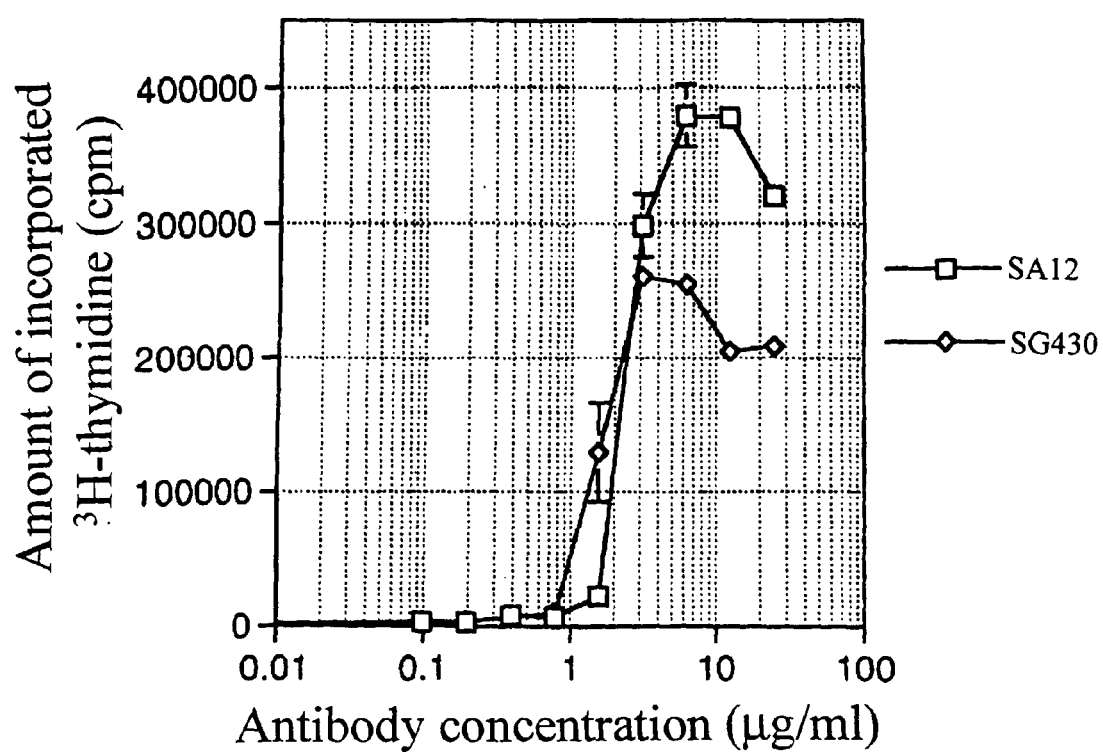

FIG. 15 shows proliferation activity of T cells derived from a normal healthy person "donor A" in the assay for the activity of transducing costimulatory signal by various mouse anti-human AILIM monoclonal antibodies using a microplate coated with anti-human CD3 monoclonal antibody together with mouse anti-human AILIM monoclonal antibody.

The vertical axis indicates the amount of cellular incorporation of [$^3$H]thymidine as an index of the degree of cell proliferation, and the horizontal axis indicates the concentration of mouse anti-human AILIM monoclonal antibody.

Figure 16:
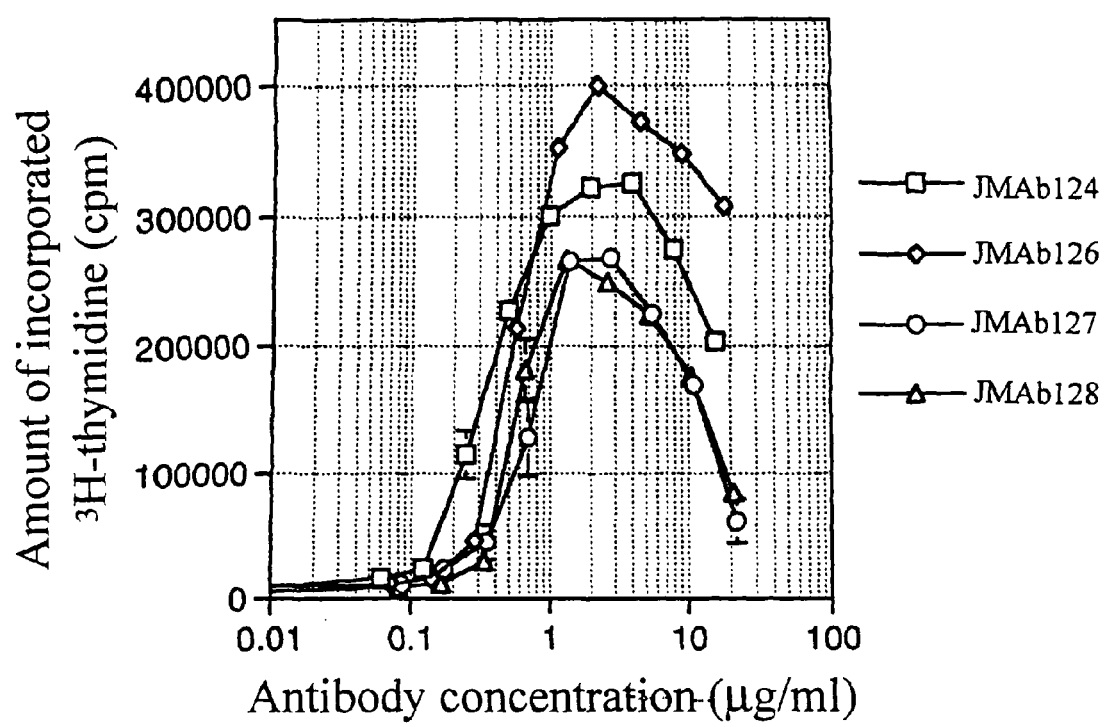

FIG. 16 shows proliferation activity of T cells derived from a normal healthy person "donor A" in the assay for the activity of transducing costimulatory signal by various human anti-human AILIM monoclonal antibodies using a microplate coated with anti-human CD3 monoclonal antibody together with human anti-human AILIM monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

Figure 17:
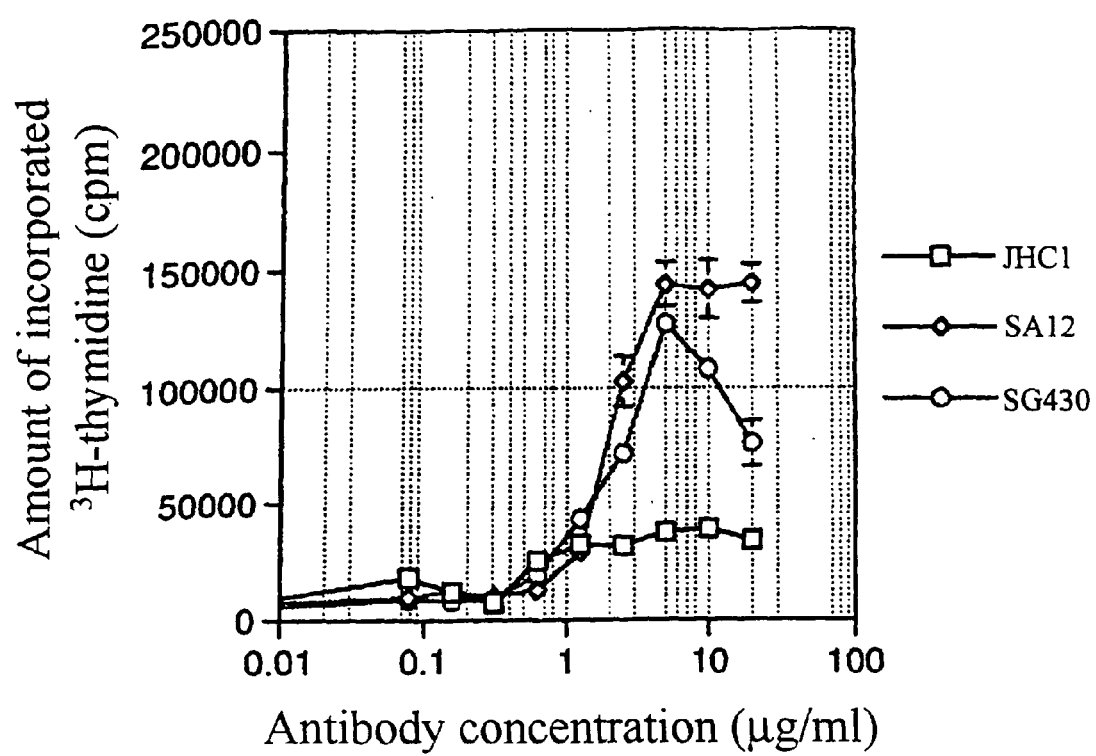

FIG. 17 shows proliferation activity of T cells derived from a normal healthy person "donor B" in the assay for the activity of transducing costimulatory signal by various mouse anti-human AILIM monoclonal antibodies using a microplate coated with anti-human CD3 monoclonal antibody together with mouse anti-human AILIM monoclonal antibody.

The vertical axis indicates the amount of cellular incorporation of [$^3$H]thymidine as an index of the degree of cell proliferation, and the horizontal axis indicates the concentration of mouse anti-human AILIM monoclonal antibody.

In this figure, "JHC1" indicated result of assay in which anti-human CETP monoclonal antibody was used as the negative control, instead of the mouse anti-human AILIM monoclonal antibody.

Figure 18:
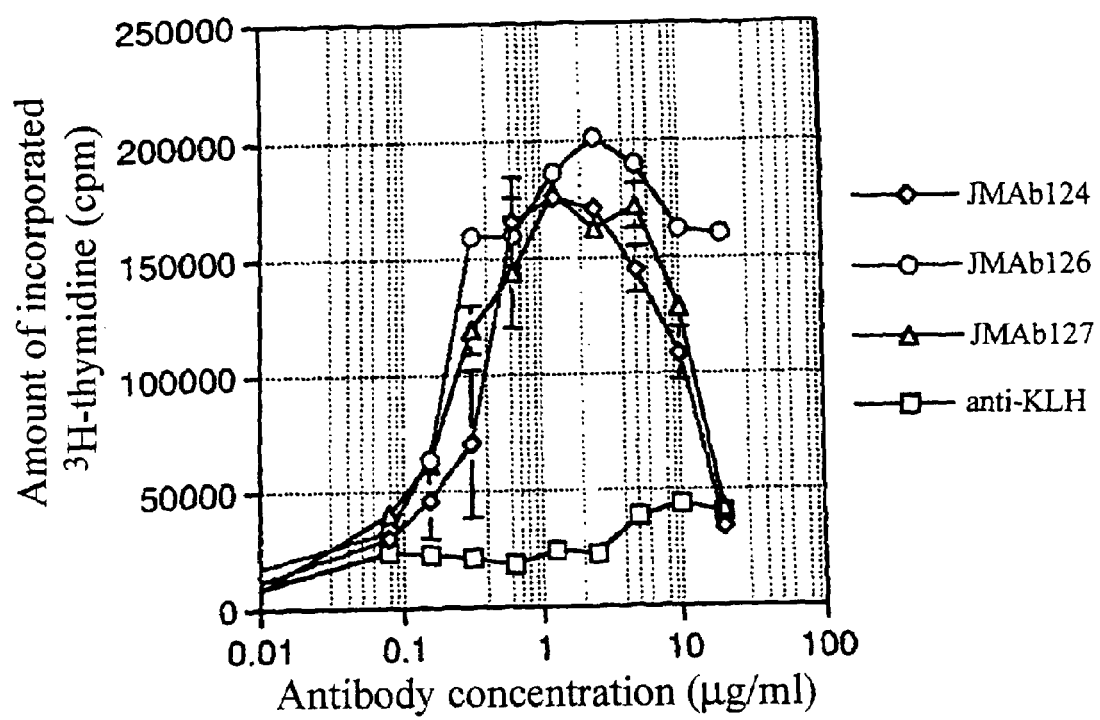

FIG. 18 shows proliferation activity of T cells derived from a normal healthy person "donor B" in the assay for the activity of transducing costimulatory signal by various human anti-human AILIM monoclonal antibodies using a microplate coated with anti-human CD3 monoclonal antibody together with human anti-human AILIM monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

In this figure, "anti-KLH" indicates result of assay in which human anti-KLH monoclonal antibody was used as the negative control, instead of the human anti-human AILIM monoclonal antibody.

Figure 19:
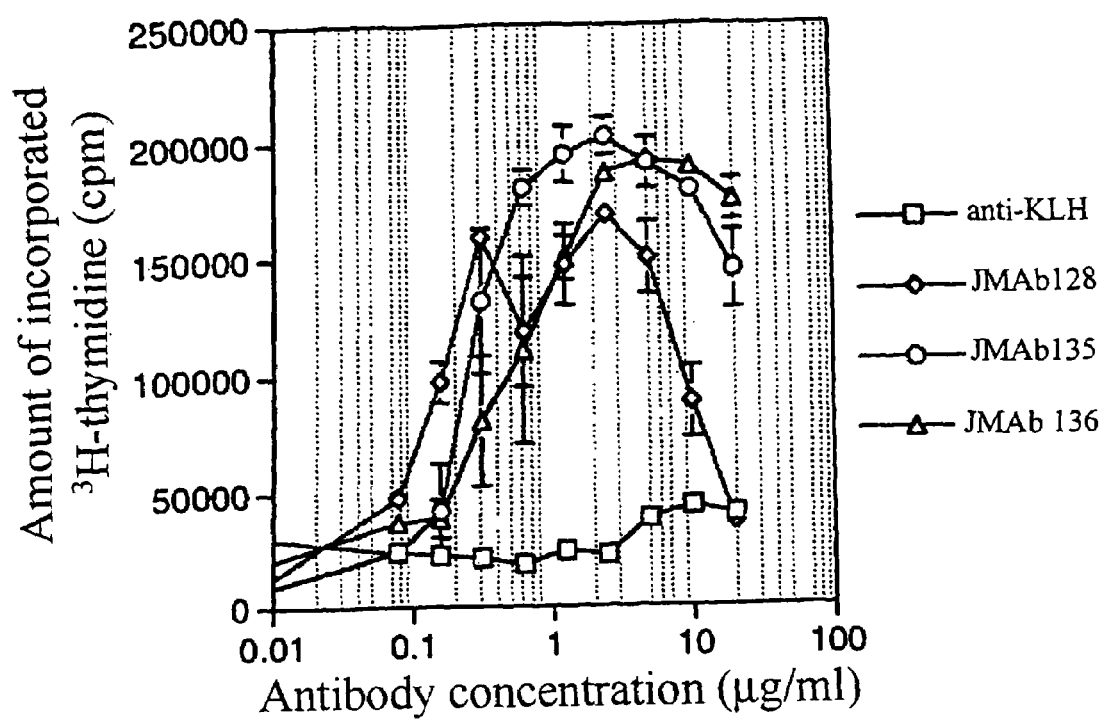

FIG. 19 shows proliferation activity of T cells derived from a normal healthy person "donor B" in the assay for the activity of transducing costimulatory signal by various human anti-human AILIM monoclonal antibodies using a microplate coated with anti-human CD3 monoclonal antibody together with human anti-human AILIM monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

In this figure, "anti-KLH" indicates result of assay in which human anti-KLH monoclonal antibody was used as the negative control, instead of the human anti-human AILIM monoclonal antibody.

Figure 20:
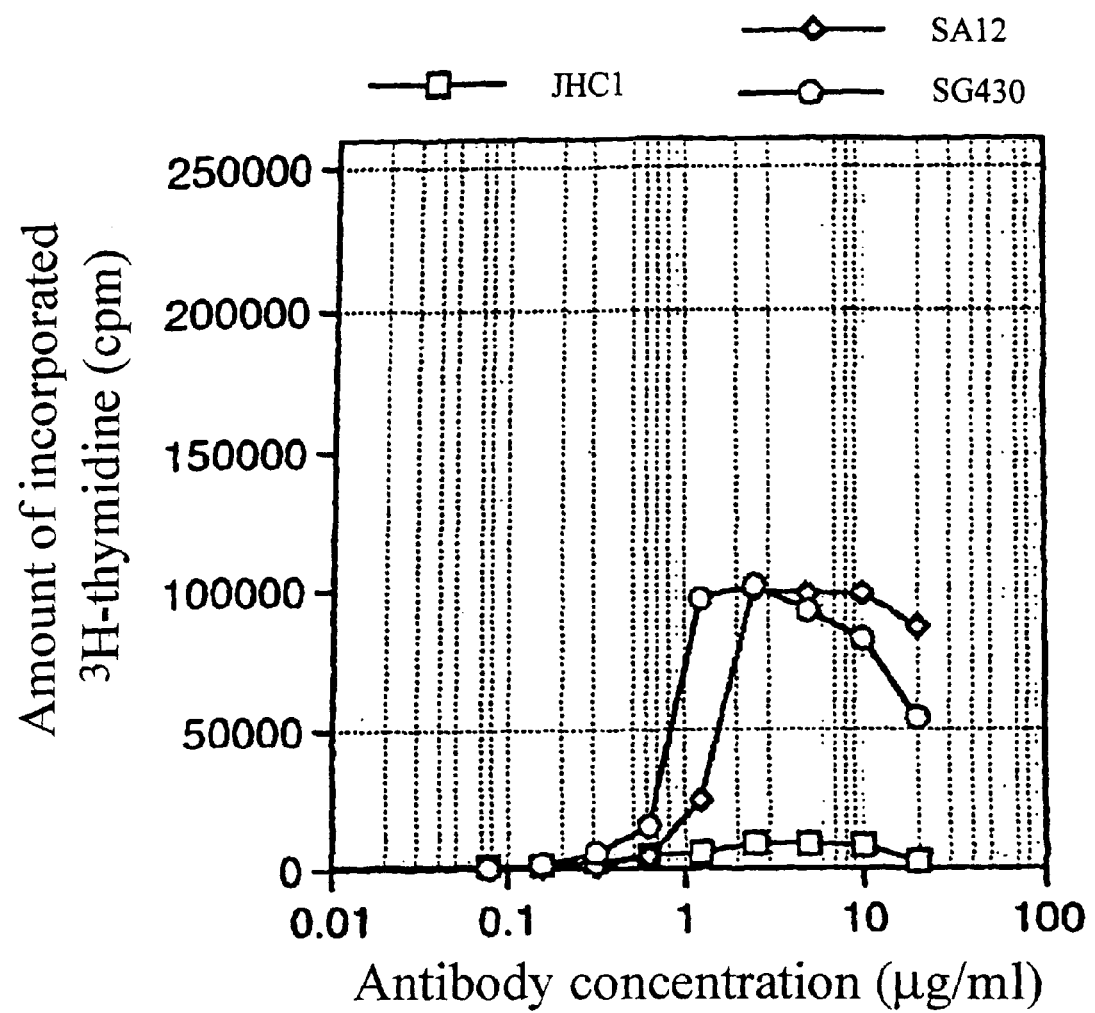

FIG. 20 shows proliferation activity of T cells derived from a normal healthy person "donor C" in the assay for the activity of transducing costimulatory signal by various mouse anti-human AILIM monoclonal antibodies using a microplate coated with anti-human CD3 monoclonal antibody together with mouse anti-human AILIM monoclonal antibody.

The vertical axis indicates the amount of cellular incorporation of [$^3$H]thymidine as an index of the degree of cell proliferation, and the horizontal axis indicates the concentration of mouse anti-human AILIM monoclonal antibody.

In this figure, "JHC1" indicates result of assay in which anti-human CETP monoclonal antibody was used as the negative control, instead of the mouse anti-human AILIM monoclonal antibody.

Figure 21:
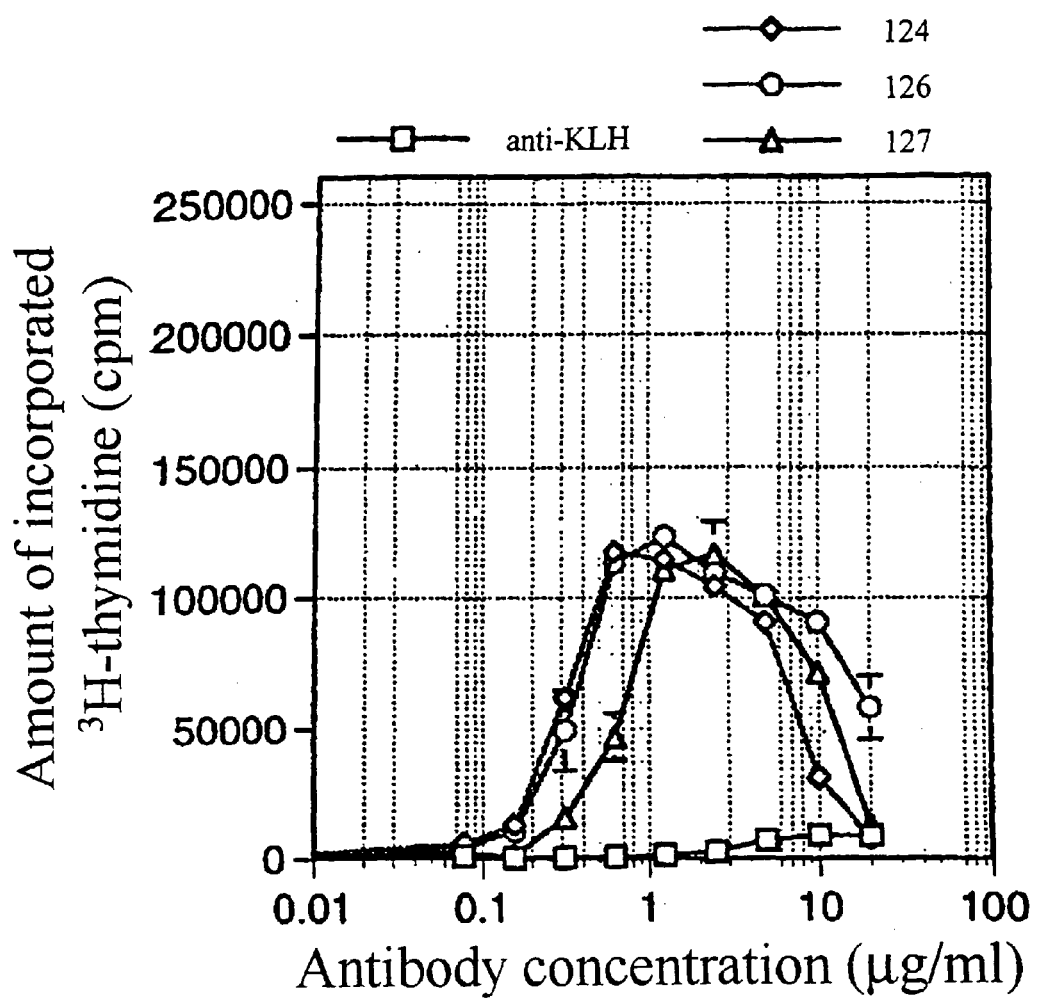

FIG. 21 shows proliferation activity of T cells derived from a normal healthy person "donor C" in the assay for the activity of transducing costimulatory signal by various human anti-human AILIM monoclonal antibodies using a microplate coated with anti-human CD3 monoclonal antibody together with human anti-human AILIM monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"124": human anti-human AILIM monoclonal antibody JMab124.

"126": human anti-human AILIM monoclonal antibody JMab126.

"127": human anti-human AILIM monoclonal antibody JMab127.

Figure 22:
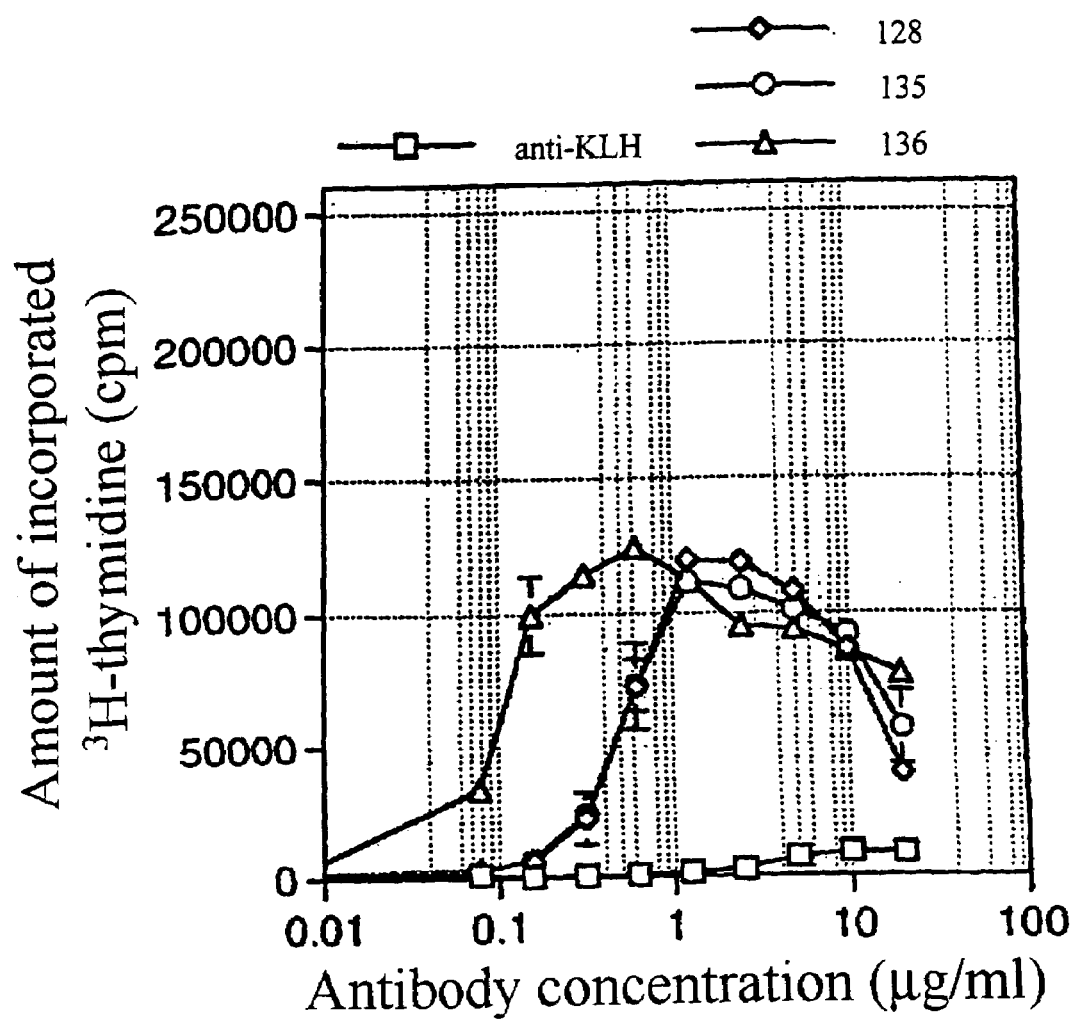

FIG. 22 shows proliferation activity of T cells derived from a normal healthy person "donor C" in the assay for the activity of transducing costimulatory signal by various human anti-human AILIM monoclonal antibodies using a microplate coated with anti-human CD3 monoclonal antibody together with human anti-human AILIM monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"128": human anti-human AILIM monoclonal antibody JMab128.

"135": human anti-human AILIM monoclonal antibody JMab135.

"136": human anti-human AILIM monoclonal antibody JMab136.

Figure 23:
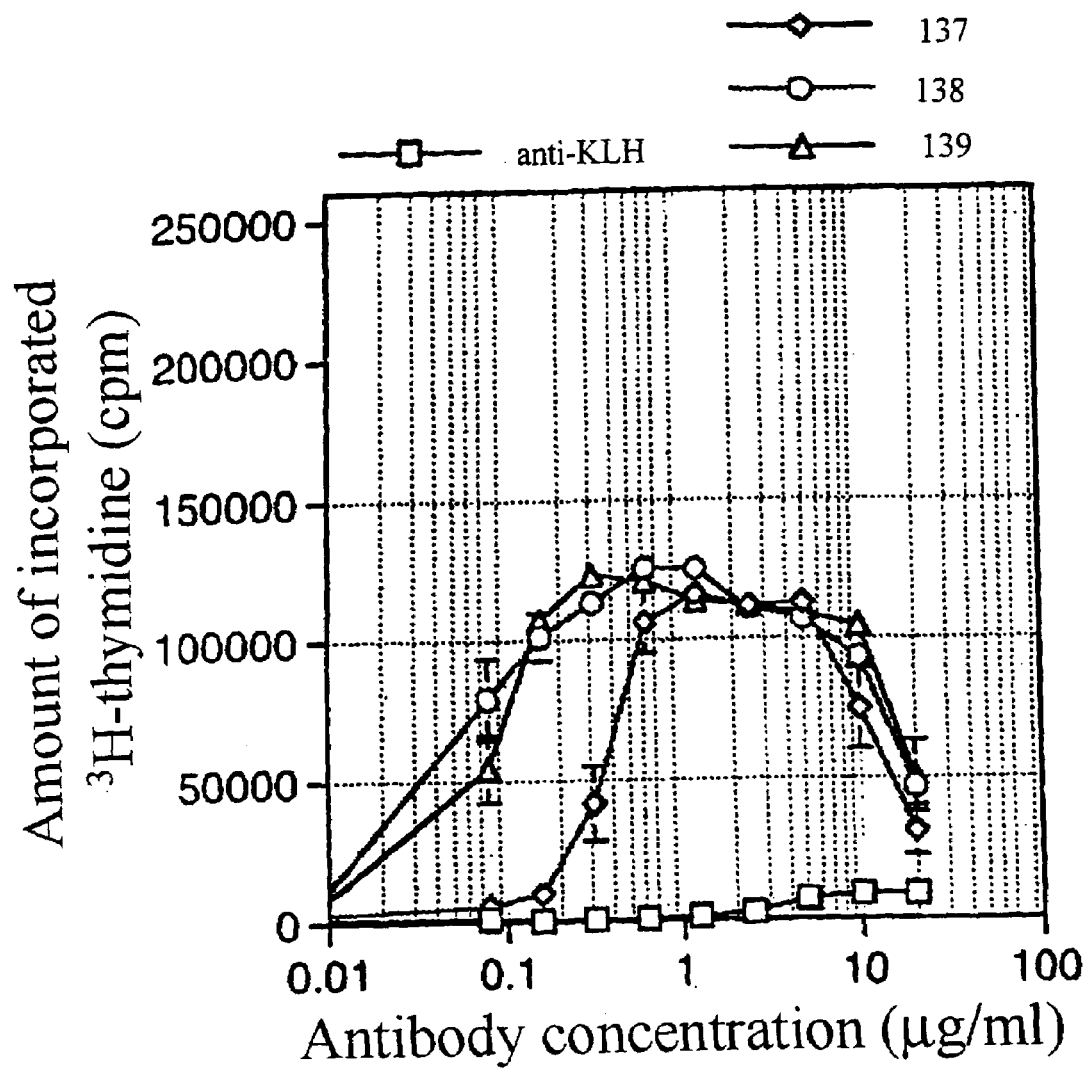

FIG. 23 shows proliferation activity of T cells derived from a normal healthy person "donor C" in the assay for the activity of transducing costimulatory signal by various human anti-human AILIM monoclonal antibodies using a microplate coated with anti-human CD3 monoclonal antibody together with human anti-human AILIM monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"137": human anti-human AILIM monoclonal antibody JMab137.

"138": human anti-human AILIM monoclonal antibody JMab138.

"139": human anti-human AILIM monoclonal antibody JMab139.

Figure 24:
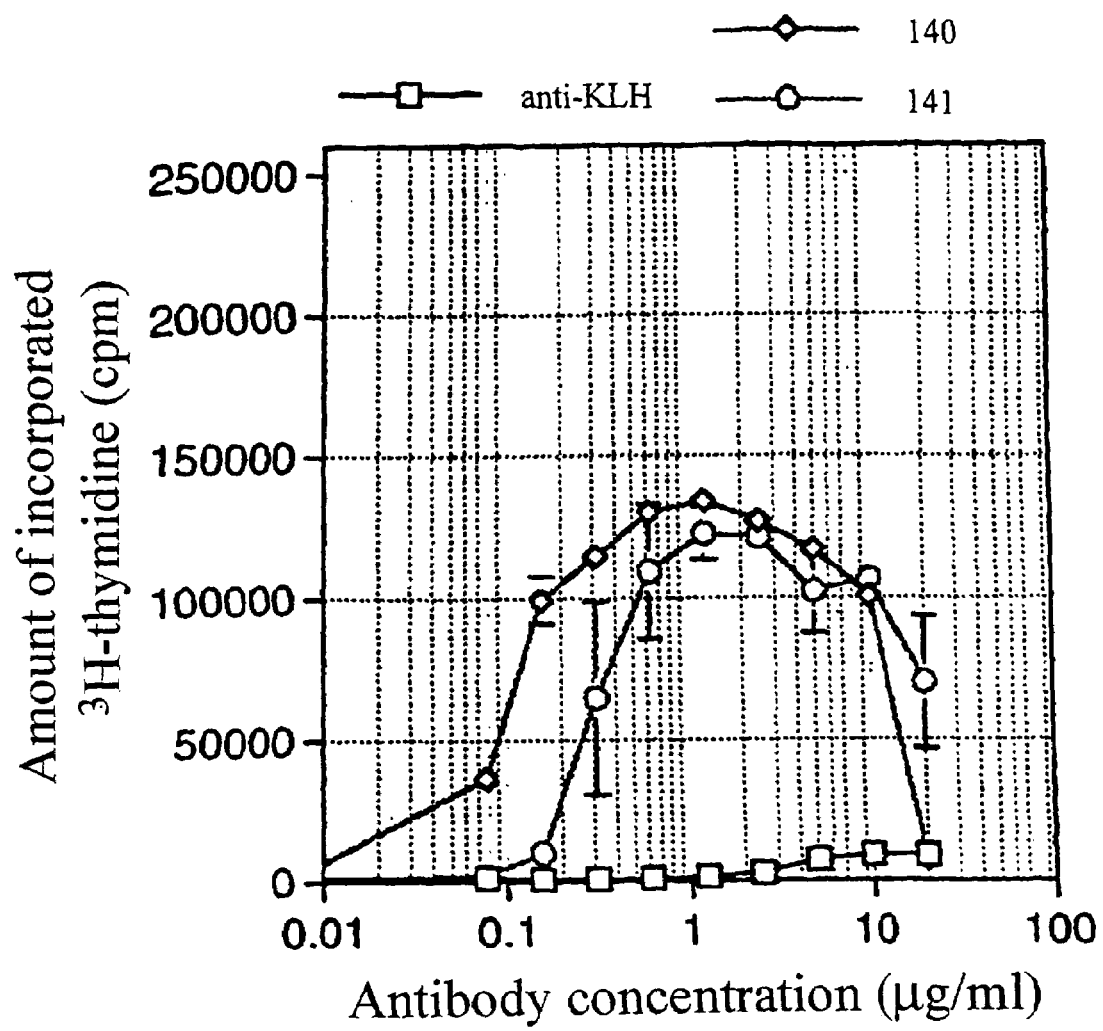

FIG. 24 shows proliferation activity of T cells derived from a normal healthy person "donor C" in the assay for the activity of transducing costimulatory signal by various human anti-human AILIM monoclonal antibodies using a microplate coated with anti-human CD3 monoclonal antibody together with human anti-human AILIM monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"140": human anti-human AILIM monoclonal antibody JMab140.

"141": human anti-human AILIM monoclonal antibody JMab141.

Figure 25:
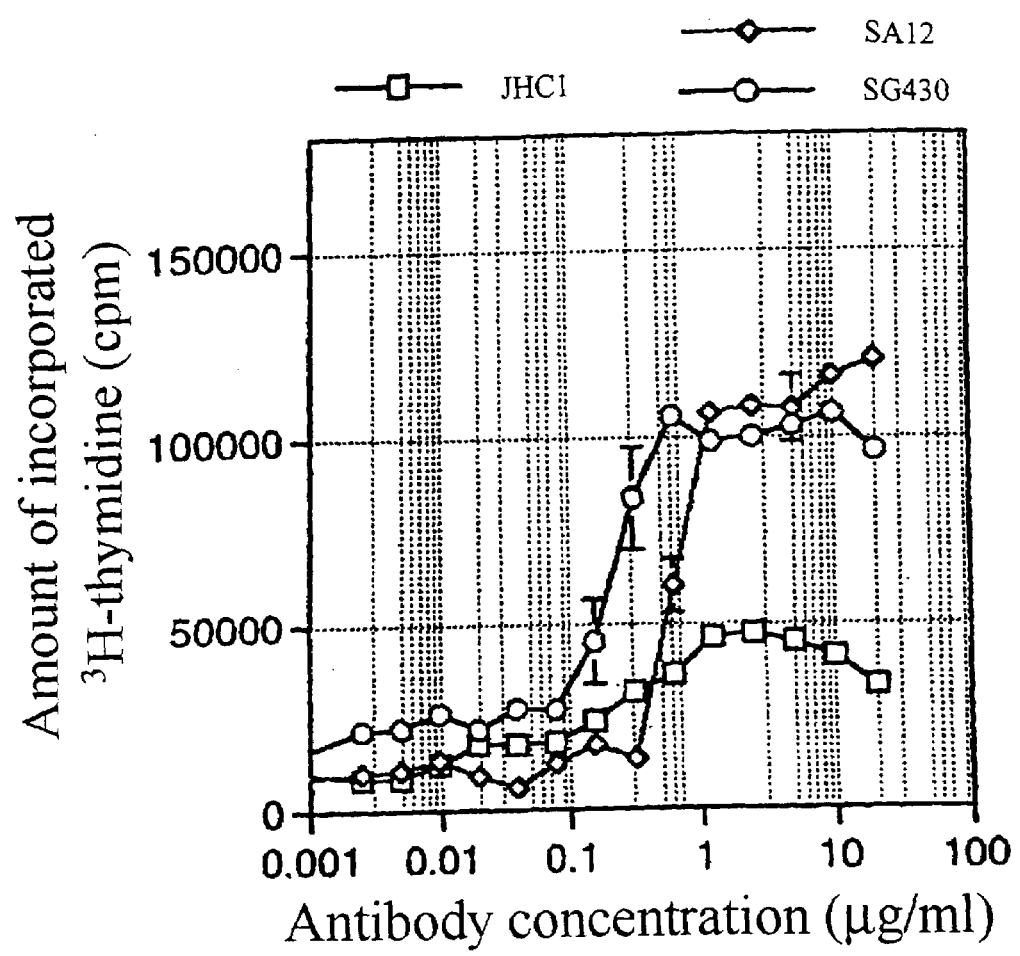

FIG. 25 shows proliferation activity of T cells derived from a normal healthy person "donor D" in the assay for the activity of transducing costimulatory signal by various mouse anti-human AILIM monoclonal antibodies using a microplate coated with anti-human CD3 monoclonal antibody together with mouse anti-human AILIM monoclonal antibody.

The vertical axis indicates the amount of cellular incorporation of [$^3$H]thymidine as an index of the degree of cell proliferation, and the horizontal axis indicates the concentration of mouse anti-human AILIM monoclonal antibody.

In this figure, "JHC1" indicates result of assay in which anti-human CETP monoclonal antibody was used as the negative control, instead of the mouse anti-human AILIM monoclonal antibody.

Figure 26:
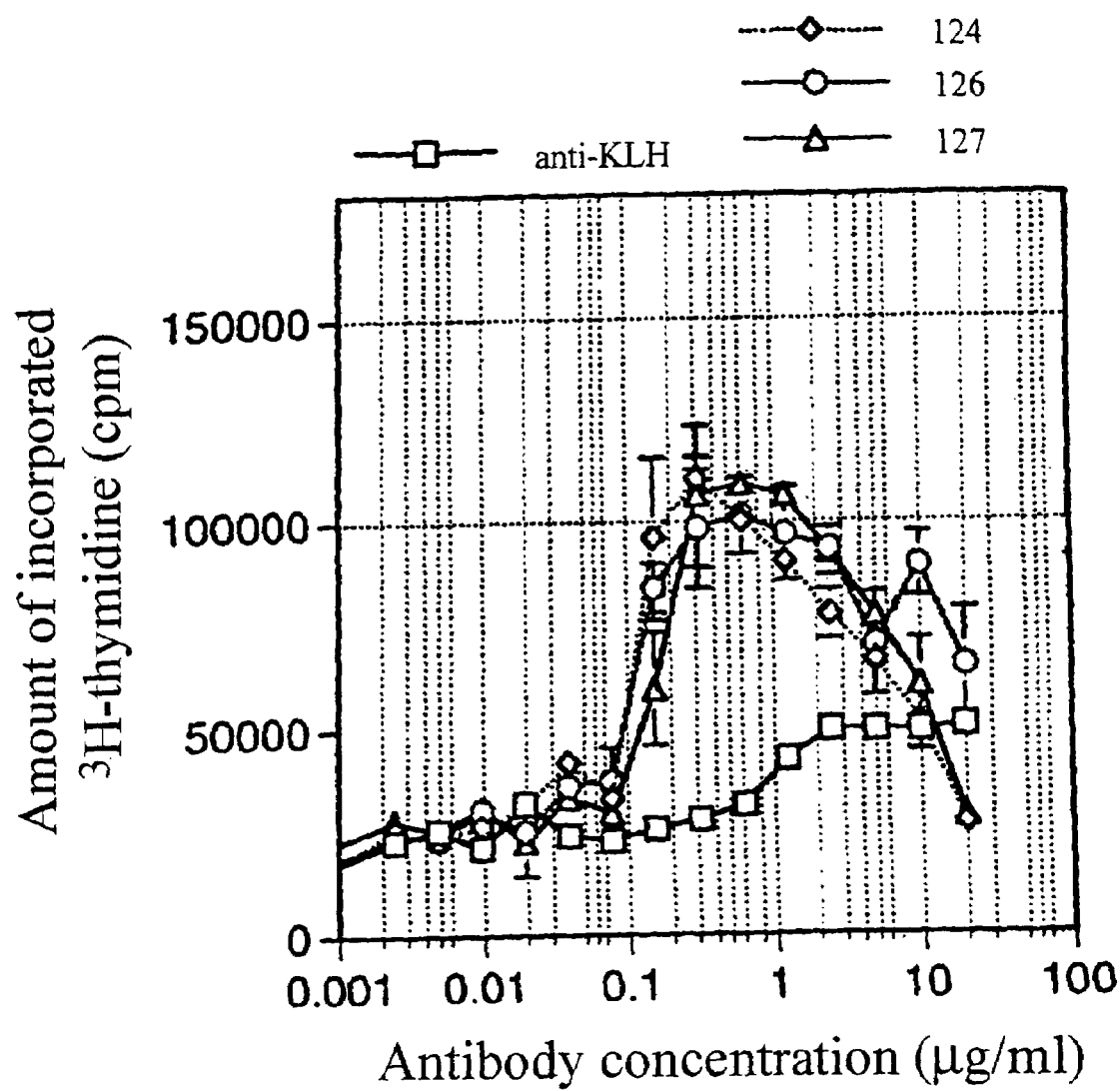

FIG. 26 shows proliferation activity of T cells derived from a normal healthy person "donor D" in the assay for the activity of transducing costimulatory signal by various human anti-human AILIM monoclonal antibodies using a microplate coated with anti-human CD3 monoclonal antibody together with human anti-human AILIM monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"124": human anti-human AILIM monoclonal antibody JMab124.

"126": human anti-human AILIM monoclonal antibody JMab126.

"127": human anti-human AILIM monoclonal antibody JMab127.

Figure 27:
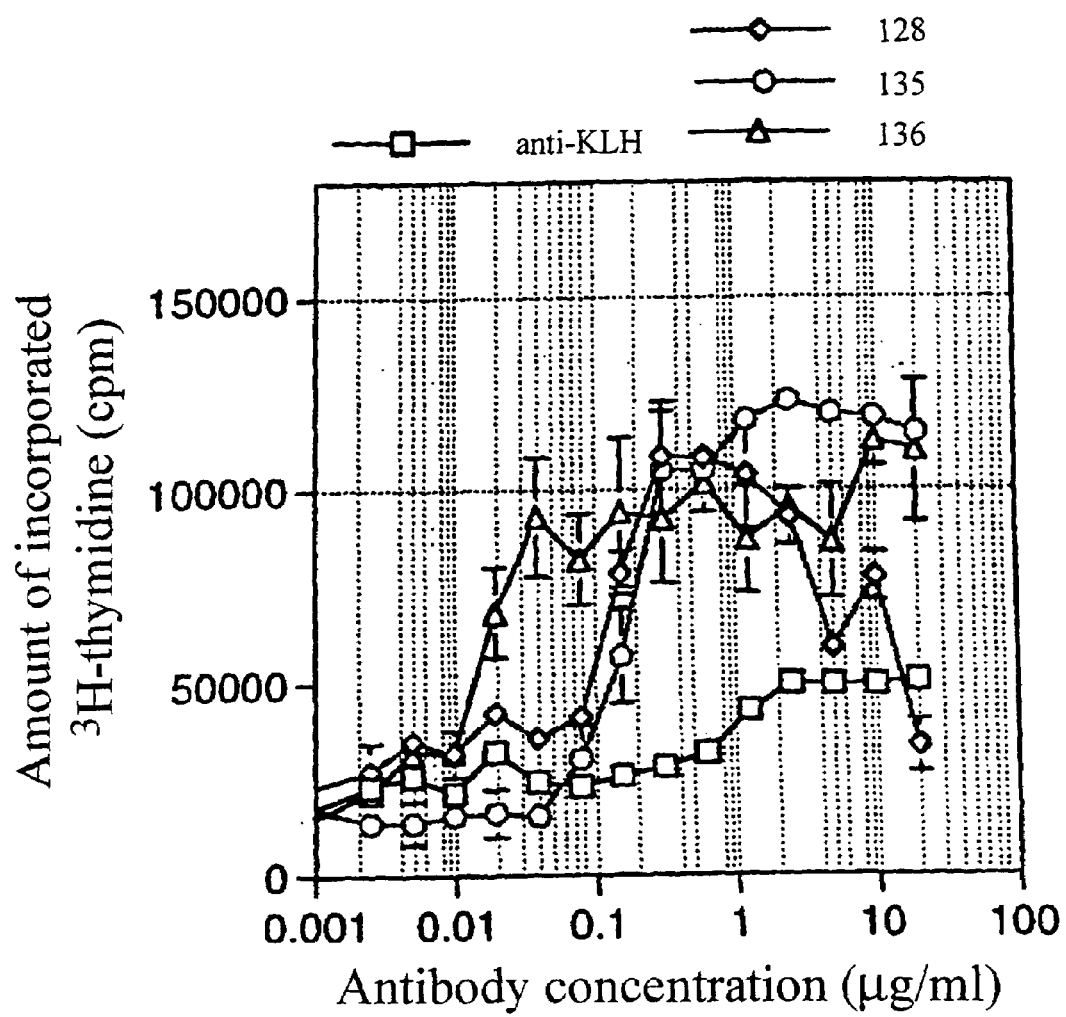

FIG. 27 shows proliferation activity of T cells derived from a normal healthy person "donor D" in the assay for the activity of transducing costimulatory signal by various human anti-human AILIM monoclonal antibodies using a microplate coated with anti-human CD3 monoclonal antibody together with human anti-human AILIM monoclonal antibody.

The vertical axis indicates the amount of cellular incorporation of [$^3$H]thymidine as an index of the degree of cell proliferation, and the horizontal axis indicates the concentration of mouse anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"128": human anti-human AILIM monoclonal antibody JMab128.

"135": human anti-human AILIM monoclonal antibody JMab135.

"136": human anti-human AILIM monoclonal antibody JMab136.

Figure 28:
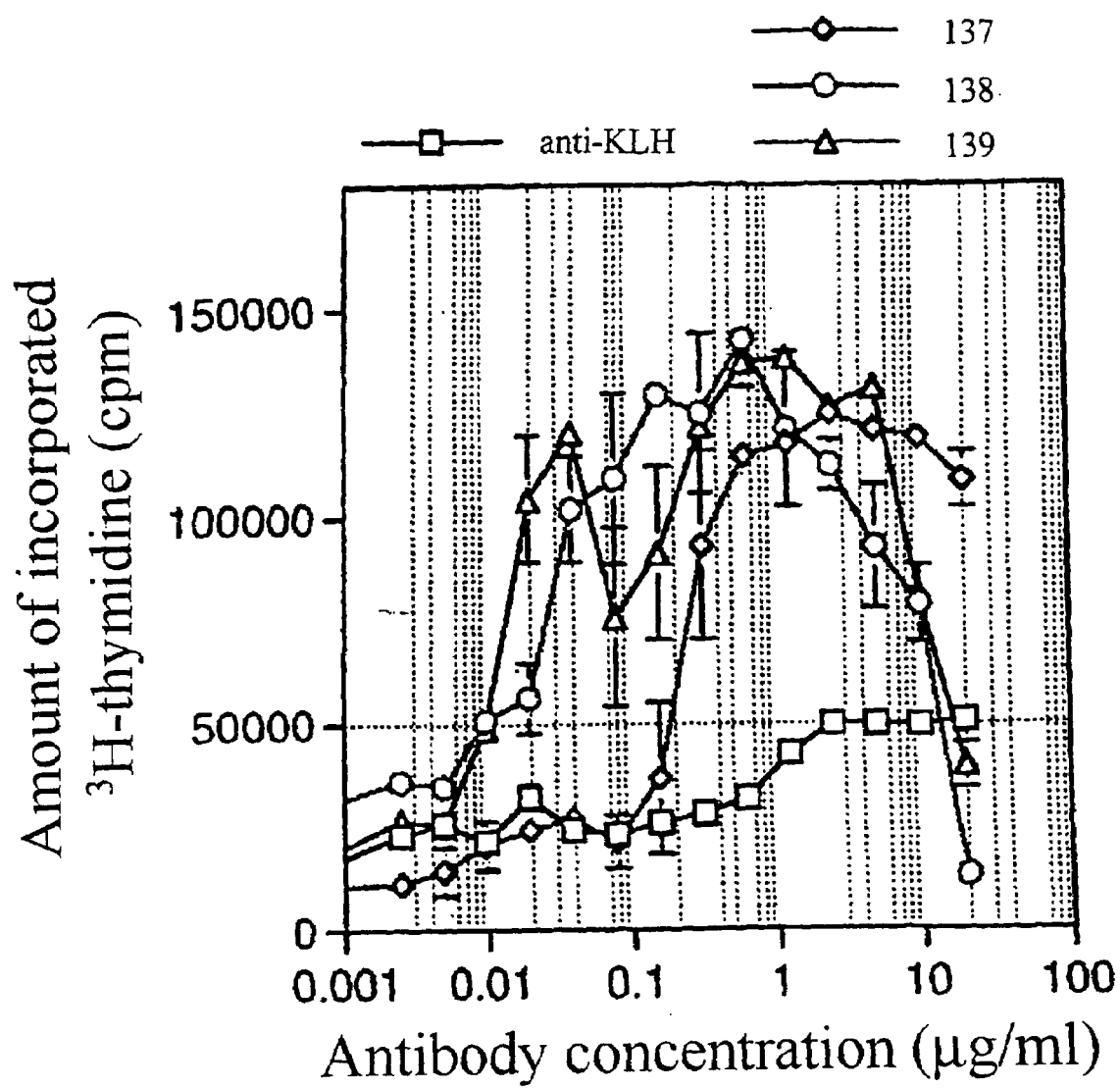

FIG. 28 shows proliferation activity of T cells derived from a normal healthy person "donor D" in the assay for the activity of transducing costimulatory signal by various human anti-human AILIM monoclonal antibodies using a microplate coated with anti-human CD3 monoclonal antibody together with human anti-human AILIM monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"137": human anti-human AILIM monoclonal antibody JMab137.

"138": human anti-human AILIM monoclonal antibody JMab138.

"139": human anti-human AILIM monoclonal antibody JMab139.

Figure 29:
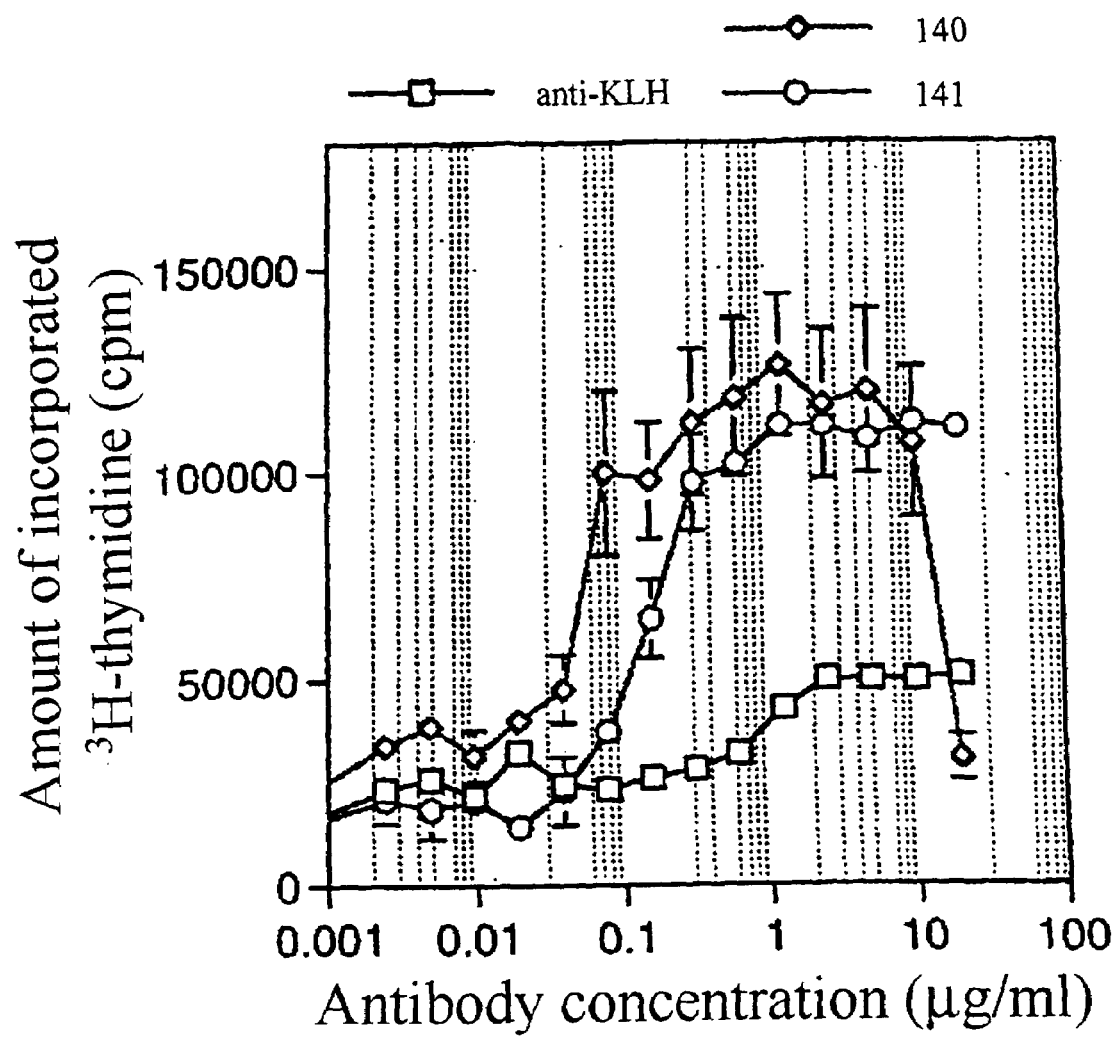

FIG. 29 shows proliferation activity of T cells derived from a normal healthy person "donor D" in the assay for the activity of transducing costimulatory signal by various human anti-human AILIM monoclonal antibodies using a microplate coated with anti-human CD3 monoclonal antibody together with human anti-human AILIM monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"140": human anti-human AILIM monoclonal antibody JMab140.

"141": human anti-human AILIM monoclonal antibody JMab141.

Figure 30:
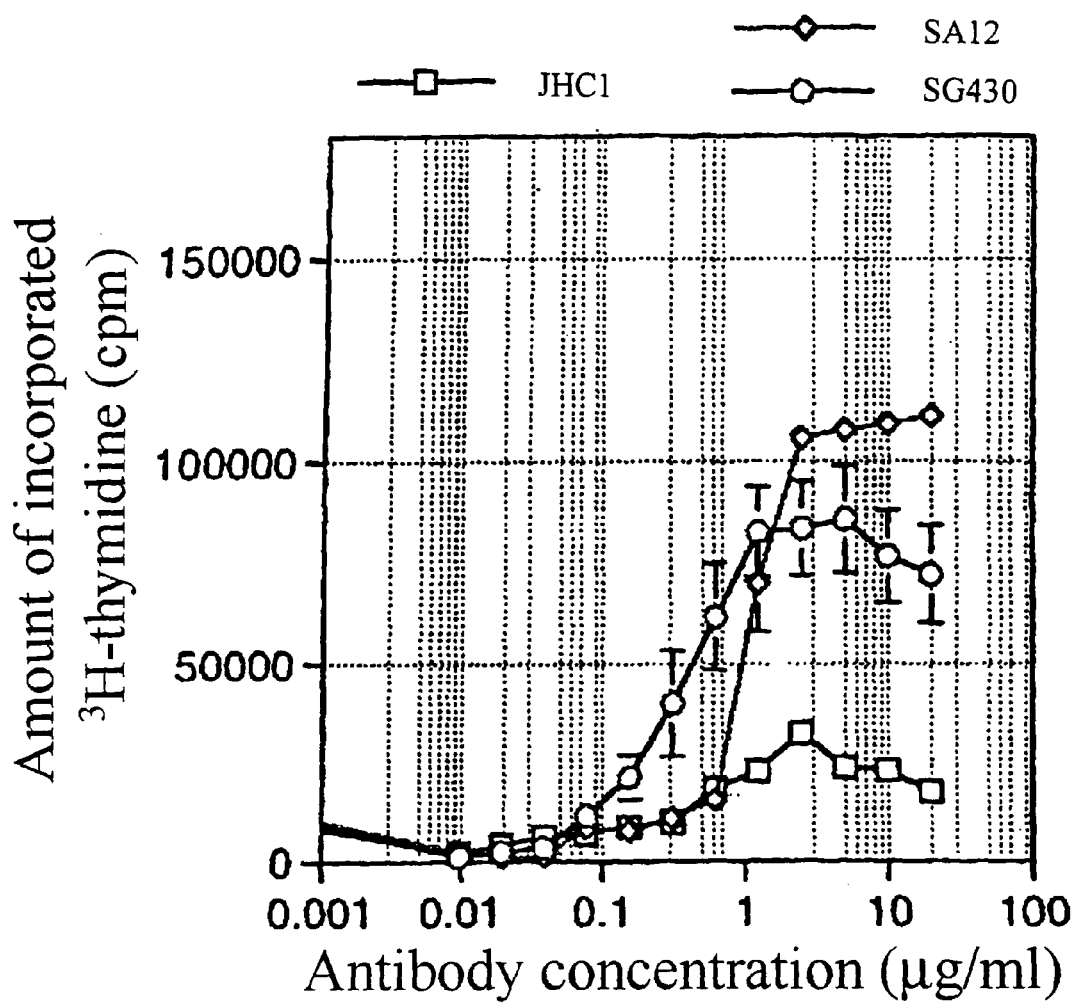

FIG. 30 shows proliferation activity of T cells derived from a normal healthy person "donor E" in the assay for the activity of transducing costimulatory signal by various mouse anti-human AILIM monoclonal antibodies using a microplate coated with anti-human CD3 monoclonal antibody together with mouse anti-human AILIM monoclonal antibody.

The vertical axis indicates the amount of cellular incorporation of [$^3$H]thymidine as an index of the degree of cell proliferation, and the horizontal axis indicates the concentration of mouse anti-human AILIM monoclonal antibody.

In this figure, "JHC1" indicates result of assay in which anti-human CETP monoclonal antibody was used as the negative control, instead of the mouse anti-human AILIM monoclonal antibody.

Figure 31:
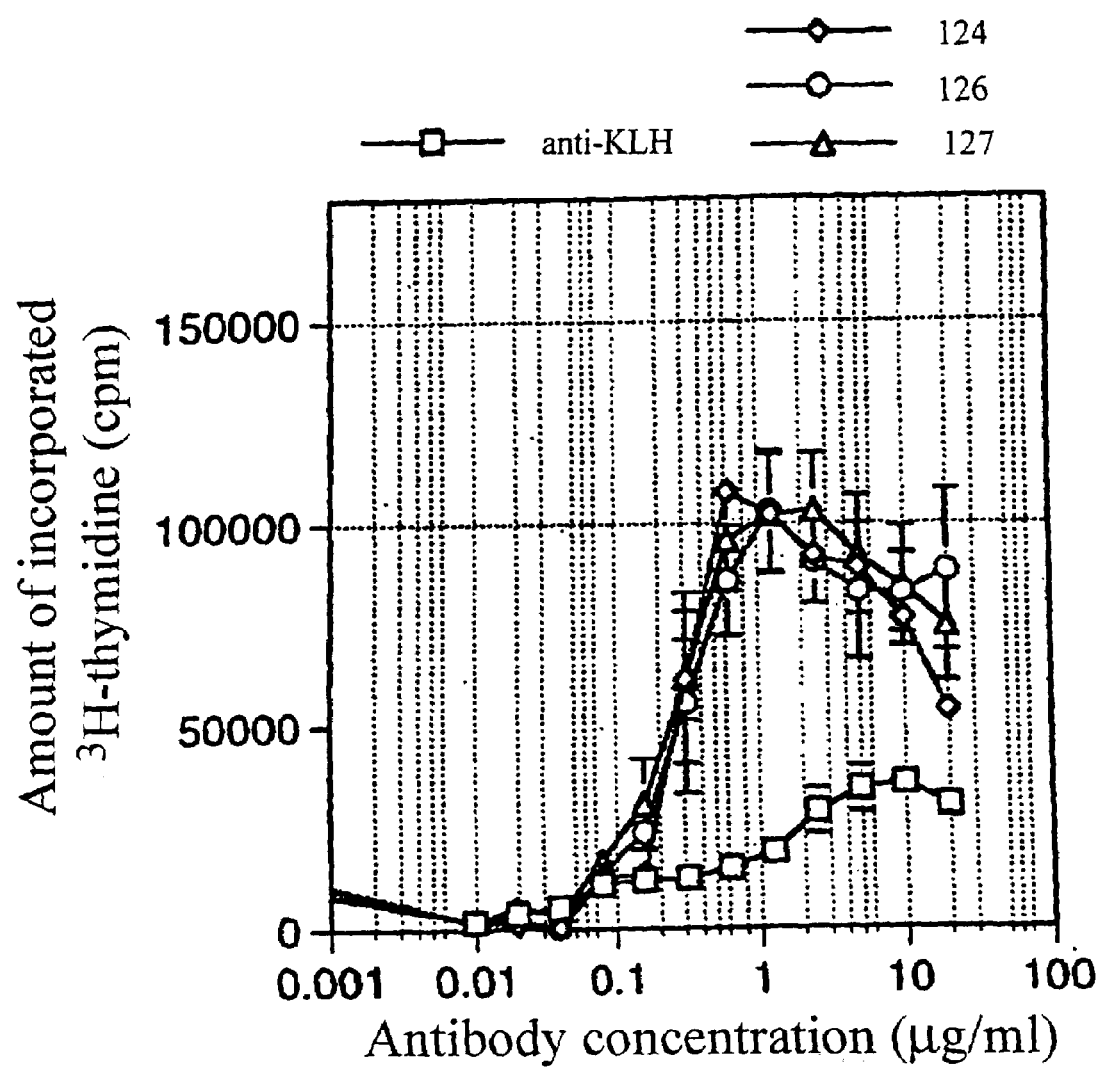

FIG. 31 shows proliferation activity of T cells derived from a normal healthy person "donor E" in the assay for the activity of transducing costimulatory signal by various human anti-human AILIM monoclonal antibodies using a microplate coated with anti-human CD3 monoclonal antibody together with human anti-human AILIM monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"124": human anti-human AILIM monoclonal antibody JMab124.

"126": human anti-human AILIM monoclonal antibody JMab126.

"127": human anti-human AILIM monoclonal antibody JMab127.

Figure 32:
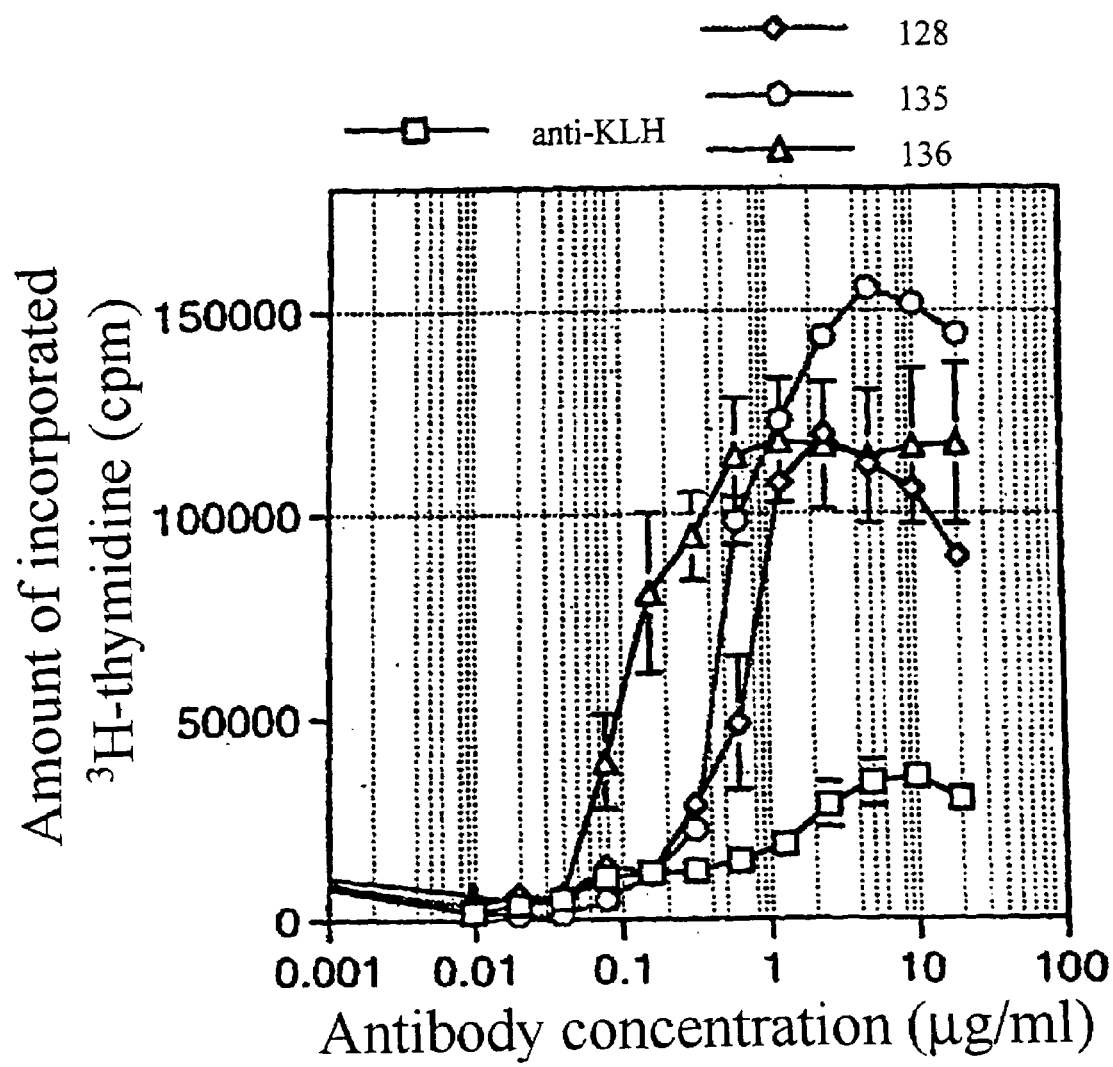

FIG. 32 shows proliferation activity of T cells derived from a normal healthy person "donor E" in the assay for the activity of transducing costimulatory signal by various human anti-human AILIM monoclonal antibodies using a microplate coated with anti-human CD3 monoclonal antibody together with human anti-human AILIM monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"128": human anti-human AILIM monoclonal antibody JMab128.

"135": human anti-human AILIM monoclonal antibody JMab135.

"136": human anti-human AILIM monoclonal antibody JMab136.

Figure 33:
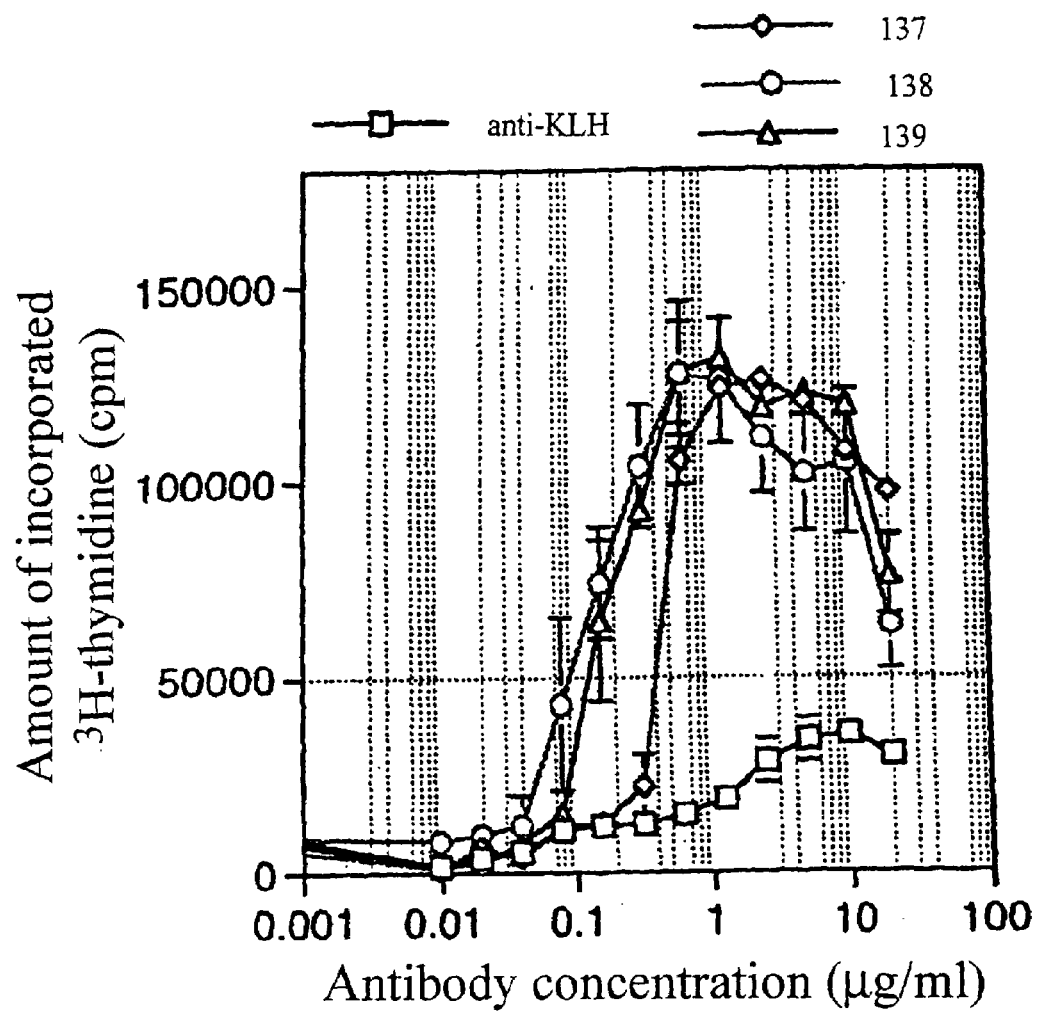

FIG. 33 shows proliferation activity of T cells derived from a normal healthy person "donor E" in the assay for the activity of transducing costimulatory signal by various human anti-human AILIM monoclonal antibodies using a microplate coated with anti-human CD3 monoclonal antibody together with human anti-human AILIM monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"137": human anti-human AILIM monoclonal antibody JMab137.

"138": human anti-human AILIM monoclonal antibody JMab138.

"139": human anti-human AILIM monoclonal antibody JMab139.

Figure 34:
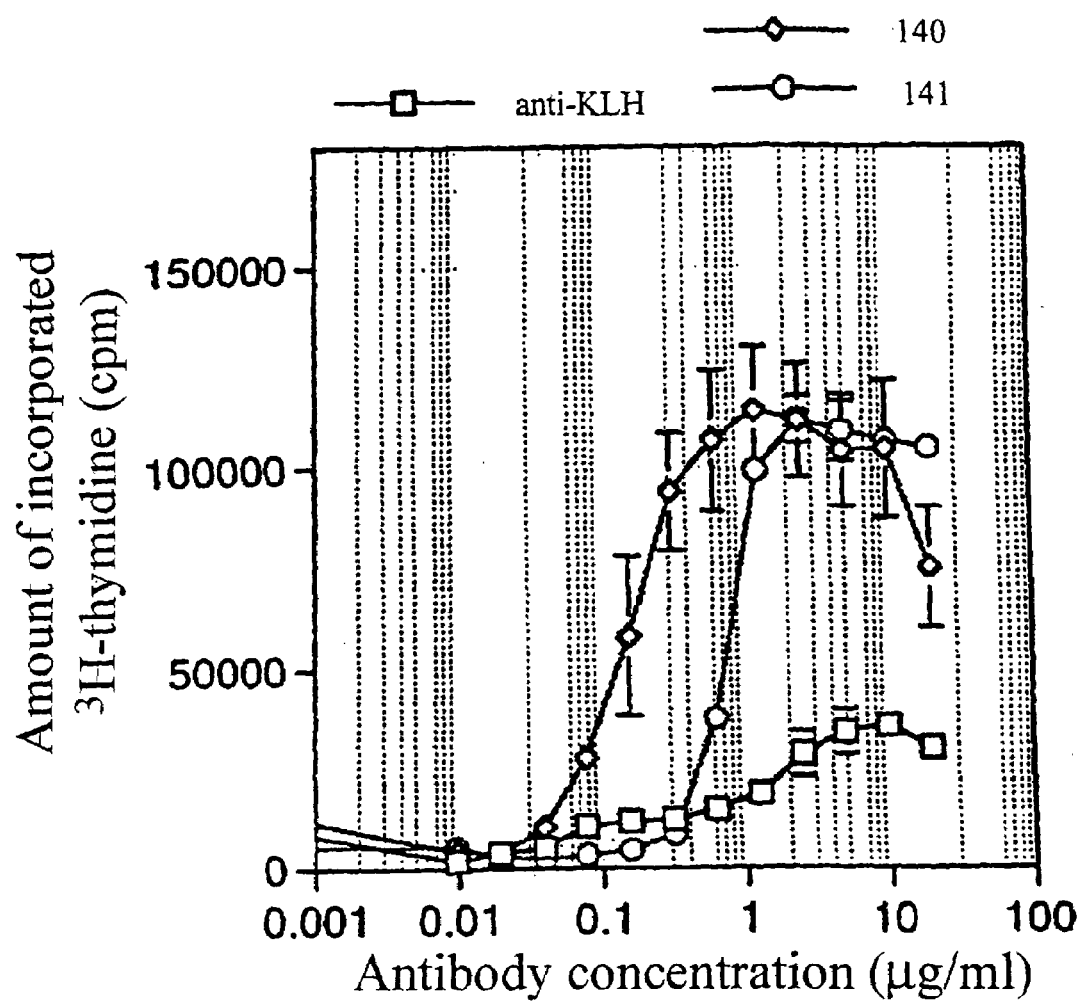

FIG. 34 shows proliferation activity of T cells derived from a normal healthy person "donor E" in the assay for the activity of transducing costimulatory signal by various human anti-human AILIM monoclonal antibodies using a microplate coated with anti-human CD3 monoclonal antibody together with human anti-human AILIM monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"140": human anti-human AILIM monoclonal antibody JMab140.

"141": human anti-human AILIM monoclonal antibody JMab141.

Figure 35:
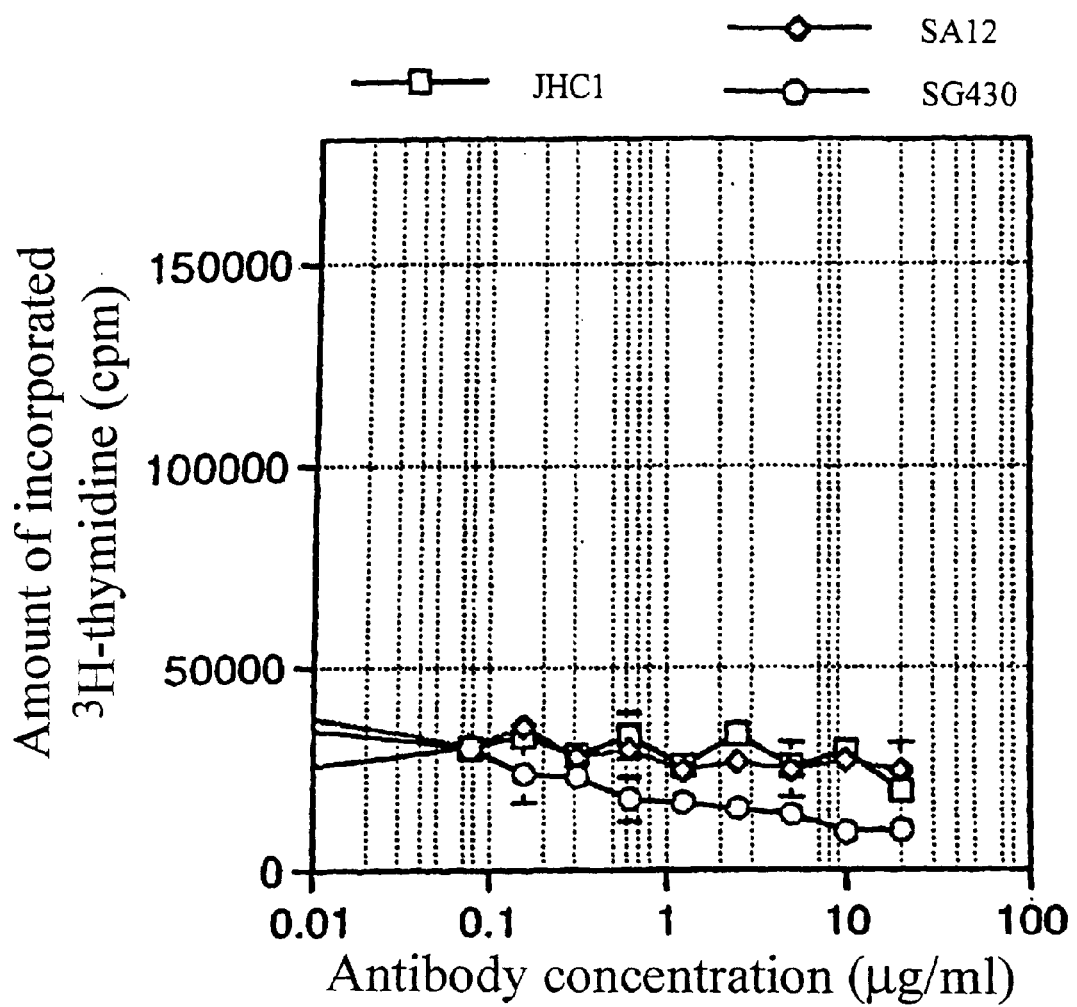

FIG. 35 shows proliferation activity of T cells derived from a normal healthy person "donor D" in the assay for the activity of various mouse anti-human AILIM monoclonal antibodies to transduce costimulatory signal, when a solution of mouse anti-human AILIM monoclonal antibody (in liquid phase) was added alone to a microplate coated with anti-human CD3 monoclonal antibody.

The vertical axis indicates the amount of cellular incorporation of [$^3$H]thymidine as an index of the degree of cell proliferation, and the horizontal axis indicates the concentration of mouse anti-human AILIM monoclonal antibody.

In this figure, "JHC1" indicates result of assay in which anti-human CETP monoclonal antibody was used as the negative control, instead of the mouse anti-human AILIM monoclonal antibody.

Figure 36:
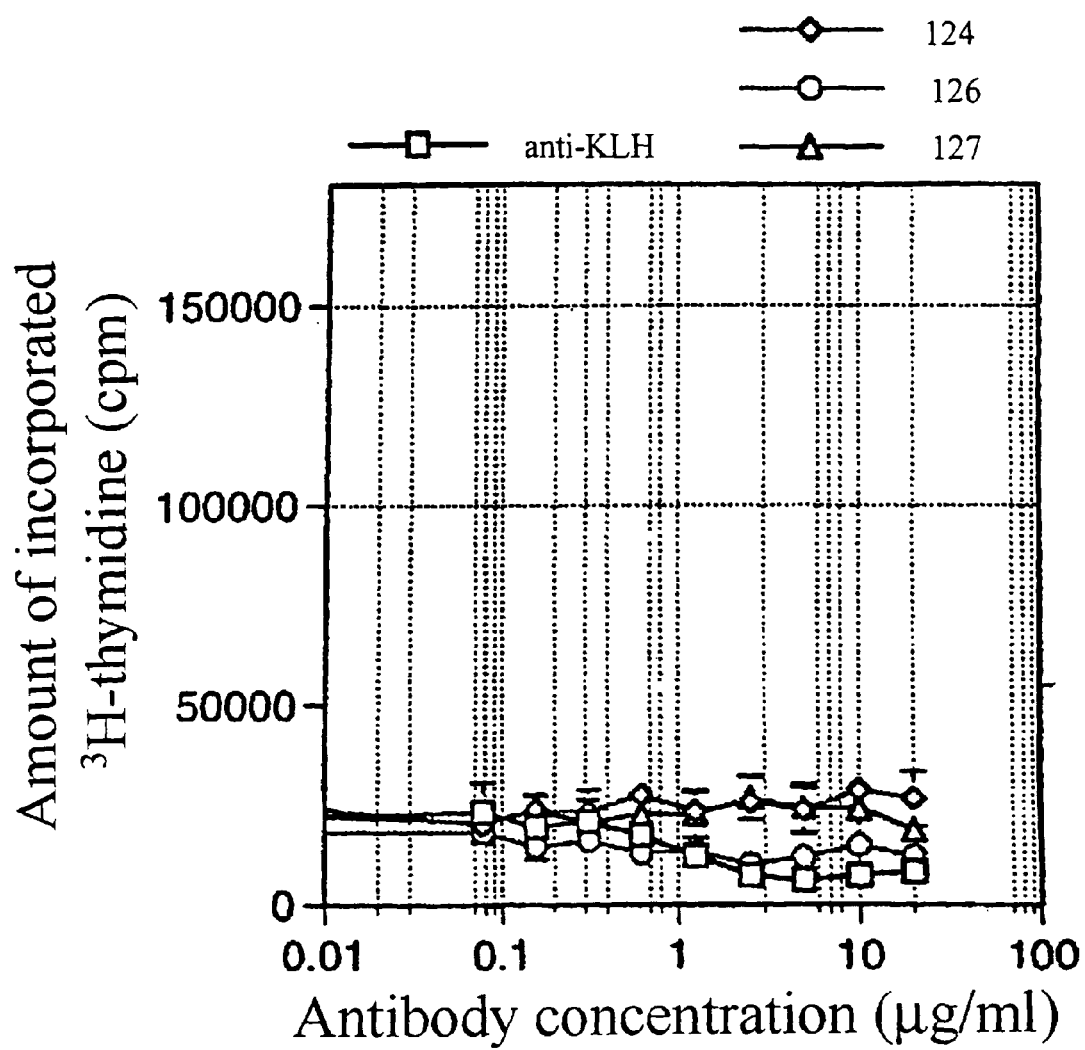

FIG. 36 shows proliferation activity of T cells derived from a normal healthy person "donor D" in the assay for the activity of various human anti-human AILIM monoclonal antibodies to transduce costimulatory signal when a solution of human anti-human AILIM monoclonal antibody (in liquid phase) was added alone to a microplate coated with anti-human CD3 monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"124": human anti-human AILIM monoclonal antibody JMab124.

"125": human anti-human AILIM monoclonal antibody JMab125.

"126": human anti-human AILIM monoclonal antibody JMab126.

Figure 37:
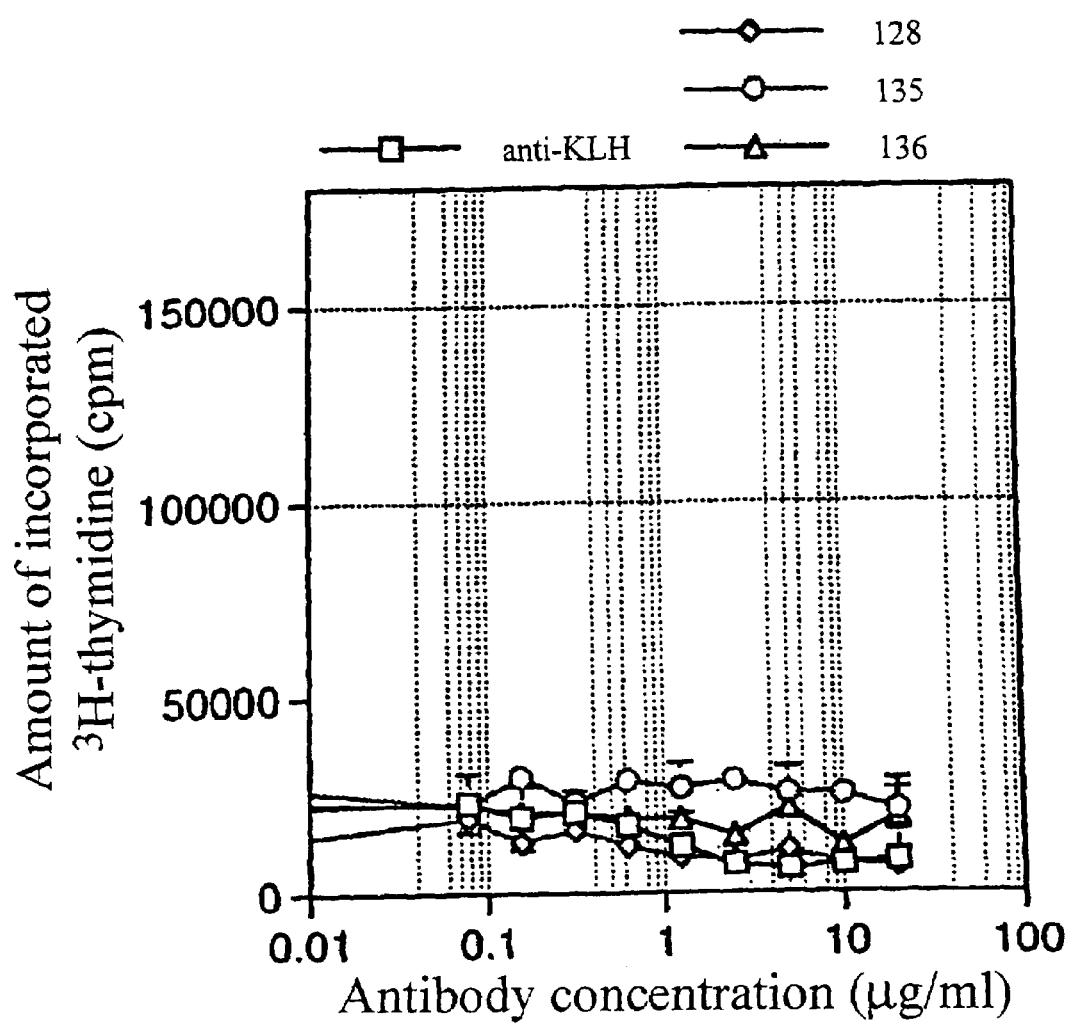

FIG. 37 shows proliferation activity of T cells derived from a normal healthy person "donor D" in the assay for the activity of various human anti-human AILIM monoclonal antibodies to transduce costimulatory signal when a solution of human anti-human AILIM monoclonal antibody (in liquid phase) was added alone to a microplate coated with anti-human CD3 monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"128": human anti-human AILIM monoclonal antibody JMab128.

"135": human anti-human AILIM monoclonal antibody JMab135.

"136": human anti-human AILIM monoclonal antibody JMab136.

Figure 38:
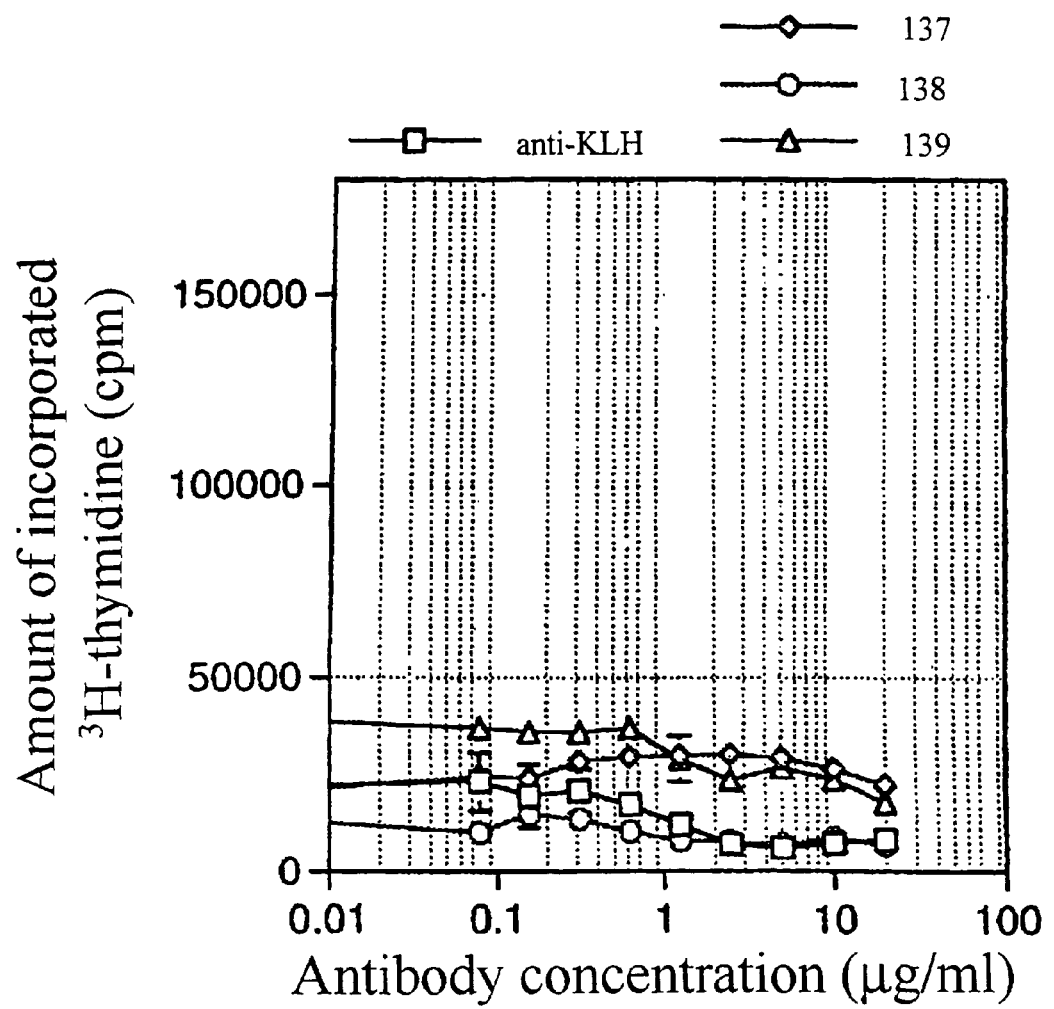

FIG. 38 shows proliferation activity of T cells derived from a normal healthy person "donor D" in the assay for the activity of various human anti-human AILIM monoclonal antibodies to transduce costimulatory signal when a solution of human anti-human AILIM monoclonal antibody (in liquid phase) was added alone to a microplate coated with anti-human CD3 monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"137": human anti-human AILIM monoclonal antibody JMab137.

"138": human anti-human AILIM monoclonal antibody JMab138.

"139": human anti-human AILIM monoclonal antibody JMab139.

Figure 39:
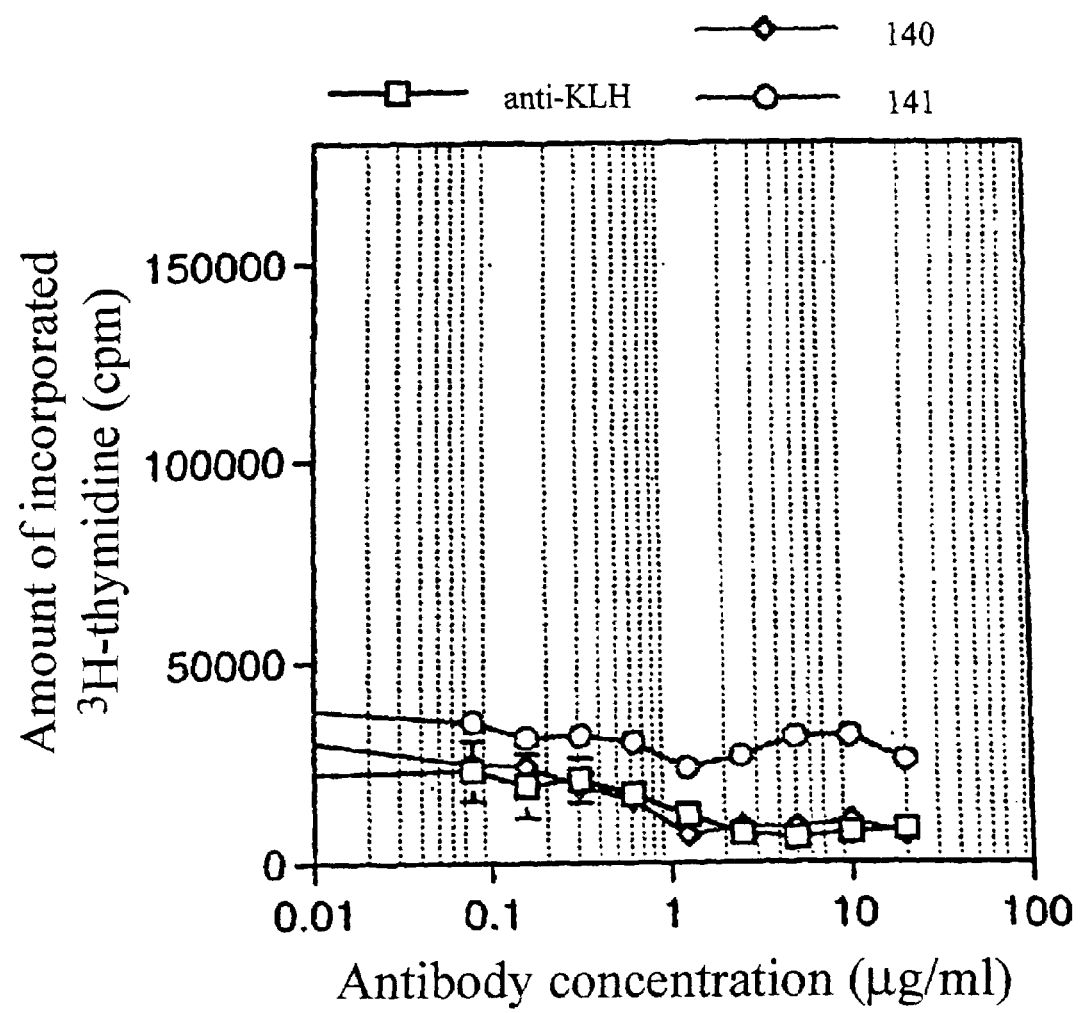

FIG. 39 shows proliferation activity of T cells derived from a normal healthy person "donor D" in the assay for the activity of various human anti-human AILIM monoclonal antibodies to transduce costimulatory signal when a solution of human anti-human AILIM monoclonal antibody (in liquid phase) was added alone to a microplate coated with anti-human CD3 monoclonal antibody.

The vertical axis indicates the amount of cellular incorporation of [$^3$H]thymidine as an index of the degree of cell proliferation, and the horizontal axis indicates the concentration of human anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"140": human anti-human AILIM monoclonal antibody JMab140.

"141": human anti-human AILIM monoclonal antibody JMab141.

Figure 40:
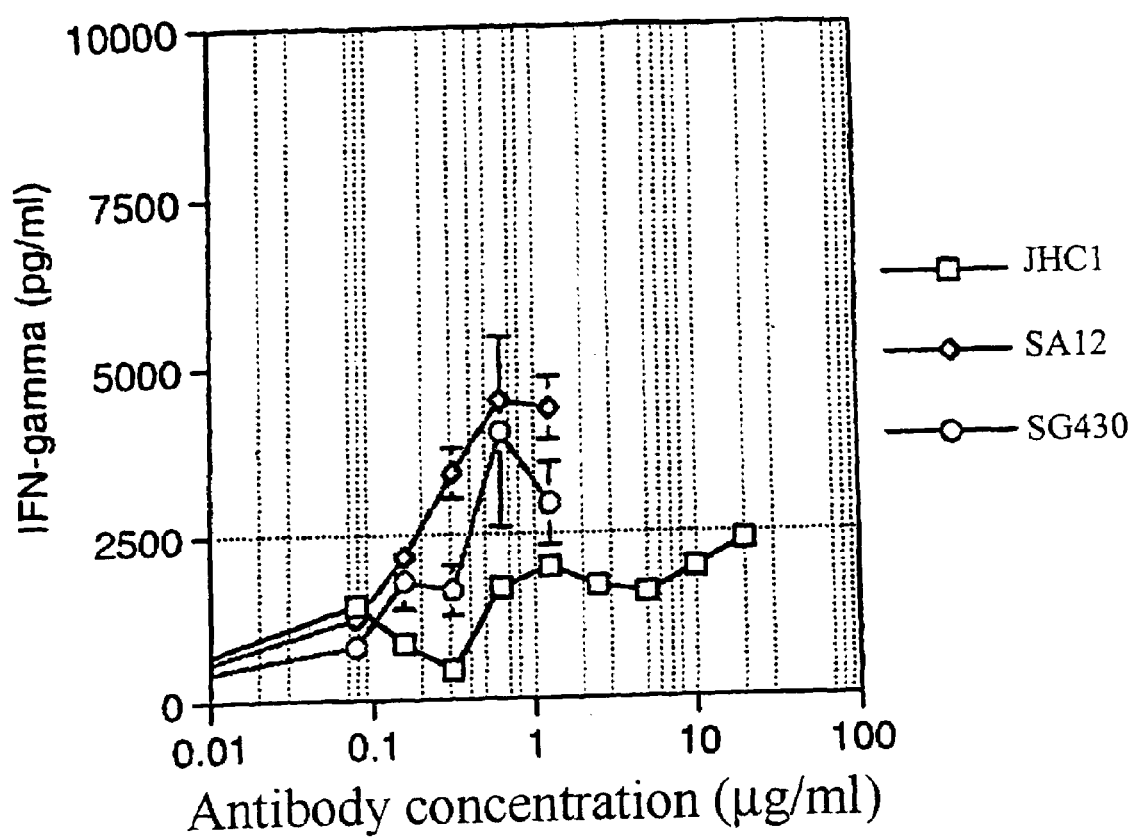

FIG. 40 shows the amount of IFN-γ produced in the culture supernatant of T cells derived from a normal healthy person "donor B," which were cultured in a microplate coated with mouse anti-human AILIM monoclonal antibody together with anti-human CD3 monoclonal antibody.

The vertical axis indicates the concentration of IFN-g, and the horizontal axis indicates the concentration of the mouse anti-human AILIM monoclonal antibody.

In this figure, "JHC1" indicates result of assay in which anti-human CETP monoclonal antibody was used as the negative control, instead of the mouse anti-human AILIM monoclonal antibody.

Figure 41:
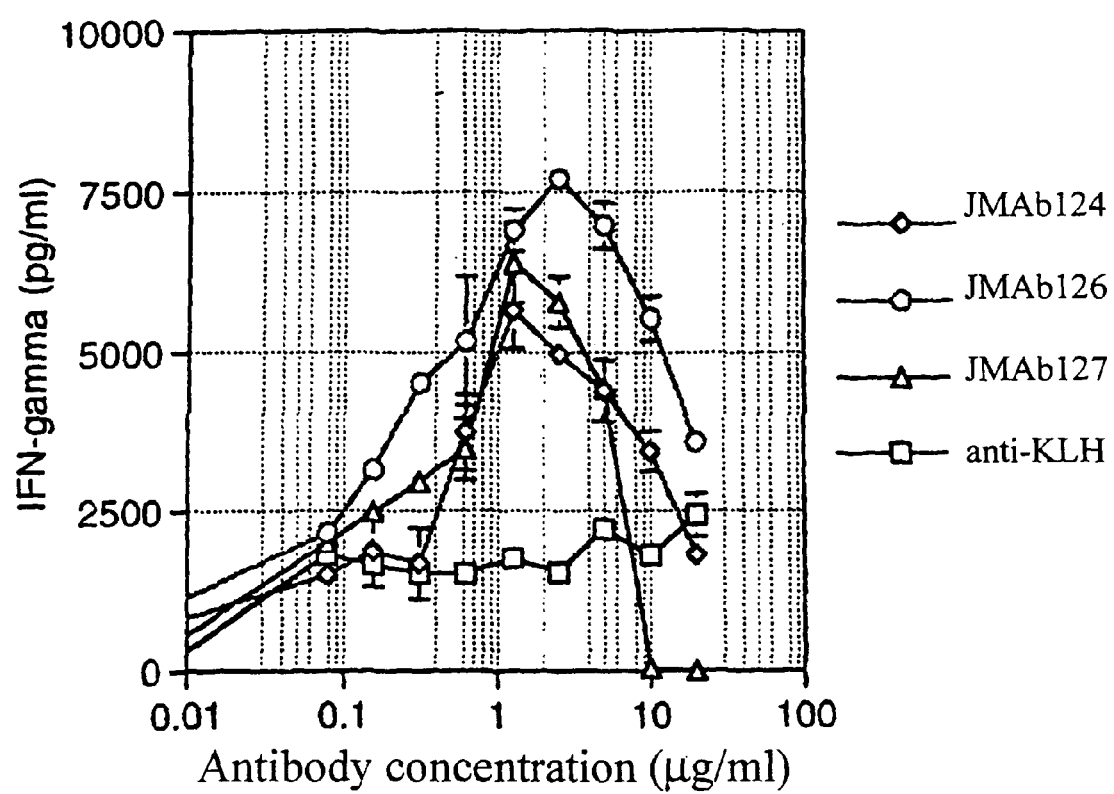

FIG. 41 shows the amount of IFN-g produced in the culture supernatant of T cells derived from a normal healthy person "donor B," which were cultured in a microplate coated with human anti-human AILIM monoclonal antibody together with anti-human CD3 monoclonal antibody.

The vertical axis indicates the concentration of IFN-γ, and the horizontal axis indicates the concentration of the mouse anti-human AILIM monoclonal antibody.

In this figure, "anti-KLH" indicates result of assay in which human anti-KLH monoclonal antibody was used as the negative control, instead of the human anti-human AILIM monoclonal antibody.

Figure 42:
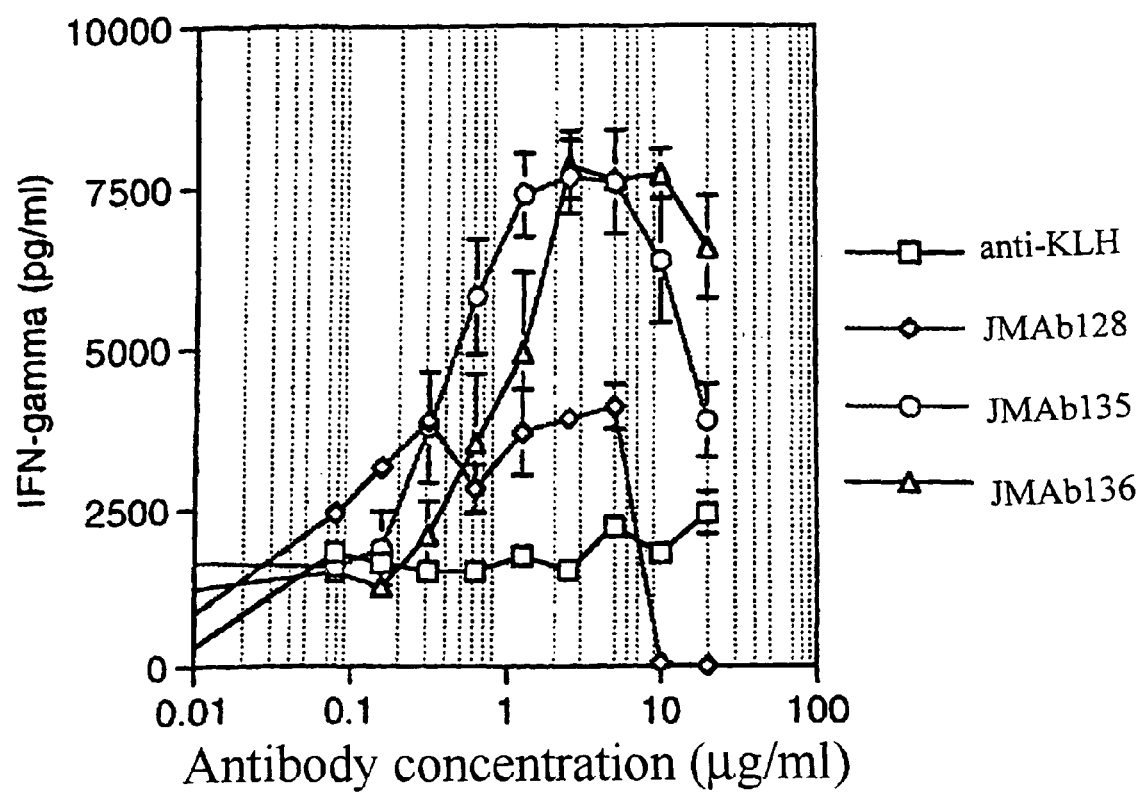

FIG. 42 shows the amount of IFN-γ produced in the culture supernatant of T cells derived from a normal healthy person "donor B," which were cultured in a microplate coated with human anti-human AILIM monoclonal antibody together with anti-human CD3 monoclonal antibody.

The vertical axis indicates the concentration of IFN-γ, and the horizontal axis indicates the concentration of the mouse anti-human AILIM monoclonal antibody.

In this figure, "anti-KLH" indicates result of assay in which human anti-KLH monoclonal antibody was used as the negative control, instead of the human anti-human AILIM monoclonal antibody.

Figure 43:
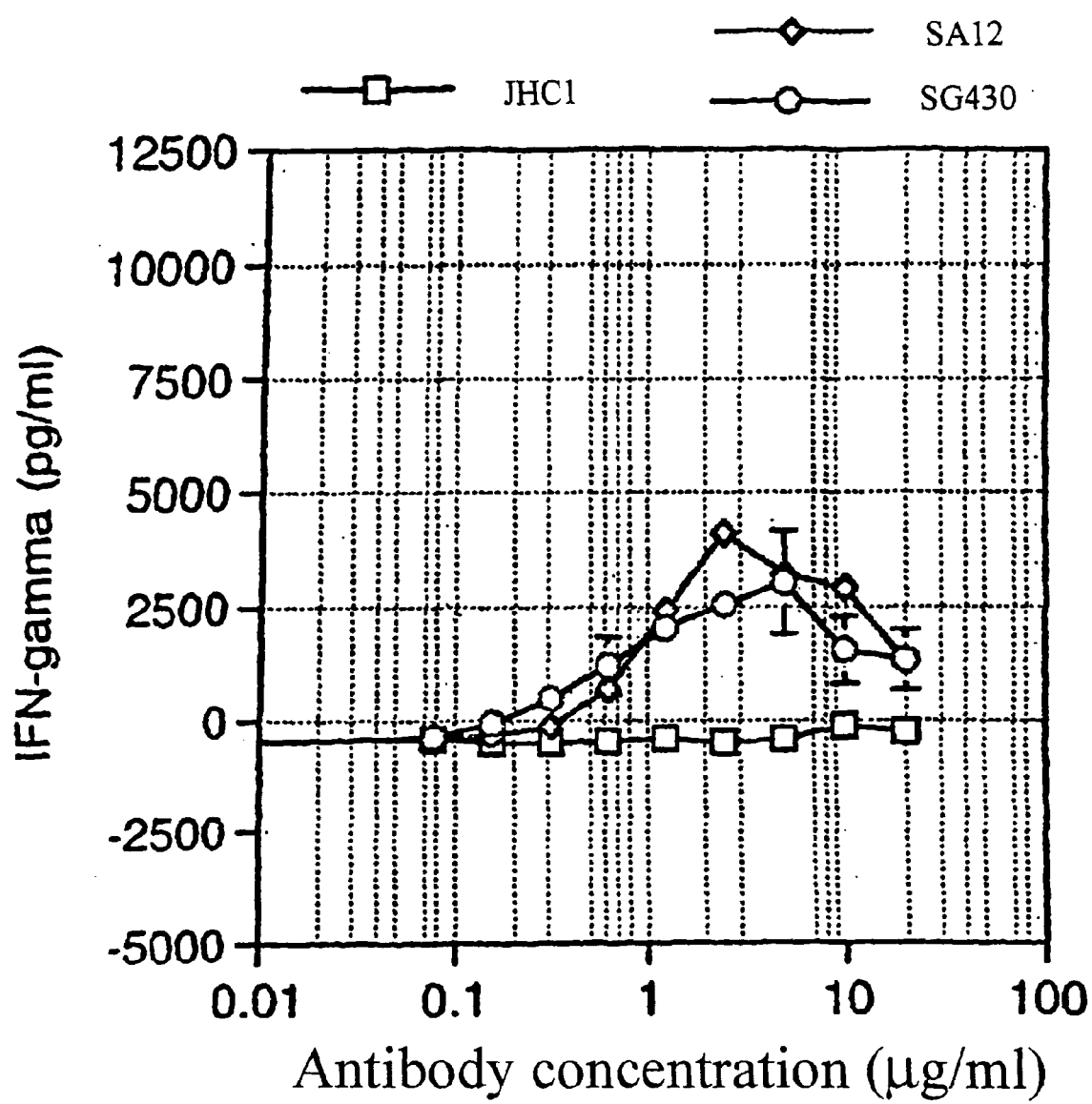

FIG. 43 shows the amount of IFN-γ produced in the culture supernatant of T cells derived from a normal healthy person "donor C," which were cultured in a microplate coated with mouse anti-human AILIM monoclonal antibody together with anti-human CD3 monoclonal antibody.

The vertical axis indicates the concentration of IFN-γ, and the horizontal axis indicates the concentration of the mouse anti-human AILIM monoclonal antibody.

In this figure, "JHC1" indicates result of assay in which anti-human CETP monoclonal antibody was used as the negative control, instead of the mouse anti-human AILIM monoclonal antibody.

Figure 44:
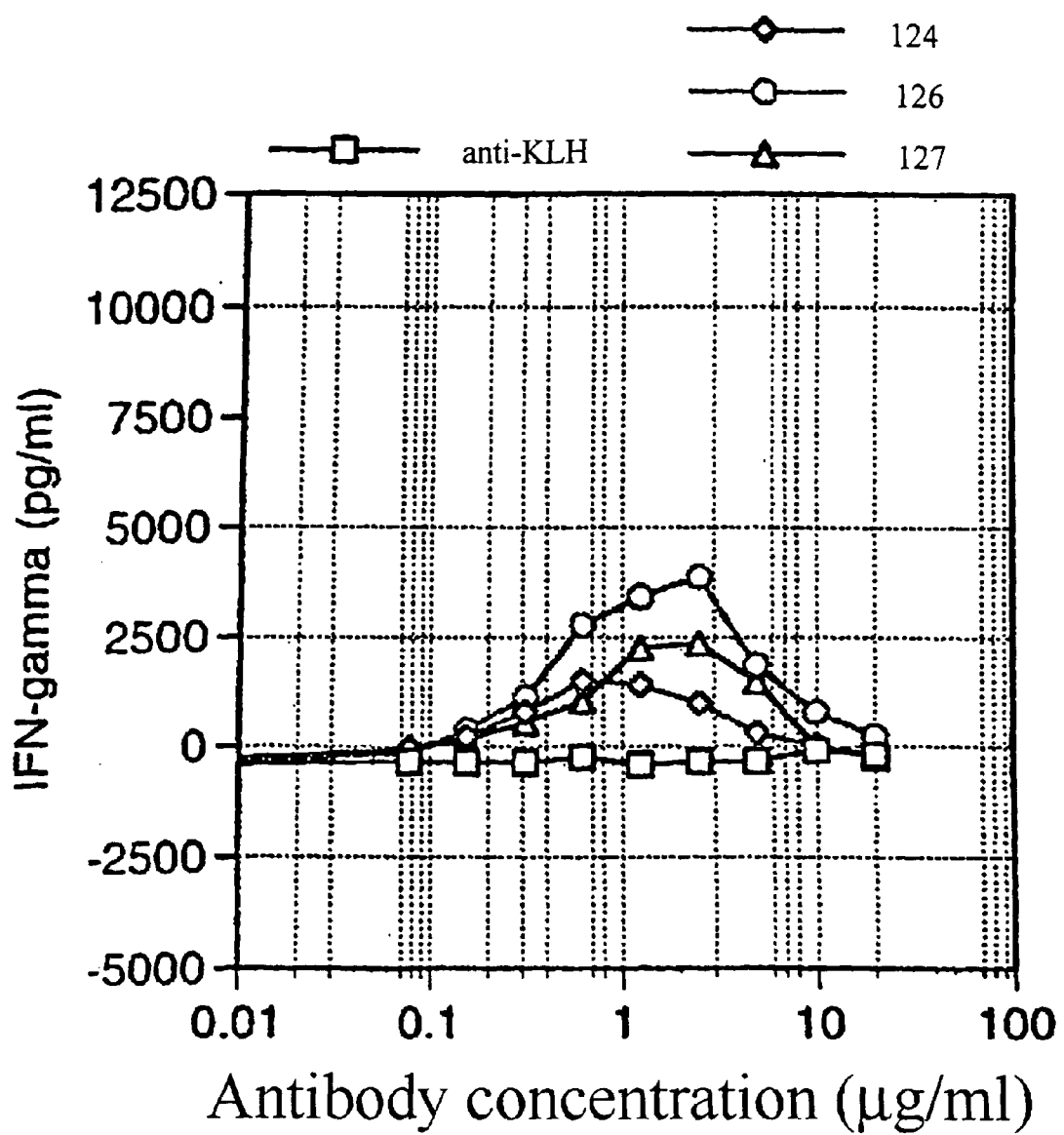

FIG. 44 shows the amount of IFN-γ produced in the culture supernatant of T cells derived from a normal healthy person "donor C," which were cultured in a microplate coated with human anti-human AILIM monoclonal antibody together with anti-human CD3 monoclonal antibody.

The vertical axis indicates the concentration of IFN-γ, and the horizontal axis indicates the concentration of the mouse anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"124": human anti-human AILIM monoclonal antibody JMab124.

"125": human anti-human AILIM monoclonal antibody JMab125.

"126": human anti-human AILIM monoclonal antibody JMab126.

Figure 45:
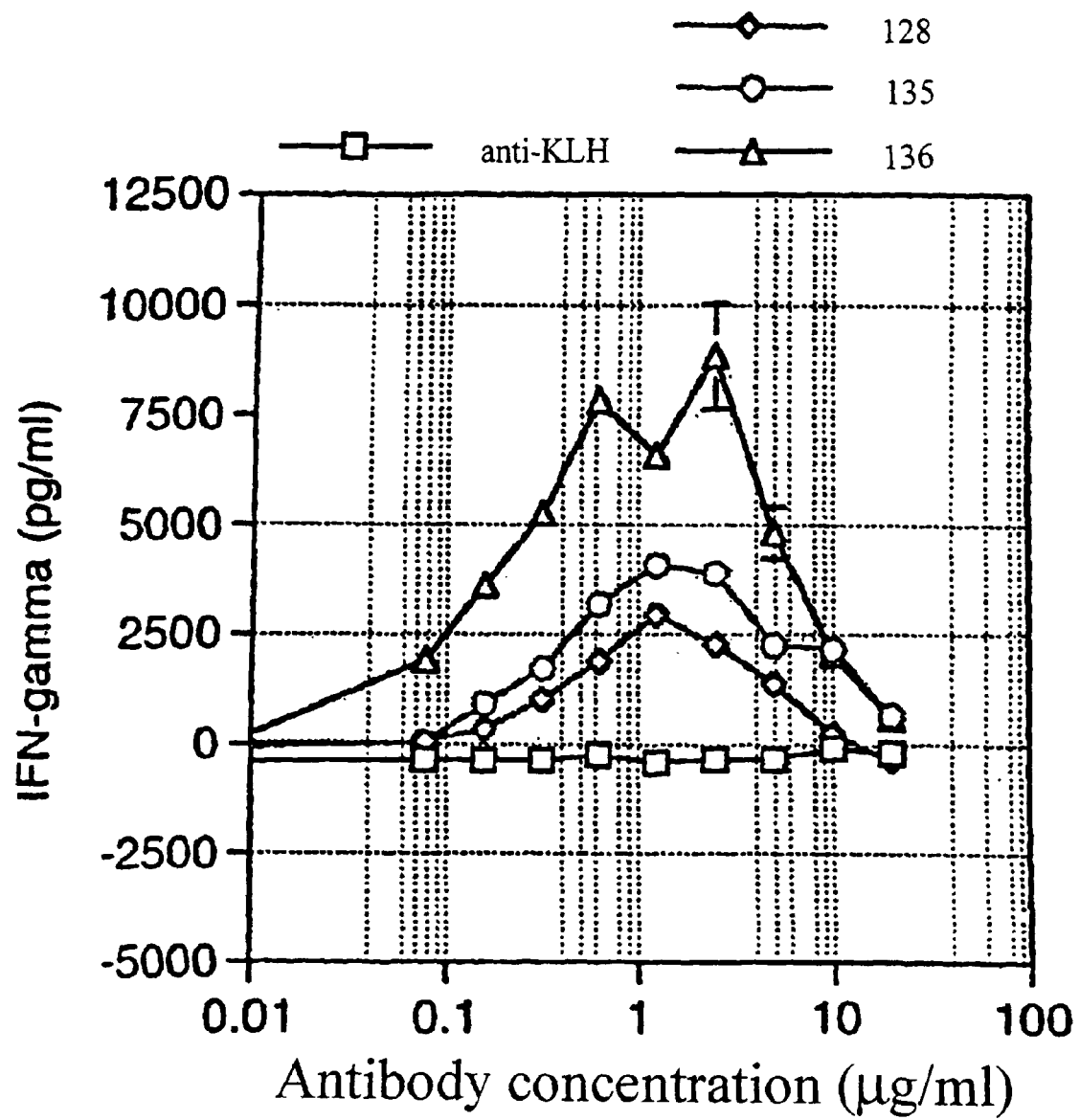

FIG. 45 shows the amount of IFN-γ produced in the culture supernatant of T cells derived from a normal healthy person "donor C," which were cultured in a microplate coated with human anti-human AILIM monoclonal antibody together with anti-human CD3 monoclonal antibody.

The vertical axis indicates the concentration of IFN-γ, and the horizontal axis indicates the concentration of the mouse anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"128": human anti-human AILIM monoclonal antibody JMab128.

"135": human anti-human AILIM monoclonal antibody JMab135.

"136": human anti-human AILIM monoclonal antibody JMab136.

Figure 46:
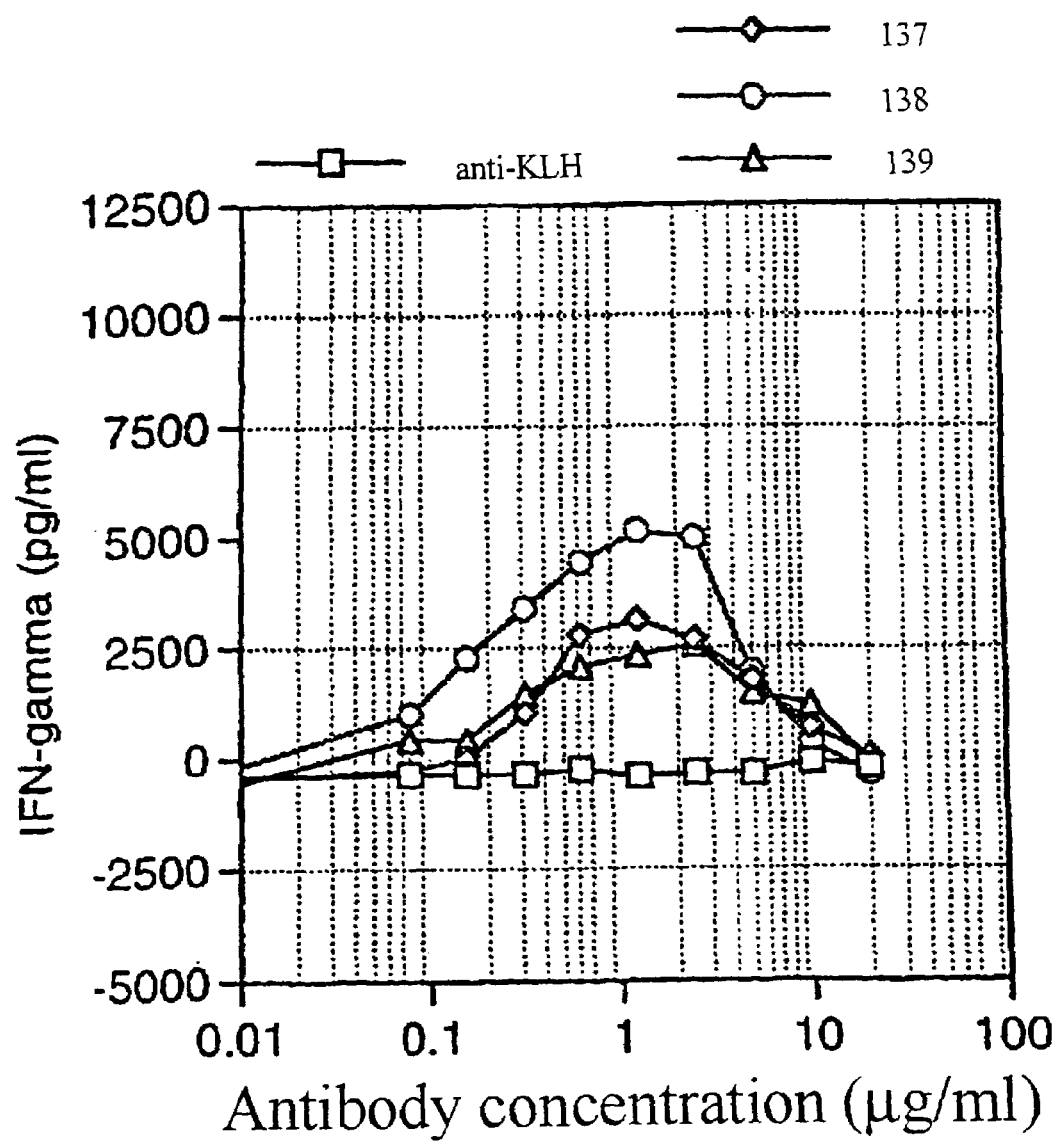

FIG. 46 shows the amount of IFN-γ produced in the culture supernatant of T cells derived from a normal healthy person "donor C," which were cultured in a microplate coated with human anti-human AILIM monoclonal antibody together with anti-human CD3 monoclonal antibody.

The vertical axis indicates the concentration of IFN-γ, and the horizontal axis indicates the concentration of the mouse anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"137": human anti-human AILIM monoclonal antibody JMab137.

"138": human anti-human AILIM monoclonal antibody JMab138.

"139": human anti-human AILIM monoclonal antibody JMab139.

Figure 47:
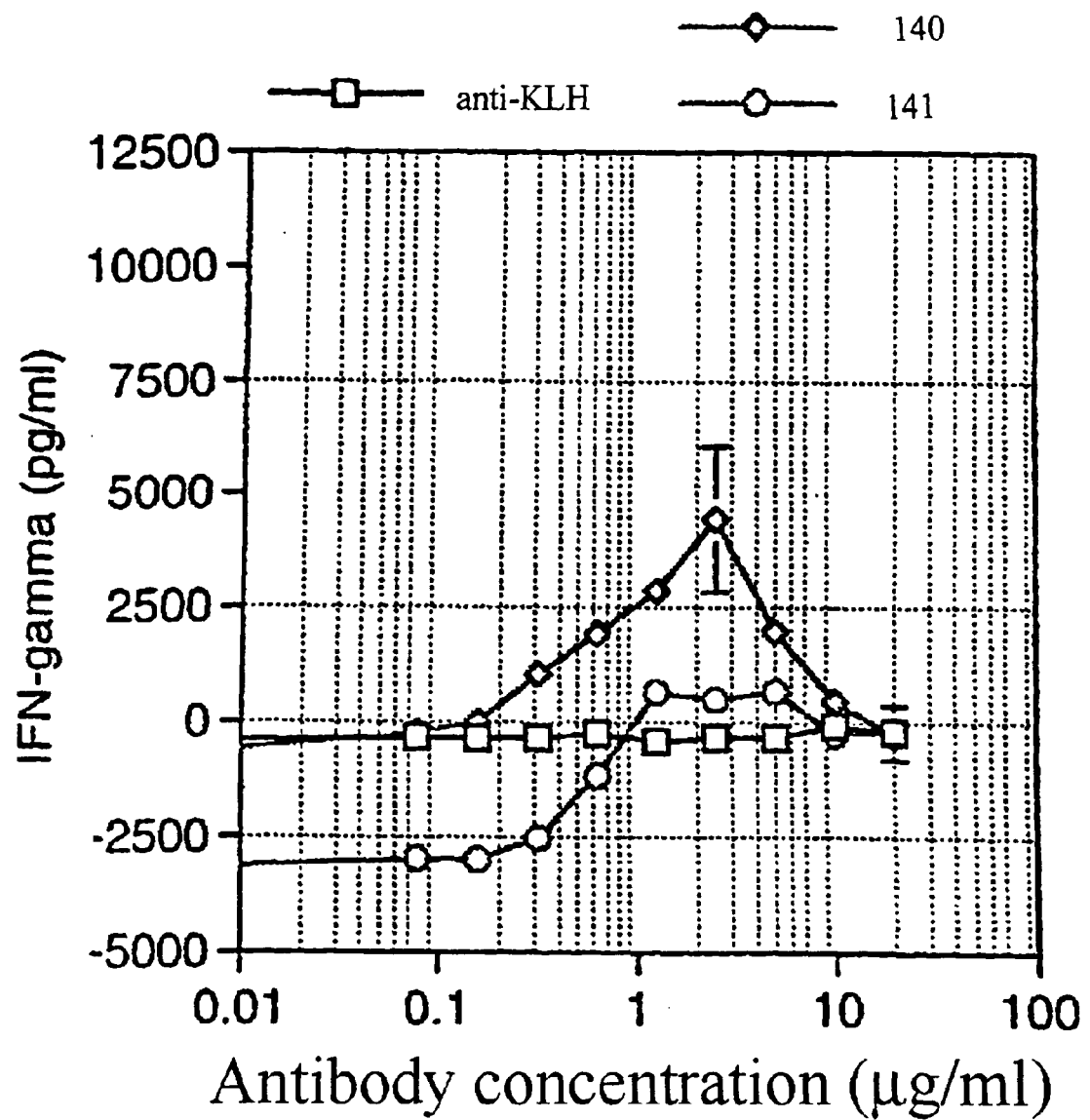

FIG. 47 shows the amount of IFN-γ produced in the culture supernatant of T cells derived from a normal healthy person "donor C," which were cultured in a microplate coated with human anti-human AILIM monoclonal antibody together with anti-human CD3 monoclonal antibody.

The vertical axis indicates the concentration of IFN-γ, and the horizontal axis indicates the concentration of the mouse anti-human AILIM monoclonal antibody.

In this figure, "anti-KLH" indicates result of assay in which human anti-KLH monoclonal antibody was used as the negative control, instead of the human anti-human AILIM monoclonal antibody.

Other notations are as follows:

"140": human anti-human AILIM monoclonal antibody JMab140.

"141": human anti-human AILIM monoclonal antibody JMab141.

Figure 48:
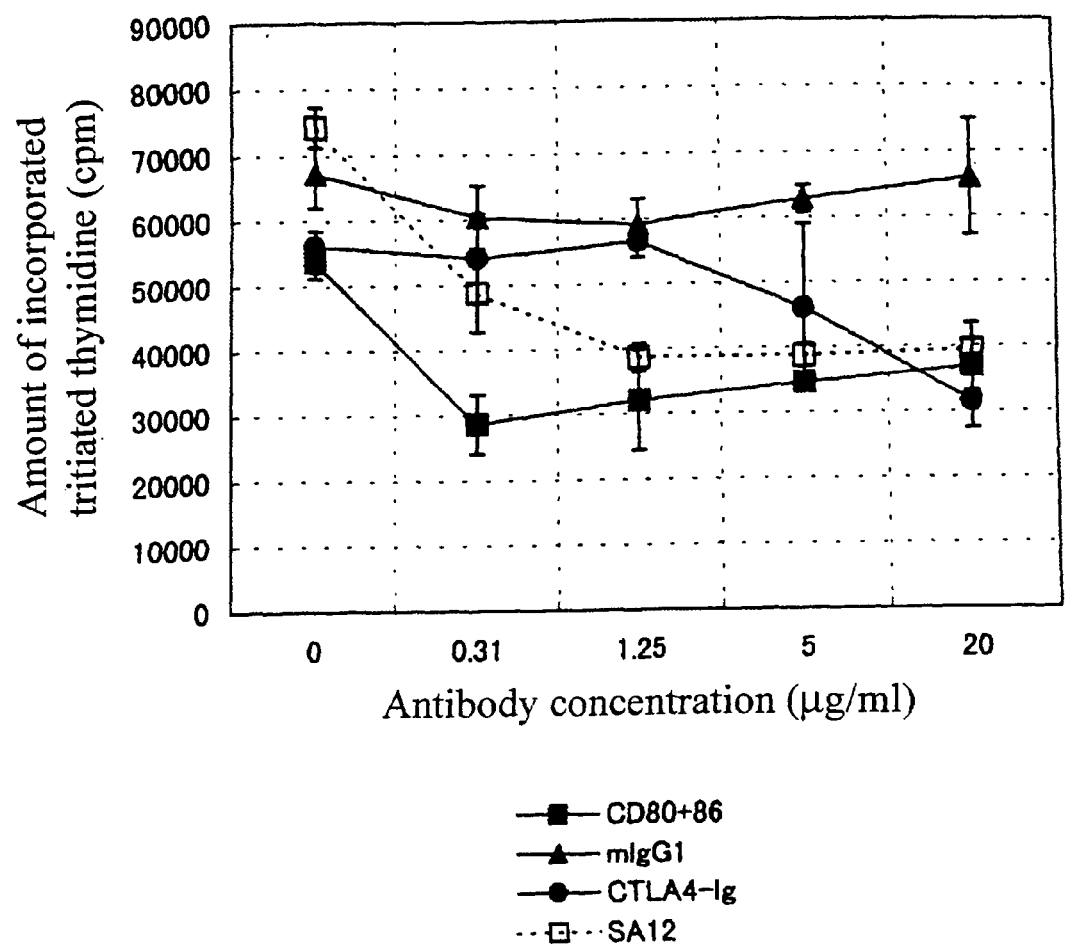

FIG. 48 shows the inhibitory effect on T cell proliferation in the case of culturing T cells from a normal healthy person "donor A", with PBMC of a normal healthy person "donor D" by various test samples in the proliferation test of the T cells through the mixed lymphocyte reactions (MLR).

The vertical axis indicates the amount of incorporation of [³H]thymidine as an index showing a level of cell proliferation, and the horizontal axis shows the concentration of the test samples.

Figure 49:
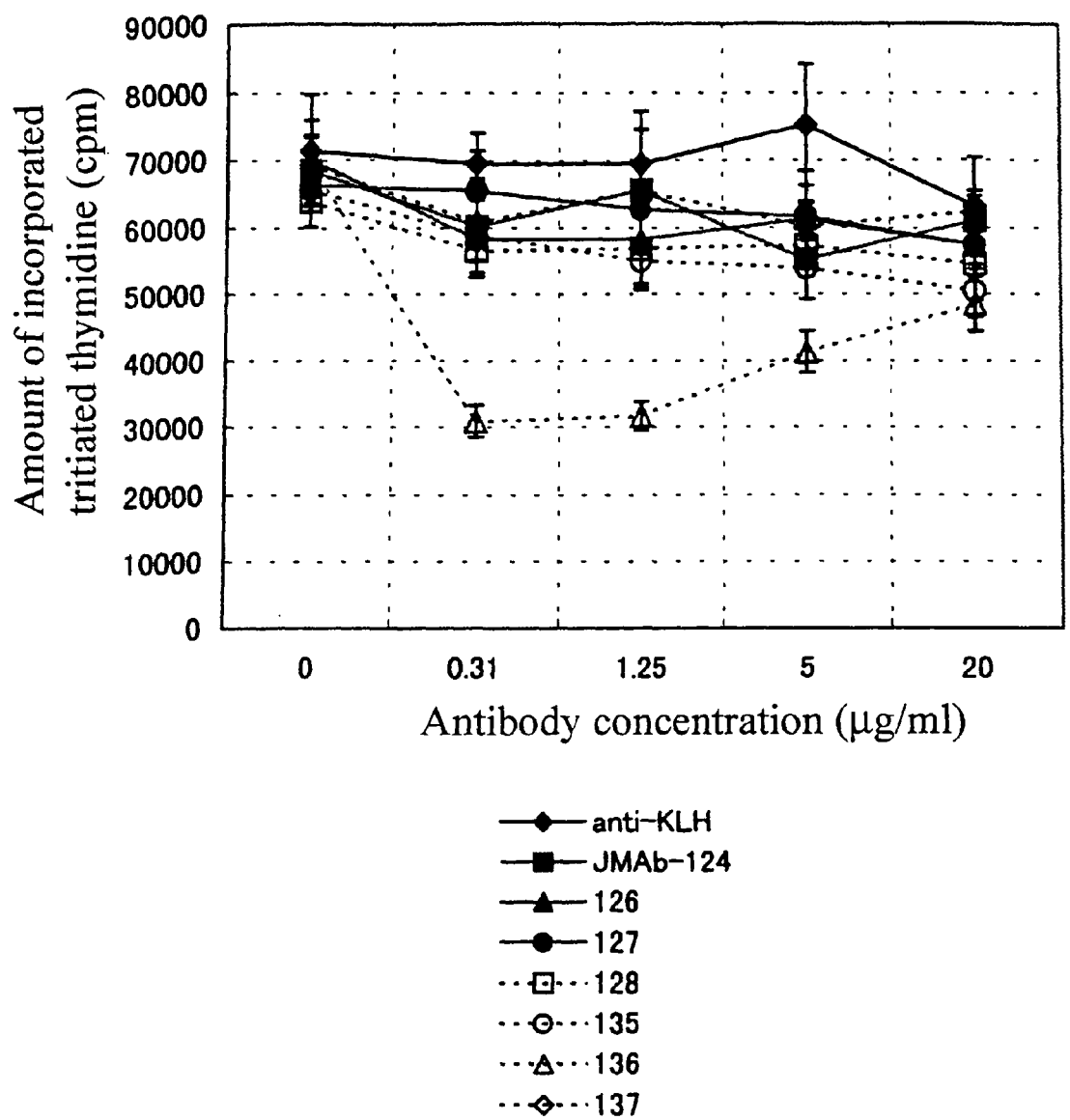

Each description in the figures shows the following.
"CD80+86": The mixture of anti-CD80 antibody and anti-CD86 antibody
"mIgG1": Anti-human CD34/IgG1 mouse monoclonal antibody
"CTLA4-Ig": Human CTLA4-IgFc chimeric molecule
"SA12": Anti-human AILIM mouse monoclonal antibody FIG. 49 shows the inhibitory effect on T cell proliferation in the case of culturing T cells from a normal healthy person "donor A", with PBMC of a normal healthy person "donor D" by various human anti-human AILIM monoclonal antibodies in the proliferation test of the T cells through the mixed lymphocyte reactions (MLR).

The vertical axis indicates the amount of incorporation of [³H] thymidine as an index showing a level of cell proliferation, and the horizontal axis shows the concentration of the test samples.

Other notations are as follows:
"anti-KLH": human anti-KLH monoclonal antibody as a negative control.
"JMab-124": human anti-human AILIM monoclonal antibody JMab124.
"126": human anti-human AILIM monoclonal antibody JMab126.
"127": human anti-human AILIM monoclonal antibody JMab127.
"128": human anti-human AILIM monoclonal antibody JMab128.
"135": human anti-human AILIM monoclonal antibody JMab135.
"136": human anti-human AILIM monoclonal antibody JMab136.
"137": human anti-human AILIM monoclonal antibody JMab137.

Figure 50:
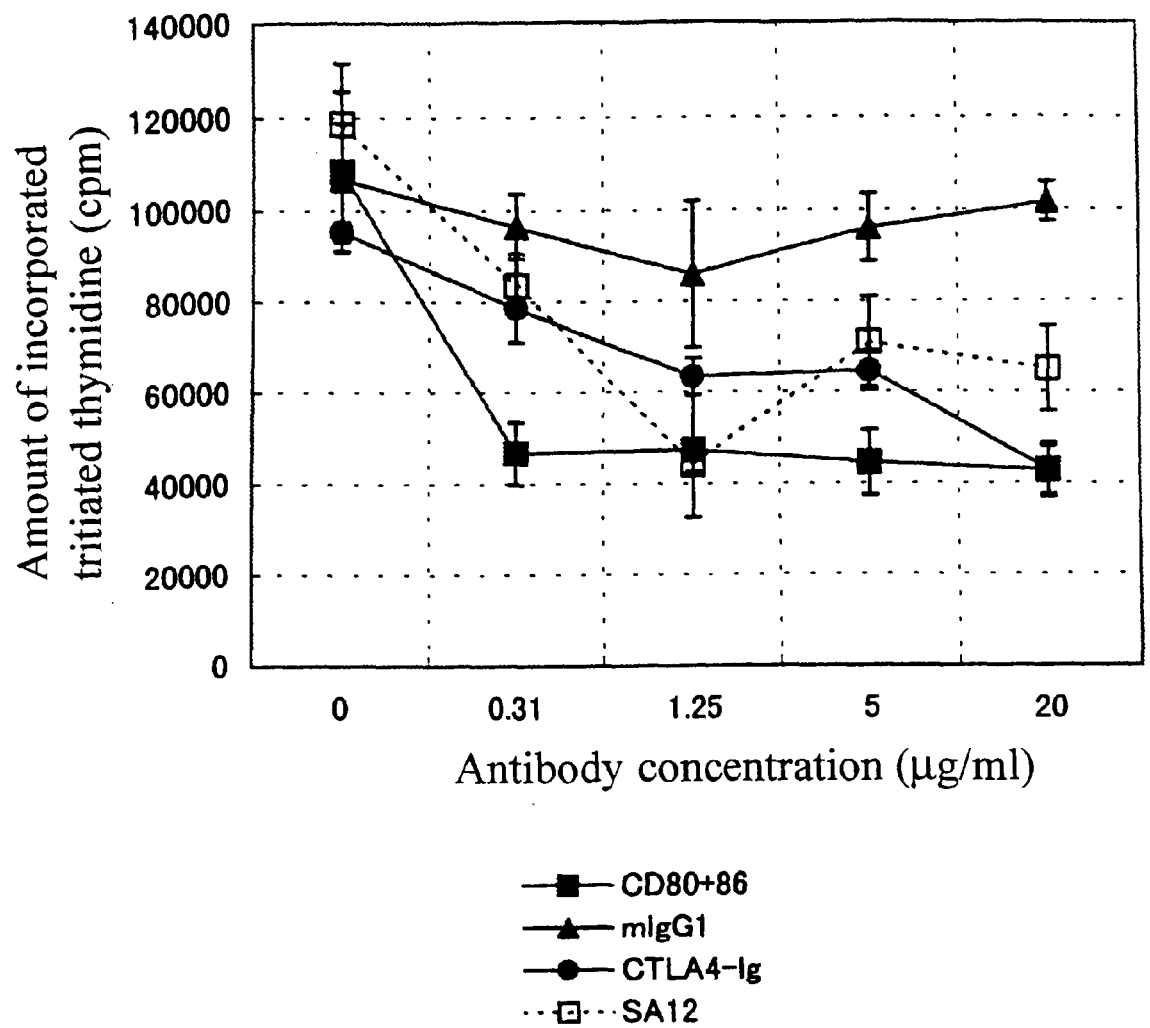

FIG. 50 shows the inhibitory effect on T cell proliferation in the case of culturing T cells from a normal healthy person "donor D", with PBMC of a normal healthy person "donor B" by various test samples in the proliferation test of the T cells through the mixed lymphocyte reactions (MLR).

The vertical axis indicates the amount of incorporation of [³H]thymidine as an index showing a level of cell proliferation, and the horizontal axis shows the concentration of the test samples.

Figure 51:
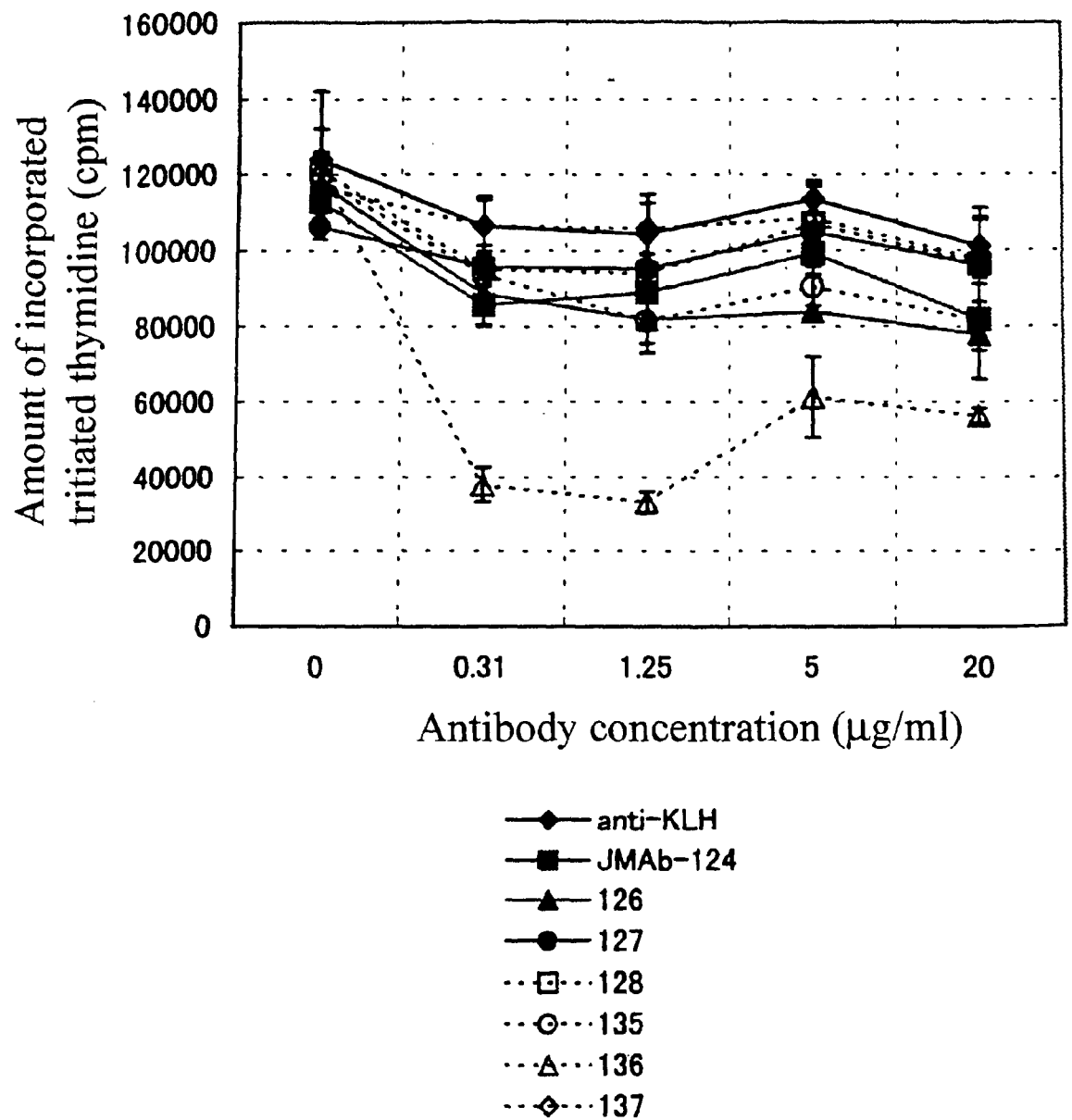

Each description in the figures shows the following.
"CD80+86": The mixture of anti-CD80 antibody and anti-CD86 antibody
"mIgG1": Anti-human CD34/IgG1 mouse monoclonal antibody
"CTLA4-Ig": Human CTLA4-IgFc chimeric molecule
"SA12": Anti-human AILIM mouse monoclonal antibody FIG. 51 shows the inhibitory effect on T cell proliferation in the case of culturing T cells from a normal healthy person "donor D", with PBMC of a normal healthy person "donor B" by various human anti-human AILIM monoclonal antibodies in the proliferation test of the T cells through the mixed lymphocyte reactions (MLR).

The vertical axis indicates the amount of incorporation of [³H]thymidine as an index showing a level of cell proliferation, and the horizontal axis shows the concentration of the test samples.

Other notations are as follows:
"anti-KLH": human anti-KLH monoclonal antibody as a negative control.
"JMab-124": human anti-human AILIM monoclonal antibody JMab124.
"126": human anti-human AILIM monoclonal antibody JMab126.
"127": human anti-human AILIM monoclonal antibody JMab127.
"128": human anti-human AILIM monoclonal antibody JMab128.
"135": human anti-human AILIM monoclonal antibody JMab135.
"136": human anti-human AILIM monoclonal antibody JMab136.
"137": human anti-human AILIM monoclonal antibody JMab137.

Figure 52:
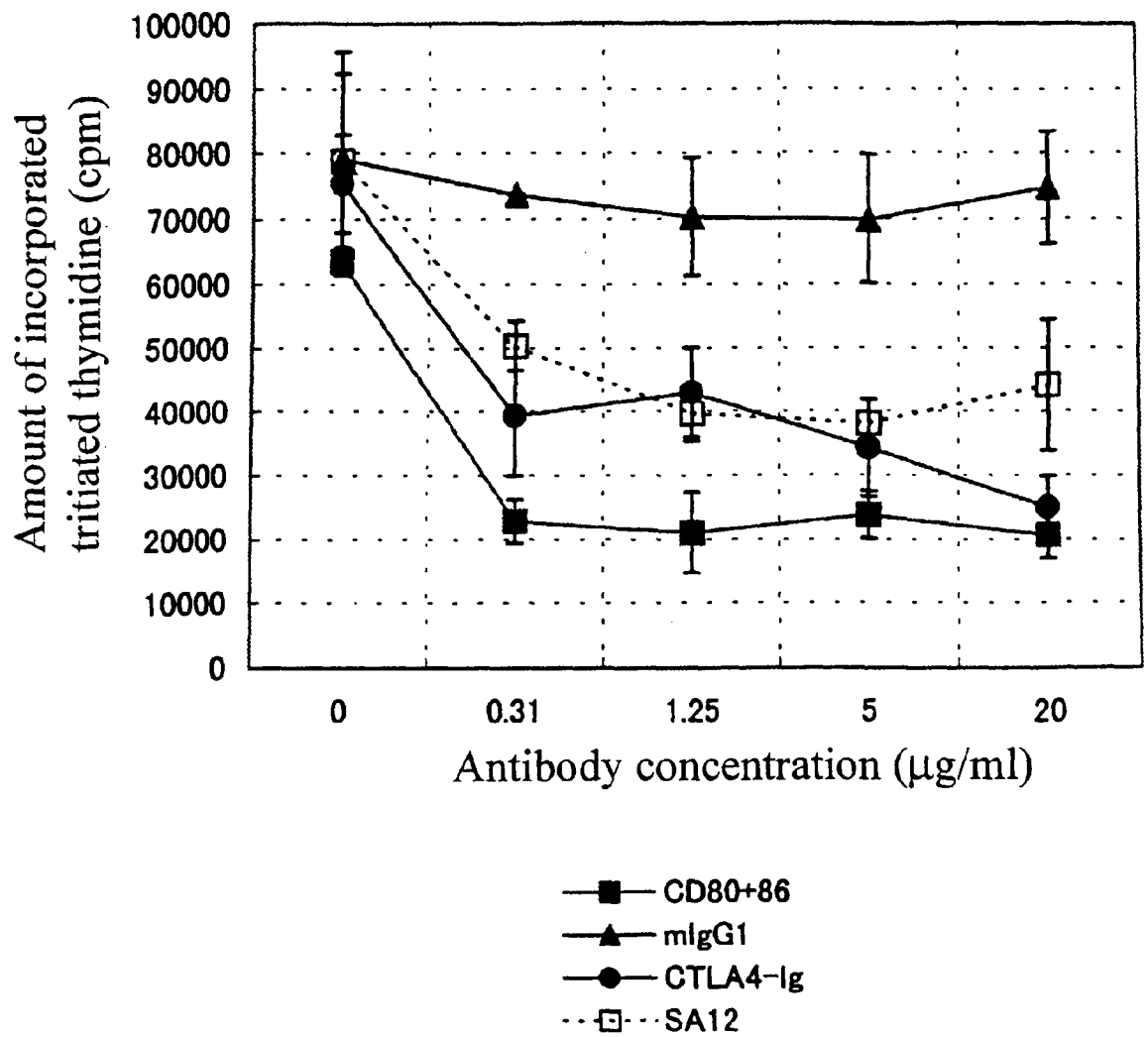

FIG. 52 shows the inhibitory effect on T cell proliferation in the case of culturing T cells from a normal healthy person "donor C", with PBMC of a normal healthy person "donor A" by various test samples in the proliferation test of the T cells through the mixed lymphocyte reactions (MLR).

The vertical axis indicates the amount of incorporation of [³H]thymidine as an index showing a level of cell proliferation, and the horizontal axis shows the concentration of the test samples.

Figure 53:
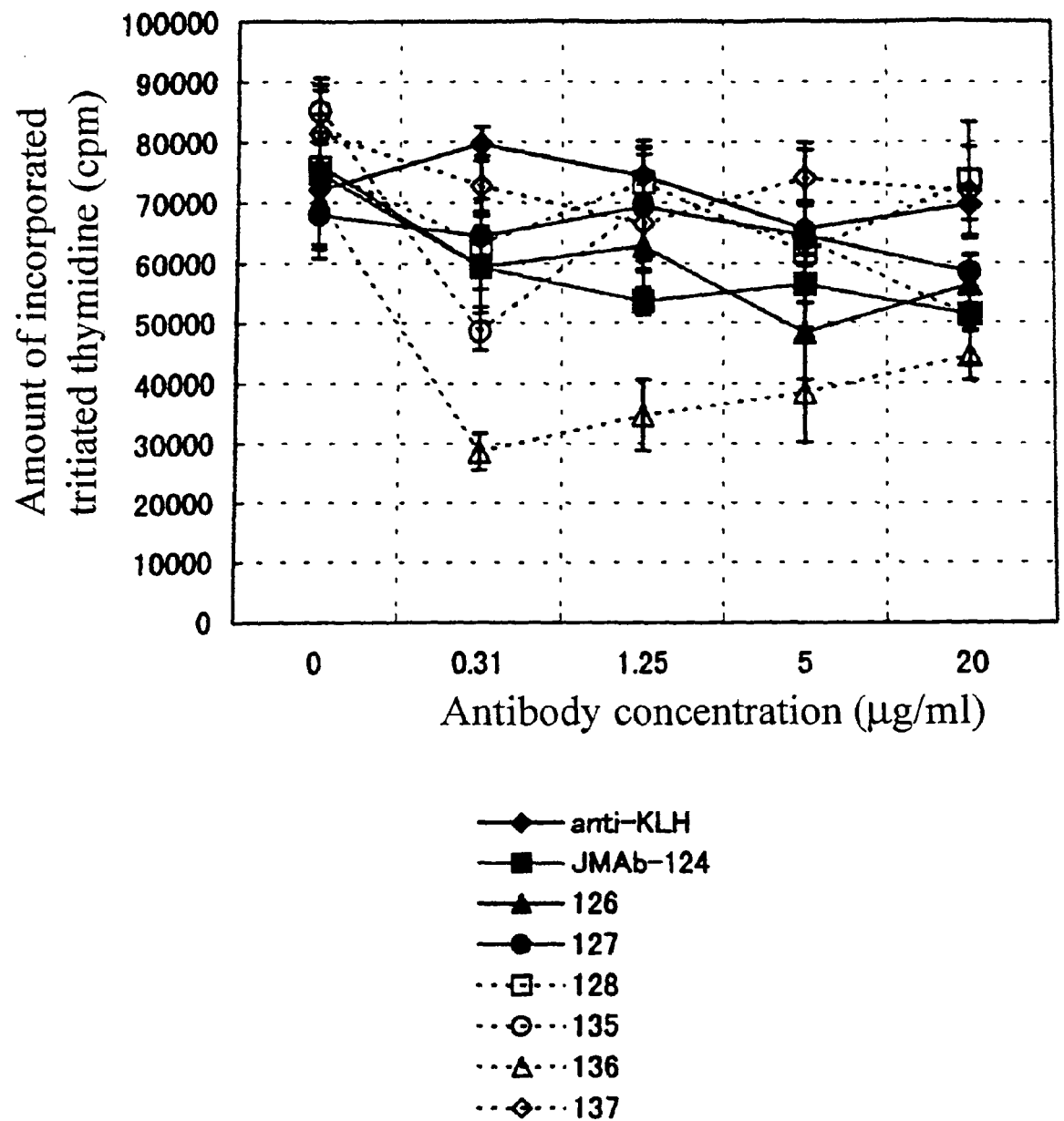

Each description in the figures shows the following.
"CD80+86": The mixture of anti-CD80 antibody and anti-CD86 antibody
"mIgG1": Anti-human CD34/IgG1 mouse monoclonal antibody
"CTLA4-Ig": Human CTLA4-IgFc chimeric molecule
"SA12": Anti-human AILIM mouse monoclonal antibody FIG. 53 shows the inhibitory effect on T cell proliferation in the case of culturing T cells from a normal healthy person "donor C", with PBMC of a normal healthy person "donor A" by various human anti-human AILIM monoclonal antibodies in the proliferation test of the T cells through the mixed lymphocyte reactions (MLR).

The vertical axis indicates the amount of incorporation of [³H]thymidine as an index showing a level of cell proliferation, and the horizontal axis shows the concentration of the test samples.

Other notations are as follows:
"anti-KLH": human anti-KLH monoclonal antibody as a negative control.
"JMab-124": human anti-human AILIM monoclonal antibody JMab124.
"126": human anti-human AILIM monoclonal antibody JMab126.
"127": human anti-human AILIM monoclonal antibody JMab127.
"128": human anti-human AILIM monoclonal antibody JMab128.
"135": human anti-human AILIM monoclonal antibody JMab135.
"136": human anti-human AILIM monoclonal antibody JMab136.
"137": human anti-human AILIM monoclonal antibody JMab137.

Figure 54:
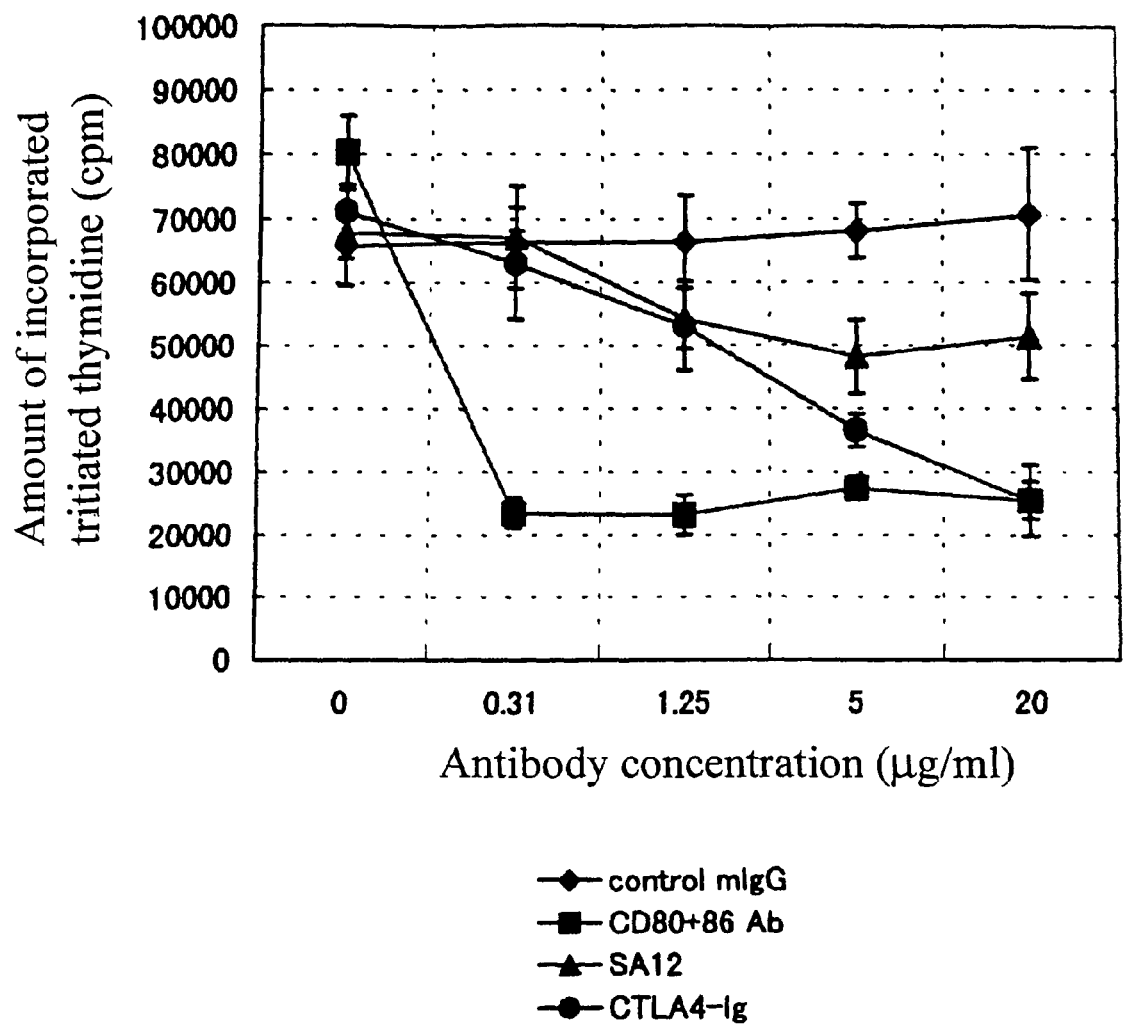

FIG. 54 shows the inhibitory effect on T cell proliferation in the case of culturing T cells from a normal healthy person "donor E", with PBMC of a normal healthy person "donor G" by various test samples in the proliferation test of the T cells through the mixed lymphocyte reactions (MLR).

The vertical axis indicates the amount of incorporation of [³H]thymidine as an index showing a level of cell proliferation, and the horizontal axis shows the concentration of the test samples.

Figure 55:
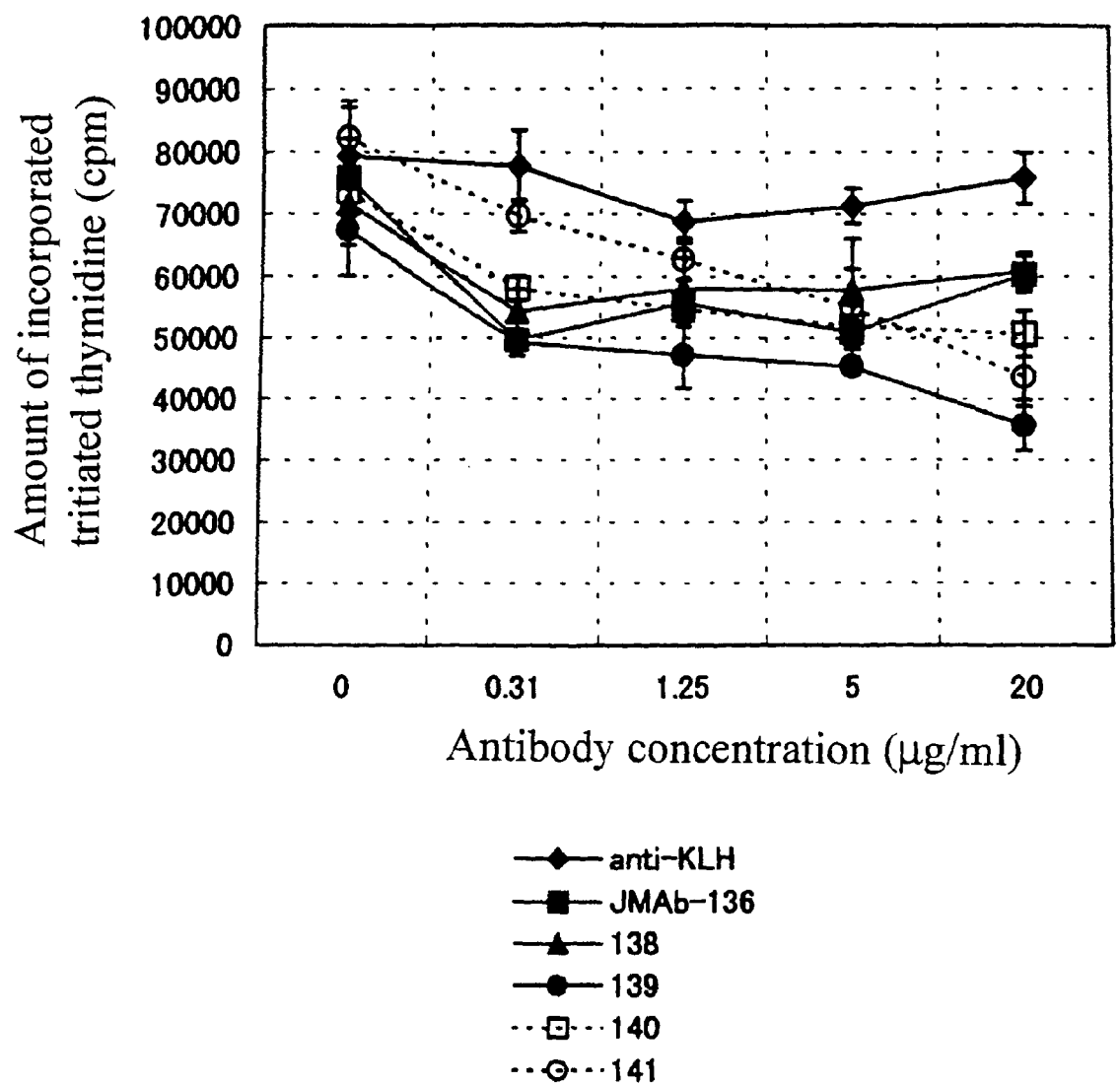

Each description in the figures shows the following.
"control mIgG": Anti-human CD34/IgG1 mouse monoclonal antibody
"CD80+86 Ab": The mixture of anti-CD80 antibody and anti-CD86 antibody
"SA12": Anti-human AILIM mouse monoclonal antibody
"CTLA4-Ig": Human CTLA4-IgFc chimeric molecule FIG. 55 shows the inhibitory effect on T cell proliferation in the case of culturing T cells from a normal healthy person "donor E", with PBMC of a normal healthy person "donor G" by various human anti-human AILIM monoclonal antibodies in the proliferation test of the T cells through the mixed lymphocyte reactions (MLR).

The vertical axis indicates the amount of incorporation of [$^3$H]thymidine as an index showing a level of cell proliferation, and the horizontal axis shows the concentration of the test samples.

Other notations are as follows:
"anti-KLH": human anti-KLH monoclonal antibody as a negative control.
"JMab-136": human anti-human AILIM monoclonal antibody JMab136.
"138": human anti-human AILIM monoclonal antibody JMab138.
"139": human anti-human AILIM monoclonal antibody JMab139.
"140": human anti-human AILIM monoclonal antibody JMab140.
"141": human anti-human AILIM monoclonal antibody JMab141.

Figure 56:
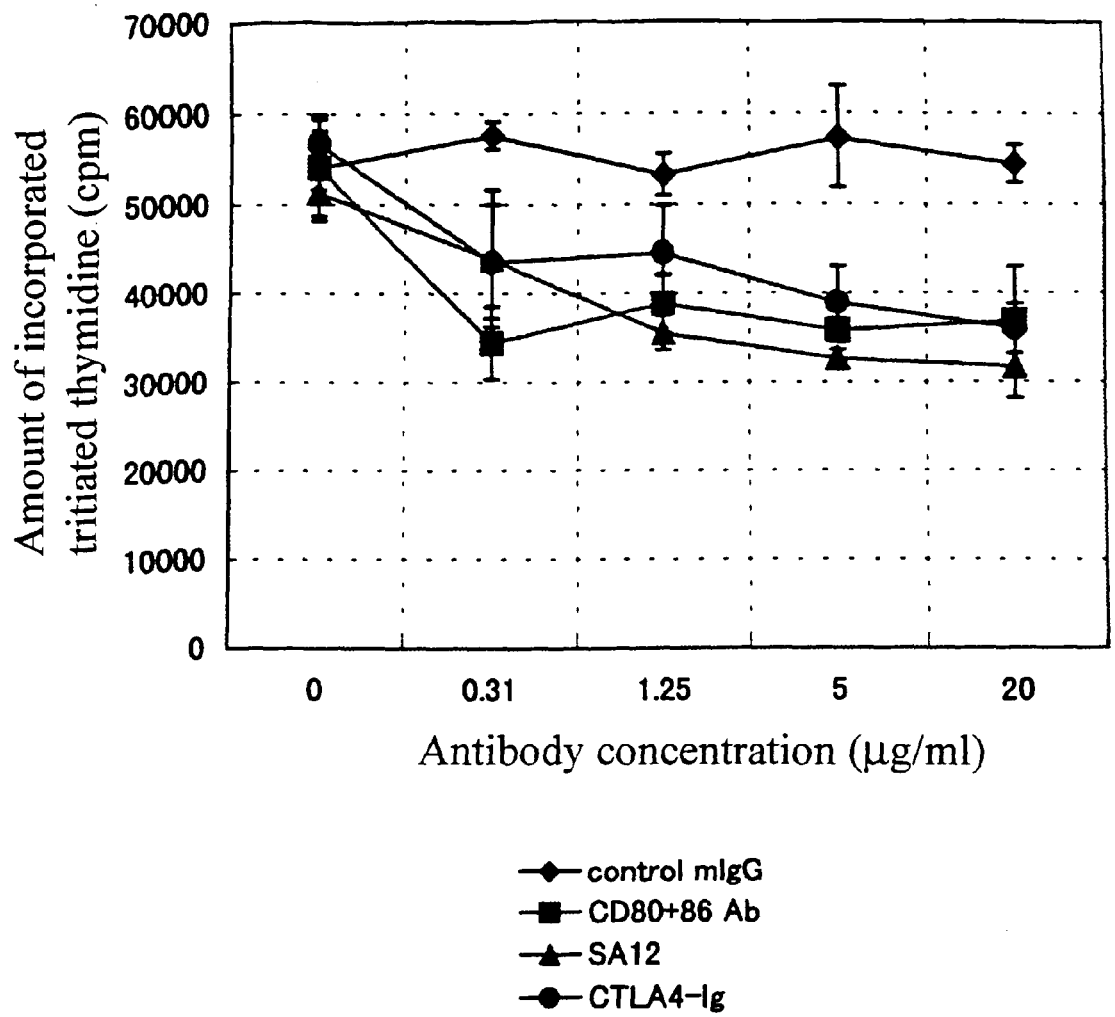

FIG. 56 shows the inhibitory effect on T cell proliferation in the case of culturing T cells from a normal healthy person "donor F", with PBMC of a normal healthy person "donor E" by various test samples in the proliferation test of the T cells through the mixed lymphocyte reactions (MLR).

The vertical axis indicates the amount of incorporation of [$^3$H]thymidine as an index showing a level of cell proliferation, and the horizontal axis shows the concentration of the test samples.

Figure 57:
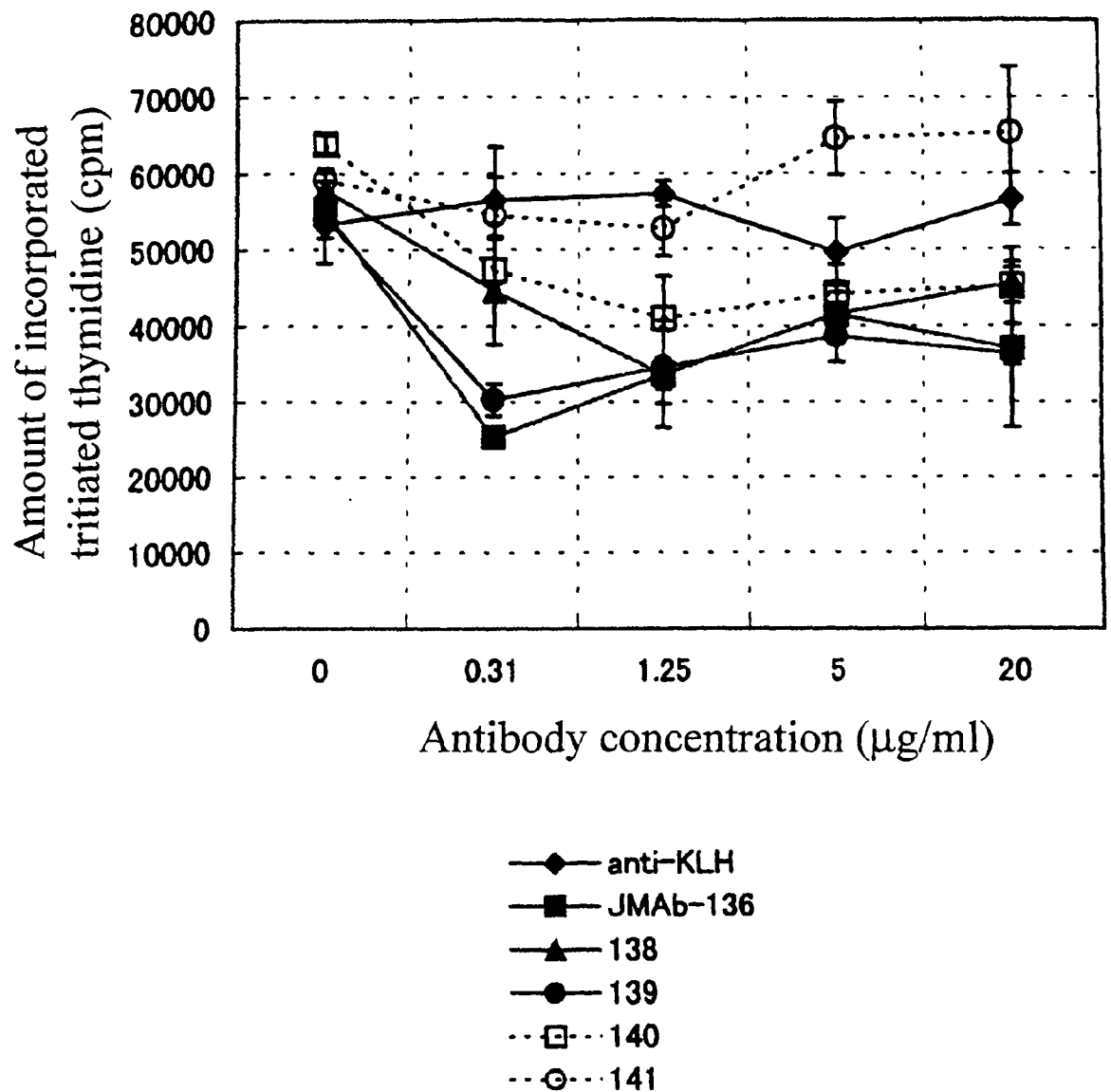

Each description in the figures shows the following.
"control mIgG": Anti-human CD34/IgG1 mouse monoclonal antibody
"CD80+86 Ab": The mixture of anti-CD80 antibody and anti-CD86 antibody
"SA12": Anti-human AILIM mouse monoclonal antibody
"CTLA4-Ig": Human CTLA4-IgFc chimeric molecule FIG. 57 shows the inhibitory effect on T cell proliferation in the case of culturing T cells from a normal healthy person "donor F", with PBMC of a normal healthy person "donor E" by various test samples in the proliferation test of the T cells through the mixed lymphocyte reactions (MLR).

The vertical axis indicates the amount of incorporation of [$^3$H]thymidine as an index showing a level of cell proliferation, and the horizontal axis shows the concentration of the test samples.

Each description in the figures shows the following.
"anti-KLH": human anti-KLH monoclonal antibody as a negative control.
"JMab-136": human anti-human AILIM monoclonal antibody JMab136.
"138": human anti-human AILIM monoclonal antibody JMab138.
"139": human anti-human AILIM monoclonal antibody JMab139.
"140": human anti-human AILIM monoclonal antibody JMab140.
"141": human anti-human AILIM monoclonal antibody JMab141.

Figure 58:
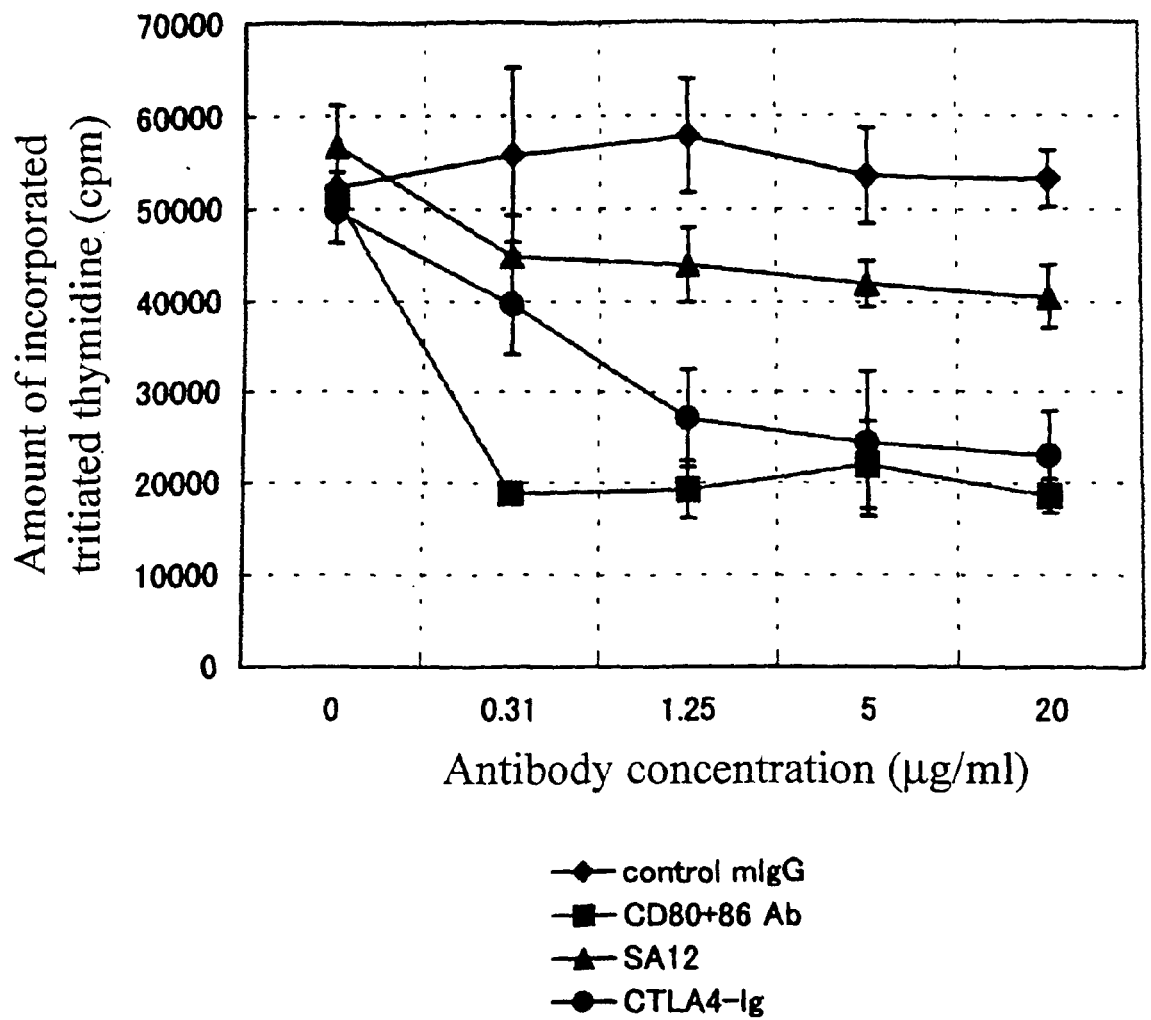

FIG. 58 shows the inhibitory effect on T cell proliferation in the case of culturing T cells from a normal healthy person "donor G", with PBMC of a normal healthy person "donor F" by various test samples in the proliferation test of the T cells through the mixed lymphocyte reactions (MLR).

The vertical axis indicates the amount of incorporation of [$^3$H]thymidine as an index showing a level of cell proliferation, and the horizontal axis shows the concentration of the test samples.

Figure 59:
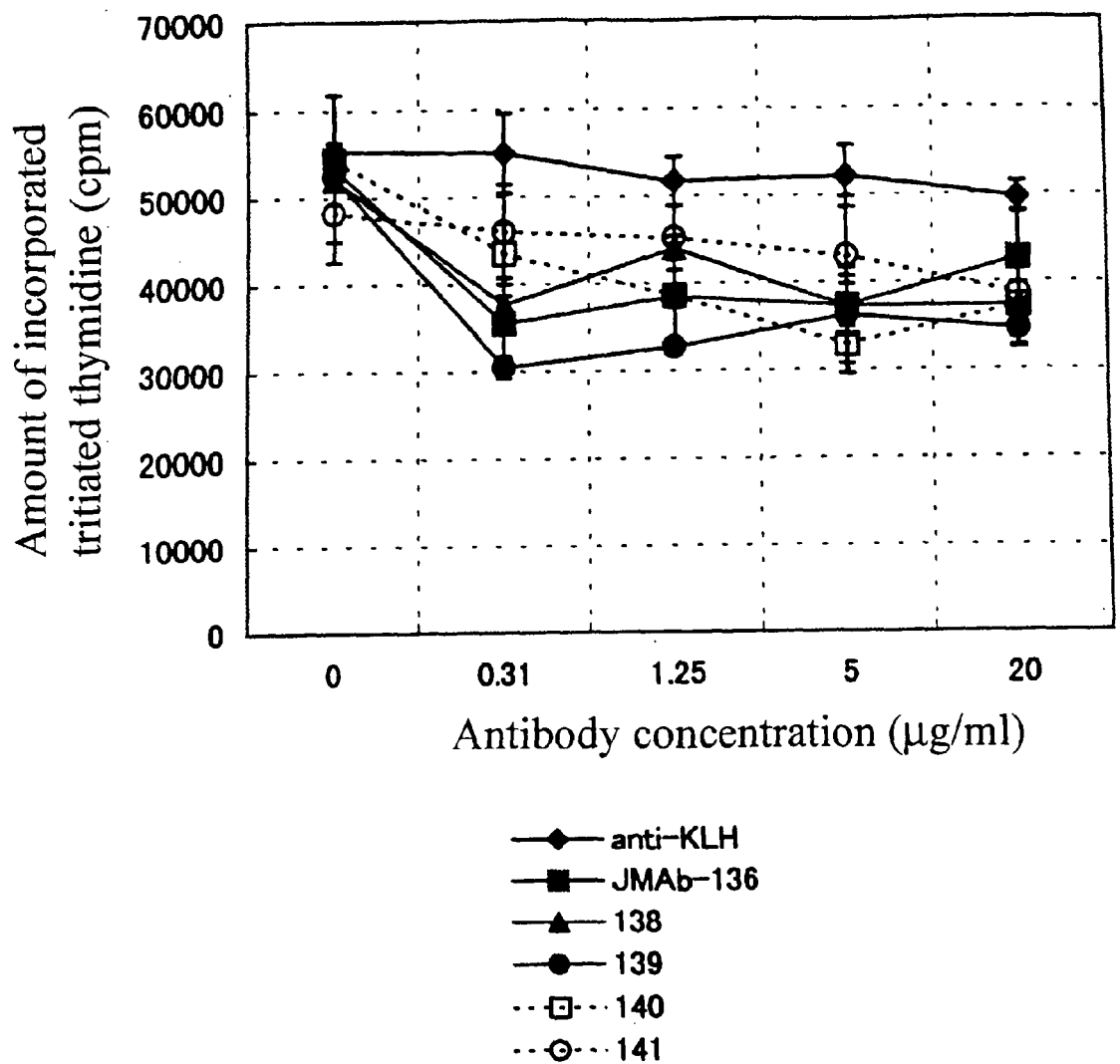

Each description in the figures shows the following.
"control mIgG": Anti-human CD34/IgG1 mouse monoclonal antibody
"CD80+86 Ab": The mixture of anti-CD80 antibody and anti-CD86 antibody
"SA12": Anti-human AILIM mouse monoclonal antibody
"CTLA4-Ig": Human CTLA4-IgFc chimeric molecule FIG. 59 shows the inhibitory effect on T cell proliferation in the case of culturing T cells from a normal healthy person "donor G", with PBMC of a normal healthy person "donor F" by various test samples in the proliferation test of the T cells through the mixed lymphocyte reactions (MLR).

The vertical axis indicates the amount of incorporation of [$^3$H]thymidine as an index showing a level of cell proliferation, and the horizontal axis shows the concentration of the test samples.

Each description in the figures shows the following.
"anti-KLH": human anti-KLH monoclonal antibody as a negative control.
"JMab-136": human anti-human AILIM monoclonal antibody JMab136.
"138": human anti-human AILIM monoclonal antibody JMab138.
"139": human anti-human AILIM monoclonal antibody JMab139.
"140": human anti-human AILIM monoclonal antibody JMab140.
"141": human anti-human AILIM monoclonal antibody JMab141.

Figure 60:
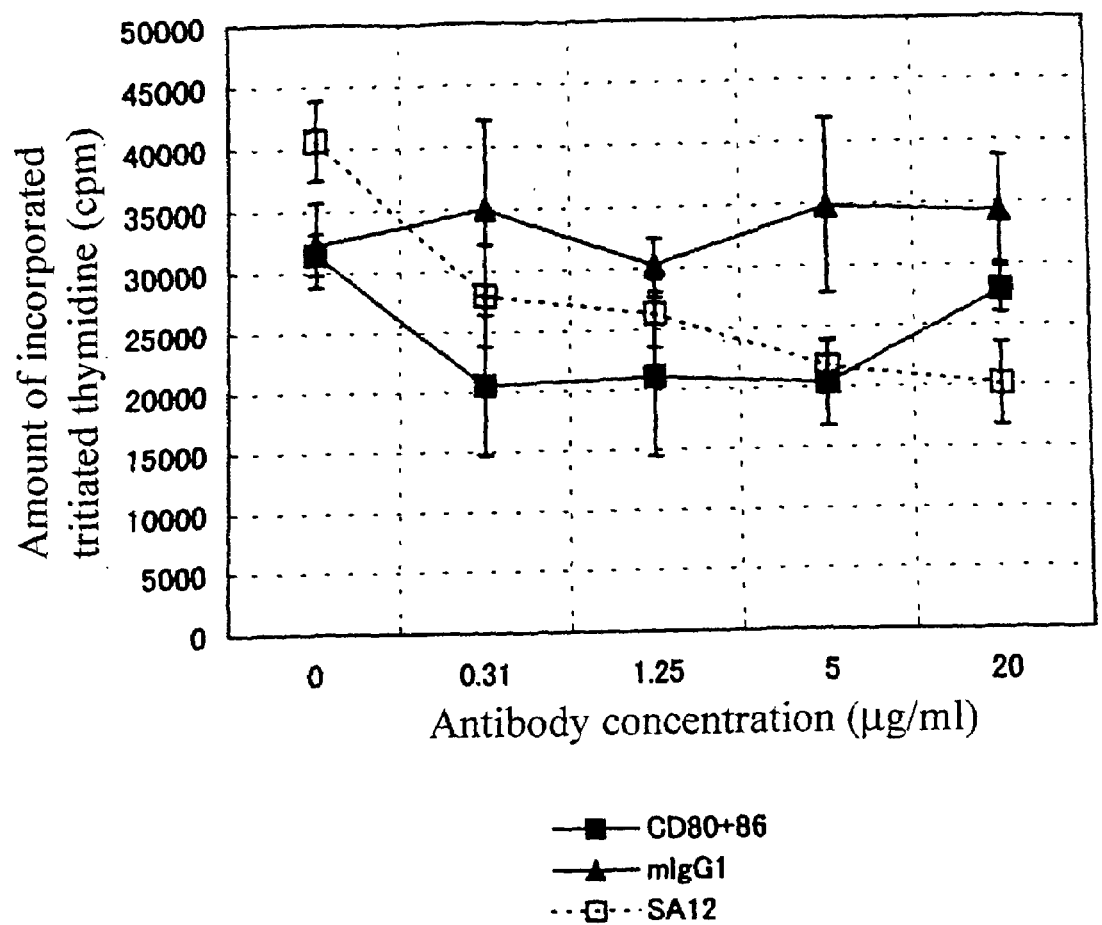

FIG. 60 shows the inhibitory effect of various control test substances on the proliferation of T cells in the assay using mixed lymphocyte reaction (MLR). T cells from a normal healthy person "donor A" were co-cultured with PBMCs from a normal healthy person "donor D" pre-cultured in the presence of human CTLA4-Ig chimeric molecule.

The vertical axis indicates the amount of cellular incorporation of [$^3$H]thymidine as an index of the degree of cell proliferation, and the horizontal axis indicates the concentrations of test substances.

Figure 61:
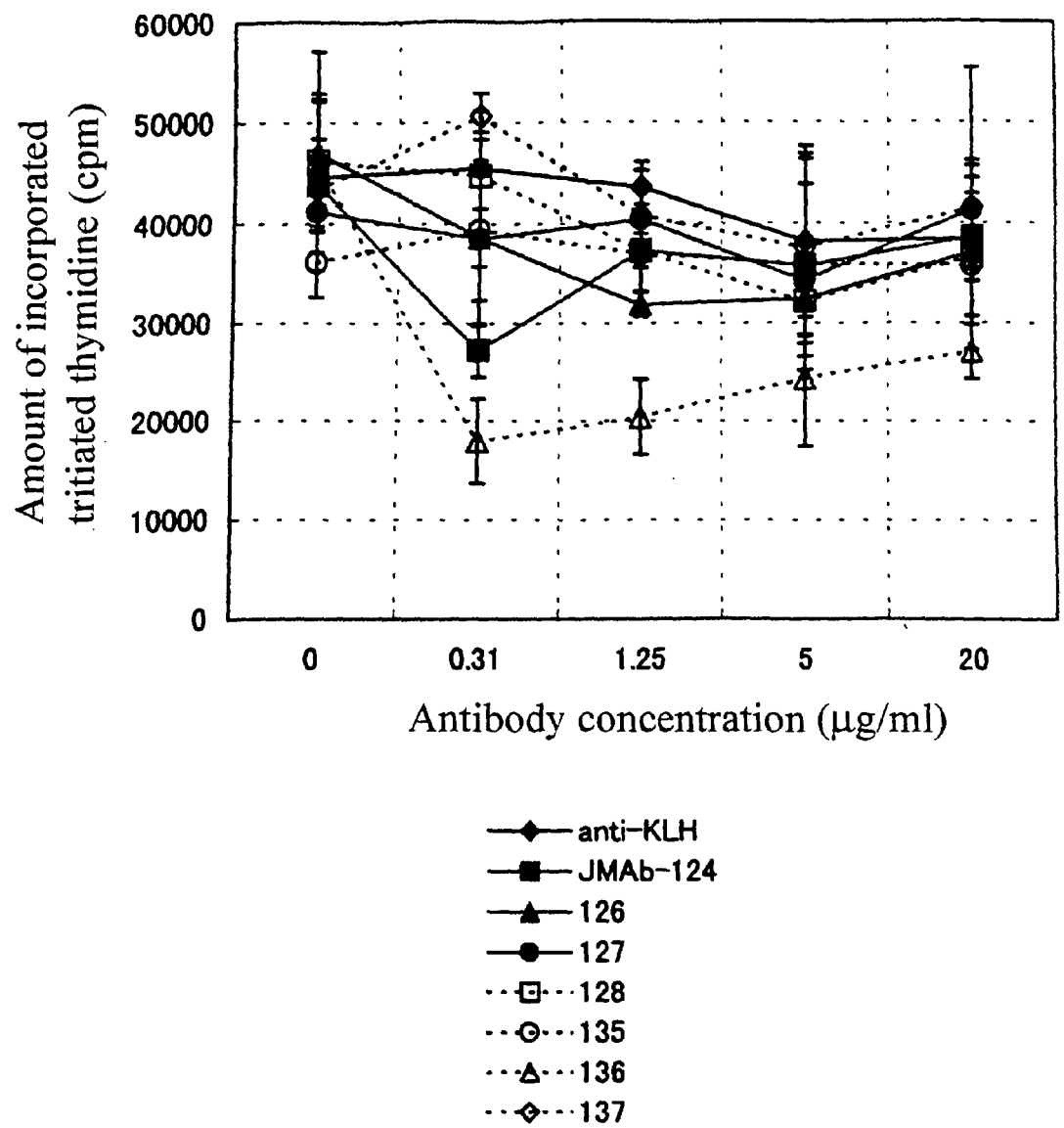

Each description in the figures shows the following.
"CD80+86": The mixture of anti-CD80 antibody and anti-CD86 antibody
"mIgG1": Anti-human CD34/IgG1 mouse monoclonal antibody
"SA12": Anti-human AILIM mouse monoclonal antibody FIG. 61 shows the inhibitory effect of various human anti-human AILIM monoclonal antibodies on the proliferation of T cells in the assay using mixed lymphocyte reaction (MLR). T cells from a normal healthy person "donor A" were co-cultured with PBMCs from a normal healthy person "donor D" pre-cultured in the presence of human CTLA4-Ig chimeric molecule.

The vertical axis indicates the amount of cellular incorporation of [$^3$H]thymidine as an index of the degree of cell proliferation, and the horizontal axis indicates the concentrations of test substances.

Other notations are as follows:

"anti-KLH": human anti-KLH monoclonal antibody as a negative control.

"JMab-124": human anti-human AILIM monoclonal antibody JMab124.

"126": human anti-human AILIM monoclonal antibody JMab126.

"127": human anti-human AILIM monoclonal antibody JMab127.

"128": human anti-human AILIM monoclonal antibody JMab128.

"135": human anti-human AILIM monoclonal antibody JMab135.

"136": human anti-human AILIM monoclonal antibody JMab136.

"137": human anti-human AILIM monoclonal antibody JMab137.

Figure 62:
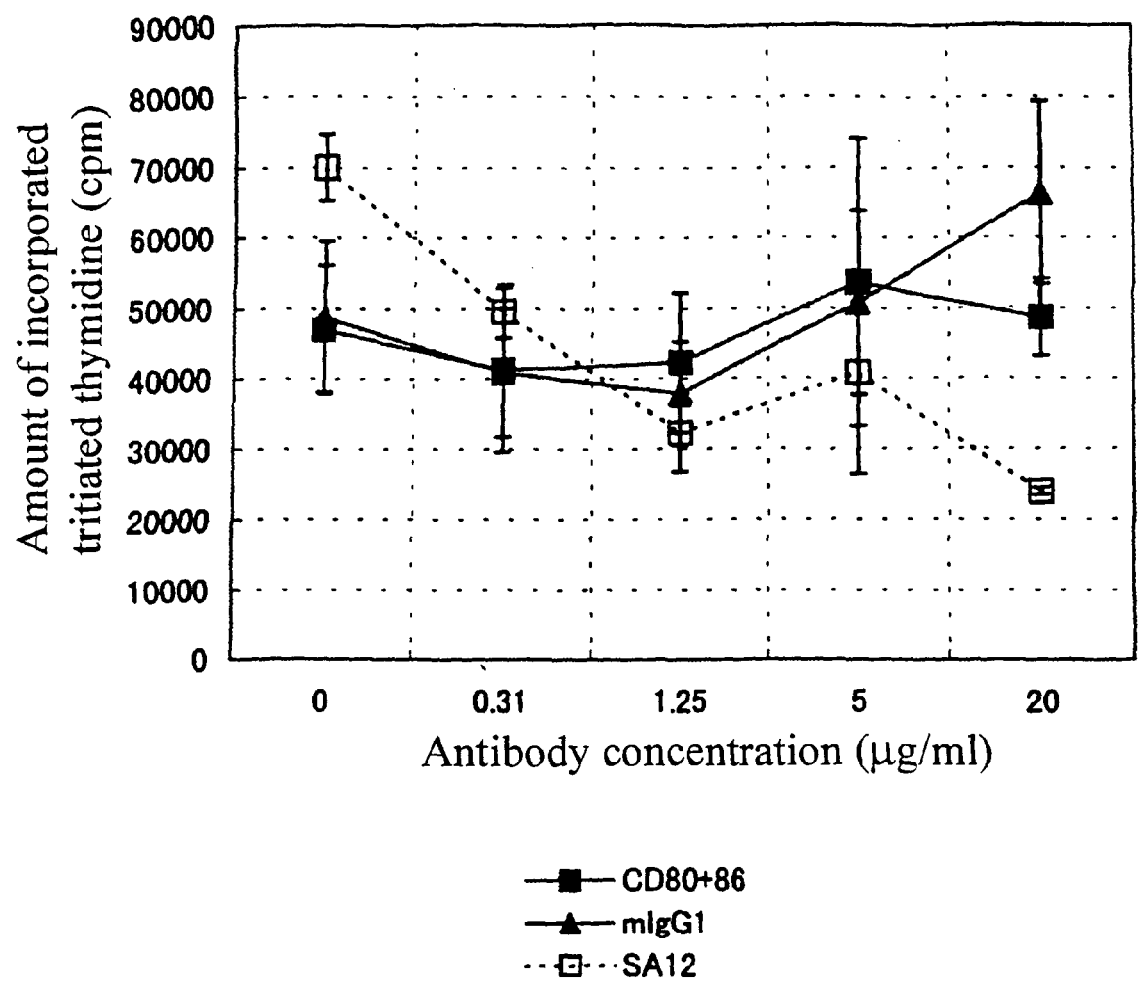

FIG. 62 shows the inhibitory effect of various control test substances on the proliferation of T cells in the assay using mixed lymphocyte reaction (MLR). T cells from a normal healthy person "donor D" were co-cultured with PBMCs from a normal healthy person "donor B" pre-cultured in the presence of human CTLA4-Ig chimeric molecule.

The vertical axis indicates the amount of cellular incorporation of [$^3$H]thymidine as an index of the degree of cell proliferation, and the horizontal axis indicates the concentrations of test substances.

Each description in the figures shows the following.

"CD80+86": The mixture of anti-CD80 antibody and anti-CD86 antibody

"mIgG1": Anti-human CD34/IgG1 mouse monoclonal antibody

"SA12": Anti-human AILIM mouse monoclonal antibody

Figure 63:
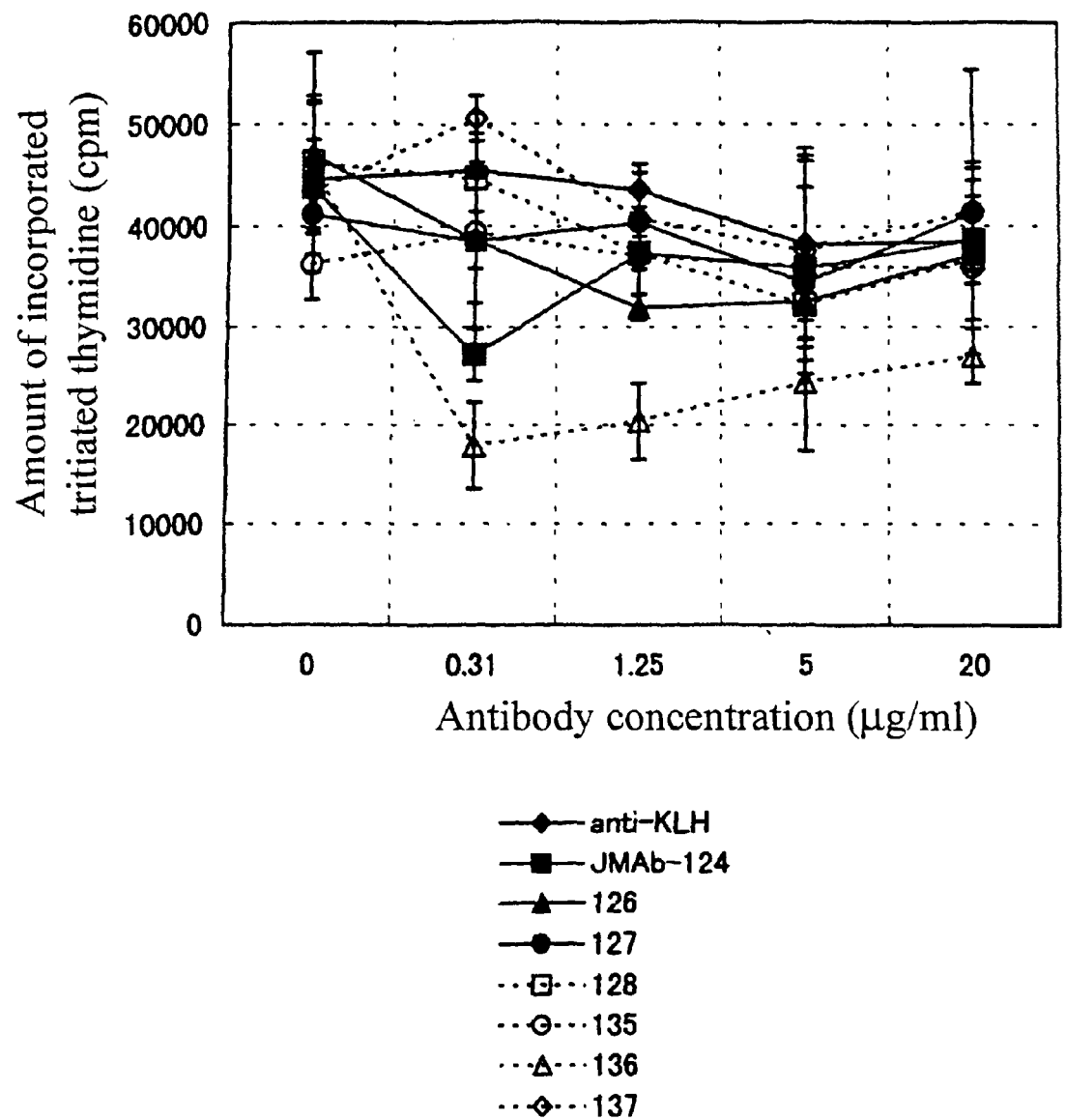

FIG. 63 shows the inhibitory effect of various human anti-human AILIM monoclonal antibodies on the proliferation of T cells in the assay using mixed lymphocyte reaction (MLR). T cells from a normal healthy person "donor D" were co-cultured with PBMCs from a normal healthy person "donor B" pre-cultured in the presence of human CTLA4-Ig chimeric molecule.

The vertical axis indicates the amount of cellular incorporation of [$^3$H]thymidine as an index of the degree of cell proliferation, and the horizontal axis indicates the concentrations of test substances.

Other notations are as follows:

"anti-KLH": human anti-KLH monoclonal antibody as a negative control.

"JMab-124": human anti-human AILIM monoclonal antibody JMab124.

"126": human anti-human AILIM monoclonal antibody JMab126.

"127": human anti-human AILIM monoclonal antibody JMab127.

"128": human anti-human AILIM monoclonal antibody JMab128.

"135": human anti-human AILIM monoclonal antibody JMab135.

"136": human anti-human AILIM monoclonal antibody JMab136.

"137": human anti-human AILIM monoclonal antibody JMab137.

Figure 64:
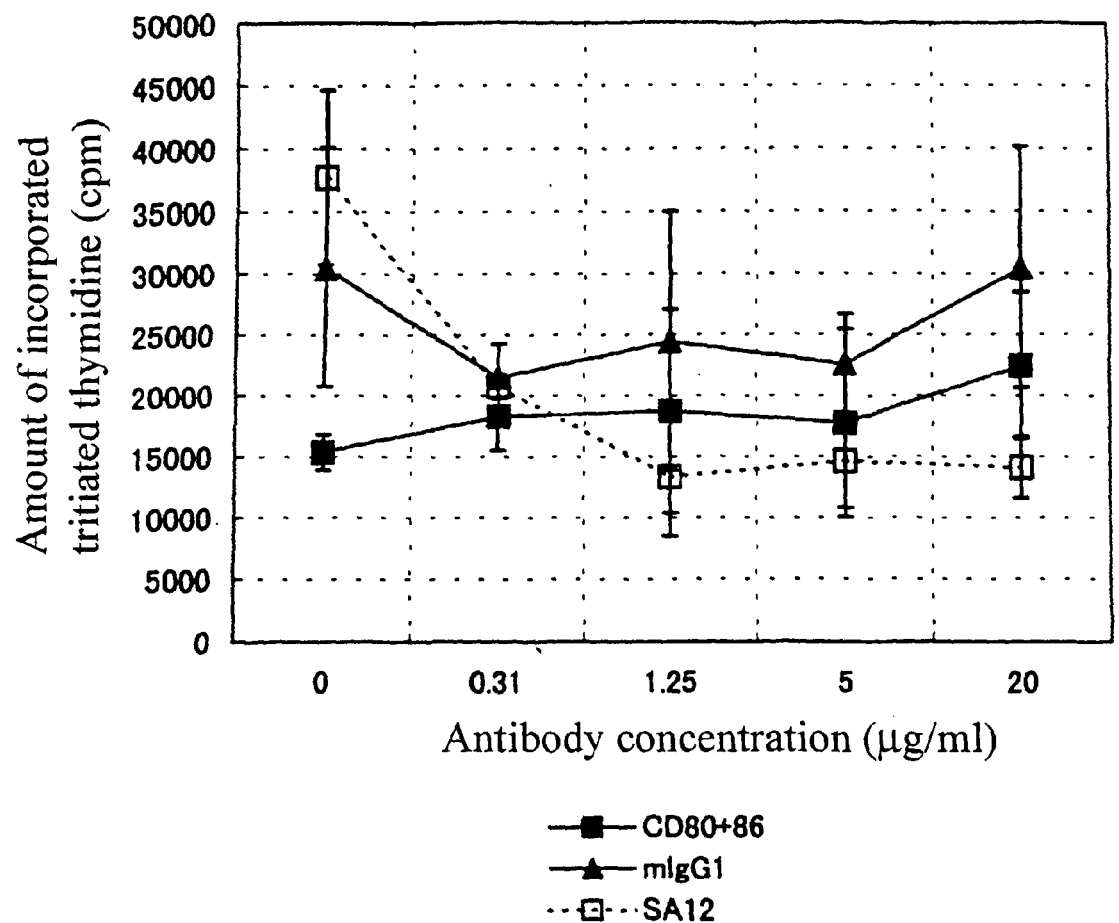

FIG. 64 shows the inhibitory effect of various control test substances on the proliferation of T cells in the assay using mixed lymphocyte reaction (MLR). T cells from a normal healthy person "donor C" were co-cultured with PBMCs from a normal healthy person "donor A" pre-cultured in the presence of human CTLA4-Ig chimeric molecule.

The vertical axis indicates the amount of cellular incorporation of [$^3$H]thymidine as an index of the degree of cell proliferation, and the horizontal axis indicates the concentrations of test substances.

Each description in the figures shows the following.

"CD80+86": The mixture of anti-CD80 antibody and anti-CD86 antibody

"mIgG1": Anti-human CD34/IgG1 mouse monoclonal antibody

"SA12": Anti-human AILIM mouse monoclonal antibody

Figure 65:
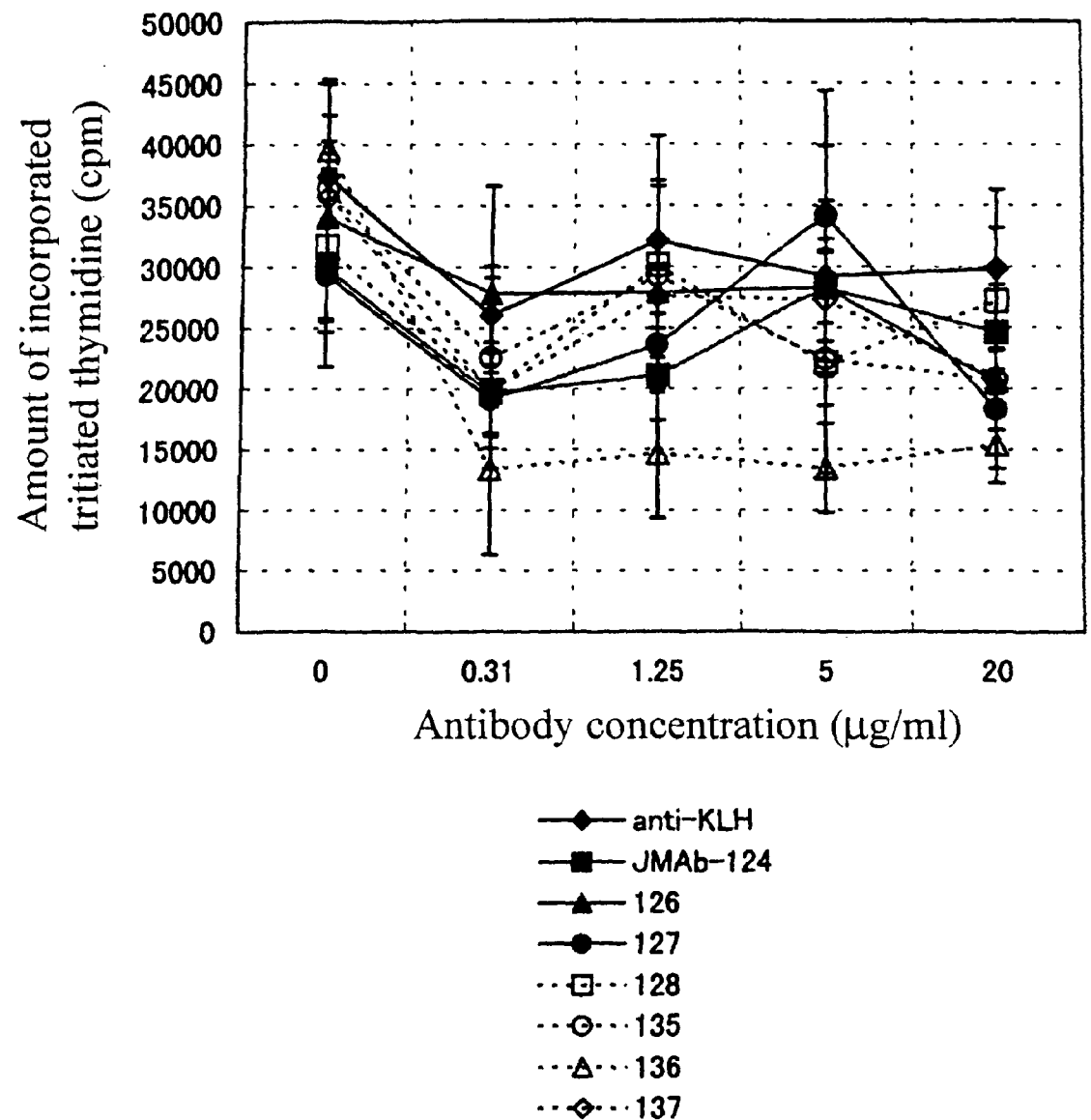

FIG. 65 shows the inhibitory effect of various human anti-human AILIM monoclonal antibodies on the proliferation of T cells in the assay using mixed lymphocyte reaction (MLR). T cells from a normal healthy person "donor C" were co-cultured with PBMCs from a normal healthy person "donor A" pre-cultured in the presence of human CTLA4-Ig chimeric molecule.

The vertical axis indicates the amount of cellular incorporation of [$^3$H]thymidine as an index of the degree of cell proliferation, and the horizontal axis indicates the concentrations of test substances.

Other notations are as follows:

"anti-KLH": human anti-KLH monoclonal antibody as a negative control.

"JMab-124": human anti-human AILIM monoclonal antibody JMab124.

"126": human anti-human AILIM monoclonal antibody JMab126.

"127": human anti-human AILIM monoclonal antibody JMab127.

"128": human anti-human AILIM monoclonal antibody JMab128.

"135": human anti-human AILIM monoclonal antibody JMab135.

"136": human anti-human AILIM monoclonal antibody JMab136.

"137": human anti-human AILIM monoclonal antibody JMab137.

Figure 66:
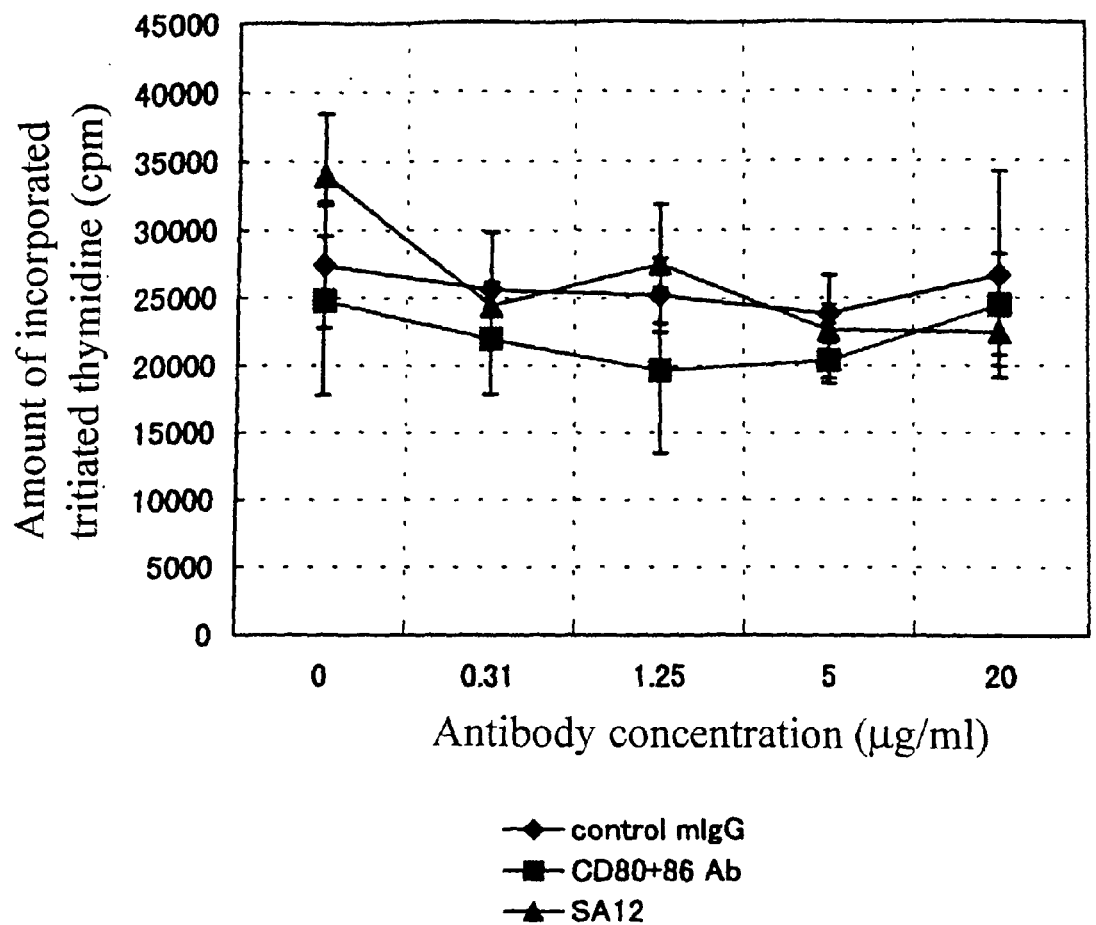

FIG. 66 shows the inhibitory effect of various control test substances on the proliferation of T cells in the assay using mixed lymphocyte reaction (MLR). T cells from a normal healthy person "donor E" were co-cultured with PBMCs from a normal healthy person "donor G" pre-cultured in the presence of human CTLA4-Ig chimeric molecule.

The vertical axis indicates the amount of cellular incorporation of [$^3$H]thymidine as an index of the degree of cell proliferation, and the horizontal axis indicates the concentrations of test substances.

Each description in the figures shows the following.

"control mIgG": Anti-human CD34/IgG1 mouse monoclonal antibody

"CD80+86 Ab": The mixture of anti-CD80 antibody and anti-CD86 antibody

"SA12": Anti-human AILIM mouse monoclonal antibody

Figure 67:
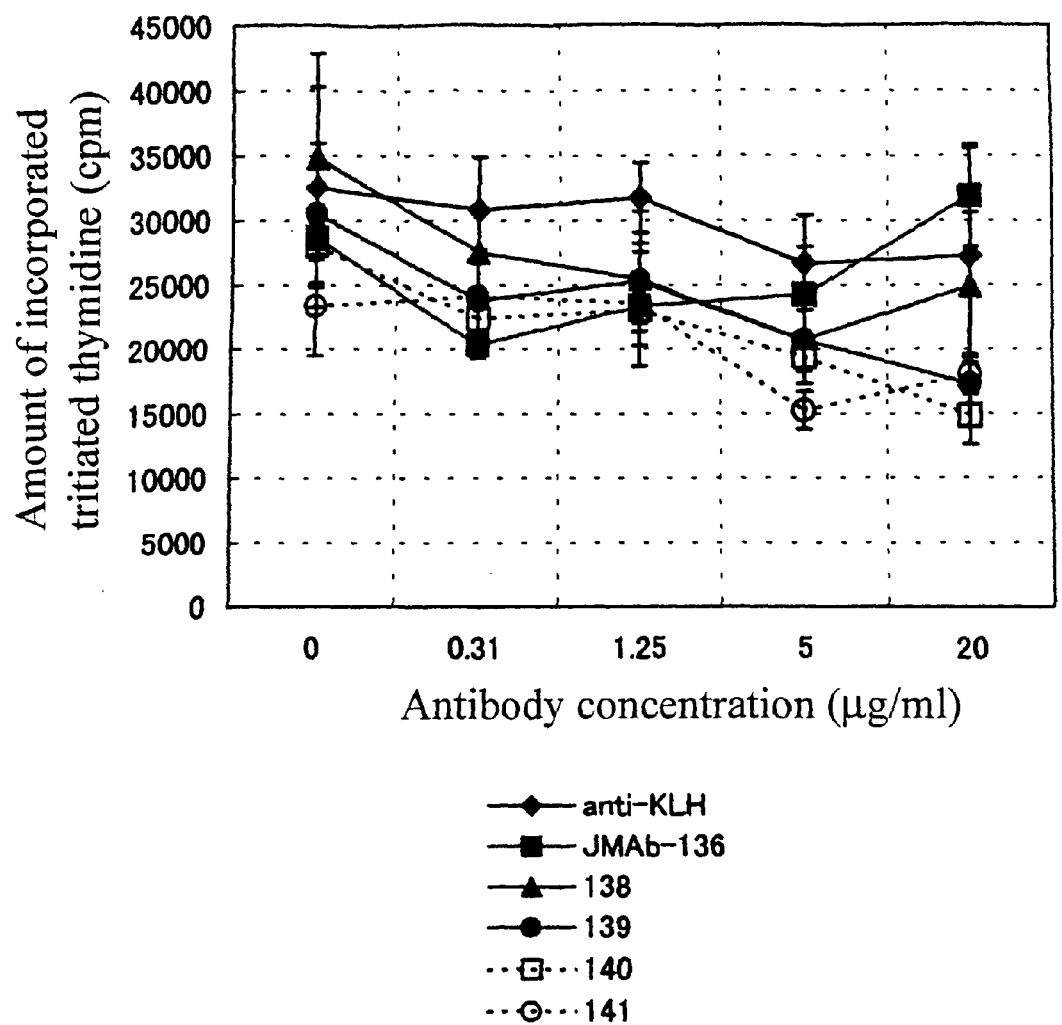

FIG. 67 shows the inhibitory effect of various human anti-human AILIM monoclonal antibodies on the proliferation of T cells in the assay using mixed lymphocyte reaction (MLR). T cells from a normal healthy person "donor E" were co-cultured with PBMCs from a normal healthy person "donor G" pre-cultured in the presence of human CTLA4-Ig chimeric molecule.

The vertical axis indicates the amount of cellular incorporation of [$^3$H]thymidine as an index of the degree of cell proliferation, and the horizontal axis indicates the concentrations of test substances.

Other notations are as follows:

"anti-KLH": human anti-KLH monoclonal antibody as a negative control.

"JMab-136": human anti-human AILIM monoclonal antibody JMab136.

"138": human anti-human AILIM monoclonal antibody JMab138.

"139": human anti-human AILIM monoclonal antibody JMab139.

"140": human anti-human AILIM monoclonal antibody JMab140.

"141": human anti-human AILIM monoclonal antibody JMab141.

Figure 68:
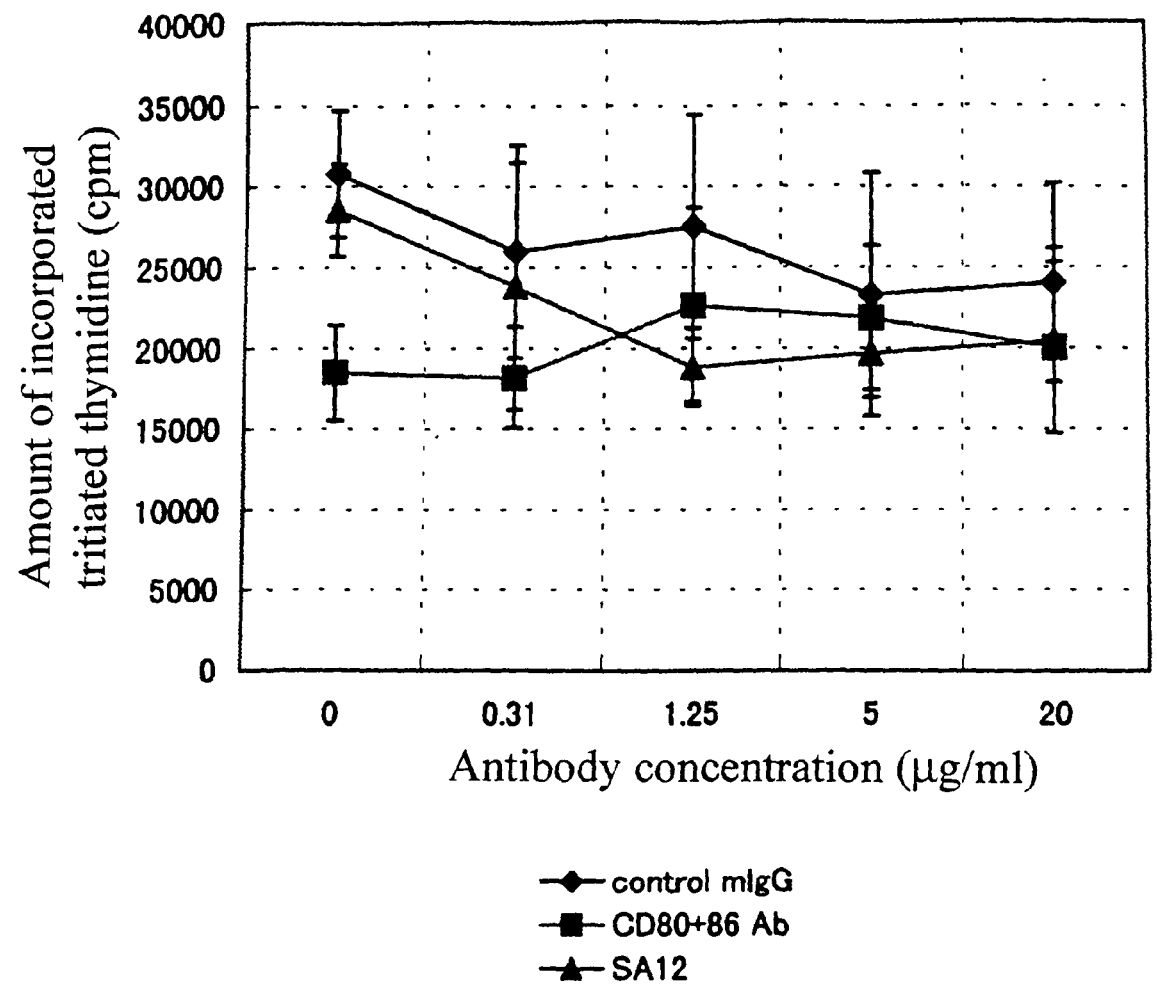

FIG. 68 shows the inhibitory effect of various control test substances on the proliferation of T cells in the assay using mixed lymphocyte reaction (MLR). T cells from a normal healthy person "donor G" were co-cultured with PBMCs from a normal healthy person "donor F" pre-cultured in the presence of human CTLA4-Ig chimeric molecule.

The vertical axis indicates the amount of cellular incorporation of [$^3$H]thymidine as an index of the degree of cell proliferation, and the horizontal axis indicates the concentrations of test substances.

Each description in the figures shows the following.

"control mIgG": Anti-human CD34/IgG1 mouse monoclonal antibody

"CD80+86 Ab": The mixture of anti-CD80 antibody and anti-CD86 antibody

"SA12": Anti-human AILIM mouse monoclonal antibody

Figure 69:
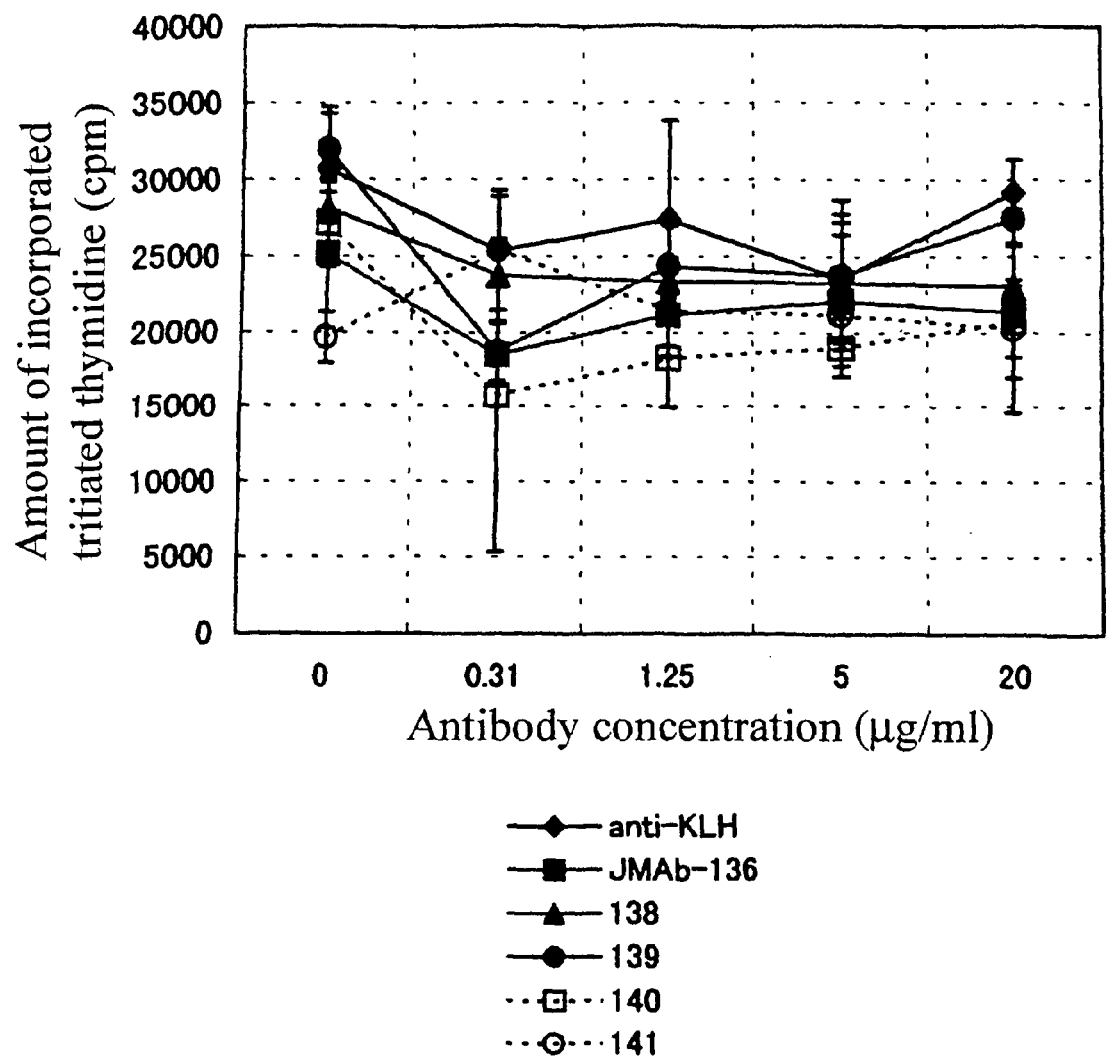

FIG. 69 shows the inhibitory effect of various human anti-human AILIM monoclonal antibodies on the proliferation of T cells in the assay using mixed lymphocyte reaction (MLR). T cells from a normal healthy person "donor G" were co-cultured with PBMCs from a normal healthy person "donor F" pre-cultured in the presence of human CTLA4-Ig chimeric molecule.

The vertical axis indicates the amount of cellular incorporation of [$^3$H]thymidine as an index of the degree of cell proliferation, and the horizontal axis indicates the concentrations of test substances.

Other notations are as follows:

"anti-KLH": human anti-KLH monoclonal antibody as a negative control.

"JMab-136": human anti-human AILIM monoclonal antibody JMab136.

"138": human anti-human AILIM monoclonal antibody JMab138.

"139": human anti-human AILIM monoclonal antibody JMab139.

"140": human anti-human AILIM monoclonal antibody JMab140.

"141": human anti-human AILIM monoclonal antibody JMab141.

Figure 70:
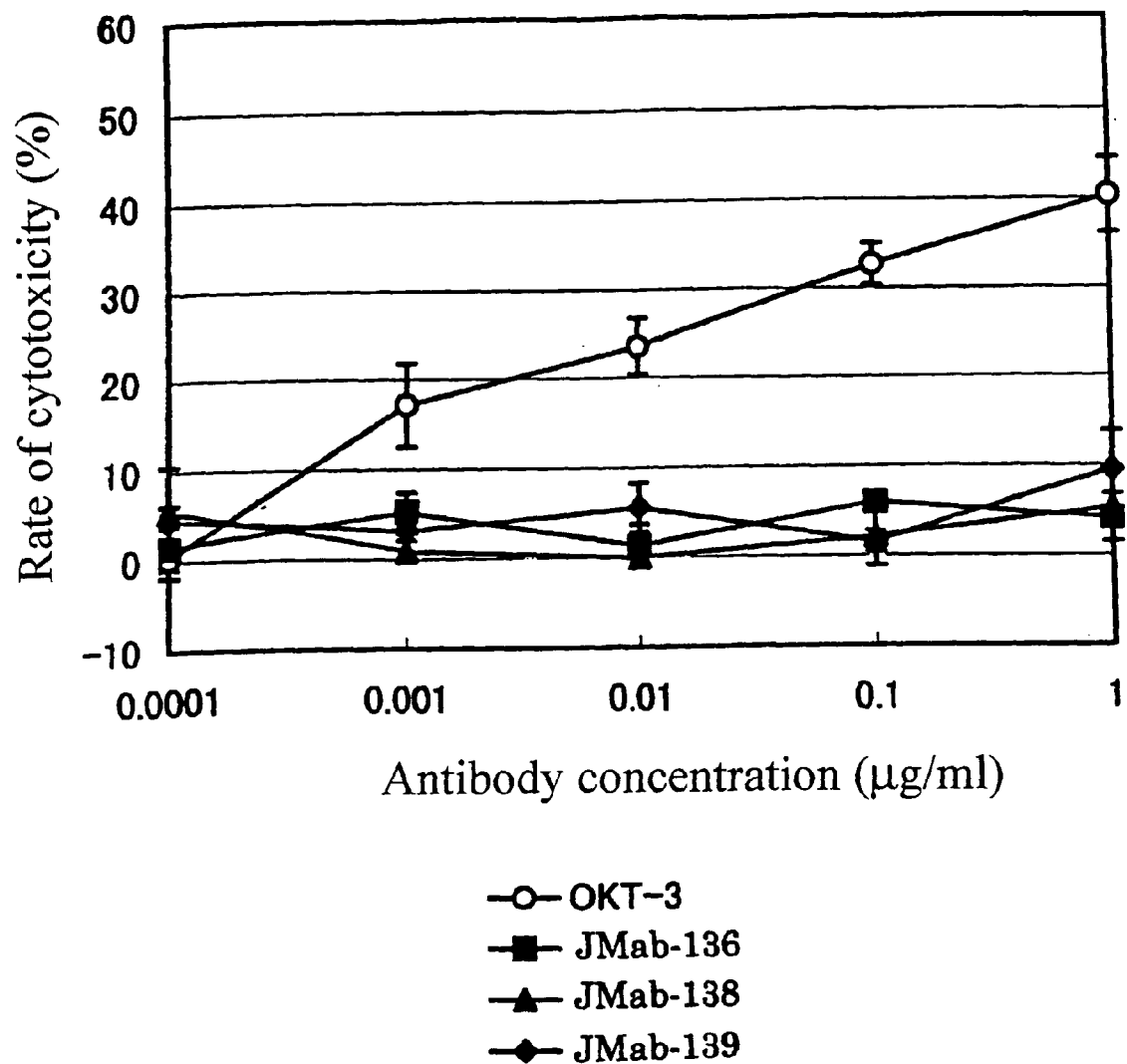

FIG. 70 shows ADCC-inducing activity of various human anti-human AILIM monoclonal antibodies and control antibodies where wild-type CHO cells were used as the target cells.

The vertical axis indicates the rate of cytotoxicity caused by ADCC-inducing activity of antibody, and the horizontal axis indicates the concentration of antibody.

Figure 71:
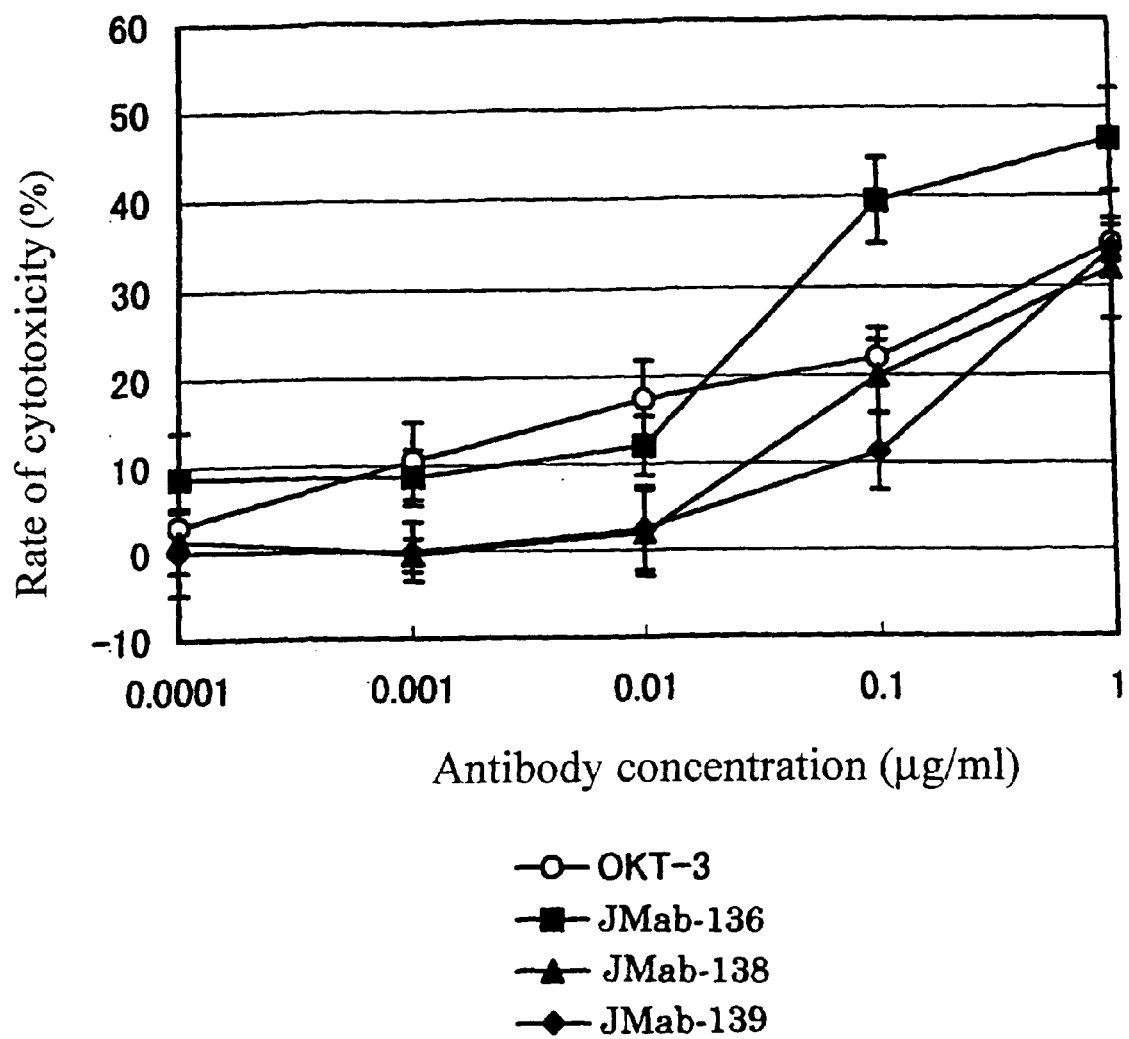

FIG. 71 shows ADCC-inducing activity of various human anti-human AILIM monoclonal antibodies and control antibody where human AILIM-overexpressing recombinant CHO cells were used as the target cells.

The vertical axis indicates the frequency of cell damage resulted from the ADCC-inducing activity of antibody, and the horizontal axis indicates the concentration of antibody.

Figure 72:
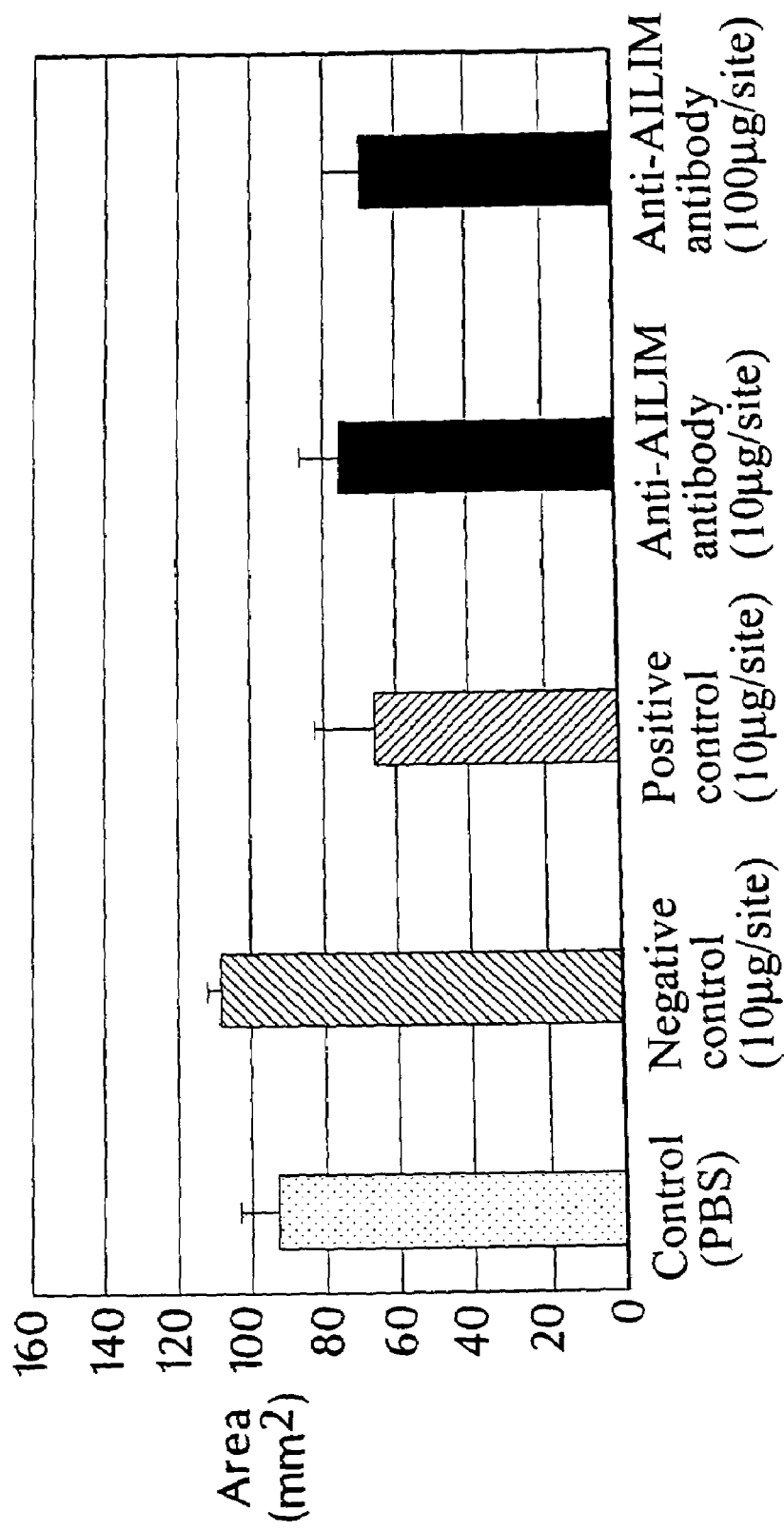

FIG. 72 shows the inhibitory effect of anti-AILIM antibody on delayed allergy.

The vertical axis indicates the size of redness measured as an index of the onset of delayed allergy, and the horizontal axis indicates the type of test sample given to animal subjects.

Figure 73:
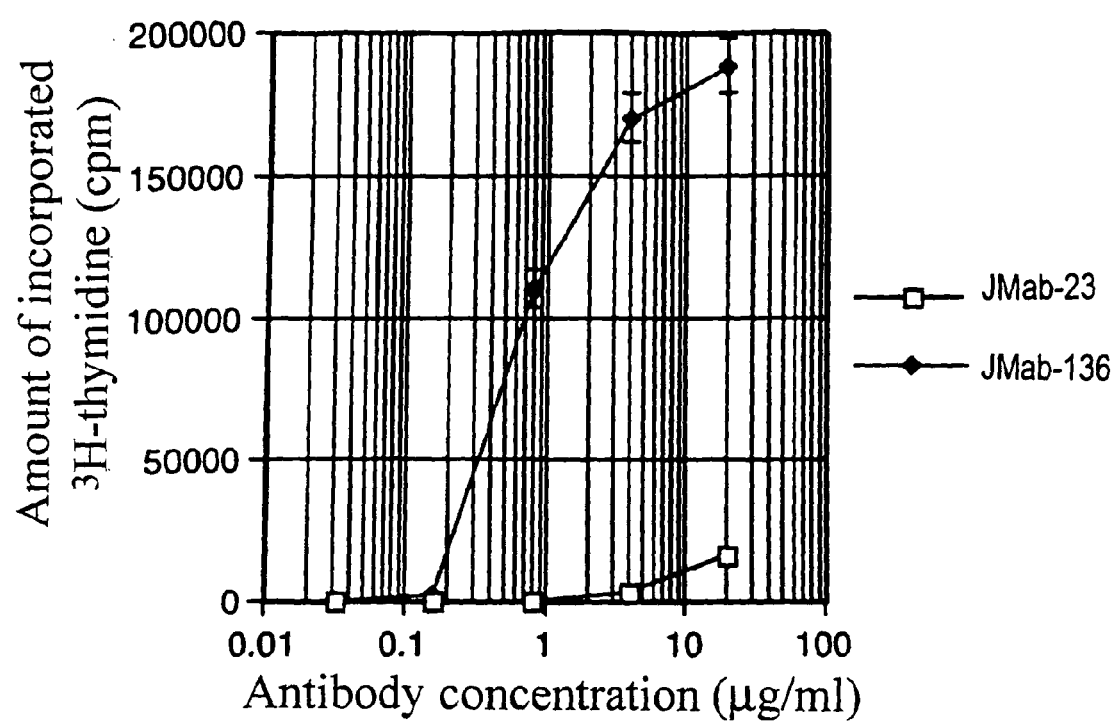

FIG. 73 shows proliferation activity of monkey T cells in the assay to determine the activity of various human anti-human AILIM monoclonal antibodies to transduce costimulatory signal, using a microplate coated with human anti-human AILIM monoclonal antibody together with anti-human CD3 monoclonal antibody.

The vertical axis indicates the amount of cellular incorporation of [$^3$H]thymidine as an index of the degree of cell proliferation, and the horizontal axis indicates the concentration of the human anti-human AILIM monoclonal antibody.

In this figure, "anti-KLH" indicates result of assay in which human anti-KLH monoclonal antibody was used as the negative control, instead of the human anti-human AILIM monoclonal antibody.

Figure 74:
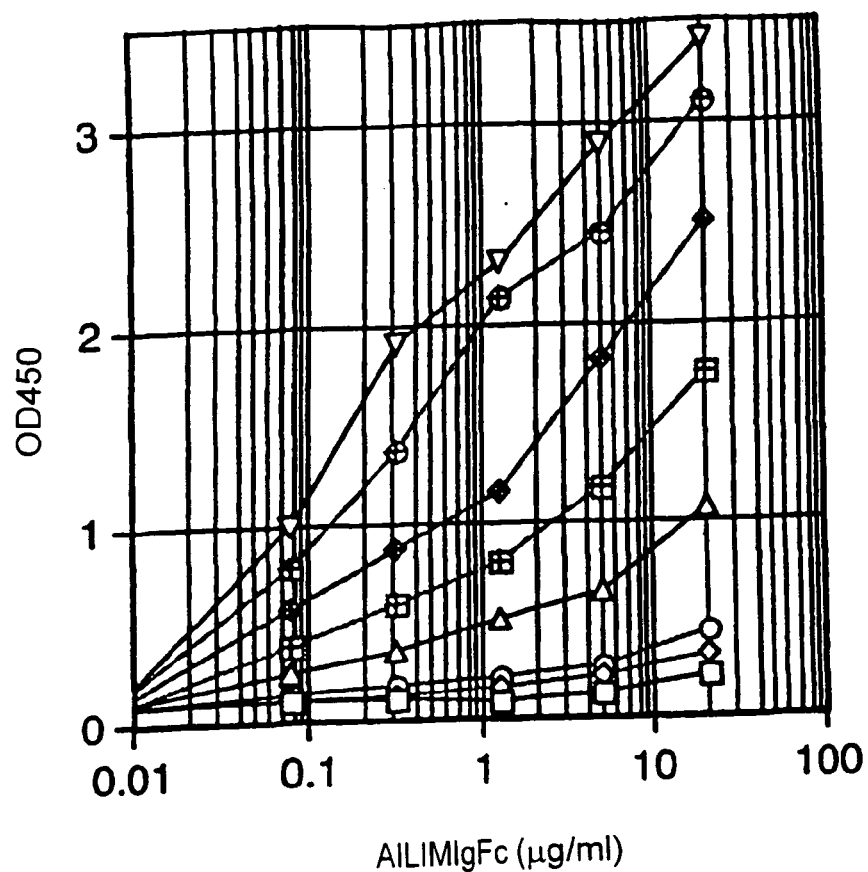

FIG. 74 shows inhibitory activity of the negative control antibody against binding between soluble AILIM ligands (hB7h-IgFc) and soluble AILIM (AILIM-IgFc) of various concentrations.

The vertical axis indicates absorbance as an index for the inhibitory activity, and the horizontal axis indicates the concentration of soluble AILIM.

Figure 75:
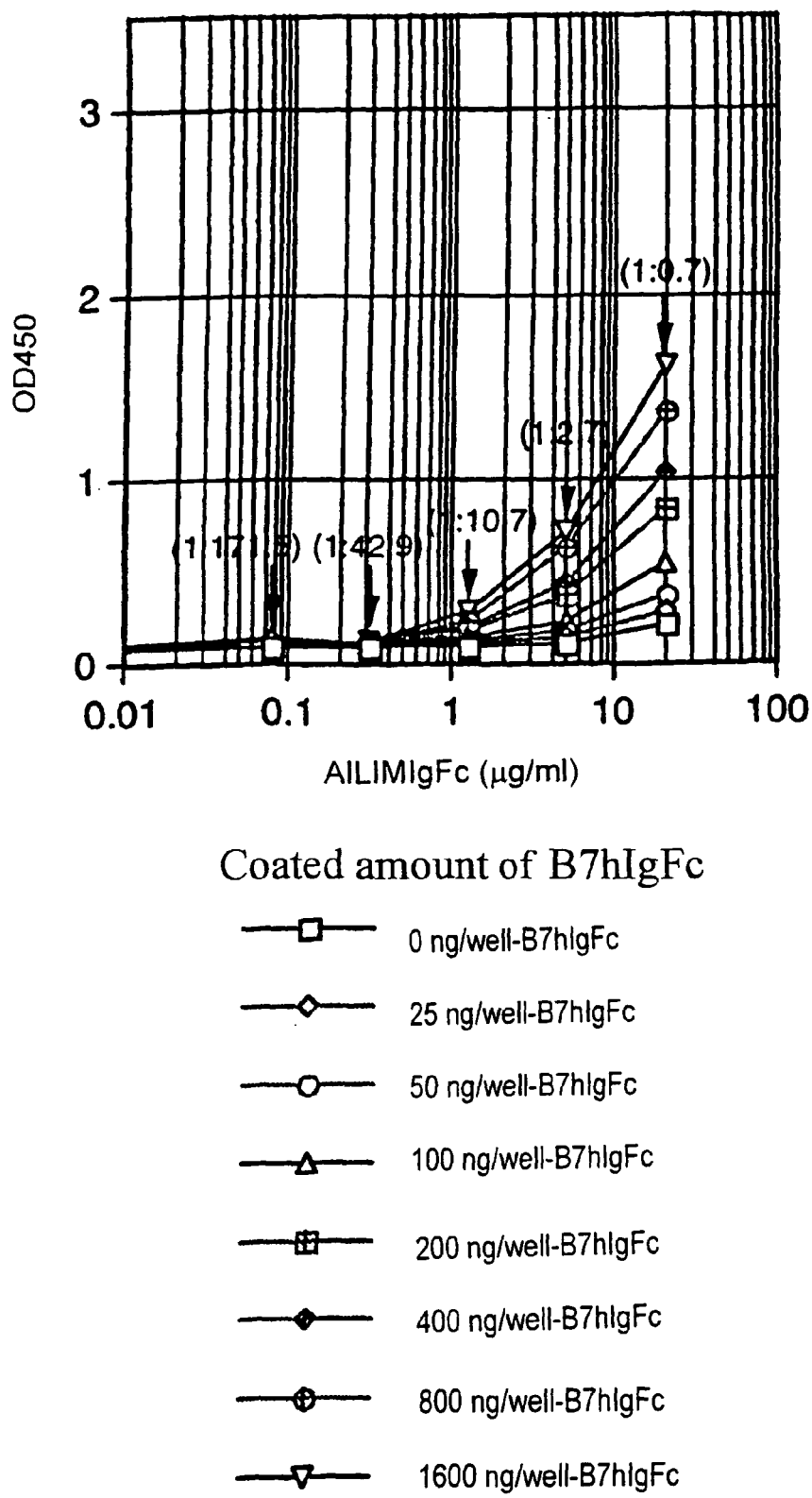

FIG. 75 shows inhibitory activity of anti AILIM antibody against binding between soluble AILIM ligands (hB7h-IgFc) and soluble AILIM (AILIM-IgFc) of various concentrations.

The vertical axis indicates absorbance as an index for the inhibitory activity, and the horizontal axis indicates the concentration of soluble AILIM.

Figure 76:
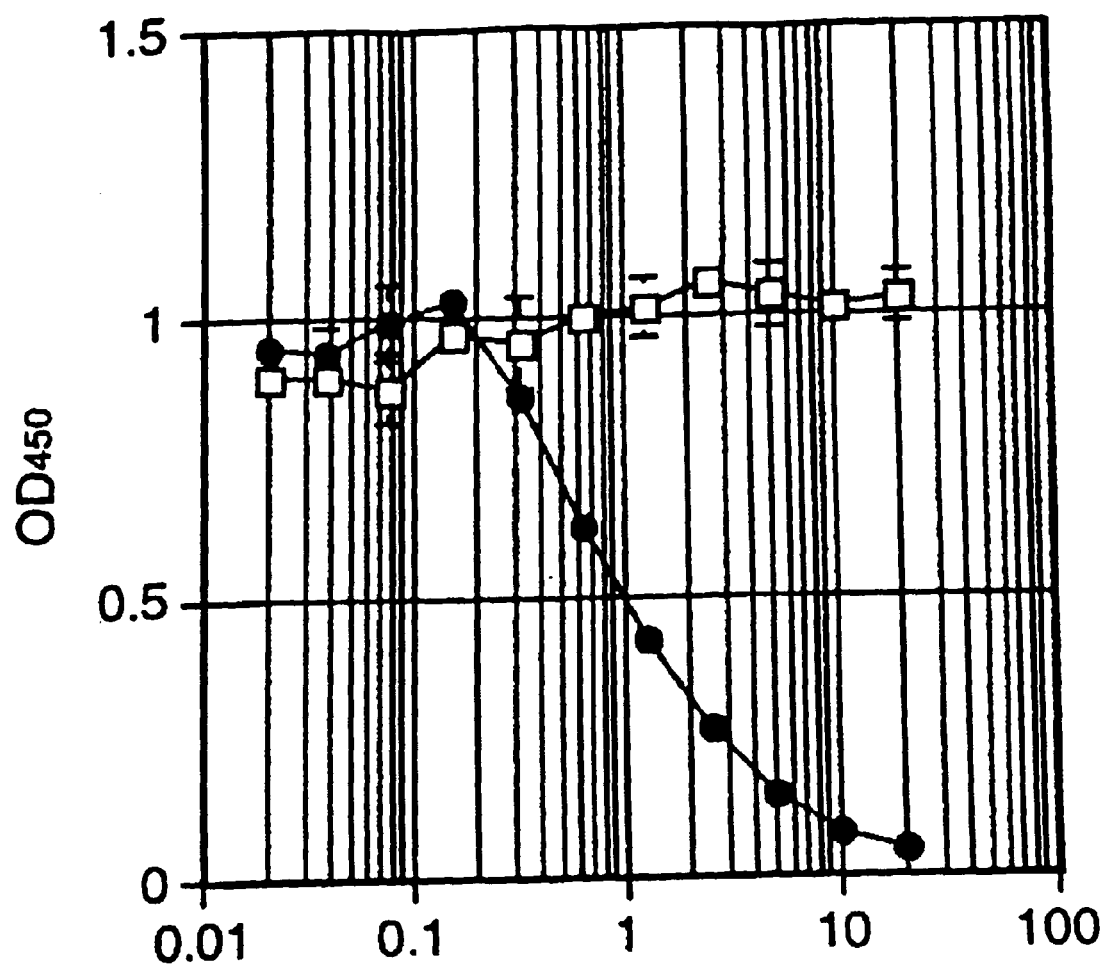

FIG. 76 shows inhibitory activity of anti AILIM antibody at various concentrations against binding between soluble AILIM ligands (hB7h-IgFc) and soluble AILIM (AILIM-IgFc).

The vertical axis indicates absorbance as an index for the inhibitory activity, and the horizontal axis indicates the concentration of soluble AILIM.

Figure 77:
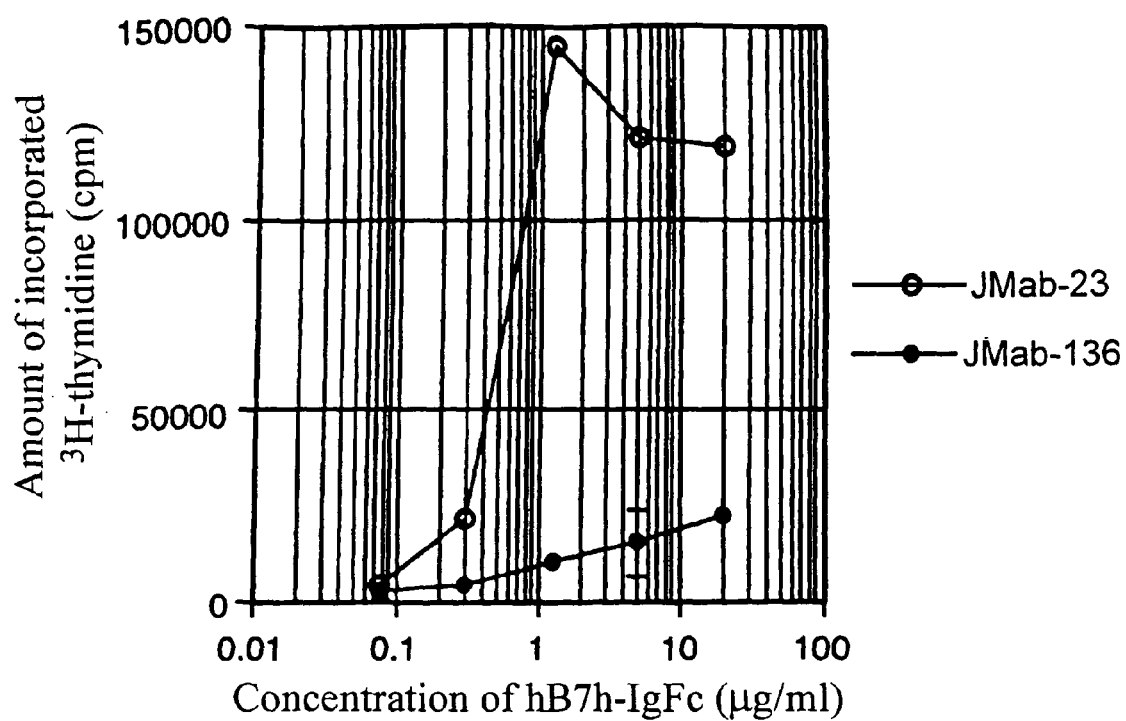

FIG. 77 shows inhibitory activity of various human anti-human AILIM monoclonal antibodies to human T cell proliferation in the assay to determine the activity of transducing costimulatory signal using a microplate coated with soluble human AILIM ligand (hB7h-IgFc) together with anti-human CD3 monoclonal antibody.

The vertical axis indicates the amount of cellular incorporation of [$^3$H]thymidine as an index of the degree of cell proliferation, and the horizontal axis indicates the concentration of antibody.

Figure 78:
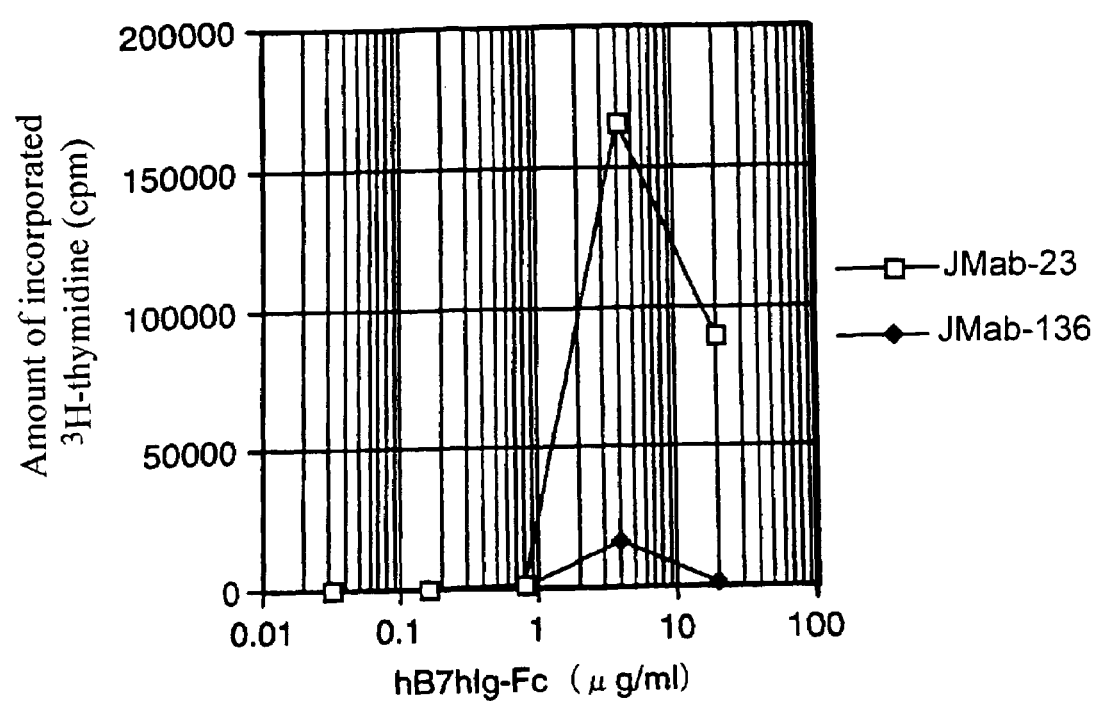

FIG. 78 shows inhibitory activity of various human anti-human AILIM monoclonal antibodies to monkey T cell proliferation in the assay to determine the activity of transducing costimulatory signal using a microplate coated with soluble human AILIM ligand (hB7h-IgFc) together with anti-human CD3 monoclonal antibody.

The vertical axis indicates the amount of cellular incorporation of [$^3$H]thymidine as an index of the degree of cell proliferation, and the horizontal axis indicates the concentration of antibody.

DETAILED DESCRIPTION OF THE INVENTION

The present inventions are described in detail herein below by defining terminologies of the present invention.

Herein, "mammal" means human, bovine, goat, rabbit, mouse, rat, hamster, and guinea pig; preferred is human, rabbit, rat, hamster, or mouse and particularly preferred is human, rat, hamster, or mouse.

The term "mammals other than humans" and "non-human mammals" used herein, are synomic to each other, meaning all mammals other than humans defined above.

The term "amino acids" used herein, means every amino acid existing in nature, preferably those described according to the alphabetical three letters system or single letter system as shown below:

glycine (Gly/G), alanine (Ala/A), valine (Val/V), leucine (Leu/L), isoleucine (Ile/I), serine (Ser/S), threonine (Thr/T), aspartic acid (Asp/D), glutamic acid (Glu/E), asparagine (Asn/N), glutamine (Gln/Q), lysine (Lys/K), arginine (Arg/R), cysteine (Cys/C), methionine (Met/M), phenylalanine (Phe/F), tyrosine (Tyr/Y), tryptophan (Trp/W), histidine (His/H), proline (Pro/P).

The term "AILIM" used herein is the abbreviation for Activation Inducible Lymphocyte Immunomodulatory Molecule, indicating a mammalian cell surface molecule having the structure and function as already described in a previous report, more preferably a human-derived AILIM in particular (for example, International Immunology, Vol. 12, No. 1, p.51–55; GenBank Accession Number: BAA82129 (human), BAA82128 (rat), BAA82127 (rat variant), and BAA82126 (mouse)).

Alternatively, this AILIM is also referred to as ICOS (Unexamined Published Japanese Patent Application (JP-A) No. Hei 11-29599, International Patent Application No. WO98/38216), and these abbreviations indicate the same molecule.

"AILIM ligand" used herein means a cell surface molecule which interacts with said co-stimulatory molecule AILIM (ICOS), and is referred to as B7h, B7RP-1, GL50 or LICOS (Nature, Vol. 402, No. 6763, p.827–832, 1999; Nature Medicine, Vol. 5, No. 12, p.1365–1369, 1999; J. Immunology, Vol. 164, p.1653–1657, 2000; Curr. Biol. Vol. 10, No. 6, p.333–336, 2000).

Moreover, "AILIM" used herein also includes a polypeptide having substantially the same amino acid sequence as that of AILIM of each mammal described in the references, and particularly preferably, that of human AILIM. Furthermore, a human AILIM variant which is similar to the rat AILIM variant already reported (GenBank Accession Number: BAA82127) is also included in "AILIM" of this invention.

"AILIM ligand" used herein is also defined to have a similar meaning as above.

Herein, "polypeptides having essentially identical amino acid sequence" means variant polypeptides as described below.

That is, as long as these variant polypeptides have biological properties essentially equivalent to the natural type AILIM (particularly preferably the human-derived AILIM), they are polypeptides of this invention. Like those having amino acid sequence of the natural type AILIM, in which a plurality of amino acid residues, preferably 1 to 10 amino acid residues, most preferably 1 to 5 amino acid residues are deleted and/or modified, and to which a plurality of amino acid residues, preferably 1 to 10 amino acid residues, most preferably 1 to 5 amino acid residues are added.

Furthermore, they may be variant polypeptides having plurality of these substitution, deletion, modification and addition of amino acid residues in the molecule.

"AILIM ligand" in this invention is also defined to have a similar meaning as above.

AILIM (particularly human AILIM) and AILIM ligand (particularly human AILIM ligand) in this invention can be prepared by, in addition to gene recombinant technique, appropriately using well-known methods in this technical field such as chemical synthesis method, cell culture method, etc. or these methods with modifications.

Such substitution, deletion, or insertion of amino acids can be achieved according to the usual method (Experimental Medicine: SUPPLEMENT, "Handbook of Genetic Engineering" (1992); and so on).

Examples of methods for producing mutant polypeptides as mentioned above are synthetic oligonucleotide site-directed mutagenesis (gapped duplex method), point mutagenesis by which a point mutation is introduced at random by treatment with nitrite or sulfite, the method by which a deletion mutant is prepared with Bal31 enzyme and the like, cassette mutagenesis, linker scanning method, miss incorporation method, mismatch primer method, DNA segment synthesis method, etc.

Synthetic oligonucleotide site-directed mutagenesis (gapped duplex method) can be, for example, performed as follows. The region desired to be mutagenized is cloned into M13 phage vector having amber mutation to prepare the single-stranded phage DNA. After RF I DNA of M13 vector without amber mutation is linearized by restriction enzyme treatment, DNA is mixed with the single-stranded phage DNA mentioned above, denatured, and annealed thereby forming "gapped duplex DNA." A synthetic oligonucleotide into which mutations are introduced is hybridized with the gapped duplex DNA and the closed-circular double-stranded DNAs are prepared by the reactions with DNA polymerase and DNA ligase. E. coli mutS cells, deficient in mismatch repair activity, are transfected with this DNA. E. coli cells without suppressor activity are infected with the grown phages, and only phages without amber mutation are screened.

The method by which a point mutation is introduced with nitrite utilizes, for example the principle as mentioned below. If DNA is treated with nitrite, bases are deaminated to change adenine into hypoxanthine, cytosine into uracil, and guanine into xanthine. If deaminated DNA is introduced into cells, "A:T" and "G:C" are replaced with "G:C" and "A:T", respectively, because hypoxanthine, uracil, and xanthine form a base pair with cytosine, adenine, and thymine, respectively, in the DNA replication. Actually, single-stranded DNA fragments treated with nitrite are hybridized with "gapped duplex DNA", and thereafter mutant strains are separated by manipulating in the same way as synthetic oligonucleotide site-directed mutagenesis (gapped duplex method).

In addition, "AILIM" herein also includes "a portion" of said AILIM. Herein, "a portion" means a polypeptide comprising any partial sequence of the above-defined AILIM amino acid sequence.

Preferably, said portion indicates the extracellular region of above-defined AILIM (particularly preferably a human AILIM) or any portion thereof.

"AILIM ligand" in this invention is also defined to have a similar meaning as above.

"Portion" of said AILIM (preferably the extracellular region of AILIM or any portion thereof) can be prepared according to well-known methods in this technical field as described below or according to their modified methods by genetic recombination technique or chemical synthesis method, or by suitably cleaving AILIM (particularly preferably a human AILIM) isolated by cell culture method using proteolytic enzymes, etc.

"Portion of AILIM ligand" can be also prepared by similar methods as described above.

"Human antibody" of this invention is a human antibody which binds to the above-defined AILIM or a portion thereof (particularly preferably a human-derived AILIM or a portion thereof). Specifically, it means a human-derived polyclonal antibody (human polyclonal antibody, human antiserum) or human-derived monoclonal antibody (human monoclonal antibody).

"Human monoclonal antibody" of this invention is a human monoclonal antibody which binds to the above-defined AILIM or a portion thereof (particularly preferably a human-derived AILIM or a portion thereof).

More specifically, all the regions comprising the variable and constant regions of the heavy chain (H-chain), and the variable and constant regions of the light chain (L-chain) consist of human immunoglobulin derived from gene encoding said human immunoglobulin. L-chain is exemplified by human κ chain or human λ chain.

Human monoclonal antibody which binds to AILIM (particularly preferably a human-derived AILIM) of this invention or a portion thereof is a human monoclonal antibody having characteristic defined in any of aforementioned (5) through (42) or (84).

More specifically, it includes various human monoclonal antibodies having various characteristics and industrial applicability as described in examples and drawings below.

A preferred embodiment of human monoclonal antibody of this invention is a human monoclonal antibody which binds to AILIM or a portion thereof defined in any of aforementioned (5) through (42) or (84).

Most preferable embodiment is a human monoclonal antibody which binds to human AILIM as described in (30) or (39).

"Human monoclonal antibody" of this invention can be prepared by immunizing following transgenic non-human mammals producing human antibody with any of the immunogens (antigens) described below.

(a) a natural cell or artificially established cell line expressing aforementioned AILIM (particularly preferably a human-derived AILIM) on the cell surface;

(b) a genetic recombinant cell prepared using genetic recombination techniques so as to express above-defined AILIM (particularly preferably a human-derived AILIM) on the cell surface;

(c) a cell lysate obtained by solubilizing cells aforementioned in (a) or (b), or a polypeptide fragment of AILIM (particularly preferably a human-derived AILIM) purified from said cell lysate;

(d) a genetic recombinant cell prepared using genetic recombination techniques so as to express a portion (particularly preferably the extracellular region or any preferable peptide thereof) of above-defined AILIM (particularly preferably a human-derived AILIM) as a soluble polypeptide;

(e) a culture supernatant obtained by culturing the genetic recombinant cell aforementioned in (d) or an extracellular region polypeptide (soluble AILIM) of AILIM (particularly preferably a human-derived AILIM) purified from said culture supernatant; or (f) a portion (particularly preferably the extracellular region or any preferable peptide thereof) of chemically synthesized AILIM (particularly preferably a human-derived AILIM).

Furthermore, monoclonal antibody of this invention can be also obtained from culture supernatant by culturing a "genetic recombinant host" [herein, said host is an eukaryotic cell other than fertilized eggs (preferably mammalian cells such as CHO, lymphocytes, and myeloma cells)], which can be prepared by transforming a host with cDNAs (preferably a vector containing said cDNAs) encoding each of the heavy and light chains of such a human monoclonal antibody of this invention using genetic recombination techniques, and which produces genetic recombinant human monoclonal antibody.

Specifically, the monoclonal antibody of this invention can be obtained by culturing genetic recombinant host described in any of aforementioned (60) through (62) or (64) through (80) of this invention (herein, said host is an eukaryotic cell other than a fertilized egg (preferably mammalian cells such as CHO, lymphocytes, and myeloma cells)).

In addition, human monoclonal antibody of this invention may be a human monoclonal antibody having any isotype belonging to IgG (IgG1, IgG2, IgG3 and IgG4), IgH, IgA (IgA1 and IgA2), IgD or IgE. Preferably, said monoclonal antibody belongs to IgG (IgG1, IgG2, IgG3 and IgG4), more preferably IgG1, IgG2 or IgG4.

Human monoclonal antibody of this invention can be prepared by immunizing transgenic non-human mammal producing human antibody such as human antibody-producing transgenic mouse described below with any of the immunogens (antigens) aforementioned in (a) through (f) according to known commonly used manufacturing method.

That is, for example, said transgenic non-human mammal producing human antibody is immunized with said antigen in combination with Freund's adjuvant as the occasion demands. Polyclonal antibody can be obtained from sera collected from said immunized animal. Monoclonal antibody can be manufactured by preparing fusion cells (hybridomas) from said antibody-producing cells isolated from said immunized animal and myeloma cells with no autoantibody-producing ability, and cloning said hybridomas to select a clone producing the monoclonal antibody with a specific affinity to the antigen used for immunizing the mammal.

More specifically, monoclonal antibody can be prepared as described below. That is, said human antibody-producing transgenic non-human mammal (particularly preferably "human antibody-producing transgenic mouse") is immunized by injecting any of the immunogens aforementioned in (a) through (c) intradermally, intramuscularly, intravenously, into the footpad, or intraperitoneally once to several times, or transplanting said immunogen into said mammal. Usually, immunizations are performed once to four times every one to fourteen days after the first immunization. Antibody-producing cells are obtained from the mammal so immunized in about one to five days after the last immunization. The frequency and interval of immunizations can be appropriately arranged depending on, e.g., property of the immunogen used.

Hybridomas that secrete a human monoclonal antibody can be prepared by the method of Köhler and Milstein (Nature, Vol. 256, pp.495–497 (1975)) and by its modified method. Namely, hybridomas are prepared by fusing antibody-producing cells contained in a spleen, lymph node, bone marrow, or tonsil obtained from the human antibody-producing transgenic non-human mammal immunized as mentioned above, preferably a spleen, with myelomas without autoantibody-producing ability, which are derived from, preferably, a mammal such as a mouse, rat, guinea pig, hamster, rabbit, or human, or more preferably, a mouse, rat, or human.

For example, mouse-derived myeloma P3/X63-AG8.653 (ATCC No. CRL-1580), P3/NSI/1-Ag4-1 (NS-1), P3/X63-Ag8. U1 (P3U1), SP2/0-Ag14 (Sp2/0, Sp2), NSO, PAI, F0, or BW5147, rat-derived myeloma 210RCY3-Ag.2.3., or human-derived myeloma U-266AR1, GM1500-6TG-A1-2, UC729-6, CEM-AGR, D1R11, or CEM-T15 can be used as a myeloma used for the cell fusion.

Cells producing monoclonal antibodies (for example, hybridomas) can be screened by cultivating the cells, for example, in microtiter plates and by measuring the reactivity of the culture supernatant in the well in which hybridoma growth is observed, to the immunogen used for the immunization mentioned above, for example, by enzyme immunoassay such as radio immunoassay (RIA) and enzyme-linked immuno-solvent assay (ELISA).

The monoclonal antibodies can be produced from hybridomas by cultivating the hybridomas in vitro or in vivo such as in the ascites fluid of a mouse, rat, guinea pig, hamster, or rabbit, preferably a mouse or rat, more preferably mouse and isolating the antibodies from the resulting the culture supernatant or ascites fluid of a mammal.

Monoclonal antibodies of this invention can be manufactured on a large scale by the following method:

(1) genes (cDNAs, etc.) encoding each of the heavy and light chains of said monoclonal antibody are cloned from said hybridomas;

(2) cloned genes encoding each of the heavy and light chains are inserted into separate vectors or a single vector to prepare the expression vector;

(3) said expression vector is transferred into a fertilized egg of a desired non-human mammal (such as goat);

(4) said fertilized egg transferred with the gene is transplanted into the uterus of a foster mother to obtain a chimeric non-human animal;

(5) by further mating said chimeric goat with another non-human mammal, a transgenic non-human mammal (cattle, goat, sheep or swine) with genes encoding each of said heavy and light chains incorporated into the endogenous gene is produced; and (6) from the milk of said transgenic non-human mammal, monoclonal antibody derived from said human monoclonal antibody gene is obtained on a large scale (Nikkei Science, April, 1997, p.78–84).

Cultivating in vitro the cells producing the monoclonal antibodies can be performed depending on, e.g., the property of cells to be cultured, the object of a test study, and the various conditions of a cultivating method, by using known nutrient media or any nutrient media derived from known basal media for growing, maintaining, and storing the hybridomas to produce monoclonal antibodies in culture supernatant.

Examples of basal media are low calcium concentration media such as Ham'F12 medium, MCDB153 medium, or low calcium concentration MEM medium, and high calcium concentration media such as MCDB104 medium, MEM medium, D-MEM medium, RPMI1640 medium, ASF104 medium, or RD medium. The basal media can contain, for example, sera, hormones, cytokines, and/or various inorganic or organic substances depending on the objective.

Monoclonal antibodies can be isolated and purified from the culture supernatant or ascites fluid mentioned above by saturated ammonium sulfate precipitation, euglobulin precipitation method, caproic acid method, caprylic acid method, ion exchange chromatography (DEAE or DE52), affinity chromatography using anti-immunoglobulin column or protein A column.

Human monoclonal antibody of this invention includes human monoclonal antibodies consisting of the heavy chain and/or light chain of which amino acid sequence for each chain have one or more amino acid residues deleted, substituted or added.

Herein, "more amino acid residues" means a plurality of amino acids, specifically 1 to 10 amino acid residues, preferably 1 to 5 amino acid residues.

A partial modification (deletion, substitution, insertion or addition) as described above can be introduced into the amino acid sequence of human monoclonal antibody of this invention by partial alteration of base sequence encoding said amino acid sequence. This partial alteration of base sequence can be introduced by standard method using known site-specific mutagenesis technique (Proc. Natl. Acad. Sci. USA, Vol. 81, p.5662–5666, 1984).

"Transgenic human antibody-producing non-human mammal", particularly human antibody-producing transgenic mouse which is a preferred embodiment, can be prepared according to published literature (Nature Genetics, Vol. 7, p.13–21, 1994; Nature Genetics, Vol. 15, p.146–156, 1997; Published Japanese Translation of International Publication No. Hei 4-504365; Published Japanese Translation of Publication No. Hei 7-509137; Nikkei Science, June, p.40–50, 1995; International Patent Publication No. WO94/25585; Nature, Vol. 368, p.856–859, 1994; and Published Japanese Translation of Publication No. Hei 6-500233, etc.)

Specifically, said human antibody-producing transgenic mice can be prepared, for example, using techniques consisting of the following processes:

(1) preparing a knockout mouse which endogenous immunoglobulin heavy chain gene is functionally inactivated by substituting at least a portion of gene locus of the mouse endogenous immunoglobulin heavy chain with a drug tolerance marker gene (such as neomycin tolerance gene) by homologous recombination;

(2) preparing a knockout mouse which endogenous immunoglobulin light chain gene (particularly the κ chain gene) is functionally inactivated by substituting at least a portion of gene locus of the mouse endogenous immunoglobulin light chain with a drug tolerance marker gene (such as neomycin tolerance gene) by homologous recombination;

(3) preparing a transgenic mouse which desired region of the human immunoglobulin heavy chain gene locus is incorporated into the mouse chromosome using a vector represented by the yeast artificial chromosome (YAC) capable of carrying a giant gene;

(4) preparing a transgenic mouse which desired region of the human immunoglobulin light chain gene locus (particularly the κ chain gene) is incorporated into the mouse chromosome using a vector represented by the yeast artificial chromosome (YAC) capable of carrying a giant gene; and (5) preparing a transgenic mouse which endogenous immunoglobulin heavy and light chains gene loci are both functionally inactivated and which chromosome is incorporated with the desired regions of both of the human immunoglobulin heavy and light chains gene loci by mating knockout and transgenic mice aforementioned in (1) through (4) in arbitrary orders.

The above-described knockout mouse can be prepared by substituting the suitable region of the mouse endogenous immunoglobulin gene locus with a foreign marker gene (such as neomycin tolerance gene) based on homologous recombination to inactivate said gene locus so as not to be rearranged. For the inactivation using said homologous recombination, for example, a method referred to as positive negative selection (PNS) can be used (Nikkei Science, May, p.52–62, 1994).

Functional inactivation of the immunoglobulin heavy chain gene locus can be achieved, for example, by introducing a lesion into a part of the J- or C-region (for example, Cµ region). And functional inactivation of the immunoglobulin light chain (for example, κ chain) can be achieved, for example, by introducing a lesion into a part of J- or C-region, or a region extending over J- and C-regions.

A transgenic mouse can be prepared according to the method as usually used for producing a transgenic animal (for example, see "Newest Manual of Animal Cell Experiment", LIC press, Chapter 7, pp.361–408, (1990)). Specifically, for example, the HPRT-negative (hypoxanthine-guanine phosphoribosyltransferase gene deficient) ES cell (embryonic stem cell) derived from a normal mouse blastocyst is fused with yeast containing the YAC vector inserted with the gene encoding said human immunoglobulin heavy chain gene locus or light chain gene locus or a portion thereof and the HPRT gene using spheroplast fusion method. ES cells whose mouse endogenous gene is integrated with said foreign gene are selected by HAT selection method. Then, the ES cells screened are microinjected into a fertilized egg obtained from another normal mouse (blastocyst) (Proc. Natl. Acad. Sci. USA, Vol.77, No.12, pp.7380–7384 (1980); U.S. Pat. No. 4,873,191). The blastocyst is transplanted into the uterus of another normal mouse as the foster mother. Then, chimeric transgenic mice are born from the foster mother mouse. By mating the chimeric transgenic mice with normal mice, heterogeneic transgenic mice are obtained. By mating the heterogeneic transgenic mice with each other, homogeneic transgenic mice are obtained according to Mendel's laws.

The "portion of a monoclonal antibody" used in the present invention means a partial region of the above-mentioned human monoclonal antibody of the present invention, and specifically, includes F(ab')$_2$, Fab', Fab, Fv (variable fragment of antibody), sFv, dsFv (disulfide stabilized Fv), or dAb (single domain antibody) (Exp. Opin. Ther. Patents, Vol.6, No.5, pp.441–456 (1996)).

"F(ab')$_2$" and "Fab'" can be produced by treating immunoglobulin (monoclonal antibody) with a protease such as pepsin and papain, and means an antibody fragment generated by digesting immunoglobulin near the disulfide bonds in the hinge regions existing between each of the two H chains. For example, papain cleaves IgG upstream of the disulfide bonds in the hinge regions existing between each of the two H chains to generate two homologous antibody fragments in which an L chain composed of $V_L$ (L chain variable region) and $C_L$ (L chain constant region), and an H chain fragment composed of $V_H$ (H chain variable region) and $C_H\gamma 1$ (γ1 region in the constant region of H chain) are connected at their C terminal regions through a disulfide bond. Each of such two homologous antibody fragments is called Fab'. Pepsin also cleaves IgG downstream of the disulfide bonds in the hinge regions existing between each of the two H chains to generate an antibody fragment slightly larger than the fragment in which the two above-mentioned Fab' are connected at the hinge region. This antibody fragment is called F(ab')$_2$.

"Binding rate constant (ka)" herein means a value indicating the binding strength (degree) of said monoclonal antibody to the target antigen calculated based on the antibody antigen reaction kinetics. "Dissociation rate constant (kd)" means a value indicating the dissociation strength (degree) of said monoclonal antibody from the target antigen. "Dissociation constant (Kd)" is a value obtained by dividing said "dissociation rate constant (kd)" by said "binding rate constant (ka)" value. These constants are used to represent the affinity of said monoclonal antibody to antigen and its activity to neutralize antigen.

Said constants can be analyzed according to various methods, and can be easily analyzed using a commercial assay kit BiacoreX (Amersham Pharmacia) or a similar kit according to the manual and experimental method attached to said kit. ka, kd and Kd values obtained using said kit are expressed in 1/M.Sec, 1/Sec and M (mol) units, respectively. Higher ka values indicate stronger antigen binding activity of monoclonal antibody tested, and smaller Kd values show stronger antigen neutralizing activity of antibody.

Human monoclonal antibody of this invention includes those having the ka, kd or Kd value as shown in following (1) through (3):

(1) human monoclonal antibody which binds to human AILIM or a portion thereof with the binding rate constant (ka) of $1.0 \times 10^4$ (1/M.Sec) or more, preferably $1.0 \times 10^5$ (1/M.Sec) or more.

(2) human monoclonal antibody which binds to human AILIM or a portion thereof with the dissociation rate constant (kd) of $1.0 \times 10^{-4}$ (1/Sec) or less, preferably $1.0 \times 10^{-5}$ (1/Sec) or less.

(3) human monoclonal antibody which has a reactivity to human AILIM or a portion thereof with the dissociation constant (Kd) of $1.0 \times 10^{-7}$ (M) or less, preferably $1.0 \times 10^{-8}$ (M) or less and more preferably $1.0 \times 10^{-9}$ (M) or less.

In this case, each value of ka, kd and Kd described above is expected to slightly fluctuate depending on various conditions at the time of measurement with a margin of error but with practically no fluctuation in indexes in general.

"Monoclonal antibody-producing cell" or genetic recombinant human monoclonal antibody-producing "genetic recombinant host" of this invention (herein, said host is a cell excluding fertilized egg) means any cell producing aforementioned human monoclonal antibody of this invention.

Specifically, for example, it includes cells described in any of following (1) through (3), but is not limited to them:

(1) human monoclonal antibody-producing B cell obtained by immunizing aforementioned human antibody-producing transgenic non-human mammal with the above-defined immunogen (antigen) and collecting the cell from said immunized animal.

(2) aforementioned fusion cell (hybridoma) resulted by fusion of the human monoclonal antibody-producing B cell thus obtained with a myeloma cell derived from mammal.

(3) genetic recombinant human monoclonal antibody-producing genetic recombinant cell obtained by transforming a cell excluding said B cell and hybridoma (for example, CHO (chinese hamster ovarian) cell, BHK (baby hamster kidney) cell, lymphocyte such as myeloma) with the gene encoding said human monoclonal antibody (gene encoding the heavy chain or that encoding the light chain, or both genes) isolated from said human monoclonal antibody-producing B cell or human monoclonal antibody-producing fusion cell (hybridoma).

Herein, the genetic recombinant human monoclonal antibody-producing genetic recombinant cell aforementioned in (3) namely means a genetic recombinant cell producing the genetic recombinant of human monoclonal antibody generated by the B cell described above in (1) or the hybridoma aforementioned in (2).

And, "host" in "genetic recombinant host" of this invention includes, in addition to various mammalian cells as described above, fertilized eggs of any non-human mammals (goat, swine, sheep, cattle, etc.). By transferring a gene (gene encoding the heavy chain or that encoding the light chain, or both genes) encoding any monoclonal antibody (preferably human monoclonal antibody) to human AILIM of this invention into this fertilized egg, a genetic recombinant fertilized egg of this invention can be obtained. This genetic recombinant fertilized egg is used to prepare transgenic animals for manufacturing the aforementioned protein from the milk on a large scale (Nikkei Science, April, 1997, p.78–84).

"A substance" composing the present invention, specifically "a substance having an activity in modulating the signal transduction mediated by AILIM", and more specifically "a substance having an activity in inhibiting proliferation of AILIM-expressing cells, or in inhibiting production of a cytokine by AILIM-expressing cells" means a natural substance present in the nature, or a artificially prepared arbitrary substance.

"Substance" related to "substance binding to AILIM" and "substance binding to AILIM ligand" herein also means any natural substance in nature or any artificially prepared substance.

Here, "the signal transduction mediated by AILIM" means the signal transduction through AILIM, leading to a change of an arbitrary phenotype in the AILIM-expressing cells (cell proliferation, activation of cells, inactivation of cells, apoptosis, and/or a change of an ability for producing an arbitrary cytokine from AILIM-expressing cells).

"The substance" can be mainly classified into "a protein substance" and "a non-protein substance".

Examples of the "protein substances" are the following polypeptide, antibody (a polyclonal antibody, a monoclonal antibody, or a portion of a monoclonal antibody, and particularly preferably the human antibody mentioned above).

When the substance is an antibody, the substance is preferably a monoclonal antibody. When the substance is a monoclonal antibody, the substance includes not only a non-human mammal derived monoclonal antibody, but also a recombinant chimeric monoclonal antibody, a recombinant humanized monoclonal antibody and human monoclonal antibody.

Here, the "recombinant chimeric monoclonal antibody" is a monoclonal antibody prepared by genetic engineering, and specifically means a chimeric antibody such as mouse/human chimeric monoclonal antibody whose variable regions are derived from immunoglobulin of an non-human mammal (mouse, rat, hamster, etc.) and whose constant regions are derived from human immunoglobulin.

The "humanized monoclonal antibody (CDR-grafted antibody)" of the present invention is a monoclonal antibody prepared by genetic engineering and specifically means a humanized monoclonal antibody wherein a portion or the whole of the complementarity determining regions of the hypervariable region are derived from the complementarity determining regions of the hypervariable region from a monoclonal antibody of an non-human mammal (mouse, rat, hamster, etc.), the framework regions of the variable region are derived from the framework regions of the variable region from human immunoglobulin, and the constant region is derived from human a constant region from immunoglobulin.

The complementarity determining regions of the hypervariable region exists in the hypervariable region in the variable region of an antibody and means three regions which directly and complementary binds to an antigen (complementarity-determining residues, CDR1, CDR2, and CDR3). The framework regions of the variable region mean four comparatively conserved regions lying upstream, downstream or between the three complementarity determining regions (framework region, FR1, FR2, FR3, and FR4).

In other words, a humanized monoclonal antibody means that in which all the regions except a portion or the whole of the complementarity determining regions of the hypervariable region of a non-human mammal-derived monoclonal antibody have been replaced with their corresponding regions derived from a human immunoglobulin.

The constant region derived from human immunoglobulin has the amino acid sequence inherent in each isotype such as IgG (IgG1, IgG2, IgG3, IgG4), IgM, IgA, IgD, and IgE. The constant region of a humanized monoclonal antibody in the present invention can be that from human immunoglobulin belonging to any isotype. Preferably, it is the constant region of human IgG. The framework regions of the constant region derived from human immunoglobulin are not particularly limited.

When the substance of the present invention is a polypeptide, the substance includes the following polypeptide, a fragment of the polypeptide (an oligopeptide), a fusion polypeptide, a chemically modified one thereof. Examples of an oligopeptide are a peptide comprising 5 to 30 amino acids, preferably 5 to 20 amino acids. The chemical modification can be designed depending on various purposes, for example, the increased half-life in blood in the case of administering in vivo, or the increased tolerance against the degradation or increased absorption in digestive tract at the oral administration.

Examples of the polypeptide are as follows:
(1) A polypeptide comprising the whole or a portion of an extracellular region of AILIM;
(2) A fusion polypeptide comprising the whole or a portion of an extracellular region of AILIM and the whole or a portion of a constant region of immunoglobulin heavy chain; or
(3) A polypeptide which binds to AILIM.

Examples of the "non-protein" are DNA, RNA, and a chemically synthesized compound.

Here, "DNA" means "DNA comprising a partial nucleotide sequence of the DNA or chemically modified DNA thereof" useful as an antisense DNA pharmaceutical designed based on a nucleotide sequence of DNA (including cDNA and genomic DNA) encoding the above AILIM (preferably human AILIM). Specifically the antisense DNA can inhibit transcription of DNA encoding the AILIM into mRNA, or translation of the mRNA into a protein by hybridizing DNA or RNA encoding AILIM.

The "partial nucleotide sequence" as referred to here indicates a partial nucleotide sequence comprising an arbitrary number of nucleotides in an arbitrary region. The partial nucleotide sequence consists of 5 to 100 consecutive nucleotides, preferably 5 to 70 consecutive nucleotides, more preferably 5 to 50 consecutive nucleotides, and still more preferably 5 to 30 consecutive nucleotides.

When the DNA is used as an antisense DNA pharmaceutical, the DNA sequence can be modified chemically in part for extending the half-life (stability) of the blood concentration of the DNA administered to patients, for increasing the intracytoplasmic-membrane permeability of the DNA, or for increasing the degradation resistance or the absorption of the orally administered DNA in the digestive organs. The chemical modification includes, for example, the modification of the phosphate bonds, the riboses, the nucleotide bases, the sugar moiety, the 3' end and/or the 5' end in the structure of the oligonucleotide DNA.

The modification of phosphate bond includes, for example, the conversion of one or more of the bonds to phosphodiester bonds (D-oligo), phosphorothioate bonds, phosphorodithioate bonds (S-oligo), methyl phosphonate (MP-oligo), phosphoroamidate bonds, non-phosphate bonds or methyl phosphonothioate bonds, or combinations thereof. The modification of the ribose includes, for example, the conversion to 2'-fluororibose or 2'-O-methylribose. The modification of the nucleotide base includes, for example, the conversion to 5-propynyluracil or 2-aminoadenine.

Here, "RNA" means "RNA comprising a partial nucleotide sequence of the RNA or chemically modified RNA thereof" useful as an antisense RNA pharmaceutical designed based on a nucleotide sequence of RNA encoding the above AILIM (preferably human AILIM). The antisense RNA can inhibit transcription of DNA encoding the AILIM into mRNA, or translation of the mRNA into a protein by hybridizing DNA or RNA encoding AILIM.

The "partial nucleotide sequence" as referred to here indicates a partial nucleotide sequence comprising an arbitrary number of nucleotides in an arbitrary region. The partial nucleotide sequence consists of 5 to 100 consecutive nucleotides, preferably 5 to 70 consecutive nucleotides, more preferably 5 to 50 consecutive nucleotides, and still more preferably 5 to 30 consecutive nucleotides.

The sequence of antisense RNA can be modified chemically in part for extending the half-life (stability) of the blood concentration of the RNA administered to patients, for increasing the intracytoplasmic-membrane permeability of the RNA, or for increasing the degradation resistance or the absorption of the orally administered RNA in the digestive organ. An example of chemical modification is the chemical modification applied to the above antisense DNA.

Examples of "a chemically synthesized compound" are an arbitrary compound except for the above DNA, RNA and protein substances, having the molecular weight of about 100 to about 1000, preferably a compound having the molecular weight of about 100 to about 800, and more preferably the molecular weight of about 100 to about 600.

A "polypeptide" included in the definition of the above "substance" means a portion (a fragment) of a polypeptide chain constituting AILIM (preferably human AILIM), preferably the whole or a portion of an extracellular region of the polypeptide constituting AILIM (1 to 5 amino acids may be optionally added into the N-terminus and/or C-terminus of the region).

AILIM involving in the present invention is a transmembrane molecule penetrating cell membrane, comprising 1 or 2 polypeptide chains.

Here, a "transmembrane protein" means a protein that connects with membrane through the hydrophobic peptide region penetrating the lipid bilayer of the membrane once or several times and whose structure is, as a whole, composed of three main regions, that is, extracellular region, transmembrane region, and cytoplasmic region, as seen in many receptors or cell surface molecules. Such a transmembrane protein constitutes each receptor or cell surface molecule in the form of a monomer, homodimer, heterodimer or oligomer with another chain(s) having the same or different amino acid sequence.

Here, an "extracellular region" means the whole or a portion from the partial structure (partial region) from the entire structure of the above-mentioned transmembrane protein where the partial structure exists outside of the membrane. In other words, it means the whole or a portion of the region of the transmembrane protein except the region incorporated into the membrane (transmembrane region) and the region existing in the cytoplasm following the transmembrane region (cytoplasmic region).

"A fusion polypeptide" included in the above "protein substance" means a fusion polypeptide comprising the whole or a portion of an extracellular region of a polypeptide constituting AILIM (preferably human AILIM), and "the whole or a portion of a constant region of immunoglobulin heavy chain (Ig, preferably human Ig)". Preferably, the fusion polypeptide is a fusion polypeptide with an extracellular region of AILIM and a portion of a constant region of human IgG heavy chain and particularly preferably, a fusion polypeptide of an extracellular region of AILIM and a region (Fc) of human IgG heavy chain comprising a hinge region, CH2 domain and CH3 domain. As IgG, IgG1 is preferable, and as AILIM, human, mouse, or rat AILIM is preferable (preferably human).

"The whole or a portion of a constant region of human immunoglobulin (Ig) heavy chain" used herein means the constant region or the Fc region of human-derived immunoglobulin heavy chain (H chain) as described, or a portion thereof. The immunoglobulin can be any immunoglobulin belonging to any class and any subclass. Specifically, examples of the immunoglobulin are IgG (IgG1, IgG2, IgG3, and IgG4), IgM, IgA (IgA1 and IgA2), IgD, and IgE. Preferably, the immunoglobulin is IgG (IgG1, IgG2, IgG3, or IgG4), or IgM. Examples of particularly preferable immunoglobulin of the present invention are those belonging to human-derived IgG (IgG1, IgG2, IgG3, or IgG4).

Immunoglobulin has a Y-shaped structural unit in which four chains composed of two homologous light chains (L chains) and two homologous heavy chains (H chains) are connected through disulfide bonds (S—S bonds). The light chain is composed of the light chain variable region ($V_L$) and the light chain constant region ($C_L$). The heavy chain is composed of the heavy chain variable region ($V_H$) and the heavy chain constant region ($C_H$).

The heavy chain constant region is composed of some domains having the amino acid sequences inherent in each class (IgG, IgM, IgA, IgD, and IgE) and each subclass (IgG1, IgG2, IgG3, and IgG4, IgA1, and IgA2).

The heavy chain of IgG (IgG1, IgG2, IgG3, and IgG4) is composed of VH, CH1 domain, hinge region, CH2 domain, and CH3 domain in this order from N terminus.

Similarly, the heavy chain of IgG1 is composed of $V_H$, $C\gamma_1 1$ domain, hinge region, $C\gamma_1 2$ domain, and $C\gamma_1 3$ domain in this order from N terminus. The heavy chain of IgG2 is composed of $V_H$, $C\gamma_2 1$ domain, hinge region, $C\gamma_2 2$ domain, and $C\gamma_2 3$ domain in this order from N terminus. The heavy chain of IgG3 is composed of $V_H$, $C\gamma_3 1$ domain, hinge region, $C\gamma_3 2$ domain, and $C\gamma_3 3$ domain in this order from N terminus. The heavy chain of IgG4 is composed of $V_H$, $C\gamma_4 1$ domain, hinge region, $C\gamma_4 2$ domain, and $C\gamma_4 3$ domain in this order from N terminus.

The heavy chain of IgA is composed of $V_H$, $C\alpha 1$ domain, hinge region, $C\alpha 2$ domain, and $C\alpha 3$ domain in this order from N terminus.

Similarly, the heavy chain of IgA1 is composed of $V_H$, $C\alpha_1 1$ domain, hinge region, $C\alpha_1 2$ domain, and $C\alpha_1 3$ domain in this order from N terminus. The heavy chain of IgA2 is composed of $V_H$, $C\alpha_2 1$ domain, hinge region, $C\alpha_2 2$ domain, and $C\alpha_2 3$ domain in this order from N terminus.

The heavy chain of IgD is composed of $V_H$, $C\delta 1$ domain, hinge region, $C\delta 2$ domain, and $C\delta 3$ domain in this order from N terminus.

The heavy chain of IgM is composed of $V_H$, $C\mu 1$ domain, $C\mu 2$ domain, $C\mu 3$ domain, and $C\mu 1$ domain in this order from N terminus and have no hinge region as seen in IgG, IgA, and IgD.

The heavy chain of IgE is composed of $V_H$, $C\epsilon 1$ domain, $C\epsilon 2$ domain, $C\epsilon 3$ domain, and $C\epsilon 4$ domain in this order from N terminus and have no hinge region as seen in IgG, IgA, and IgD.

If, for example, IgG is treated with papain, it is cleaved at the slightly N terminal side beyond the disulfide bonds existing in the hinge region where the disulfide bonds connect the two heavy chains to generate two homologous Fab, in which a heavy chain fragment composed of $V_H$ and CH1 is connected with one light chain through a disulfide bond, and one Fc, in which two homologous heavy chain fragments composed of the hinge region, CH2 domain, and CH3 domain are connected through disulfide bonds (See "Immunology Illustrated", original 2nd ed., Nankodo, pp.65–75 (1992); and "Focus of Newest Medical Science 'Recognition Mechanism of Immune System'", Nankodo, pp.4–7 (1991); and so on).

Namely, "a portion of a constant region of immunoglobulin heavy chain" mentioned above means a portion of a constant region of an immunoglobulin heavy chain having the structural characteristics as mentioned above, and preferably, is the constant region without C1 domain, or the Fc region. Specifically, example thereof is the region composed of hinge region, C2 domain, and C3 domain from each of IgG, IgA, and IgD, and is the region composed of C2 domain, C3 domain, and C4 domain from each of IgM and IgE. A particularly preferable example thereof is the Fc region of human-derived IgG1.

The fusion polypeptide mentioned above has the advantage that the fusion polypeptide can be purified extremely easily by using affinity column chromatography using the property of protein A, which binds specifically to the immunoglobulin fragment because the fusion polypeptide of the present invention has a portion of a constant region (for example Fc) of an immunoglobulin such as IgG as mentioned above as a fusion partner. Moreover, since various antibodies against the Fc of various immunoglobulins are available, an immunoassay for the fusion polypeptides can be easily performed with antibodies against the Fc.

"A polypeptide which binds to AILIM" is included in "a polypeptide" included in the definition of the above "substance".

Specific examples of "a polypeptide which binds to AILIM" are the whole or a portion of a polypeptide constituting known B7h, B7RP-1, GL50 or a molecule called LICOS which are ligands interacting with AILIM (Nature, Vol.402, No.6763, pp.827–832, 1999; Nature Medicine, Vol.5, No.12, pp.1365–1369, 1999; J. Immunology, Vol.164, pp.1653–1657, 2000; Curr. Biol., Vol.10 No 6, pp.333–336, 2000).

Preferably, the polypeptide is a polypeptide comprising the whole or a portion of an extracellular region of the above ligands (B7h, B7RP-1, GL50, LICOS), or a fusion polypeptide comprising the polypeptide, and the whole or a portion of a constant region of immunoglobulin heavy chain (preferably human immunoglobulin). Here, the terms "an extracellular region" and "a constant region of immunoglobulin heavy chain" have the same meaning as the above.

The polypeptide, a portion of the polypeptide (fragment), and fusion polypeptide mentioned above can be produced not only by recombinant DNA technology as mentioned below but also by a method well known in the art such as a chemical synthetic method and a cell culture method, or a modified method thereof.

The "antibody" of the present invention can be a polyclonal antibody (antiserum) or a monoclonal antibody against mammalian AILIM (particularly preferably human AILIM) defined above, and preferably a monoclonal antibody.

Specifically the antibody is an antibody having an activity in inhibiting proliferation of AILIM-expressing cells by biding to AILIM, or inhibiting production of interferon γ or interleukin 4 by AILIM-expressing cells through biding to AILIM.

"Delayed type allergy" herein this allergy mediated by cellular immunity (particularly mediated by Th1-type T cell), that is, the allergy is mediated by T cell sensitized with antigen (memory T cell memorizing antigen) and is referred to any allergy, which takes approximately 24 to 48 hours to exhibit allergic reaction accompanied with inflammation caused by said memory T cell when the living organism sensitized with an antigen is re-contacted with the same antigen.

This delayed type allergy includes allergy to an infectious pathogenic antigen such as tuberculin allergy derived from *Mycobacterium tuberculosis*, a transient Jones-Mote delayed type allergy to a minute quantity of protein, contact allergy to chemicals such as picryl chloride or plant toxin such as lacquer, or allergy related to graft rejection to graft observed in the allograft.

"Pharmaceutical composition" herein means a composition useful as a drug comprising as the effective ingredients antibody (preferably human antibody), which binds to AILIM (preferably human AILIM) or a portion thereof, or monoclonal antibody (preferably human monoclonal antibody) or a portion thereof and a "pharmacologically acceptable carrier".

The "pharmaceutically acceptable carrier" includes a excipient, a diluent, an expander, a decomposition agent, a stabilizer, a preservative, a buffer, an emulsifier, an aromatic, a colorant, a sweetener, a viscosity increasing agent, a flavor, a solubility increasing agent, or other additives.

Using one or more of such carriers, a pharmaceutical composition can be formulated into tablets, pills, powders, granules, injections, solutions, capsules, troches, elixirs, suspensions, emulsions, or syrups.

The pharmaceutical composition can be administered orally or parenterally. Other forms for parenteral administration include a solution for external application, suppository for rectal administration, and pessary, prescribed by the usual method, which comprises one or more active ingredient.

The dosage can vary depending on the age, sex, weight, and symptom of a patient, effect of treatment, administration route, period of treatment, or the kind of active ingredient (polypeptide or antibody mentioned above) contained in the pharmaceutical composition. Usually, the pharmaceutical composition can be administered to an adult in a dose of 10 μg to 1000 mg (or 10 μg to 500 mg) per one administration. Depending on various conditions, the dosage less than that mentioned above may be sufficient in some cases, and the dosage more than that mentioned above may be necessary in other cases.

In particular, the injection can be produced by dissolving or suspending the antibody in a non-toxic, pharmaceutically acceptable carrier such as physiological saline or commercially available distilled water for injection with adjusting a concentration to 0.1 µg antibody/ml carrier to 10 mg antibody/ml carrier.

The injection thus produced can be administered to a human patient in need of treatment in a dose of 1 µg to 100 mg/kg body weight, preferably 50 µg to 50 mg/kg body weight once or more times a day. Examples of administration route are medically appropriate administration routes such as intravenous injection, subcutaneous injection, intradermal injection, intramuscular injection, or intraperitoneal injection, preferably intravenous injection.

The injection can also be prepared into a non-aqueous diluent (for example, propylene glycol, polyethylene glycol, vegetable oil such as olive oil, and alcohol such as ethanol), suspension, or emulsion.

The injection can be sterilized by filtration with a bacteria-non-penetrated filter, by mixing bacteriocide, or by irradiation. The injection can be produced in the form that is prepared upon use. Namely, it is freeze-dried to be a sterile solid composition, and can be dissolved in sterile distilled water for injection or another solvent before use.

Pharmaceutical compositions comprising the human antibodies of this invention are useful as pharmaceutical preparations, without inducing host immunorejection due to HAMA (human anti-mouse antibody), to control a variety of biological reactions (e.g., proliferation of cells expressing AILIM, cytokine production by cells expressing AILIM, immune cytolysis or death (apoptosis) of cells expressing AILIM and others) that are associated with AILIM-mediated transduction of costimulatory signal (secondary signal) to AILIM-expressing cells, and/or as pharmaceutical preparations to treat or prevent various diseases by suppressing and inhibiting the onset and/or progress of diseases associated with AILIM-mediated signal transduction.

The term "immune cytolysis" herein indicates a biological phenomenon as follows.

Lysis of the cell (cytolysis) can be induced by an antibody (particularly cell-lysing antibody) as well as by binding with killer cells. The cell-lysing antibody is a cytotoxic antibody, which particularly has lysing activity on cells such as immune cells, tissue cell or sperms. When the antibody binds to the cell-surface antigen, it causes a cytotoxic effect on the cell or induces cytolysis in the presence of the complement.

This immune cytolysis is induced by the action of the complement in conjunction with specific binding of the antibody to cell-surface antigen. The antibody bound to the surface antigen activates C1 complement (C1). Subsequently cell damage sites are formed through a series of complement-fixation reactions with C2 to C9 complements ($C_2$–$C_9$), and then cellular contents are released from the cells thereby lysing the cells.

The term "antibody-dependent cellular cytotoxicity" herein indicates a biological event that is also abbreviated as "ADCC," and is a cytotoxic action on target cells by effector cells such as lymphocytes, macrophages or polymorphonuclear leucocytes, which requires not only effector cells and target cells but also an antibody participating in the induction of the cytotoxic event.

The term "mixed lymphocyte reaction" herein means a biological phenomenon abbreviated as "MLR." The reaction is also referred to as mixed leukocyte reaction.

Allogenic leukocytes or lymphocytes derived from distinct individuals are mixed with each other and cultured for several days, thereby allowing blast formation of the cells and DNA synthesis in the cells (i.e., cell proliferation). This reaction is referred to as MLR (allogenic MLR).

DNA synthesis (cell proliferation) can be analyzed by arresting proliferation of either of the lymphocytes. The arrest can be accomplished by treatment with irradiation or mitomycin. Analysis can be carried out by measuring the amount of DNA synthesized in the other lymphocyte.

The amount of synthesized DNA can be analyzed by measuring incorporation of thymidine, labeled with radioisotope such as tritium, into the nucleus of the cell.

DNA encoding AILIM (particularly preferably human AILIM) of the present invention can be obtained according to a commonly used method by using procedures for cloning cDNA from mRNA encoding AILIM; procedure for isolating genomic DNA and splicing them; procedure for preparing the DNA by PCR using a cDNA sequence or mRNA sequence as a template; or procedure for chemically synthesizing the DNA.

DNA encoding the AILIM ligand in accordance with the present invention can also be obtained in the same manner as described above.

DNA encoding AILIM (particularly preferably the human AILIM) of the present invention can be prepared by cutting (digesting) DNA comprising DNA encoding AILIM prepared as such with appropriate restriction enzymes, and as required, ligating the resultant DNA fragment with a linker DNA or tag by using an appropriate DNA polymerase or the like. The DNA encoding AILIM ligand can also be prepared in the same manner.

An exemplary method will be shown below to clone the cDNA encoding AILIM (particularly preferably the human AILIM; the protein is hereinafter referred to as the protein of interest) from the mRNA.

A DNA encoding AILIM ligand can also be cloned in the same manner.

First, messenger RNA encoding the protein of interest is prepared from tissues or cells expressing and producing the protein of interest. mRNA can be prepared isolating total RNA by a known method such as quanidine-thiocyanate method (Chirgwin, J. M. et al., Biochemistry, Vol.18, p5294, 1979), hot phenol method, or AGPC method, and subjecting it to affinity chromatography using oligo-dT cellulose or poly-U Sepharose.

Then, with the mRNA obtained as a template, cDNA is synthesized, for example, by a well-known method using reverse transcriptase such as the method of Okayama et al. (Mol. Cell. Biol. Vol.2, p.161 (1982); ibid. Vol.3, p.280 (1983)) or the method of Hoffman et al. (Gene Vol.25, p.263 (1983)), and converted into double-stranded cDNA. A cDNA library is prepared by transforming E. coli with plasmid vectors, phage vectors, or cosmid vectors having this cDNA or by transfecting E. coli after in vitro packaging.

The plasmid vectors used in this invention are not limited as long as they are replicated and maintained in hosts. Any phage vectors that can be replicated in hosts can also be used. Examples of usually used cloning vectors are pUC19, λgt10, λgt11, and so on. When the vector is applied to immunological screening as mentioned below, the vector having a promoter that can express a gene encoding the polypeptide of the present invention in a host is preferably used.

cDNA can be inserted into a plasmid by, for example, the method of Maniatis et al. (Molecular Cloning, A Laboratory Manual, second edition, Cold Spring Harbor Laboratory, p.1.53, 1989). cDNA can be inserted into a phage vector by, for example, the method of Hyunh et al. (DNA cloning, a practical approach, Vol.1, p.49 (1985)). These methods can be simply performed by using a commercially available cloning kit (for example, a product from Takara Shuzo). The recombinant plasmid or phage vector thus obtained is introduced into appropriate host cells such as a prokaryote (for example, *E. coli*: XL1Blue MRF', DH5α, HB101, MC1061/ P3, etc.).

Examples of a method for introducing a plasmid into a host are calcium chloride method, calcium chloride/rubidium chloride method described in Molecular Cloning, A Laboratory Manual (second edition, Cold Spring Harbor Laboratory, p.1.74 (1989)), and electroporation method. Phage vectors can be introduced into host cells by, for example, a method in which the phage DNAs are introduced into grown hosts after in vitro packaging. In vitro packaging can be easily performed with a commercially available in vitro packaging kit (for example, a product from Stratagene or Amersham).

The cDNA encoding the polypeptide of the present invention can be isolated from the cDNA library so prepared according to the method mentioned above by combining general cDNA screening methods.

For example, a clone comprising the desired cDNA can be screened by a known colony hybridization method (Crunstein et al. Proc. Natl. Acad. Sci. USA, Vol.72, p.3961 (1975)) or plaque hybridization method (Molecular Cloning, A Laboratory Manual, second edition, Cold Spring Harbor Laboratory, p.2.108 (1989)) using $^{32}$P-labeled chemically synthesized oligonucleotides as probes, which are corresponding to the amino acid sequence of the polypeptide of the present invention. Alternatively, a clone having a DNA fragment encoding a specific region within the polypeptide of the present invention can be screened by amplifying the region by PCR with synthetic PCR primers.

When a cDNA library prepared using a cDNA expression vector (for example, λZAPII phage vector) is used, the desired clone can be screened by the antigen-antibody reaction using an antibody against the polypeptide of the present invention. A screening method using PCR method is preferably used when many clones are subjected to screening.

The nucleotide sequence of the DNA thus obtained can be determined by Maxam-Gilbert method (Maxam et al. Proc. Natl. Acad. Sci. USA, Vol.74, p.560 (1977)) or the dideoxynucleotide synthetic chain termination method using phage M13 (Sanger et al. Proc. Natl. Acad. Sci. USA, Vol.74, pp.5463–5467 (1977)). The whole or a portion of the gene encoding the polypeptide of the present invention can be obtained by excising the clone obtained as mentioned above with restriction enzymes and so on.

The DNA encoding the polypeptide of the present invention can be isolated from the genomic DNA derived from the cells expressing the polypeptide of the present invention as mentioned above by the following methods.

Such cells are solubilized preferably by SDS or proteinase K, and the DNAs are deproteinized by repeating phenol extraction. RNAs are digested preferably with ribonuclease. The DNAs obtained are partially digested with appropriate restriction enzymes, and the DNA fragments obtained are amplified with appropriate phage or cosmid to generate a library. Then, clones having the desired sequence are detected, for example, by using radioactively labeled DNA probes, and the whole or a portion of the gene encoding the polypeptide of the present invention is obtained from the clones by excision with restriction enzyme and so on.

Preparation of DNA encoding the protein of interest by PCR can be carried out by using known mRNA or cDNA encoding the protein of interest as the template according to a usual method ("PCR techniques for gene amplification—fundamental and new technologies" KYORITSU SHUPPAN, 1992, etc.).

The DNA encoding the protein of interest can also be chemically synthesized by the usual method, based on the nucleotide sequence encoding the protein of interest.

AILIM of the invention (particularly preferably the human AILIM) or a portion thereof (preferably, the extracellular region) can be prepared as a recombinant protein according to a usual method with commonly used genetic recombination techniques, using DNA obtained by cutting DNA encoding AILIM (cDNA or intron-containing genomic DNA) based on the method illustrated above with appropriate restriction enzymes to give a DNA fragment encoding the AILIM, and then as required, ligating the resultant DNA fragment with a linker DNA or tag, by using an appropriate DNA polymerase or the like.

The AILIM ligand (particularly preferably the human AILIM ligand) or a portion thereof (preferably, the extracellular region) can be prepared in the same manner.

A specific example is illustrated below. Namely, the DNA prepared as described above is inserted into a vector, which will be described later in detail, to yield an expression vector. Then the expression vector is used to transform a host cell as described below to obtain a transformant. The transformant is cultured and allowed to produce the protein of interest into the culture supernatant. The protein of interest in the culture supernatant can easily be purified by using column chromatography and such.

There is no particular limitation on the type of expression vector for the production of the recombinant AILIM (or its extracellular region), as far as the vector is replicated and maintained or produced autonomously in any of various hosts such as prokaryotic cells and/or eukaryotic cells. Such expression vectors include plasmid vectors and phage vectors (Cloning Vectors: A Laboratory Manual, Elsevier, N.Y., 1985).

The expression vector can easily be prepared by ligating the DNA encoding AILIM (or its extracellular region) with a vector for recombination available in the art (plasmid DNA and bacteriophage DNA) by the usual method. Specific examples of the vectors for recombination used are *E. coli*-derived plasmids such as pBR322, pBR325, pUC12, pUC13, and pUC19, yeast-derived plasmids such as pSH19 and pSH15, and *Bacillus subtilis*-derived plasmids such as pUB110, pTP5, and pC194. Examples of phages are a bacteriophage such as λ phage, and an animal or insect virus (pVL1393, Invitrogen) such as a retrovirus, vaccinia virus, and nuclear polyhedrosis virus.

Plasmid vectors are useful, when a DNA encoding AILIM of the invention (particularly preferably the human AILIM) or its soluble extracellular region is intended to be expressed in a host cell and thereby expressing the AILIM on the surface of the host cell, or alternatively the soluble extracellular region of the AILIM (particularly preferable the human AILIM) is intended to be produced. There is no particular limitation on such plasmid vectors, as far as the vectors can express the gene encoding AILIM (particularly preferably the human AILIM) or its soluble extracellular region and produce the encoded protein in various host cells such as prokaryotic cells and/or eukaryotic cells. For example, such plasmids include pMAL C2, pcDNA3.1 (−), pEF-BOS (Nucleic Acid Research, Vol.18, p.5322, 1990; etc.), pME18S ("Handbook for genetic engineering," Experimental Medicine, supplement, 1992; etc.), etc.

When bacteria, particularly *E. coli* are used as host cells, an expression vector is generally comprised of, at least, a promoter-operator region, an initiation codon, the DNA encoding the protein of the present invention, termination codon, terminator region, and replicon.

When yeast, animal cells, or insect cells are used as hosts, an expression vector is preferably comprised of, at least, a promoter, an initiation codon, the DNA encoding the AILIM (particularly preferably human AILIM) of the present invention or its extracellular region, and a termination codon. It may also comprise the DNA encoding a signal peptide, enhancer sequence, 5'- and 3'-untranslated region of the gene encoding the AILIM of the present invention, splicing junctions, polyadenylation site, selectable marker region, and replicon. The expression vector may also contain, if required, a gene for gene amplification (marker) that is usually used.

A promoter-operator region to express the AILIM (particularly preferably human AILIM) of the present invention or its extracellular region in bacteria comprises a promoter, an operator, and a Shine-Dalgarno (SD) sequence (for example, AAGG). For example, when the host is $Escherichia$, it preferably comprises Trp promoter, lac promoter, recA promoter, λPL promoter, lpp promoter, tac promoter, or the like.

Examples of a promoter to express the AILIM (particularly preferably human AILIM) of the present invention or its extracellular region in yeast are PH05 promoter, PGK promoter, GAP promoter, ADH promoter, and so on. When the host is $Bacillus$, examples thereof are SL01 promoter, SP02 promoter, penP promoter and so on.

When the host is a eukaryotic cell such as a mammalian cell, examples thereof are SV40-derived promoter, retrovirus promoter, heat shock promoter, and so on. As a matter of course, the promoter is not limited to the above examples. In addition, to use an enhancer is effective for expression.

A preferable initiation codon is, for example, a methionine codon (ATG).

The commonly used termination codon (for example, TAG, TGA, TAA, and so on) is illustrated as a termination codon. Usually used natural or synthetic terminators are used as a terminator region.

A replicon means a DNA capable of replicating the whole DNA sequence in host cells, and includes a natural plasmid, an artificially modified plasmid (DNA fragment prepared from a natural plasmid), a synthetic plasmid, and so on. Examples of a preferable plasmids are pBR322 or its artificial derivatives (DNA fragment obtained by treating pBR322 with appropriate restriction enzymes) for $E.\ coli$, yeast 2μ plasmid or yeast chromosomal DNA for yeast, and pRSVneo ATCC 37198, pSV2dhfr ATCC 37145, pdBPV-MMTneo ATCC 37224, pSV2neo ATCC 37149, pSV2bsr, etc. for mammalian cells.

An enhancer sequence, polyadenylation site, and splicing junction that are usually used in the art, such as those derived from SV40 can be also used.

A selectable marker usually used can be used according to the usual method. Examples thereof are resistance genes for antibiotics, such as tetracycline, ampicillin, or kanamycin, and thymidine kinase gene.

Examples of a gene for gene amplification are dihydrofolate reductase (DHFR) gene, thymidine kinase gene, neomycin resistance gene, glutamate synthase gene, adenosine deaminase gene, ornithine decarboxylase gene, hygromycin-B-phophotransferase gene, aspartate transcarbamylase gene, etc.

The expression vector of the present invention can be prepared by continuously and circularly linking at least the above-mentioned promoter, initiation codon, DNA encoding the protein of the present invention, termination codon, and terminator region, to an appropriate replicon. If desired, appropriate DNA fragments (for example, linkers, restriction sites generated with other restriction enzyme), can be used by the usual method such as digestion with a restriction enzyme or ligation using T4 DNA ligase.

Transformants of the present invention can be prepared by introducing the expression vector mentioned above into host cells.

Host cells used in the present invention are not limited as long as they are compatible with an expression vector mentioned above and can be transformed. Examples thereof are various cells such as natural cells or artificially established recombinant cells usually used in technical field of the present invention (for example, bacteria ($Escherichia$ and $Bacillus$), yeast ($Saccharomyces$, $Pichia$, etc.), animal cells, or insect cells.

$E.\ coli$ or animal cells are preferably used. Specific examples are $E.\ coli$ (DH5a, DH10B, TB1, HB101, XL-2Blue, etc.), mouse-derived cells (COP, L, C127, Sp2/0, NS-1, NIH 3T3, etc.), rat-derived cells, hamster-derived cells (BHK, CHO, etc.), monkey-derived cells (COS1, COS3, COS7, CV1, Velo, etc.), and human-derived cells (Hela, diploid fibroblast-derived cells, myeloma, Namalwa, etc.).

An expression vector can be introduced (transformed (transduced)) into host cells by known method.

Transformation can be performed, for example, according to the method of Cohen et al. (Proc. Natl. Acad. Sci. USA, Vol.69, p.2110 (1972)), protoplast method (Mol. Gen. Genet., Vol.168, p.111 (1979)), or competent method (J. Mol. Biol., Vol.56, p.209 (1971)) when the hosts are bacteria ($E.\ coli,\ Bacillus\ subtilis$, etc.), the method of Hinnen et al. (Proc. Natl. Acad. Sci. USA, Vol.75, p.1927 (1978)), or lithium method (J. Bacteriol., Vol.153, p.163 (1983)) when the host is $Saccharomyces\ cerevisiae$, the method of Graham (Virology, Vol.52, p.456 (1973)) when the hosts are animal cells, and the method of Summers et al. (Mol. Cell. Biol., Vol.3, pp.2156–2165 (1983)) when the hosts are insect cells.

The extracellular region of the AILIM (particularly preferably human AILIM) of the present invention (soluble AILIM) can be produced by cultivating transformants (in the following this term includes transductants) comprising an expression vector prepared as mentioned above in nutrient media. AILIM ligand can be produced in the same way.

The nutrient media preferably comprise carbon source, inorganic nitrogen source, or organic nitrogen source necessary for the growth of host cells (transformants). Examples of the carbon source are glucose, dextran, soluble starch, and sucrose, and examples of the inorganic or organic nitrogen source are ammonium salts, nitrates, amino acids, corn steep liquor, peptone, casein, meet extract, soy bean cake, and potato extract. If desired, they may comprise other nutrients (for example, an inorganic salt (for example, calcium chloride, sodium dihydrogenphosphate, and magnesium chloride), vitamins, antibiotics (for example, tetracycline, neomycin, ampicillin, kanamycin, etc.).

Cultivation is performed by a method known in the art. Cultivation conditions such as temperature, pH of the media, and cultivation time are selected appropriately so that the protein of the present invention is overproduced.

Specific media and cultivation conditions used depending on host cells are illustrated below, but are not limited thereto.

When the hosts are bacteria, actinomycetes, yeasts, filamentous fungi, liquid media comprising the nutrient source mentioned above are appropriate. The media with pH 5 to 8 are preferably used.

When the host is E. coli, examples of preferable media are LB media, M9 media (Miller et al. Exp. Mol. Genet., Cold Spring Harbor Laboratory, p.431 (1972)), YT media, etc. Using these media, cultivation can be performed usually at 14 to 43° C. for about 3 to 24 hours with aeration and stirring, if necessary.

When the host is Bacillus, cultivation can be performed usually at 30 to 40° C. for about 16 to 96 hours with aeration and stirring, if necessary.

When the host is yeast, examples of media are Burkholder minimal media (Bostian, Proc. Natl. Acad. Sci. USA, Vol.77, p.4505 (1980)). The pH of the media is preferably 5 to 8. Cultivation can be performed usually at 20 to 35° C. for about 14 to 144 hours with aeration and stirring, if necessary.

When the host is an animal cell, examples of media are MEM media containing about 5 to 20% fetal bovine serum (Science, Vol.122, p.501 (1952)), DMEM media (Virology, Vol.8, p.396 (1959)), RPMI1640 media (J. Am. Med. Assoc., Vol.199, p.519 (1967)), 199 media (Proc. Soc. Exp. Biol. Med., Vol.73, p.1 (1950)), HamF12 media, etc. The pH of the media is preferably about 6 to 8. Cultivation can be performed usually at about 30 to 40° C. for about 15 to 72 hours with aeration and stirring, if necessary.

When the host is an insect cell, an example of media is Grace's media containing fetal bovine serum (Proc. Natl. Acad. Sci. USA, Vol.82, p.8404 (1985)). The pH thereof is preferably about 5 to 8. Cultivation can be performed usually at about 20 to 40° C. for 15 to 100 hours with aeration and stirring, if necessary.

The extracellular region (soluble AILIM) of AILIM of the invention (particularly preferably the human AILIM) can be produced by culturing the above-mentioned transformed cells (particularly, animal cell or E. coli) and allowing the secretion of the protein in the culture supernatant. Namely, a culture filtrate (supernatant) is obtained by the method such as filtration or centrifugation of the obtained culture, and the polypeptide or polypeptide fragment of the present invention is purified and isolated from the culture filtrate by the usual method commonly used in order to purify and isolate a natural or synthetic protein.

Examples of the isolation and purification method are a method utilizing specific affinity, such as affinity chromatography, a method utilizing solubility, such as salting out and solvent precipitation method, a method utilizing the difference in molecular weight, such as dialysis, ultrafiltration, gel filtration, and sodium dodecyl sulfate-polyacrylamide gel electrophoresis, a method utilizing charges, such as ion exchange chromatography and hydroxylapatite chromatography, a method utilizing the difference in hydrophobicity, such as reverse phase high performance liquid chromatography, and a method utilizing the difference in isoelectric point, such as isoelectric focusing.

When the protein of interest exists in the periplasm or cytoplasm of cultured transformants, first, the fungus bodies or cells are harvested by the usual method such as filtration or centrifugation and suspended in appropriate buffer. After the cell wall and/or cell membrane of the cells and so on are disrupted by the method such as lysis with sonication, lysozyme, and freeze-thawing, the membrane fraction comprising the polypeptide of the present invention is obtained by the method such as centrifugation or filtration. The membrane fraction is solubilized with a detergent such as Triton-X100 to obtain the crude extract. Finally, the polypeptide or the polypeptide fragment is isolated and purified from the crude extract by the usual method as illustrated above.

In the present invention, the term "insoluble carrier" means a carrier which is used to immobilize polypeptides on them by physical adsorption or chemical linking. For example, the carrier can be (1) plate, test tube, tube, or the like having internal space, bead, ball, filter, membrane, or the like made of water-insoluble materials including plastics such as polystyrene resin, polycarbonate resin, silicon resin or nylon resin, or glass, and (2) insoluble carrier used in affinity chromatography such as cellulose carrier, agarose carrier, polyacrylamide carrier, dextran carrier, polystyrene carrier, polyvnylalcohol carrier, poly amino acid carrier, porous silica carrier, etc.

The "labeling substance capable of giving detectable signal" in accordance with the present invention includes, for example, enzyme, fluorescent material, luminescent material, biotin, avidin or radioisotope, more specifically, enzymes such as peroxidase (e.g., horseradish peroxidase), alkaline phosphatase, β-D-galactosidase, glucoseoxidase, glucose-6-phosphate dehydrogenase, alcohol dehydrogenase, malate dehydrogenase, penicillinase, catalase, apoglucose oxidase, urease, luciferase, acetylcholine esterase, etc.; fluorescent materials such as fluorescein isothiocyanate, phycobilin protein, rare earth metal chelating agents, dansyl chloride, tetramethyl rhodamine isothiocyanate, etc.; radioisotopes such as $^3$H, $^{14}$C, $^{125}$I, $^{131}$I, etc.; biotin, avidin, and luminescent material.

Among them, radioisotope or fluorescent material can give detectable signal even when used alone. On the other hand, when used alone, enzyme, luminescent material, biotin or avidin provide no detectable signal, but when allowed to react with one or more substances, it can provide detectable signal. For example, when the label is an enzyme, at least a substrate is necessary for the detection. Various types of substrates can be used depending on the type of method for measuring enzyme activity (colorimetry, fluoroscopy, method using bioluminescence or chemical luminescence, etc.). For example, when the label is peroxidase, hydrogen peroxide can be used as a substrate. Alternatively, when the label is biotin, avidin or enzyme-modified avidin is commonly used but is not limited to them. As required, a variety of luminescent substances can be utilized depending on the type of substrate to be used.

Any of the above-mentioned labels can be utilized in the present invention. However, preferred label is an enzyme such as peroxidase or biotin with consideration given to sensitivity of detection or assay as well as the convenience of manipulation.

A "method for identifying a substance capable of binding to AILIM or AILIM ligand" in accordance with the invention is constructed based on the principle of immunoassay.

Specifically, the principles of various methods as described in "Immunoassay (3$^{rd}$ Edition, eds., Eiji Ishikawa et al, Igakushoin, 1987)" can be applied.

Examples of principles preferably used include solid-phase one-antibody method, liquid-phase two-antibody method, solid-phase two-antibody method, sandwich method, and one-pot method as described in Examined Published Japanese Patent Application (JP-B) No. Hei 2-39747. Further, assay method employing antigen-antibody reaction is exemplified by EMIT method (enzyme multiplied immunoassay technique), enzyme channeling immunoassay, enzyme modulator mediated enzyme immunoassay (EM-MIA), enzyme inhibitor immunoassay, immunoenzymometric assay, enzyme enhanced immunoassay and proximal linkage immunoassay.

In the present invention, any of such principles of immunoassay may be selected properly in accordance with the purpose. However, with consideration given to the convenience of procedure and/or economic advantage, and particularly clinical versatility, the principle of sandwich method, one-pot method, or solid-phase one-antibody method, more preferably sandwich method or one-pot method is preferably utilized. Particularly preferred is sandwich method using multi-well microtiter plate having many wells such as 96-well microplate, or one-pot method using beads on which polypeptide is immobilized and also using a counterpart labeled with enzyme such as peroxidase or with biotin.

The human monoclonal antibodies of the invention capable of binding to human AILIM are of human origin, and therefore these antibody induces no serious immunorejection due to antigenicity to human, i.e., HAMA (Human anti-mouse antigenicity) in a host, which has been a serious therapeutic problem (side effect) in antibody pharmaceutical preparations comprising non-human mammal-derived antibody such as mouse-derived antibody. The antibody of the invention is thus of great value as an antibody pharmaceutical.

Thus, the human monoclonal antibody of the invention against AILIM (particularly human AILIM) and pharmaceutical compositions comprising the human monoclonal antibody do not induce host immunorejection caused by HAMA at all; and thus can be used as pharmaceutical preparations capable of controlling a variety of biological reactions (e.g., proliferation of cells expressing AILIM, cytokine production by AILIM-expressing cells, immune cytolysis or cell death (apoptosis) of cells expressing AILIM, and activity of inducing antibody-dependent damage of cells expressing AILIM) associated with the transduction of AILIM-mediated costimulatory signal (secondary signal) to cells expressing AILIM; and/or can be used to treat or prevent various diseases associated with the transduction of the AILIM-mediated signal, controlling and inhibiting the onset and/or progress of the diseases.

Specifically, by providing pharmaceutical preparations containing the human anti-AILIM monoclonal antibody of the invention or a portion thereof as an active ingredient, it is possible to inhibit or treat and prevent, for example, a variety of diseases (e.g., rheumatoid arthritis, multiple sclerosis, autoimmune thyroiditis, allergic contact dermatitis, lichen planus as a chronic inflammatory skin disease, systemic lupus erythematosus, insulin dependent diabetes mellitus and psoriasis, etc.) classified into autoimmune diseases or allergic diseases (particularly, autoimmune diseases and delayed allergies by cellular immunity); arthropathies (e.g., rheumatoid arthritis (RA), osteoarthritis (OA)), inflammation (e.g., hepatitis); graft versus host reaction (GVH reaction); graft versus host disease (graft versus host disease; GVHD); immunorejection associated with transplantation (allogenic graft or heterogenous graft) of tissues (tissues such as skin, cornea and bone) or organs (liver, heart, lung, kidney, pancreas, etc.); immune response to foreign antigen or self antigen (for example, production of antibody against the antigen, cell proliferation, cytokine production, etc.); and diseases that are potentially caused by abnormality in gut immunity (specifically, inflammatory bowel disease (particularly, Crohn's disease and ulcerative colitis); and alimentary allergy, etc.

The pharmaceutical compositions in accordance with the present invention make it possible to treat or prevent some inflammations for which various steroidal drugs are used as anti-inflammatory drugs, for example, inflammation associated with various arthritides (rheumatoid arthritis, osteoarthritis, etc.), pneumonia, hepatitis (including viral hepatitis), inflammation associated with infectious diseases, inflammatory bowel disease, enteritis, nephritis (glomerular nephritis, inflammation associated with kidney fibrosis, gastritis, vasculitis, pancreatitis, peritonitis, bronchitis, myocarditis, encephalitis, inflammation associated with ischemia-reperfusion injury (myocaridial ischemia-reperfusion injury, etc.), inflammation associated with immunorejection after transplantation of tissues or organs, scald, various skin inflammations (psoriasis, allergic contact dermatitis, lichen planus as a chronic inflammatory skin disease), inflammation associated with multiple organ failure, inflammation after operation of PTCA or PTCR, and inflammation associated with atherosclerosis, autoimmune thyroiditis, etc.

In addition, with respect to the above-mentioned inhibition and treatment of immunorejection associated with transplantation of tissues or organs as described above, the pharmaceutical compositions in accordance with the present invention can be used in conjunction with known immunosuppressant used to inhibit the immunorejection in transplantation therapy thereby increasing the effect of the known drug to inhibit the graft rejection.

Further, by the use of the method of identifying substances capable of binding to AILIM or AILIM ligand, which is within the scope of the present invention, it is possible to control the signal transduction associated with the interaction between AILIM and AILIM ligand through the binding to AILIM or AILIM ligand, and thereby achieving screening and selection of pharmaceutical agents (synthetic chemical compound and antibody) having potential activity to treat the above-mentioned various diseases.

The present invention is illustrated in more detail below with reference to Examples, but is not to be construed as being limited thereto.

EXAMPLE 1

Preparation of Immunogen

<1-1> Preparation of Recombinant Cell Expressing Human AILIM

Two types of recombinant cells (CHO cell and HPB-ALL cell) overexpressing human AILIM were prepared according to the method as described in earlier applications (JP-A No. Hei 11-29599 and WO98/38216), as well as in a previous report (Int. Immunology, Vol.12, No.1, p.51–55, 2000) of one of the present inventors, Tezuka. Specifically, the method is as follows:

A cDNA (GenBank Accession Number: AB023135 (cDNA); BAA82129 (amino acid)) containing the full-length ORF encoding human AILIM was inserted into a vector pEF-neo. Then the resulting recombinant expression vector was introduced into Chinese hamster ovary cells (CHO cell) and cells of a human thymoma line, HPB-ALL, according to a commonly used method using electroporation (960 μF, 320V) with a Gene Pulser (BioRad). Respective cells were cultured in RPMI1640 medium containing Geneticin (0.8 mg/ml; Gibco BRL) and 10% FCS to select drug-resistant transformed cells.

<1-2> Selection of Recombinant HPB-ALL Cells Overexpressing Human AILIM

Culture of the drug-resistant HPB-ALL cells selected in <1-1> described above were centrifuged to give cell pellets. A mouse anti-human AILIM monoclonal antibody named "SA12" (mouse anti-human JTT-1 antigen monoclonal antibody), which had been established and reported previously (JP-A 11-29599 (Example 12) and WO98/38216 (Example 12)) by the present inventors, was added to the cell pellet (concentration: antibody solution (10 μg/ml) diluted with EDTA-BSA/PBS was added at a ratio of 100 μl/$10^5$ cells). The resulting mixtures were incubated at 4° C. for 30 minutes. The cells were washed twice with above-mentioned EDTA-BSA/PBS (200 ml), and then phycoerythrin-labeled streptavidin (SA-PE; 100 μl of 500-fold diluted solution) was added thereto. Resulting mixtures were incubated at 4° C. for 30 minutes. After incubation, cells were washed 3 times with EDTA-BSA/PBS, and cell suspensions were prepared.

Expression levels of human AILIM of respective cells in the cell suspensions were analyzed in a flow cytometer, FACSort (Beckton-Dichinson), to select recombinant HPB-ALL cells overexpressing human AILIM. Selected cells were cultured to confluence in RPMI1640 medium containing 10% FCS and G418 (1 mg/ml).

<1-3> Selection of Recombinant CHO Cells Overexpressing Human AILIM

Culture of the drug-resistant CHO cells selected in <1-1> described above were centrifuged to give cell pellets. The above-mentioned mouse anti-human AILIM monoclonal antibody SA12, which had been labeled with FITC, was added to each cell pellet (antibody solution (100 μg/ml) diluted with EDTA-BSA/PBS). Resulting mixtures were incubated at 4° C. for 30 minutes. Cells were washed with above-mentioned EDTA-BSA/PBS, and then cell suspensions were prepared by adding EDTA-BSA/PBS (500 μl) to the cell pellets.

Expression levels of human AILIM of respective cells in the cell suspensions were analyzed in a flow cytometer, FACSort (Beckton-Dichinson), to select recombinant HPB-ALL cells overexpressing human AILIM. Selected cells were cultured to confluence in RPMI1640 medium containing 10% FCS and G418 (1 mg/ml).

<1-4> Preparation of Immunogen from HPB-ALL Cells Overexpressing Human AILIM

The HPB-ALL cells overexpressing human AILIM, which had been obtained in <1-2> described above, were centrifuged. Recovered cell pellet was washed 4 times with phosphate buffer (PBS; Nikken Seibutsu) and then resuspended in a protease inhibitor-containing buffer (containing 25 mM HEPES (pH 7.4), 10 mM $MgCl_2$, 0.25 M Sucrose, and protease inhibitor (10 U/ml Aprotinine, 2 μg/ml Pepstatin, 50 μg/ml Leupeptin, and 0.35 mg/ml PMSF)). Cell suspension was treated in a Potter-type homogenizer, and centrifuged at a low speed (at 1,500 rpm at 4° C. for 10 minutes). Subsequently, resulting supernatant was subjected to ultracentrifugation (under 100,000 g at 4° C. for 1 hour). Precipitated membrane fraction was recovered, and suspended in phosphate buffer (concentration of the membrane fraction was adjusted so that 1 ml PBS contains membrane fraction derived from $1\times10^7$ cells). The suspension was stored at −80° C. The suspension containing cell membrane fraction was used as the antigen (immunogen) to prepare human antibody of the present invention, which will be described later.

<1-5> Preparation of Immunogen from CHO Cells Overexpressing Human AILIM

The CHO cells overexpressing human AILIM, which had been obtained in <1-3> described above, were dispersed with a scraper and were centrifuged. Recovered cell pellet was washed 4 times with phosphate buffer (PBS; Nikken Seibutsu) and then resuspended in a protease inhibitor-containing buffer (containing 25 mM HEPES (pH 7.4), 10 mM $MgCl_2$, 0.25 M Sucrose, and protease inhibitor (10 U/ml Aprotinine, 2 μg/ml Pepstatin, 50 μg/ml Leupeptin, and 0.35 mg/ml PMSF)). The cell suspension was treated in a Potter-type homogenizer, and centrifuged at a low speed (at 1,500 rpm at 4° C. for 10 minutes). Subsequently, resulting supernatant was subjected to ultracentrifugation (under 100,000 g at 4° C. for 1 hour). Precipitated membrane fraction was recovered, and suspended in phosphate buffer (concentration of the membrane fraction was adjusted so that 1 ml PBS contains membrane fraction derived from $1\times10^7$ cells). The suspension was stored at −80° C. The suspension containing cell membrane fraction was used as the antigen (immunogen) to prepare human antibody of the present invention, which will be described later.

EXAMPLE 2

Preparation of Hybridoma Producing Human Anti-human AILIM Monoclonal Antibody

In the present Example, preparation of monoclonal antibody was carried out according to a typical method as described in "Experimental Medicine (supplement), Handbook for Cell Technology" (eds., T. Kuroki et al., Yodosha, pp.66–74, 1992) and "Experimental Manual for Monoclonal Antibody" (T. Ando et al., Kodansha, 1991).

Cell membrane fraction prepared from recombinant cells overexpressing human AILIM provided in Example 1 was used as the immunogen of human AILIM.

Animals subjected to immunization were human antibody-producing transgenic mice created by above-described method (Nature Genetics, Vol.7, p.13–21, 1994; Nature Genetics, Vol.15, p.146–156, 1997; Published Japanese Translation of International Application No. Hei 4-504365; Published Japanese Translation of International Application No. Hei 7-509137; Nikkei Science, June, pp. 40–50, 1995; etc.).

Multi-well microplates were used for cell culture.

<2-1> Immunization and Preparation of Hybridoma

Either of the immunogens (100 μl/mouse/administration) prepared in <1-4> (derived from HPB-ALL) and in <1-5> (derived from CHO) described above was given to the above-mentioned human antibody-producing transgenic mouse. The immunogen was injected together wit Freund's complete adjuvant (ICN/CAPPEL) in the footpad as primary immunization (day 0).

After primary immunization, either of the two immunogens was additionally injected to the footpad at 1-week interval as secondary and/or tertiary immunization. In the same manner, injection was further carried out for final immunization two days before preparation of lymphocytes, which is described below.

Two days after final immunization, lymphocytes were prepared from (subinguinal and subgenual) lymph nodes and spleens of respective transgenic mice subjected to immunization. The lymphocytes and mouse myeloma cells P3/X63-AG8.653 (ATCC No. CRL-1580) were mixed at a ratio of 5:1, and polyethylene glycol 1500 (Boehringer Mannheim) was added thereto as a fusion agent. Then, the mixture was diluted with 10 volumes of serum-free basal medium EX-CELL301 (JRH Bioscience). Subsequently, the mixed cells were washed with the basal medium and then suspended in HAT medium (1 L of basal medium contained 13.61 mg of hypoxanthine, 176 μg of aminopterin, and 3.88 mg of thymidine). The cells were plated on 96-well microplates and cultured for 10–14 days to complete cell fusion. The cell fusion treatment yielded many hybridomas.

<2-2> Screening of Human Monoclonal Antibody-Producing Hybridoma

A number of hybridomas prepared in <2-1> described above were screened with cell ELISA as described below to select hybridomas producing human monoclonal antibody against human AILIM.

Respective recombinant HPB-ALL cells and recombinant CHO cells overexpressing human AILIM, which are described above, were plated in each well of ELISA 96-well microplates ($1\times10^5$ cell/well). Incubation was carried out at 37° C. for 2 days.

Subsequently, supernatant of each well was discarded, samples of supernatant of each hybridoma culture was added thereto (50 µl/well), and the mixture was incubated for 1 hour. After the reaction was completed, the mixed sample solution was discarded and each well was washed 3 times with PBS containing 1% BSA (Sigma).

Subsequently, peroxidase-conjugated goat anti-human immunoglobulin (Fc) antibody (50 µl of the 2000-fold dilute per well; Ameircan Corex; 1% BSA/PBS) was added to each well in order to detect the heavy chain of human immunoglobulin (human monoclonal antibody) in the hybridoma supernatant. The mixture was incubated at room temperature for 1 hour.

On the other hand, peroxidase-conjugated goat anti-human immunoglobulin κ chain antibody (50 µl of the 2000-fold dilute per well) was added to each well in order to detect the light chain of human immunoglobulin (human monoclonal antibody) in the hybridoma supernatant. The mixture was incubated at room temperature for 15 minutes.

The anti-human IgFc antibody or anti-human Igκ antibody was removed from each well of the microplates, and then the plates were washed 3 times with PBS containing 1% BSA. Tetramethylbenzidine (3,3',5,5',-tetramethylbenzidine (TMB), 100 µl/well, BIO-RAD) was added to each well, and the resulting mixture was incubated at room temperature for 15 minutes.

Subsequently, 1N $H_2SO_4$ was added to each well (50 µl/well) to quench the reaction. The reaction was monitored for absorbance at a wavelength of 450 nm by a microplate reader (Model 3550 Microplate Reader, BIO-RAD).

Control ELISA experiment was performed in the same manner as described above by using the following items:

(1) Wild-type HPB-ALL cells, instead of human AILIM expressing recombinant HPB-ALL cells;

(2) Wild-type CHO cells, instead of human AILIM expressing recombinant CHO cells;

(3) Mouse monoclonal antibodies against human AILIM (SA12 or SG430; JP-A 11-29599 (Example 12) and WO98/38216 (Example 12)) instead of hybridoma supernatant;

(4) Human monoclonal antibody against KLH (keyhole limpet hemocyanin, PIERCE) instead of hybridoma supernatant.

The human anti-KLH monoclonal antibody was prepared according to the same manner as described above in <2-1>, by immunizing above-mentioned human antibody-producing transgenic mice with KLH (keyhole limpet hemocyanin, PIERCE).

Many hybridomas producing human monoclonal antibody capable of binding to human AILIM were selected by said screening.

<2-3> Primary Cloning of Hybridoma

Many types of hybridoma monoclones were established from the various hybridomas (parental cell lines), which had been selected in <2-2> described above, producing human monoclonal antibody against human AILIM by the following assay procedure.

Respective hybridomas selected in <2-2> described above were plated in 24-well microplates. Cell count of hybridoma in each well was determined by pipetting. Subsequently, 10% fetal calf serum (FCS; Trace Bioscience PTY), 1% penicillin/streptomycin (Sigma), 1% HT Supplement (Gibco BRL) and 2.5% T-STIM Culture Supplement (Collaborative Biomedical Products) were added to EX-CELL301 medium (JRH Bioscience) containing 4.0 mM L-glutamine and lipid. The resulting modified medium was used to dilute hybridomas to $1\times10^4$ cells/ml and the cells were suspended in each well.

Cell suspension (300 µl or 600 µl) of each well was combined and mixed well with the modified medium (150 ml or 300 ml), and then a 200 µl aliquot of the cell suspension was added to each well of multiple 96-well microplates such that each well contained 4 cells of the hybridoma. The above-mentioned modified medium (50 ml or 100 ml) was freshly added to the remaining cell suspension, which was mixed well, and then the resulting cell suspension was added to each well of other freshly prepared multiple 96-well microplates such that each well contained 2 cells of the hybridoma.

Cultivation was continued for 1 to 2 weeks. After cultivation, single colonies derived from a single hybridoma were found in many wells.

With the cell ELISA as described above in <2-2>, it was verified that human monoclonal antibody against human AILIM was produced in the culture supernatant in each well containing the colony.

<2-4> Secondary Cloning of Hybridoma

Subcloning (secondary cloning) of each clone from the various hybridoma clones obtained in <2-3> described above was performed according to the same method as described above in <2-3>.

Cell density of each well in a 96-well microplate was adjusted to 1 cell/well in the present experiment.

The screening yielded many hybridoma monoclones producing human monoclonal antibody against human AILIM. Part of the clones included were as below:

(Clone Name)

AIF34 (JMab124), AIF182 (JMab-126), AIF348 (JMab-127),

AIF620 (JMab-128), AIF1052 (JMab-135), AIH5D3 (JMab-136),

AIH386 (JMab-137), AII289 (JMab-138), AII394 (JMab-139),

AII488 (JMab-140), AIJ40 (JMab-141),

The names shown above are used through the present application, namely in all Examples described below including the present Example, and in Figures and Tables containing the assay result obtained in this Example.

EXAMPLE 3

Analysis of Properties of Monoclonal Antibody

<3-1> Analyses of the Heavy Chain and Light Chain

By using ELISA and flow cytometry described below, it was verified that the monoclonal antibody against human AILIM produced by each hybridoma clone, which had been cloned in <2-4> described above, was indeed a human monoclonal antibody.

The recombinant HPB-ALL cells overexpressing human AILIM, which had been prepared in Example 1, were plated in each v-shaped well of microplate ($3\times10^4$ cell/well). Cells were cultured at 37° C. in RPMI640 medium containing 10% FCS.

After the culture was completed, the plate was centrifuged (at 1,800 rpm for 2 minutes) to precipitate the cells, and then the resulting supernatant was discarded. Subsequently, supernatant sample (50 ml/well) from the culture of each hybridoma cloned in <2-4> described above, or mouse anti-human AILIM monoclonal antibody SA12 (2 μg/50 μl) or alternatively human anti-KLH monoclonal antibody (50 μl/well) as a control antibody was added to each well. The mixture was reacted for 30 minutes in a refrigerator. After reaction, the sample solution was discarded and each well was washed with phosphate buffer (0.5% BSA-PBS containing 5 mM EDTA).

Subsequently, any one of the secondary antibodies below was added to each well (diluted 1000 times with the above phosphate buffer and added at a quantity of 50 μl/well) in order to suspend the cells. The suspension was reacted for 30 minutes in a refrigerator.

(Secondary Antibody)
Biotin-labeled anti-human IgG antibody (Zymed);
Biotin-labeled anti-human IgG antibody (Protos);
Biotin-labeled anti-human IgFc antibody (EY Laboratories); or
Biotin-labeled anti-human Igκ antibody (Vector).

After reaction, the secondary antibody was discarded and each well of the plate was washed with the above-mentioned phosphate buffer. Subsequently, phycoerythrin-labeled streptavidin (Streptavidin-PE; Pharmingen; diluted 500 time with the above-mentioned phosphate buffer and added at a quantity of 50 μl/well) was added to each well. The mixture was reacted for 30 minutes in a refrigerator. After reaction, each well was washed with the above-mentioned phosphate buffer. Then, the above-mentioned phosphate buffer was added to each well (200 μl/well) in order to suspend the cells.

Analysis was performed to determine the reactivity of the anti-human AILIM monoclonal antibody in the culture supernatant of each hybridoma clone to the HPB-ALL cells overexpressing human AILIM in each well.

Control assay was performed in the same manner as described above by using following items:

(1) Wild-type HPB-ALL cells, instead of human AILIM expressing recombinant HPB-ALL cells;

(2) Human monoclonal antibody against KLH (keyhole limpet hemocyanin, PIERCE) instead of hybridoma supernatant.

The human anti-KLH monoclonal antibody was prepared according to the same manner as described above in <2-1>, by immunizing the above-mentioned human antibody-producing transgenic mice with KLH (keyhole limpet hemocyanin, PIERCE).

Based on the result, all of the hybridoma clones described above in <2-4> were verified to be human monoclonal antibodies consisting of human-derived heavy chain and human-derived κ light chain.

An example of the result is illustrated in FIG. 1, which involves assay result for hybridoma clones AIH5D3 (JMab-136), AII289 (JMab-138), and AII394 (JMab-139).

<3-2> Isotyping of Human Monoclonal Antibody

The isotype was determined for each of the human anti-human AILIM monoclonal antibodies produced by the hybridomas that had been cloned in <2-4> and analyzed in <3-1> described above. Determination was carried out using a Human Monoclonal Antibody Isotyping Kit (American Qualex) according to the experimental protocol attached to the kit.

All the human anti-human AILIM monoclonal antibodies were determined to be IgG2/κ.

EXAMPLE 4

Preparation of Human Monoclonal Antibody Against Human AILIM (Human Anti-human AILIM Monoclonal Antibody) on Large Scale and Its Purification <4-1> Method 1

Cells of each hybridoma clone producing human anti-human AILIM monoclonal antibody, which had been prepared in <2-4> described above, were added to a tissue culture flask (50 ml, FALCON), and cultured in ASF104 medium (Ajinomoto) containing 10% Ultra Low Bovine IgG FBS (GIBCO-BRL) to be confluence under an atmosphere of 5% $CO_2$ at 37° C.

Subsequently, the whole culture liquid was transferred into a new tissue culture flask (750 ml, FALCON), and the cells were cultured in ASF104 medium (Ajinomoto) containing 10% Ultra Low Bovine IgG FBS (GIBCO-BRL) to be confluent under an atmosphere of 5% $CO_2$ at 37° C.

10 to 20 days after the culture, the culture supernatant of each hybridoma was recovered and transferred into a 50-ml polypropylene conical tube (FALCON). The tube was centrifuged under 500×g for 5 minutes.

Subsequently, resulting centrifugal supernatant was filtered through a Sterilization Filter Unit (NALGEN), and the filtrate was recovered.

The filtrate was loaded onto a HiTrap Protein G column (HiTrap affinity column Protein G; Amersham Pharmacia) pre-equilibrated with phosphate buffer (30 ml) at a flow rate of 3 ml/min.

Subsequently, the column was washed with phosphate buffer (20 ml), and then the antibody of interest was eluted by loading 100 mM citrate buffer (pH 2.0) onto the column at a low rate of about 1 ml/min. Subsequently, the eluted solution was neutralized with a solution (pH 9.0) of 750 mM Tris-HCl, and then filtered through a filter (Millipore) to remove white precipitate. The resulting filtrate was dialyzed against phosphate buffer (overnight) and filtered through a filter (Millipore). Thus purified anti-AILIM human monoclonal antibody was obtained from each hybridoma line.

Protein concentration was determined from the absorbance at $A_{280}$ measured by using a photospectrometer ($1A_{280}$=1.41 mg/ml).

<4-2> Method 2

Cells of each hybridoma clone, which had been prepared in <2-4> described above, were conditioned in ASF104 medium (Ajinomoto) containing 10% Ultra Low Bovine IgG FBS (GIBCO-BRL) ($1-2\times10^6$ Cells/ml each), and were plated and cultured in Integra Cell Line 1000 (INTEGRA CL1000, INTEGRA BIOSCIENCE). 7 to 10 days after cultivation, when the cell density reached $1\times10^8$ cells/ml, the supernatant of each hybridoma culture was recovered.

Each culture supernatant was loaded onto a HiTrap Protein G column (HiTrap affinity column Protein G; Amersham Pharmacia) pre-equilibrated with phosphate buffer (30 ml) at a flow rate of 3 ml/min.

Subsequently, the column was washed with phosphate buffer (20 ml), and then 100 mM citrate buffer (pH 2.0) was loaded onto the column at a flow rate of about 1 ml/min to elute the antibody. Then, a solution (pH 9.0) of 750 mM Tris-HCl was added to neutralize the eluted solution, and the resulting solution was filtered through a filter (Millipore) to remove white precipitate. The resulting filtrate was dialyzed against phosphate buffer (overnight) and then filtered through a filter (Millipore). Thus purified anti-AILIM human monoclonal antibody was obtained from each hybridoma line.

EXAMPLE 5

Reactivity of Human Anti-human AILIM Monoclonal Antibody to Human AILIM, and Cross-reactivity of that to Mouse AILIM and Rat AILIM Purified various human anti-human AILIM monoclonal antibodies above were analyzed for their reactivity to human AILIM as well as cross-reactivity to mouse AILIM and rat AILIM by utilizing cell ELISA method.

<5-1> Establishment of ELISA System to Determine IgG Antibody Concentration and Preparation of Calibration Curves Because all the above-mentioned purified human anti-human AILIM monoclonal antibodies were IgG (IgG2) antibody, ELISA system was established to determine the concentration of IgG antibody.

Goat anti-human IgG (Fc) antibody (1.2 μg/ml in PBS; 100 μl/well; Organon Teknika) was added to each well of a 96-well ELISA microplate (Nunc). The plate was incubated at room temperature for 2 hours to adsorb the anti-IgG (Fc) antibody on the microplate. Subsequently, the supernatant was discarded, and the plate was washed 3 times with phosphate buffer (PBS) containing 0.05% Tween20. A blocking reagent (PBS containing 0.5% bovine serum albumin (BSA) and 0.1% Tween20) was added to each well (200 μl/well) and the plate was incubated at room temperature for 2 hours to block the anti-IgG (Fc) antibody-free sites on the plate. Then, the blocking reagent was discarded, and each well was washed twice with PBS.

Human-derived IgG2 antibody (50 μl/well; The Binding Site), which was used as a standard antibody, was added at various concentrations (0 to 100 ng/ml) to respective wells of the plate and the plate was incubated at room temperature for 2 hours. Surplus solutions of standard antibody were removed and each well was washed 3 times with phosphate buffer containing 0.05% Tween20.

Subsequently, peroxidase-conjugated goat anti-human IgG/κ antibody was added to each well (4,000 times diluted, 100 μl/well, Protos), and the plate was incubated at room temperature for 1 hour.

The supernatant was discarded and the microplate was washed 3 times with phosphate buffer containing 0.05% Tween20. A buffer containing substrate (composition: ortho-phenylenediamine (O-phenylenediamine, OPD; 20 mg)/citrate-phosphate buffer (pH 5.0, 50 ml)/aqueous solution of 30% hydrogen peroxide (15 μl)) was added to each well (100 μl/well) and the plate was incubated at room temperature for about 7 minutes.

Subsequently, 2 M sulfuric acid was added to each well (50 μl/well) to stop the reaction. Calibration curves were made (FIG. 2) based on the values of absorbance measured at a wavelength of 490 nm by using a microplate reader.

Control assays were performed with culture medium alone or BSA solution alone as a test substance in the same manner as described above.

<5-2> Analyses for the Reactivity of Various Purified Human Anti-human AILIM Monoclonal Antibodies to Human AILIM as well as for Cross-reactivity of that to Mouse AILIM and Rat AILIM <5-2-1> Preparation of Reagents Reagents to be used in this cell ELISA were prepared as follows:

<5-2-1-1> Preparation of Recombinant CHO Cell Overexpressing Mouse AILIM

Recombinant CHO cells overexpressing mouse AILIM were prepared and obtained in the same manner as described above in <1-1> and <1-3>.

cDNA (GenBank Accession Number: AB023132 (cDNA); BAA82126 (amino acid)) containing the full-length ORF of mouse AILIM was inserted into a vector pEF-neo, and then the resulting recombinant expression vector was introduced into Chinese hamster ovary cells (CHO cell) by a commonly used method for electroporation (960 μF, 320 V) using a Gene Pulser (BioRad). The cells were cultured in RPMI1640 medium containing Geneticin (0.8 mg/ml; Gibco BRL) and 10% FCS to select drug-resistant transformed cells, thereby obtaining mouse AILIM-overexpressing recombinant CHO cells.

<5-2-1-2> Preparation of Recombinant CHO Cell Overexpressing Rat AILIM

Recombinant CHO cells overexpressing rat AILIM were prepared and obtained in the same manner as described above in <1-1> and <1-3>.

A cDNA (GenBank Accession Number: AB023134 (cDNA); BAA82128 (amino acid)) containing the full-length ORF of rat AILIM was inserted into a vector pEF-neo, and then the resulting recombinant expression vector was introduced into Chinese hamster ovary cells (CHO cell) by a commonly used method for electroporation (960 μF, 320 V) using a Gene Pulser (BioRad). The cells were cultured in RPMI1640 medium containing Geneticin (0.8 mg/ml; Gibco BRL) and 10% FCS to select drug-resistant transformed cells, thereby obtaining rat AILIM-overexpressing recombinant CHO cells.

<5-2-1-3> Preparation of Monoclonal Antibody Against Mouse AILIM

The recombinant CHO cells overexpressing mouse AILIM, which had been prepared in <5-2-1-1> described above were homogenized, and subjected to ultracentrifugation (100,000×g). Resulting pellet containing cell membrane fraction was recovered and then suspended in PBS. Resulting cell membrane fraction was injected together with Freund's complete adjuvant to Wistar rats in the footpad for primary immunization (day 0). The antigen of cell membrane fraction was further given to the rats into the footpad on the $7^{th}$ day, $14^{th}$ day and $28^{th}$ day after the primary immunization. The lymph node cells were collected from them 2 days after the final immunization.

The lymph node cells and mouse myeloma cell PAI (JCR No.B0113; Res. Disclosure, Vol.217, p.155, 1982) were combined at a ratio of 5:1. The cells were fused to each other by using polyethylene glycol 4000 (Boehringer Mannheim) as a fusion agent to prepare monoclonal antibody-producing hybridomas. Selection of hybridomas was achieved by culturing them in ASF104 medium (Ajinomoto) containing HAT, 10% fetal calf serum and aminopterin.

Reactivity of rat monoclonal antibody in the culture supernatant of each hybridoma to mouse AILIM was determined by reacting the culture supernatant with the above-mentioned CHO cells expressing mouse AILIM and then measuring the fluorescence intensity of cells stained with FITC-labeled anti-rat IgG (Cappel) in a EPICS-ELITE flow cytometer. The screening yielded multiple hybridomas producing monoclonal antibody having reactivity against mouse AILIM.

Among them, a hybridoma line was named "B10.5." Cells of this hybridoma were intraperitoneally injected ($10^6$ to $10^7$ cells/0.5 ml/mouse) to ICR nu/nu mice (female, 7 to 8-weeks old). 10 to 20 days after the injection, the ascites was collected from each mouse by laparotomy under anesthesia according to a commonly used method. The rat anti-mouse AILIM monoclonal antibody B10.5 (IgG1) was prepared from the ascites on a large scale.

<5-2-2> The Reactivity of the Antibody to Human, Mouse and Rat AILIM

Concentrations of human anti-human AILIM monoclonal antibody and control antibody to be used in the ELISA described below were determined based on the ELISA and calibration curves in <5-1> described above.

Each cells ($7 \times 10^3$ cells/well) of the recombinant CHO cell overexpressing human AILIM prepared in Example 1, the recombinant CHO cell overexpressing mouse AILIM prepared in <5-2-1-1> described above, and the recombinant CHO cell overexpressing rat AILIM prepared in <5-2-1-2> described above were plated in wells of 96-well ELISA microplates and cultured to be confluent at 37° C.

Subsequently, the supernatant was discarded, and then any one of the purified various human anti-human AILIM monoclonal antibodies or control antibody prepared above were added to each well (antibody concentrations: antibody of 200 μg/ml was diluted, with PBS containing 1% BSA, 3 times, $3^2$ times, $3^3$ times, $3^4$ times, $3^5$ times, $3^6$ times, $3^7$ times, $3^8$ times, $3^9$ times, $3^{10}$ times, $3^{11}$ times, and $3^{12}$ times) in a quantity of 50 μl/well, and the plates were reacted at room temperature for 2 hours. The solutions of the monoclonal antibodies were discarded, and each well was washed 3 times with phosphate buffer containing 1% BSA (Sigma).

Subsequently, horseradish peroxidase-conjugated anti-human IgG (Fc) antibody was added to each well (diluted 1,000 times, 50 μl/well; American Qualex), and the plates were incubated at room temperature for 1 hour.

Surplus solution of the labeled antibody was discarded and the microplates were washed 3 times with phosphate buffer containing 1% BSA. Buffer containing substrate (composition: ortho-phenylenediamine (O-phenylenediamine, OPD; 20 mg)/citrate-phosphate buffer (pH 5.0, 50 ml)/aqueous solution of 30% hydrogen peroxide (15 μl)) was added to each well (100 μl/well) and the plates were incubated at room temperature for about 7 minutes.

Subsequently, 2 M sulfuric acid was added to each well (50 μl/well) to stop the reaction. Absorbance was measured at a wavelength of 490 nm by using a microplate reader (Bio-Rad).

Control ELISA assay was performed with the following control antibodies to evaluate the above-mentioned antibodies in the same manner as described above:

(1) Mouse monoclonal antibody SA12 or SG430 against human AILIM (JP-A 11-29599 (Example 12) and WO98/38216 (Example 12));

(2) Rat monoclonal antibody B10.5 against mouse AILIM (<5-2-1-3> described above);

(3) Mouse monoclonal antibody JTT2 against rat AILIM (monoclonal antibody produced by a hybridoma, which has been deposited internationally on Oct. 11, 1996, under the international accession number FERM BP-5708 in The National Institute of Bioscience and Human-Technology, The Agency of Industrial Science and Technology, The Ministry of International Trade and Industry)), which is an international depositary authority under the Budapest Treaty; JP-A 11-29599 (Examples 1 and 2) and WO98/38216 (Examples 1 and 2)).

(4) The above-prepared human monoclonal antibody against KLH (keyhole limpet hemocyanin, PIERCE) instead of hybridoma supernatant.

Control ELISA experiment was performed in the same manner as described above using wild-type CHO cell shown below, instead of AILIM-expressing recombinant CHO cell.

The result is shown in FIGS. 3 to 14.

Based on the result obtained, 50%-effective concentration (ED50:ng/ml) was calculated as an index for the reactivity of each human anti-human AILIM monoclonal antibody to human AILIM (recombinant CHO cell overexpressing human AILIM), mouse AILIM (recombinant CHO cells overexpressing mouse AILIM), or rat AILIM (recombinant CHO cell overexpressing rat AILIM). The results obtained by the calculation are shown below.

(A) ED50 for CHO Over-Expressing Human AILIM

| | |
|---|---|
| AIF 34 (JMab-124): | 5.3 ng/ml |
| AIF182 (JMab-126): | 3.6 ng/ml |
| AIF348 (JMab-127): | 9.1 ng/ml |
| AIF620 (JMab-128): | 10.1 ng/ml |
| AIF1052 (JMab-135): | 2.0 ng/ml |
| AIH5D3 (JMab-136): | 7.5 ng/ml |
| AIH386 (JMab-137): | 9.6 ng/ml |
| AII289 (JMab-138): | 10.5 ng/ml |
| AII394 (JMab-139): | 10.6 ng/ml |
| AII488 (JMab-140): | 11.0 ng/ml |
| AIJ 40 (JMab-141): | 3.7 ng/ml |
| SA 12: | 1.8 ng/ml |
| SG430: | 1.2 ng/ml |

(B) ED50 for CHO Overexpressing Mouse AILIM

| | |
|---|---|
| AIF 34 (JMab-124): | 42 ng/ml |
| AIF348 (JMab-127): | 81 ng/ml |
| AIF620 (JMab-128): | 100 ng/ml |
| AII289 (JMab-138): | 53 ng/ml |
| AII394 (JMab-139): | 60 ng/ml |
| AII488 (JMab-140): | 70 ng/ml |

(C) ED50 for CHO Overexpressing Rat AILIM

| | |
|---|---|
| AIF 34 (JMab-124): | 45 ng/ml |
| AIF348 (JMab-127): | 62 ng/ml |
| AIF620 (JMab-128): | 97 ng/ml |
| AII289 (JMab-138): | 57 ng/ml |
| AII394 (JMab-139): | 90 ng/ml |
| AII488 (JMab-140): | 90 ng/ml |

The result showed that the human anti-human AILIM monoclonal antibodies of the present invention exhibited significantly high specificities to human AILIM.

Further, it has been revealed that 6 types of human anti-human AILIM monoclonal antibodies (shown above in (B) and (C)) are reactive to both mouse AILIM and rat AILIM (binding capability, cross-reactivity).

EXAMPLE 6

Determination of Affinity and Neutralizing Activity of Human Anti-human AILIM Monoclonal Antibody Against the Antigen (Human AILIM)

Association rate constant (ka), dissociation rate constant (kd) and dissociation constant (Kd) with respect to the reaction between each of the purified various human anti-human AILIM monoclonal antibodies prepared above and human AILIM were determined using a commercially available kit Biacore X (Amersham Pharmacia).

<6-1> Preparation of Antigen to be Immobilized on Sensor Chip

Antigen to be immobilized on sensor chip in the kit was prepared as a recombinant chimeric antigen (hereinafter referred to as "human AILIM-IgFc") consisting of the extracellular region of human AILIM and the constant region (Fc) of human IgG1.

Human AILIM-IgFc was prepared by further purifying the antigen obtained according to the method as described in earlier applications (JP-A 11-29599 (Example 16 (2)) and WO98/38216 (Example 16 (2)) by one of the present inventors, Tezuka.

The culture supernatant of recombinant cells producing the human AILIM-IgFc was loaded onto a HiTrap Protein G column (HiTrap affinity column Protein G; Amersham-Pharmacia) pre-equilibrated with phosphate buffer (30 ml) at a flow rate of 3 ml/min to adsorb the human AILIM-IgFc in the culture supernatant on the column.

Subsequently, the column was washed with phosphate buffer (20 ml), and then 100 mM citrate buffer (pH 2.0) was loaded onto the column at a flow rate of about 1 ml/min to elute the human AILIM-IgFc. Subsequently, the eluted solution was neutralized with a solution (pH 9.0) of 750 mM Tris-HCl, and then dialyzed against phosphate buffer (overnight). Then, the solution dialyzed was filtered through a filter (Millipore). Thus purified anti-human AILIM-IgFc was obtained.

Protein concentration was determined from the absorbance at $A_{280}$ measured by using a photospectrometer ($1A_{280}=1$ mg/ml). The concentration of human AILIM-IgFc was determined to be 0.28 mg/ml.

Purified chimeric protein consisting of the extracellular region of rat AILIM and the constant region (Fc) of human IgG1 (rat AILIM-IgFc; JP-A 11-29599 (Example 16 (2)) and WO98/38216 (Example 16 (2)) was also prepared according to the same manner as described above. The concentration of the rat AILIM-IgFc obtained was determined to be 0.45 mg/ml.

<6-2> Determination of Affinity and Neutralizing Activity

Experimental procedures except for immobilization of antigen (human AILIM-IgFc) on the sensor chip, which is described below, were based on the instruction manual and experimental protocol attached to the commercially available assay kit Biacore X (Amersham-Pharmacia).

HBS buffer (containing 0.01 M HEPES, 0.15 M NaCl, 3 mM EDTA and 0.005% detergent P20, (pH 7.0)) was allowed to flow through a Flow Cell-1 attached to the kit at a flow rate of 5 µl/min. Subsequently, a solution (15 µl) containing 0.005 M NHS (N-hydroxysuccinimide) and 0.2 M EDC (N-ethyl-N'-(dimethylaminopropyl) carbodiimide) was added to activate carboxyl groups of CM coated on the surface of the sensor chip.

Subsequently, 23 µl of human AILIM-IgFc solution (10 µg/ml; dissolved in 10 mM sodium acetate buffer (pH 5.0)) was added to the to immobilize the human AILIM-IgFc on the sensor chip. Subsequently, unreacted activated carboxyl groups were blocked by adding 35 ml of 1 M ethanol amine hydrochloride. The amounts of human AILIM-IgFc immobilized by the immobilization treatment performed twice was 2,444RU (resonance unit) and 2,213 RU, respectively. The unit, RU, corresponds to the mass per unit area; 1 RU=1 pg/mm².

Flow Cell-2, which is a reference flow cell, was subjected to the capping treatment in the absence of human AILIM-IgFc in the same manner as described above.

Phosphate buffer was allowed to flow through the flow cell (sensor chip) at a flow rate of 20 µl/min, and each of purified human anti-human AILIM monoclonal antibodies, which had been prepared in the Example above, was added thereto (10 to 50 µg/ml, 60 µl).

Standard condition for the measurement was: association phase for 3 minutes and dissociation phase for 10 minutes. Respective amounts of antibody bound to and released from the antigen were monitored over time to obtain a sensorgram. Dissociation of antibody from the antigen was achieved by running PBS through the sensor chip at a flow rate of 20 µl/min.

Based on the resulting sensorgram data, association rate constant (ka), dissociation rate constant (kd) and dissociation constant (Kd; Kd=kd/ka) were computed by using the analytical software (BIAevaluation 3.0) attached to the kit.

The affinity and the neutralizing activity of mouse monoclonal antibodies SA12 and SG430 to the human AILIM prepared in the Example described above were also analyzed in the same manner as described above.

Respective values obtained are shown below.

| <clone name> | <ka (1/M.Sec)> | <kd [1/Sec]> | <Kd (M)> |
|---|---|---|---|
| AIF 34 (JMab-124) | $1.6 \times 10^4$ | $1.0 \times 10^{-4}$ | $6.3 \times 10^{-9}$ |
| AIF182 (JMab-126) | $3.2 \times 10^4$ | $2.8 \times 10^{-5}$ | $8.8 \times 10^{-10}$ |
| AIF348 (JMab-127) | $1.9 \times 10^4$ | $6.4 \times 10^{-5}$ | $3.4 \times 10^{-9}$ |
| AIF620 (JMab-128) | $1.1 \times 10^4$ | $1.1 \times 10^{-4}$ | $1.0 \times 10^{-8}$ |
| AIF1052 (JMab-135) | $1.6 \times 10^4$ | $6.3 \times 10^{-5}$ | $3.9 \times 10^{-9}$ |
| AIH5D3 (JMab-136) | $2.8 \times 10^4$ | $4.9 \times 10^{-6}$ | $1.8 \times 10^{-10}$ |
| AIH386 (JMab-137) | $1.2 \times 10^5$ | $3.1 \times 10^{-4}$ | $2.6 \times 10^{-9}$ |
| AII289 (JMab-138) | $3.7 \times 10^4$ | $4.2 \times 10^{-5}$ | $1.1 \times 10^{-9}$ |
| AII394 (JMab-139) | $3.1 \times 10^4$ | $2.4 \times 10^{-5}$ | $7.7 \times 10^{-10}$ |
| AII488 (JMab-140) | $2.3 \times 10^4$ | $3.5 \times 10^{-5}$ | $1.5 \times 10^{-9}$ |
| AIJ 40 (JMab-141) | $1.9 \times 10^4$ | $1.9 \times 10^{-5}$ | $1.0 \times 10^{-9}$ |
| SA 12 | $7.8 \times 10^3$ | $7.9 \times 10^{-5}$ | $1.0 \times 10^{-8}$ |
| SG430 | $2.2 \times 10^4$ | $1.5 \times 10^{-4}$ | $6.8 \times 10^{-9}$ |

The result shows that all of the human anti-human AILIM monoclonal antibodies and anti-human AILIM mouse monoclonal antibodies exhibit markedly high binding affinity and neutralizing activity to human AILIM.

EXAMPLE 7

Activity of Human Anti-human AILIM Monoclonal Antibody to Transduce Costimulatory Signal in Human T Cell It was analyzed whether or not the human anti-human AILIM monoclonal antibodies in accordance with the present invention had the capability of controlling (enhancing and/or inhibiting) human T cell responses (production of cytokines such as IFN-γ and IL-4, cell proliferation, etc.), in other words, whether or not the antibodies exhibited regulatory activity on cellular transduction of AILIM-mediated costimulatory signal. Analysis was performed based on the amount of cytokines (IFN-γ and IL-4) produced in human T cells as well as the degree of human T cell proliferation as an index.

<7-1> Dilution of Antibody

Anti-human CD3 monoclonal antibody OKT3 (ATCC CRL-8001) was diluted with phosphate buffer (PBS) to final concentration of 8 μg/ml.

Each of the various human anti-human AILIM monoclonal antibodies prepared above was diluted with PBS to a final concentration of 40 μg/ml. The antibody solutions were further diluted with PBS to prepare various concentrations of antibodies (40 μg/ml–0.0049 μg/ml).

<7-2> Coating of Microplate with Antibody

Each well of 96-well microplates was coated with (1) anti-human CD3 monoclonal antibody OKT3 (8 μg/ml; 25 μl to each well) and any one of the various human anti-human AILIM monoclonal antibodies (40 μg/ml–0.0049 μg/ml; 25 μl to each well), or (2) anti-human CD3 monoclonal antibody OKT3 (8 μg/ml; 25 μl to each well) alone. The plates were incubated at 37° C. for 2 hours. Subsequently, the antibody solutions were discarded, and each well was washed 3 times with PBS. After the wash, RPMI1640 medium containing 10% FCS was added to each well (100 μl/well), and the plates were incubated at 37° C. for 1 hour. Thus, respective wells of the plates were coated with the antibodies mentioned above in (1) or (2).

Control experiments were carried out in the same manner by using plates coated with the following respective monoclonal antibodies as control antibodies instead of the human anti-human AILIM monoclonal antibodies.

(1) Mouse monoclonal antibody SA12 or SG430 against human AILIM (JP-A 11-29599 (Example 12) and WO98/38216 (Example 12));

(2) Mouse anti-human CETP monoclonal antibody JHC1 (also referred to as JMab109; JP-A 9-20800); and (3) Human anti-KLH monoclonal antibody (also referred to as JMab23; the above-mentioned Example).

The microplates coated with the antibodies were used in the following assays.

<7-3> Preparation of Human T Cell Suspension

Peripheral blood was collected from each normal healthy persons (5 persons; donor A, B, C, D and E). Fraction containing mononuclear cells was prepared by density-gradient centrifugation using LymphoPrep (Nycomed). Human T cells were separated from the human mononuclear cell fraction according to the manual for experimental procedure by using a Pan-T cell Isolation Kit (Miltenyi) and Magnetic Sorter. T cell count was determined using a hemacytometer. Human T cells were suspended in RPMI1640 medium containing 10% FCS to prepare human T cell suspension ($1 \times 10^6$ cell/ml).

<7-4> Cell Culture (1) Culture using Microplate Coated with Anti-human CD3 Antibody and Anti-human AILIM Antibody Human T cell suspension (donor A, B, C, D or E; 100 μl/well; $1 \times 10^5$ cells/well) was added to each well of the microplate coated with the antibody mentioned above and the plate was incubated at 37° C. for 3 days in a $CO_2$ incubator.

After cultivation, aliquots of the resulting culture supernatants (50 μl) were stored at −20° C. and then used in the assay described later (assay for IFNγ). After sampling aliquots of the culture supernatants, respective microplates were used for the following assay:

(2) Culture Using Microplate Coated with Anti-human CD3 Antibody Alone

Human T cell suspension (donor D; 100 μl/well; $1 \times 10^5$ cells/well) was added to each well of the microplates coated with the above-mentioned antibody, and then any one of the various human anti-human AILIM monoclonal antibodies was added thereto (25 μl of the antibody of 40 μg/ml–0.0049 μg/ml). The plates were incubated at 37° C. for 3 days in a $CO_2$ incubator.

<7-5> Determination of Proliferation Activity of T Cell

Methyl [$^3$H]thymidine (0.5 μCi/well; Amersham-Pharmacia) was added to each well of the plates after incubation, and the plates were incubated at 37° C. for 6 hours in a $CO_2$ incubator. After incubation, cells were trapped on GF/C filters (Packard) using Cell Harvester. Subsequently, the filters were dried at 40° C. for 3 hours or longer, and then Microscinti 0 (20 μl/well; Packard) was added thereto. Radioactivity of $^3$H incorporated of the cells trapped on the filters was measured by a β-counter (TOP COUNT) to analyze the degree of T cell proliferation after cultivation.

Results are shown in FIGS. 15 to 39.

Result of this assay showed that human T cells were significantly proliferated depending on the concentration of the cells when microplates were coated with anti-human AILIM monoclonal antibody (human monoclonal antibody or mouse monoclonal antibody) together with anti-human CD3 antibody. Further, there were some differences in the degree of cell proliferation among the donors.

On the other hand, human T cells did not grow significantly when plates had been coated with anti-human CD3 antibody alone and anti-human AILIM monoclonal antibody (human monoclonal antibody or mouse monoclonal antibody) in solution (liquid phase) was used during culturing the cells.

<7-6> Quantification of IFNγ in Culture Supernatant of T Cell

For respective cultures of T cells (donors B and C) described in (1) of <7-4>, the amounts of IFNγ in the culture supernatants were determined by a commercially available human IFNγ ELISA KIT (Amersham-Pharmacia; Endogen).

Results are shown in FIGS. 40 to 47.

Result of this assay showed that the production of IFNγ increased significantly depending on the concentration of anti-human AILIM monoclonal antibody (human monoclonal antibody or mouse monoclonal antibody).

EXAMPLE 8

Regulatory Activity of Human Anti-human AILIM Monoclonal Antibody on Mixed Lymphocyte Reaction (MLR)

It was tested whether or not the human anti-human AILIM monoclonal antibodies of the present invention were capable of controlling (enhancing and/or inhibiting) T cell responses (production of cytokines such as IFN-γ and IL-4, cell proliferation, etc.), in other words, capable of regulating the transduction of AILIM-mediated costimulatory signal into cells, by analyzing the activity (namely, DNA synthesis in cells) of controlling T cell proliferation associated with allogenic mixed lymphocyte reaction (allogenic MLR) as an index.

<8-1> Preparation of Human PBMC and T Cell

Peripheral blood (200 ml) collected from each normal healthy persons (7 persons; donor A, B, C, D, E, F and G) was dispensed on the layers of Lymphoprep (15 ml; Nycomed) in microtubes (50 ml; Falcon). After centrifugation (at 1600 rpm for 10 minutes), intermediate layers were recovered. Recovered cells were diluted 2 times or further with phosphate buffer, and then centrifuged (at 1,800 rpm for 10 minutes). Thus, PBMC (peripheral blood mononuclear cell; $2\times10^8$–$5\times10^8$ cell) was prepared. Cell count was determined by using a hemacytometer. An aliquot of the cells to be used in MLR assay ($1.08\times10^8$ cell/9 microplates) were taken and kept on ice. Remaining cells were used for the separation of T cells described below.

PanT Isolation kit (Miltenyi Biotech) was used for the separation of T cells from PBMC. According to the manual attached to the kit, remaining PBMCs were added to the solution attached to the kit, and the solution was incubated. Subsequently, cells were washed with PBS containing 5 mM EDTA and 0.5% BSA and then re-suspended in PBS. Subsequently, the cell suspension was added to a Positive Selection Column VS+ (Miltenyi Biotech) swollen with PBS, and unadsorbed fraction was recovered. Further, PBS was loaded onto the column, and the wash solution was recovered. The same treatment was repeated once. Recovered solutions were combined together to give a T cell fraction. After centrifugation of the T cell fraction, cells were re-suspended in PBS. Cell count of the resulting T cells was determined by using a hemacytometer. The cells were used in the following assay.

<8-2> Mixed Lymphocyte Reaction (MLR)

As described above, two signaling pathways one between CD28 and CD80(B7-1)/CD86(B7-2) and the other between CTLA4 and CD80(B7-1)/CD86(B7-2), for which comparatively detailed analysis have been previously made, are known as costimulatory signaling pathways required for the activation of lymphocytes such as T cell, etc.

Namely, the proliferation of T cell in response to mixed lymphocyte reaction (MLR) can be induced by the signal transduction through each of the two known pathways.

Thus, by using the substances indicated below, test of this invention was conducted to analyze (1) the inhibition of MLR by blocking the CTLA4-mediated signaling pathway; (2) the inhibition of MLR by blocking the CD80 (B7-1)/CD86(B7-2)-mediated signaling pathway; (3) the inhibition of MLR by blocking both CTLA4-mediated pathway and CD80 (B7-1)/CD86 (B7-2)-mediated signaling pathway; (4) the inhibition of MLR by blocking the tertiary signaling pathway associated with AILIM; and (5) the inhibition of MLR by blocking both CTLA4-mediated pathway and AILIM-mediated pathway.

Following test substances were used.

(1) Human anti-human AILIM monoclonal antibody (prepared in the Example described above);

(2) Mouse anti-human AILIM monoclonal antibody SA12 (same as in the above Example);

(3) Human anti-KLH monoclonal antibody (negative control; same as in the above Example);

(4) Mouse IgG antibody (anti-human CD34; negative control; Immunotech);

(5) A mixture of anti-human CD80 monoclonal antibody (Pharmingen) and anti-human CD86 monoclonal antibody (Pharmingen); and (6) Human CTLA4-IgFc chimera molecule (Ancell).

Mixed lymphocyte reaction (MLR) was conducted on the following 6 combinations using PBMCs and T cells prepared from the donors described above in <8-1>.

(i) T cell (donor A)/PBMC (donor D)
(ii) T cell (donor D)/PBMC (donor B)
(iii) T cell (donor C)/PBMC (donor A)
(iv) T cell (donor E)/PBMC (donor G)
(v) T cell (donor F)/PBMC (donor E)
(vi) T cell (donor G)/PBMC (donor F)

The concentrations of PBMCs and T cells to be used in the test were adjusted as described below.

PBMCs were suspended in PBS, and then transferred into culture dishes (60 mm). The cells were subjected to X-ray irradiation (50 Gy) with an irradiator (Hitachi MEDICO). Cells were recovered, centrifuged and then added to PRMI1640 medium containing 10% FCS. Cell count was adjusted to $2\times10^5$ cells/50 μl.

Resulting T cells from each donor were also added to PRMI1640 medium containing 10% FCS and the cell count was adjusted to $1\times10^5$ cells/50 μl.

<8-2-1> Inhibition of MLR by Human Anti-human AILIM Monoclonal Antibody

PRMI1640 medium containing 10% FCS was added to each well of a 96-well microplate having U-shaped wells. A solution of human anti-human AILIM monoclonal antibody or mouse anti-human AILIM monoclonal antibody SA12 was diluted with PRMI1640 medium containing 10% FCS to prepare solutions with various concentrations of the antibody. Diluted antibody solutions were added to the wells (final concentration: 0, 0.31, 1.25, 5 and 20 μg/ml). Subsequently, T cells (50 μL) were added to the wells. The plate was incubated at 37° C. for 1 hour in a $CO_2$ incubator (NAPCO). After the reaction was completed, PBMCs (50 μl) derived from a different donor were added to the wells to initiate MLR.

When MLR was conducted using an antibody other than human anti-human AILIM antibody (described above in (3) to (6)) as the test substance, T cells derived from a different donor were allowed to react after the incubation of PBMCs with the test substance.

On the fifth day of the culture, tritium-labeled thymidine ($^3$H-Thymidine; 20 μl; 1 μCi/well) diluted with PRMI1640 medium containing 10% FCS was added to each well. Cultivation was continued for one day. After the culture was completed, the cells were harvested using a Cell Harvester (Packard). Radioactivity of $^3$H incorporated of the cells was measured in a β-counter (TOP COUNT; Packard) to analyze the rate of T cell proliferation after the culture.

Results are shown in FIGS. 48 to 59.

<8-2-2> Inhibition of MLR by Human Anti-human AILIM Monoclonal Antibody in MLR System where CTLA4-Mediated Signaling Pathway has been Previously Blocked PRMI1640 medium containing 10% FCS was added to each well of a 96-well microplate having U-shaped wells. A solution of human anti-human AILIM monoclonal antibody or mouse anti-human AILIM monoclonal antibody SA12 was diluted with PRMI1640 medium containing 10% FCS to prepare solutions with various concentrations of the antibody. The diluted antibody solutions were added to the wells (final concentration: 0, 0.31, 1.25, 5 and 20 μg/ml). Subsequently, T cells (50 μl) were added to the wells. The plate was incubated at 37° C. for 1 hour in a $CO_2$ incubator (NAPCO).

In addition to the culture of the T cells, PBMCs (in RPMI1640 medium containing 10% FCS) derived from other donors were cultured independently after adding human CTLA4-IgFc to the PBMCs. Cultivation was performed at 37° C. for 1 hour in a $CO_2$ incubator (NAPCO). Concentration of CTLA4-IgFc was adjusted to 20 µg/ml at the start of the MLR.

Subsequently, PBMCs (50 µl) were added to the T cell culture described above to initiate MLR.

When MLR was conducted using an antibody other than human anti-human AILIM antibody (described above in (3) to (5)) as the test substance, T cells derived from a different donor were allowed to react after the incubation of PBMCs, which had been cultured in the presence of CTLA4-IgFc, with the test substance.

On the fifth day of the culture, tritium-labeled thymidine (3H-Thymidine; 20 µl; 1 µCi/well) diluted with PRMI1640 medium containing 10% FCS was added to each well. Cultivation was continued for one day. After the culture was completed, the cells were harvested by using a Cell Harvester (Packard). Radioactivity of $^3H$ incorporated of the cells was measured in a β-counter (TOP COUNT; Packard) to analyze the rate of T cell proliferation after the culture.

Results are shown in FIGS. 60 to 69.

The results obtained from the two tests described above are summarized as follows:

(1) CTLA4-IgFc blocks the CTLA-4-mediated signal transduction, and thereby inhibiting the allogenic MLR-induced proliferation of T cell.

(2) Anti-CD80 antibody and anti-CD86 antibody inhibit the signal transduction mediated by CD80/CD86, which is a ligand for CTLA4 and CD28, and thereby inhibiting the allogenic MLR-induced proliferation of T cell.

(3) A monoclonal antibody against human AILIM, like CTLA4-IgFc, anti-CD80 antibody and anti-CD86 antibody, significantly inhibits the allogenic MLR-induced T cell proliferation associated with the AILIM-mediated signal transduction in an antibody concentration-dependent manner.

In other words, these results show that a tertiary pathway mediated by AILIM and the ligand thereof in addition to the known pathways mediated by CTLA4/CD80/CD86 and mediated by CD28/CD80/CD86 exist as a costimulatory signaling pathways required for T cell activation, as well as that the AILIM-mediated signaling pathway is inhibited by antibody against AILIM.

Furthermore, it raises the possibility that contribution of AILIM-mediated pathway to the signal transduction may be comparable to those of CTLA4/CD80/CD86-mediated pathway and CD28/CD80/CD86-mediated pathway.

EXAMPLE 9

Activity of Human Anti-human AILIM Monoclonal Antibody to Induce Antibody-Dependent Cellular Cytotoxicity (ADCC)

Biological activities caused by antibodies include induction of antibody-dependent cellular cytotoxicity (ADCC). ADCC is a cytotoxic action that requires the antibody in addition to effector cells and target cells, that induces damage on the target cells induced by the effector cells such as lymphocyte, macrophage or polymorphonuclear leucocyte.

The activity of the anti-human AILIM monoclonal antibody of the present invention to induce ADCC was analyzed as follows:

$^{51}Cr$ (0.1 mCi/$10^6$ cells; Amersham-Pharmacia) was added to the culture of human AILIM-overexpressing recombinant HPB-ALL cells prepared in the Example described above, and the mixture was incubated at 37° C. for 2 hours. The cells were washed 8 times with RPMI1640 medium. The isotope-labeled cells obtained were used as target cells.

Control experiments were performed using wild-type human HPB-ALL cells labeled with the isotope as control cells in the same manner as described above.

By using Lymphosepar I (IBL), PBMC fractions were separated from peripheral blood collected from normal healthy persons. The resulting human PBMCs were used as effector cells.

The target cells ($1\times10^4$ cells/well; 25 µl/well) were plated on each well of a 96-well microplate (Nunc) having U-shaped wells. Subsequently, any one of various concentrations of human anti-human AILIM monoclonal antibodies diluted with RPMI1640 medium containing 5% FBS (0.0001–1.0 µg/ml; 25 µl/well), the medium alone (25 µl/well) or 1% Nonidet P-40 (25 µl/well; detergent having cell-lysing activity) was added to each well and the plate was incubated at room temperature for 20 minutes.

Cultivation was carried out using anti-human CD3 monoclonal antibody OKT3 (ATCC CRL-8001) as a positive control antibody instead of anti-human AILIM antibody in the same manner as described above.

Subsequently, the effector cells (E/T ratio=50; $1\times10^5$ cells/well; 50 µl/well) were added to each well and the plate was incubated at 37° C. for 16 hours under an atmosphere of 5% $CO_2$ in an incubator.

After cultivation, samples were centrifuged (at 1,500 rpm at 4° C. for 10 minutes). Resulting supernatant was recovered. Radioactivity in the centrifugal supernatant was measured by a γ-counter. The radioactivity represents the amount of $^{51}Cr$ released from the cells into the culture supernatant by the damage of cell membrane by ADCC.

Percentage of cell membrane damage (percentage cell lysis), which was caused by ADCC induced by anti-AILIM antibody or anti-CD3 antibody, was determined under an assumption that the radioactivity observed with the medium alone corresponds to 0% with respect to the cell membrane damage (0) and that with Nonidet corresponds to 100% with respect to the cell membrane damage.

Results are shown in FIGS. 70 and 71.

The result of the test showed that human anti-human AILIM monoclonal antibody of the present invention exhibited ADCC-inducing activity in a concentration-dependent manner.

EXAMPLE 10

Determination of Gene and Amino Acid Sequences of Human Anti-human AILIM Monoclonal Antibody and Analysis of the Same Sequences of cDNAs encoding the heavy chains as well as cDNAs encoding the light chains of various human anti-human AILIM monoclonal antibodies, which had been prepared in the Example described above, were determined as described below. Structural features of the genes were also analyzed.

By using Quick Prep mRNA Purification Kit (Amersham-Pharmacia), PolyA $^+$RNAs were extracted and purified from each of hybridomas (clones: AIH5D3 (JMab-136), AII289 (JMab-138) and AII394 (JMab-139)), which produce human monoclonal antibody against human AILIM prepared in the Example described above.

The hybridoma cells were suspended in a cell lysis buffer (Lysis Buffer), and lysed by using a syringe to solubilize them. Oligo (dT) resin was added to the solubilized material and the mixture was shaken gently. Subsequently, Oligo (dT) resin was washed, and then PolyA $^+$RNA was eluted with Elution Buffer. Eluted PolyA $^+$RNA was precipitated with ethanol, and then dissolved in Tris-EDTA buffer. Concentration of PolyA $^+$RNA obtained was determined by absorbance at a wavelength of 260 nm.

Double-stranded cDNA was synthesized by using PolyA $^+$RNA as a template according to M-MLV Reverse Transcriptase method using a commercially available cDNA synthesis kit (GIBCOBRL) and synthetic oligo DNA NotI-T (SEQ ID NO:1) as a primer.

Specifically, single-stranded cDNA was synthesized in a solution (about 50 µl) containing PolyA $^+$RNA (about 5 µg) purified from the hybridomas as a template, the primer (about 400 pmole) and M-MLV Reverse Transcriptase at 37° C. for 1 hour. Subsequently, dNTP, DNA polymerase I, RNaseH, DNA ligase, buffer and distilled water were added to the reaction solution (4 µl), and the mixture was incubated at 16° C. for 2 hours to synthesize double-stranded cDNA. The resulting double-stranded cDNA was extracted with phenol/chloroform and then precipitated with ethanol.

Subsequently, EcoRI linker DNA (about 300 pmole) and DNA ligase (Ligation High; 33 µl; TOYOBO) was added to the solution containing the double-stranded cDNA in TE buffer (about 50 µl) and the mixture was incubated at 16° C. for about 80 minutes to ligate the cDNA with the linker DNA. The linker DNA used was a double-stranded DNA consisting of oligo DNA (20adp; SEQ ID NO:2) and oligo DNA (24adp; SEQ ID NO:3), which had been 5'-phosphorylated and annealed to each other by a commonly used method.

The DNA ligate was extracted with phenol/chloroform, and then precipitated with ethanol. Subsequently, the DNA reactant was digested with a commercially available restriction enzyme NotI (TOYOBO), and then incubated with a commercially available ATP solution (GIBCO BRL) and T4 kinase (TOYOBO) at 37° C. for 30 minutes to phosphorylate the 5' end thereof.

The resulting DNA was precipitated with ethanol-, and then fractionated by polyacrylamide gel electrophoresis. A piece of gel containing DNA of about 500 bp to 2000 bp was cut out. Cutting of the gel was carried out while the DNA stained with ethidium bromide was being visualized by irradiating UV light in a photographic device.

The gel cut off was crushed and then suspended in TE buffer. The suspension was centrifuged and the resulting supernatant was recovered.

The DNA recovered was ligated to a commercially available lambda phage vector λEXcell (0.25 µg; Amersham Pharmacia) in the presence of commercially available DNA Ligase (Ligation High; TOYOBO) (at 16° C. for 30 minutes). In the next step, the DNA ligate was packaged into lambda phage using a commercially available lambda phage packaging kit Gigapack III Gold (STRATAGENE) and the resulting phage particles were infected to E. coli NM522 as a host to prepare a cDNA library. All the manipulations were carried out according to the experimental protocol attached to the kit.

Subsequently, the cDNA library was screened by a plaque hybridization method (Maniatis et al., "Molecular Cloning: A Labolatory Manual," Cold Spring Harbor Laboratory, Cold Spring Harbor, N.Y.) as follows:

The cDNA library (1×10$^4$ plaques) was plated on agar plates and replica filters thereof were prepared by using Hybond-N nylon membranes (Amersham Pharmacia). These replica filters were subjected to hybridization treatment using probes labeled by using γ$^{32}$P-ATP in a hybridization buffer according to the plaque hybridization method. Probes used were HIGLC (SEQ ID NO:4) for antibody light chain and NHCc2 (SEQ ID NO:5) for antibody heavy chain. Single-plaque isolation was carried out from the positive clones obtained in the primary screening and secondary screening.

Each of heavy chain and light chain of the antibody was amplified by PCR using a single PCR primer and Taq PCR kit (TAKARA) by utilizing phage suspension from each positive clone as a template DNA. A pair of primers used for antibody light chain were ExcellE (SEQ ID NO:6) and ck117 (SEQ ID NO:7), and a pair of primers used for antibody heavy chain were ExcellE (SEQ ID NO:6) and NHCc2 (SEQ ID NO:5). The resulting PCR products were fractionated according to a usual method using agarose gel electrophoresis. Pieces of gel containing DNAs of about 600 bp corresponding to the heavy chain and light chain were cut out. Nucleotide sequences of the DNAs purified from the gel were analyzed by using a DNA Sequencer (373A; PE-Applied Biosystems), ABI PRISM Sequencing Software (PE-Applied Biosystems) and ABI PRISM Auto Assembler (PE-Applied Biosystems). DNA from each positive clone was verified to have sufficient length of nucleotide sequence.

λPhage from the plaque of each positive clone was infected to E. coli NP66 for in vivo excision of plasmid DNA of interest, and the resulting filamentous phages were plated on ampicillin-containing plates to give colonies. Subsequently, plasmid DNAs were recovered and purified from the colonies by a commonly used method, and E. coli JM109 was transformed with the plasmids. Subsequently, the transformed cells were plated on ampicillin-containing nutrient agar plates to form colonies.

Subsequently, bacterial suspension in ampicillin-containing LB medium derived from each colony was transferred to a liquid nutrient medium and the bacteria were cultured at 37° C. for 24 hours. The bacteria were harvested from the culture, and then the plasmid DNA was purified by a plasmid purification kit (Quiagen). Each of the plasmid DNAs was digested with restriction enzymes EcoRI/NotI to verify the presence of vector DNA and insert DNA (heavy chain cDNA or light chain cDNA).

Each nucleotide sequence of cDNA encoding heavy chain and antibody light chain of the antibody, which was inserted in each purified plasmid, was determined by a commonly used method using DNA Sequencer (377A; PE-Applied Biosystems), ABI PRISM Sequencing Software (PE-Applied Biosystems) and ABI PRISM Auto Assembler (PE-Applied Biosystems).

Primers used for the sequence determination were as follows:

<Primers Used for the Determination of Heavy Chain cDNA>

M13R primer (SEQ ID NO:8; STRATAGENE), ExcellE (SEQ ID NO:6), 136H (SEQ ID NO:9), 138/9H (SEQ ID NO:10), AILIMHC1 (SEQ ID NO:11), HCc1 (SEQ ID NO:12), NHCc2 (SEQ ID NO:5), HCc7 (SEQ ID NO:13), HCc8 (SEQ ID NO:14), HCc3 (SEQ ID NO:15), HCc4 (SEQ ID NO:16), HCc6 (SEQ ID NO:17), HIGHC (SEQ ID NO:18), HCc9 (SEQ ID NO:19), HCc5 (SEQ ID NO:20) and polyA (SEQ ID NO:21).

<Primers Used for the Determination of Light Chain cDNA>

M13R primer (SEQ ID NO:8; STRATAGENE), ExcellE (SEQ ID NO:6), AILIMLC1 (SEQ ID NO:22), AILIMLC2 (SEQ ID NO:23), LCc1 (SEQ ID NO:24), ck117 (SEQ ID NO:7), HIGLC (SEQ ID NO:4), LCc2 (SEQ ID NO:25), HIK (SEQ ID NO:26), and polyA (SEQ ID NO:21).

Sequence Listing shown below contains cDNA sequence encoding heavy chain and cDNA sequence encoding light chain of human monoclonal antibody against human AILIM, which are produced by each hybridoma mentioned above, as well as amino acid sequences deduced from the cDNA sequences.

Clone AIH5D3 (JMab-136)

<Heavy Chain>

DNA sequence: SEQ ID NO:27 (signal sequence: nucleotide number 69 to 125, V region: nucleotide number 126 to 419)

Amino acid sequence: SEQ ID NO:28 (comprising signal sequence: amino acid number 1 to 19, variable region: amino acid number 20 to 117)

<Light Chain>

DNA sequence: SEQ ID NO:29 (signal sequence: nucleotide number 39 to 104, V region: nucleotide number 105 to 386)

Amino acid sequence: SEQ ID NO:30 (comprising signal sequence: amino acid number 1 to 22, variable region: amino acid number 23 to 116)

Clone AII289 (JMab-138)

<Heavy Chain>

DNA sequence: SEQ ID NO:31 (comprising signal sequence: nucleotide number 94 to 150, V region: nucleotide number 151 to 441)

Amino acid sequence: SEQ ID NO:32 (comprising signal sequence: amino acid number 1 to 19, variable region: amino acid number 20 to 116)

<Light Chain>

DNA sequence: SEQ ID NO:33 (comprising signal sequence: nucleotide number 28 to 87, V region: nucleotide number 88 to 375)

Amino acid sequence: SEQ ID NO:34 (comprising signal sequence: amino acid number 1 to 20, variable region: amino acid number 21 to 116)

Clone AII394 (JMab-139)

<Heavy Chain>

DNA sequence: SEQ ID NO:35 (signal sequence: nucleotide number 96 to 152, V region: nucleotide number 153 to 443)

Amino acid sequence: SEQ ID NO:36 (comprising signal sequence: amino acid number 1 to 19, variable region: amino acid number 20 to 116)

<Light Chain>

DNA sequence: SEQ ID NO:37 (signal sequence: nucleotide number 33 to 92, V region: nucleotide number 93 to 380)

Amino acid sequence: SEQ ID NO:38 (comprising signal sequence: amino acid number 1 to 20, variable region: amino acid number 21 to 116)

By using analytical software for gene sequence, the library V BASE Sequence for human immunoglobulin variable region genes constructed by Tomlinson et al. (Immunol. Today, Vol.16, No.5, p.237–242, 1995) was searched for each of the DNA sequences determined herein.

Result showed that the V-region genes of the respective heavy chain and light chain of the above-mentioned human monoclonal antibodies consisted of the following segments.

<Heavy Chain V-Region Gene>
clone AIH5D3 (JMab-136): 1-02
clone AII289 (JMab-138): 3-13
clone AII394 (JMab-139): 3-13
<Light Chain V-Region Gene>
clone AIH5D3 (JMab-136): L5
clone AII289 (JMab-138): A27
clone AII394 (JMab-139): A27

EXAMPLE 11

Inhibitory Effect of Human Anti-human AILIM Monoclonal Antibody on Delayed-Type Hypersensitivity (DTH)

The biological system of immune response, the function of which is to eliminate harmful antigens (pathogenic microorganisms such as virus, bacterium and parasite, foreign body, etc.) to the living bodies, and can be broadly divided into congenital immunity and acquired immunity.

The former is a system of elimination based on non-specific recognition including phagocytosis by phagocytes (polymorphonuclear leukocyte, monocyte, macrophage, etc.), attack by natural killer (NK) cells, and opsonization of antigen by complement, etc.

The latter, acquired immune response, is a system of elimination by lymphocytes (mainly, T cell and B cell) which acquired specificity (activation) to the antigen.

Further, acquired immune response can broadly be divided into cellular immunity and humoral immunity.

Unlike antibody-dependent humoral immunity, cellular immunity is an immune response expressed in general by the direct action of T cell on an antigen as the target. Cellular immunity is known to be involved in immune response to virus or tumor, immune response induced after transplantation of tissue or organ, hypersensitivity to some drugs, and some of autoimmune diseases.

Most typical phenomenon belonging to cellular immunity is the well-known tuberculin allergy (almost synonymous with tuberculin hypersensitivity). Tuberculin allergy is a delayed allergy triggered by the infection by tubercle bacillus. The allergy is due to the infection by tubercle bacillus and can be induced by causing immune response by intracutaneously injecting, to a living body, tuberculin protein produced in culture supernatant of tubercle bacillus.

Delayed allergy is an allergy mediated by T cell (memory T cell memorizing antigen) sensitized with an antigen. The allergy is called "delayed type," because it takes 24 to 48 hours for a living body sensitized with the antigen to express allergic response with inflammation induced by the memory T cell when contacted again with the antigen.

The phenomenon of tuberculin allergy, which is a representative of delayed allergies, has generally been utilized in "tuberculin test" to diagnose whether or not sensitization by the infection of tubercle bacillus has already been established in an animal. Specifically, the test is conducted as follows: purified tuberculin (purified protein derivative; PPD; 0.1 ml of the derivative of 0.05 μg/0.1 ml (2.5 TU) for general diagnostic use), which is tuberculin protein purified from the culture of tubercle bacillus, is intracutaneously given to an animal; the major axis of skin redness at the injection site is measured 48 hours after the injection; and the presence of infection of tubercle bacillus can be diagnosed based on the major axis measured. If the major axis of the redness is shorter than 4 mm, then the subject is negative; if it is within the range of 4–9 mm then the subject is false positive; and if it is 10 mm or longer then the subject is decided positive.

Delayed allergies associated with cellular immunity include, for example, Jones-Mote type hypersensitivity transiently induced by a small amount of protein or the like, contact allergy to drugs such as picryl chloride or plant toxins such as Japanese lacquer, or allergy associated with graft rejection (e.g., allogenic graft) as well as the above-mentioned allergy to antigen from infectious pathogen such as tuberculin allergy caused by tubercle bacillus described above.

In this test, the inhibitory effect of anti-AILIM antibody on delayed-type hypersensitivity (delayed allergy) was evaluated by utilizing the above-mentioned tuberculin test. The test was conducted as follows:

Each of cynomolgus monkeys (male, body weight: 6.0–8.5 kg, Environmental Biological Life Science Research Center Inc.; 3 individuals in each group), which had been sensitized with BCG (Bacille de Calmette et Guerin), which is an attenuated live bacterium of bovine-type tubercle bacillus, was anesthetized with ketamine hydrochloride (10 mg/kg, intramuscular injection), and then any one of the test samples indicated below was intracutaneously given with a quantity of 0.1 ml to each injection site (6 injection sites/ individual) in the chest. The distances between the injection sites of the sample were 3 cm or longer.

(1):1 mixed solution of human anti-human AILIM monoclonal antibody (JMab-136; 0.2 mg; 10 µg at each injection site) and tuberculin (4 µg/1 ml of physiological saline);

(2) 1:1 mixed solution of human anti-human AILIM monoclonal antibody (JMab-136; 2 mg; 100 µg at each injection site) and tuberculin (4 µg/1 ml of physiological saline);

(3) phosphate buffer (PBS (–)) as a control;

(4) 1:1 mixed solution of a commercially available steroidal anti-inflammatory agent, Prednisolone (0.2 mg; 10 µg at each injection site) and tuberculin (4 µg/1 ml of physiological saline) as a positive control;

(5) 1:1 mixed solution of human anti-KLH monoclonal antibody (Example <2-2>; 0.2 mg; 10 µg at each injection site) and tuberculin (41 g/1 ml of physiological saline) as a negative control.

24 hours after injection of each sample, the major axis and minor axis of redness at each injection site were measured to determine the area of the redness.

The result is shown in FIG. 72.

The result showed that redness due to delayed allergy was significantly inhibited in any groups subjected to injection of the anti-AILIM antibodies, as compared with the control and negative control groups. The inhibitory effect was comparable to that of the steroidal anti-inflammatory drug used as a positive control.

EXAMPLE 12

Analysis for the Expression of AILIM in Various Tissues of Patients with Graft Versus Host Disease (GVHD)

Expression of AILIM in a variety of tissues obtained of biopsy from patients, who were recipients subjected to transplantation of allogenic graft from donors and had been diagnosed clinically to be affected with acute or chronic graft versus host disease (GVHD) after the transplantation, was analyzed by a commonly used method. Tissues were stained with HE and human anti-human AILIM monoclonal antibody (JMab-36) prepared in the Example described above.

Analysis was carried out using 33 samples form various tissues collected from acute GVHD patients (28 cases) as well as 5 samples from chronic GVHD patient (5 cases).

Results were as follows: AILIM-positive reaction was found in 15 of 29 samples of skin tissue; in 1 of 3 samples of stomach tissue; and in 1 of 1 sample of colon tissue; which were all obtained from acute GVHD patients. AILIM-positive reaction was found in 1 of 3 samples of skin tissue; in 2 of 2 samples of colon tissue; which were all obtained from chronic GVHD patients. Further, AILIM-positive reaction was found in 10 of 13 samples in which significant lymphocyte infiltration had been observed.

EXAMPLE 13

Activity of Human Anti-human AILIM Monoclonal Antibody to Transduce Costimulatory Signal in Monkey T Cell The experiment conducted in Example 7 has demonstrated that the human anti-human AILIM monoclonal antibodies of the present invention are capable of enhancing the proliferation of human T cell via controlling the human T cell response, specifically, controlling the transduction of AILIM-mediated costimulatory signal to the cell. In this test, it was analyzed whether or not the human monoclonal antibodies exhibit activity of enhancing cell proliferation of monkey T cell by the same method as described in Example 7.

<13-1> Dilution of Antibody

Anti-human CD3 monoclonal antibody SP34 (BD-Pharmingen) was diluted with phosphate buffer (PBS) to a final concentration of 1 µg/ml.

The above-prepared human anti-human AILIM monoclonal antibody JMAb136 was diluted with PBS to a final concentration of 40 µg/ml. The antibody solutions were further diluted with PBS to prepare various concentrations of antibodies (40 µg/ml–0.064 µg/ml).

<13-2> Coating of Microplate with Antibody

Each well of 96-well microplates was coated with anti-human CD3 monoclonal antibody SP34 (1 µg/ml; 25 µl to each well) and the human anti-human AILIM monoclonal antibody JMAb136 (40 µg/ml–0.064 µg/ml; 25 µl to each well). The plates were incubated at 37° C. for 2 hours. Subsequently, the antibody solutions were discarded, and each well was washed 3 times with PBS. After the wash, RPMI1640 medium containing 10% FCS was added to each well (100 µl/well), and the plates were incubated at 37° C. for 1 hour. Thus respective wells of the plates were coated with the antibodies mentioned above.

Control experiments were carried out in the same manner using plates coated with human anti-KLH monoclonal antibody (JMab23; see the previous Examples) as control antibodies instead of the human anti-human AILIM monoclonal antibodies.

The microplates coated with the antibodies were used in the following assays.

<13-3> Preparation of Monkey T Cell Suspension

Peripheral blood was collected from cynomolgus monkeys and mononuclear cells were fractionated by density gradient centrifugation using NycoPrep1.077A (Nycomed). According to the experimental manual, monkey T cells were separated from the cynomolgus monkey mononuclear cells by using anti-human CD4 antibody M-T477 (BD-Pharmingen), anti-human CD8 antibody RPA-T8 (BD-Pharmingen), anti-mouse IgG microbead (Miltenyi) and a Magnetic Sorter. T cell count was determined using a hemacytometer. Monkey T cells were suspended in RPMI1640 medium containing 10% FCS. Thus monkey T cell suspension (1×10$_6$ cell/ml) was prepared.

<13-4> Cell Culture (1) Culture Using Microplate Coated with Anti-human CD3 Antibody and Anti-human AILIM Antibody Simian T cell suspension was added to each well of a microplate coated with the antibody mentioned above and the plate was incubated at 37° C. for 2 days in a $CO_2$ incubator.

After the culture was completed, respective microplates were used in the following assays:

<13-5> Determination of Proliferation Activity of T Cell

Methyl [$^3$H]thymidine (0.5 µCi/well; Amersham-Pharmacia) was added to each well of the plates after incubation, and the plates were incubated at 37° C. for 6 hours in a $CO_2$ incubator. After incubation, the cells were trapped on GF/C filters (Packard) by using a Cell Harvester. Subsequently, the filters were dried at 40° C. for 3 hours or longer, and then Microscinti 0 (20 µl/well; Packard) was added thereto. Radioactivity of $^3$H incorporated in the cells trapped on the filters was measured by a β-counter (TOP COUNT) to analyze the degree of T cell proliferation after the culture.

The result is shown in FIG. 73.

The result of this assay showed that simian T cells were significantly proliferated depending on the concentration of the cells when microplates were coated with anti-human AILIM monoclonal antibody (human monoclonal antibody or mouse monoclonal antibody) together with anti-human CD3 antibody.

The result also suggests that the human anti-human AILIM monoclonal antibodies of the present invention can bind to monkey AILIM and have the activity to regulate the function of monkey AILIM.

EXAMPLE 14

Establishment of Method for Identifying and Quantifying Substances Capable of Binding to AILIM or AILIM Ligand A method of ELISA (Enzyme-linked Immuno solvent assay) was established to identify or quantify a substance capable of binding to AILIM (ICOS) or AILIM ligand (B7h/B7RP1/GL50/LICOS).

The principle of the method described below in detail as an example is based on estimating, by ELISA, the degree of inhibition on the binding between soluble human AILIM (hAILIM-IgFc) and soluble human AILIM ligand (hB7h-IgFc) caused by the substance.

<14-1> Sample

The following samples were used:

(1) Streptavidin-HRP (Southern Biotechnology Associates, Inc.);

(2) Soluble human AILIM ligand (fusion protein between the extracellular region of human B7h and the constant region of human IgG1);

The protein was prepared by the method described below in <14-2>;

(3) Biotin-labeled soluble AILIM-IgFc;

The AILIM-IgFc was prepared by further purifying the antigen obtained according to the same method as described in earlier applications (JP-A 11-29599 (Example 16 (2)) and WO98/38216 (Example 16 (2))) of one of the present inventors, Tezuka;

(4) Human anti-human AILIM monoclonal antibody (JMab-136; described above);

(5) Human anti-KLH monoclonal antibody (negative control antibody; JMab-23; described above);

(6) Phosphate buffer (PBS (−); Nikken Seibutsu);

(7) PRMI1640 medium (Nikken Seibutsu);

(8) Fetal calf serum (FCS; JRH-Bioscience);

(9) 30% Bovine serum albumin (BSA; Sigma);

(10) Tween20 (BioRad);

(11) TMB+substrate chromogen (Dako).

<14-2> Preparation of Soluble Human AILIM Ligand (Fusion Protein (hB7h-IgFc) of the Extracellular Region of Human B7h and the Constant Region of Human IgG1)

Total RNA was prepared from human peripheral blood-derived mononuclear cells in the same manner as described in the Example above. cDNA was synthesized from the obtained total RNA (5 µg) as a template and by using Superscript Preamplification System for First Strand cDNA Synthesis (GIBCO-BRL).

Subsequently, 5'primer (5'-GAGGTCTCCGCCCTC-GAGATGCGGCTGGGCAGTCC-3', SEQ ID NO:39) having XhoI restriction site and 3'primer (5'-CACAGGA-CAGCCAGGGGATCCCACGTGGCCGCG-3', SEQ ID NO:40) having BamHI restriction site at their respective ends were designed and synthesized to amplify cDNA encoding the extracellular region of human AILIM ligand (hB7h) by PCR. By using the cDNA as a template and the primer pair, PCR was conducted to prepare a DNA having XhoI and BamHI at respective ends thereof containing cDNA encoding the extracellular region of human B7h. The resulting PCR products were digested with XhoI and BamHI, and fractioned by agarose gel electrophoresis to isolate a band corresponding to about 720-bp cDNA fragment, that was predicted to encode the extracellular region of interest. The isolated cDNA fragment was subcloned into plasmid pBluescript II SK (+) (Stratagene) pre-digested with XhoI and BamHI. It was verified that the cDNA fragment contained the portion encoding the extracellular region of human B7h by sequencing analysis using an automated fluorometric DNA sequencer (Applied Biosystems).

On the other hand, DNA encoding Fc of human IgG1 as a fusion partner was prepared as a BamHI-XbaI DNA fragment (about 1.3 kb) by digesting a plasmid (see, Cell, Vol.61, p.1303–1313, 1990; prepared by Dr. Seed et al., at the Massachusetts General Hospital) with BamHI and XbaI. This fragment contained exons encoding the hinge regions of human IgG1, Cγ12, and Cγ13.

The XhoI-BamHI fragment encoding the extracellular region of human B7h (hB7h), and the BamHI-XbaI fragment containing exons encoding Fc (abbreviated as "IgFc") of human IgG1, prepared as described above, were subcloned into a plasmid pBluescript II SK (+) (Stratagene) pre-digested with XhoI and XbaI.

Subsequently, the plasmid was digested with XhoI and XbaI to prepare a DNA fragment about 1.8-kb containing fusion DNA between the extracellular region of human B7h and human IgFc. By using T4 DNA ligase, this fusion DNA fragment was inserted into an expression vector pME18S (Medical Immunology, Vol.20, No.1, p.27–32, 1990, and "Handbook for Genetic Engineering," Experimental Medicine, supplement, Yodosha, pp. 101–107, 1992) between XhoI and XbaI sites, to construct a plasmid phB7h-IgFc.

Monolayer COS7 cells (ATCC CRL-1651) cultured to be sub-confluent in DMEM medium containing 10% fetal calf serum and ampicillin, were transformed with the plasmid phB7h-IgFc by electroporation to yield transformed cells.

The transformed cells were allowed to expresshB7h-IgFc by culturing them in serum-free ASF104 medium for 72 hours.

HB7h-IgFc was purified by using a Protein G Sepharose affinity column (Amersham Pharmacia) as follows:

The above-mentioned culture supernatant was centrifuged to obtain centrifugal supernatant. The resulting supernatant was loaded onto a Protein G Sepharose affinity column pre-equilibrated with a binding buffer. Subsequently, the column was washed with the binding buffer, and then elution was performed with an elution buffer. The eluted solution was recovered and then dialyzed against phosphate buffer. The outer dialyzing buffer was changed twice or more. Thus purified hB7h-IgFc was obtained.

<14-3> Dilution of Antibody and Soluble Human AILIM (□AILIM-IgFc) and Reaction Thereof Original solutions (20 µg/ml) of anti-human AILIM monoclonal antibody (JMab-136) and human anti-KLH monoclonal antibody (JMab-23) as a negative control antibody were diluted in a series of 11 levels, and each sample (200 µl) was combined and mixed well with 200 µl of RPMI1640 medium containing 10% FCS. Thus various concentrations of antibody solutions were prepared. Biotin-labeled hAILIM-IgFc (2 µl/tube; final concentration 1 µg/ml) was added to each of the prepared solutions with various concentrations. The resulting solutions were mixed well and incubated at room temperature for 30 minutes.

<14-4> Assay for the Activity of Anti-AILIM Monoclonal Antibody to Inhibit the Binding Between hAILIM-IgFc and hB7h-IgFc hB7h-IgFc was added to each well of a 96-well microplate (50 µl/well (800 ng/well)). The plate was sealed and then incubated at 37° C. for 1 hour. Solution was removed from each well, and the wells were washed 3 times with PBS (120 µl). Subsequently, PBS containing 0.5% BSA (100 µl/well) was added to each well to block the unreacted sites. The plate was sealed and incubated at 37° C. for 1 hour. After incubation, the solution was removed, and then the wells were washed 3 times with PBS (120 µl). Subsequently, each sample (50 µl/well) prepared in <14-3> was added to the wells. The plate was sealed and incubated at 37° C. for 1 hour. Solution was removed from each well. The wells were washed 3 times with RPMI1640 medium containing 10% FCS (120 µl) pre-heated at 37° C. Subsequently, PBS containing 3.7% formalin (100 µl/well) was added to each well, and the plate was incubated on ice for 5 minutes. Solution was removed from each well, and the wells were washed 3 times with 0.1% Tween20 (120 µl). Subsequently, Streptavidin-HRP (50 µl/well) was added to each well. The plate was sealed and incubated at room temperature for 30 minutes. Solution was removed from each well, and the plate was washed 3 times with PBS containing 0.1% Tween20 (120 µl). Subsequently, TMB+substrate chromogen (50 µl/well) was added to each well and the plate was incubated at room temperature for 20 minutes. Subsequently, 2N sulfuric acid (50 µl/well) was added to each well to stop the reaction. Absorbance of each well was measured at a wavelength of 450 nm by a THERMO max (Molecular Devices).

Results are shown in FIGS. 74 to 76.

The results showed that anti-AILIM antibody had the activity of inhibiting the binding between hAILIM-IgFc and hB7h-IgFc in a dosage-dependent manner.

Accordingly, this Example indicates that an assay system illustrated by the present method can be utilized to screen and identify substances capable of binding to AILIM or AILIM ligand (for example, antibody or synthetic low molecular weight compound).

EXAMPLE 15

Activity of Human Anti-human AILIM Monoclonal Antibody to Inhibit the Proliferation of Human T Cell Associated with the Transduction of AILIM-AILIM Ligand-Mediated Costimulatory Signal It was analyzed whether or not the anti-human AILIM monoclonal antibodies of the present invention had regulating activity on the transduction of signal mediated by AILIM on the surface of human T cell, based on the measurement of inhibitory effect of the human anti-human AILIM monoclonal antibody on cell proliferation induced by contacting human T cell with AILIM ligand (B7h/B7RP1/GL50/LICOS).

<15-1> Dilution of Antibody

Anti-human CD3 monoclonal antibody OKT3 (ATCC CRL-8001) was diluted with phosphate buffer (PBS) to a final concentration of 8 µg/ml.

The soluble human AILIM ligand (hB7h-IgFc) prepared above was diluted with PBS to a final concentration of 40 µg/ml. The antibody solutions were further diluted with PBS to prepare various concentrations of antibodies (40 µg/ml–0.064 µg/ml).

<15-2> Coating of Microplate with Antibody

Each well of 96-well microplates was coated with (1) anti-human CD3 monoclonal antibody OKT3 (8 µg/ml; 25 µl in each well) and hB7h-IgFc (40 µg/ml–0.064 µg/ml; 25 µl in each well). The plates were incubated at 37° C. for 2 hours. Subsequently, the antibody solutions were discarded, and each well was washed 3 times with PBS. After the wash, RPMI1640 medium containing 10% FCS was added to each well (100 µl/well), and the plates were incubated at 37° C. for 1 hour. Thus respective wells of the plates were coated.

<15-3> Preparation of Human T Cell Suspension

Peripheral blood was collected from normal healthy persons and the mononuclear cells were fractionated by density-gradient centrifugation using LymphoPrep (Nycomed). According to the experimental manual, human T cells were separated from the human mononuclear cells by using a Pan-T cell Isolation Kit (Miltenyi) and a Magnetic Sorter. T cell count was determined by using a hemacytometer. Human T cells were suspended in a RPMI1640 medium containing 10% FCS supplied with human anti-human AILIM monoclonal antibody JMab136 (20 µg/ml). Human T cell suspension ($1\times10^6$ cells/ml) prepared was incubated at room temperature for 30 minutes.

Human anti-KLH monoclonal antibody JMAb23 (20 µg/ml) was used as a negative control antibody.

<15-4> Cell Culture

In the same manner as described above, human T cell suspension (100 µl/well; $1\times10^5$ cells/well) was added to each well of a microplate coated with anti-human CD3 antibody and hB7h-IgFc, and the plate was incubated at 37° C. for 3 days in a $CO_2$ incubator.

<15-5> Determination of Proliferation Activity of T Cell

Methyl [$^3$H]thymidine (0.5 µCi/well; Amersham-Pharmacia) was added to each well of the plates after cultivation, and the plates were incubated at 37° C. for 6 hours in a $CO_2$ incubator. After incubation, the cells were trapped on GF/C filters (Packard) by using a Cell Harvester. Subsequently, the filters were dried at 40° C. for 3 hours or longer, and then Microscinti 0 (20 µl/well; Packard) was added thereto. Radioactivity of $^3$H incorporated in the cells trapped on the filters was measured by a β-counter (TOP COUNT) to analyze the degree of T cell proliferation after the culture.

The result is shown in FIG. 77.

The result obtained in this test showed that human T cells grew significantly depending on the concentration of human B7h-IgFc (in the assay using the negative control antibody). In addition, the anti-human AILIM monoclonal antibody significantly inhibited the proliferation of human T cells.

EXAMPLE 16

Activity of Human Anti-human AILIM Monoclonal Antibody to Inhibit the Proliferation of Monkey T Cell Associated with the Transduction of AILIM-AILIM Ligand-Mediated Costimulatory Signal The same test was conducted by using monkey T cells instead of human T cells used in Example 15 described above.

<16-1> Dilution of Antibody and Others

Anti-human CD3 monoclonal antibody SP34 (BD-Pharmingen) was diluted with phosphate buffer (PBS) to a final concentration of 1 µg/ml.

The human B7h-IgFc prepared above was diluted with PBS to a final concentration of 40 µg/ml. The antibody solution was further diluted with PBS to prepare various concentrations of the antibody (40 µg/ml–0.0064 µg/ml).

<16-2> Coating of Microplate with Antibody

Each well of 96-well microplates was coated with (1) anti-human CD3 monoclonal antibody SP34 (BD-Pharmingen) (1 µg/ml; 25 µl in each well) and human B7h-IgFc (40 µg/ml–0.0064 µg/ml; 25 µl in each well). The plates were incubated at 37° C. for 2 hours. Subsequently, the antibody solution was discarded, and each well was washed 3 times with PBS. After the wash, RPMI1640 medium containing 10% FCS was added to each well (100 µl/well), and the plates were incubated at 37° C. for 1 hour. Thus, respective wells of the plates were coated with the antibody.

<16-3> Preparation of Monkey T Cell Suspension

Peripheral blood was collected from cynomolgus monkeys. A fraction containing mononuclear cells was prepared by density-gradient centrifugation using NycoPrep1.077A (Nycomed). According to the experimental manual, monkey T cells were separated from the cynomolgus monkey mononuclear cells by using anti-human CD4 antibody M-T477 (BD-Pharmingen), anti-human CD8 antibody RPA-T8 (BD-Pharmingen), anti-mouse IgG microbead (Miltenyi) and a Magnetic Sorter. T cell count was determined by using a hemacytometer. Monkey T cells were suspended in RPMI 1640 medium containing human anti-human AILIM monoclonal antibody JMab-136 (20 µg/ml) and 10% FCS to prepare monkey T cell suspension ($1 \times 10^6$ cells/ml). The suspension was incubated at room temperature for 30 minutes.

Human anti-KLH monoclonal antibody JMab-23 (20 µg/ml) was used as a negative control antibody.

<16-4> Cell Culture

In the same manner as described above, monkey T cell suspension (100 µl/well; $1 \times 10^5$ cells/well) was added to each well of a microplate coated with anti-human CD3 antibody and hB7h-IgFc, and the plate was incubated at 37° C. for 3 days in a $CO_2$ incubator.

<16-5> Determination of Activity of T Cell Proliferation

Methyl [$^3$H]thymidine (0.5 µCi/well; Amersham-Pharmacia) was added to each well of the plates after the cultivation, and the plates were incubated at 37° C. for 6 hours in a $CO_2$ incubator. After the incubation, the cells were trapped on GF/C filters (Packard) by using a Cell Harvester. Subsequently, the filters were dried at 40° C. for 3 hours or longer, and then Microscinti 0 (20 µl/well; Packard) was added thereto. Radioactivity of $^3$H incorporated into the cells trapped on the filters was measured by a b-counter (TOP COUNT) to analyze the degree of T cell proliferation after the culture.

The result is shown in FIG. 78.

The result obtained in this test showed that monkey T cells grew significantly depending on the concentration of human B7h-IgFc (in the assay using the negative control antibody). In addition, the anti-human AILIM monoclonal antibody significantly inhibited the proliferation monkey T cells.

Sequence Listing Free Text

SEQ ID NO:1
Other Information: Description of Artificial Sequence: Artificially synthesized primer sequence, NotI-T.

SEQ ID NO:2
Other Information: Description of Artificial Sequence: Artificially synthesized linker sequence, 20 adp SEQ ID NO:3
Other Information: Description of Artificial Sequence: Artificially synthesized linker sequence, 24 adp.

SEQ ID NO:4
Other Information: Description of Artificial Sequence: Artificially synthesized primer sequence, HIGLC.

SEQ ID NO:5
Other Information: Description of Artificial Sequence: Artificially synthesized primer sequence, NHCc2.

SEQ ID NO:6
Other Information: Description of Artificial Sequence: Artificially synthesized primer sequence, ExcellE.

SEQ ID NO:7
Other Information: Description of Artificial Sequence: Artificially synthesized primer sequence, ck117.

SEQ ID NO:8
Other Information: Description of Artificial Sequence: Artificially synthesized primer sequence, M13R.

SEQ ID NO:9
Other Information: Description of Artificial Sequence: Artificially synthesized primer sequence, 136H.

SEQ ID NO:10
  Other Information: Description of Artificial Sequence: Artificially synthesized primer sequence, 138/9H.

SEQ ID NO:11
  Other Information: Description of Artificial Sequence: Artificially synthesized primer sequence, AILIMHC1.

SEQ ID NO:12
  Other Information: Description of Artificial Sequence: Artificially synthesized primer sequence, HCc1.

SEQ ID NO:13
  Other Information: Description of Artificial Sequence: Artificially synthesized primer sequence, HCc7.

SEQ ID NO:14
  Other Information: Description of Artificial Sequence: Artificially synthesized primer sequence, HCc8.

SEQ ID NO:15
  Other Information: Description of Artificial Sequence: Artificially synthesized primer sequence, HCc3.

SEQ ID NO:16
  Other Information: Description of Artificial Sequence: Artificially synthesized primer sequence, HCc4.

SEQ ID NO:17
  Other Information: Description of Artificial Sequence: Artificially synthesized primer sequence, HCc6.

SEQ ID NO:18
  Other Information: Description of Artificial Sequence: Artificially synthesized primer sequence, HIGHC.

SEQ ID NO:19
  Other Information: Description of Artificial Sequence: Artificially synthesized primer sequence, HCc9.

SEQ ID NO:20
  Other Information: Description of Artificial Sequence: Artificially synthesized primer sequence, HCc5.

SEQ ID NO:21
  Other Information: Description of Artificial Sequence: Artificially synthesized primer sequence, polyA.

SEQ ID NO:22
  Other Information: Description of Artificial Sequence: Artificially synthesized primer sequence, AILIMLC1.

SEQ ID NO:23
  Other Information: Description of Artificial Sequence: Artificially synthesized primer sequence, AILIMLC2.

SEQ ID NO:24
  Other Information: Description of Artificial Sequence: Artificially synthesized primer sequence, LCc1.

SEQ ID NO:25
  Other Information: Description of Artificial Sequence: Artificially synthesized primer sequence, LCc2.

SEQ ID NO:26
  Other Information: Description of Artificial Sequence: Artificially synthesized primer sequence, HIK.

SEQ ID NO:39
  Other Information: Description of Artificial Sequence: Artificially synthesized primer sequence SEQ ID NO:40
  Other Information: Description of Artificial Sequence: Artificially synthesized primer sequence

What is claimed is:

1. A method of treating an inflammatory disorder in a subject, the method comprising administering to the subject an effective amount of a pharmaceutical composition comprising (i) a pharmaceutically acceptable carrier and (ii) a human monoclonal antibody or portion thereof that binds to human AILIM, wherein:
   (a) a V region DNA encoding a heavy chain variable region of the human monoclonal antibody or portion thereof is from human immunoglobulin heavy chain V gene segment 1-02 or 3-13;
   (b) a V region DNA encoding a light chain variable region of the human monoclonal antibody or portion thereof is from human immunoglobulin light chain V gene segment L5 or A27; or
   (c) a V region DNA encoding a heavy chain variable region of the human monoclonal antibody or portion thereof is from human immunoglobulin heavy chain V gene segment 1-02 or 3-13, and a V region DNA encoding a light chain variable region of the human monoclonal antibody or portion thereof is from human immunoglobulin light chain V gene segment L5 or A27.

2. A method of treating an inflammatory disorder in a subject, the method comprising administering to the subject an effective amount of a pharmaceutical composition comprising (i) a pharmaceutically acceptable carrier and (ii) a human monoclonal antibody or portion thereof that binds to human AILIM, wherein a heavy chain variable region of the human monoclonal antibody or portion thereof comprises an amino acid sequence selected from the group consisting of:
   (a) amino acids from position 20 through 117 of SEQ ID NO:28;
   (b) amino acids from position 20 through 117 of SEQ ID NO:28 in which one to ten amino acid residues are deleted, substituted, or added;
   (c) amino acids from position 20 through 116 of SEQ ID NO:32;
   (d) amino acids from position 20 through 116 of SEQ ID NO:32 in which one to ten amino acid residues are deleted, substituted, or added;
   (e) amino acids from position 20 through 116 of SEQ ID NO:36; and
   (f) amino acids from position 20 through 116 of SEQ ID NO:36, in which one to ten amino acid residues are deleted, substituted, or added.

3. A method of treating an inflammatory disorder in a subject, the method comprising administering to the subject an effective amount of a pharmaceutical composition comprising (i) a pharmaceutically acceptable carrier and (ii) a human monoclonal antibody or portion thereof that binds to human AILIM, wherein a light chain variable region of the human monoclonal antibody or portion thereof comprises an amino acid sequence selected from the group consisting of:
   (a) amino acids from position 23 through 116 of SEQ ID NO:30;
   (b) amino acids from position 23 through 116 of SEQ ID NO:30 in which one to ten amino acid residues are deleted, substituted, or added;
   (c) amino acids from position 21 through 116 of SEQ ID NO:34;
   (d) amino acids from position 21 through 116 of SEQ ID NO:34 in which one to ten amino acid residues are deleted, substituted, or added;
   (e) amino acids from position 21 through 116 of SEQ ID NO:38; and
   (f) amino acids from position 21 through 116 of SEQ ID NO:38 in which one to ten amino acid residues are deleted, substituted, or added.

4. A method of inhibiting proliferation, production of interferon gamma or interleukin 4, or AILIM-mediated signal transduction in an AILIM-expressing cell, the method comprising contacting the cell with an effective amount of a composition comprising a human monoclonal antibody or portion thereof that binds to human AILIM, wherein:
   (a) a V region DNA encoding a heavy chain variable region of the human monoclonal antibody or portion thereof is from human immunoglobulin heavy chain V gene segment 1-02 or 3-13;
   (b) a V region DNA encoding a light chain variable region of the human monoclonal antibody or portion thereof is from human immunoglobulin light chain V gene segment L5 or A27; or
   (c) a V region DNA encoding a heavy chain variable region of the human monoclonal antibody or portion thereof is from human immunoglobulin heavy chain V gene segment 1-02 or 3-13, and a V region DNA encoding a light chain variable region of the human monoclonal antibody or portion thereof is from human immunoglobulin light chain V gene segment L5 or A27.

5. A method of inhibiting proliferation, production of interferon gamma or interleukin 4, or AILIM-mediated signal transduction in an AILIM-expressing cell, the method comprising contacting the cell with an effective amount of a composition comprising a human monoclonal antibody or portion thereof that binds to human AILIM, wherein a heavy chain variable region of the human monoclonal antibody or portion thereof comprises an amino acid sequence selected from the group consisting of:
  (a) amino acids from position 20 through 117 of SEQ ID NO:28;
  (b) amino acids from position 20 through 117 of SEQ ID NO:28 in which one to ten amino acid residues are deleted, substituted, or added;
  (c) amino acids from position 20 through 116 of SEQ ID NO:32;
  (d) amino acids from position 20 through 116 of SEQ ID NO:32 in which one to ten amino acid residues are deleted, substituted, or added;
  (e) amino acids from position 20 through 116 of SEQ ID NO:36; and
  (f) amino acids from position 20 through 116 of SEQ ID NO:36, in which one to ten amino acid residues are deleted, substituted, or added.

6. A method of inhibiting proliferation, production of interferon gamma or interleukin 4, or AILIM-mediated signal transduction in an AILIM-expressing cell, the method comprising contacting the cell with an effective amount of a composition comprising a human monoclonal antibody or portion thereof that binds to human AILIM, wherein a light chain variable region of the human monoclonal antibody or portion thereof comprises an amino acid sequence selected from the group consisting of:
  (a) amino acids from position 23 through 116 of SEQ ID NO:30;
  (b) amino acids from position 23 through 116 of SEQ ID NO:30 in which one to ten amino acid residues are deleted, substituted, or added;
  (c) amino acids from position 21 through 116 of SEQ ID NO:34;
  (d) amino acids from position 21 through 116 of SEQ ID NO:34 in which one to ten amino acid residues are deleted, substituted, or added;
  (e) amino acids from position 21 through 116 of SEQ ID NO:38; and
  (f) amino acids from position 21 through 116 of SEQ ID NO:38 in which one to ten amino acid residues are deleted, substituted, or added.

7. The method of claim 1, wherein a V region DNA encoding a heavy chain variable region of the human monoclonal antibody or portion thereof is from human immunoglobulin heavy chain V gene segment 1-02 or 3-13.

8. The method of claim 1, wherein a V region DNA encoding a light chain variable region of the human monoclonal antibody or portion thereof is from human immunoglobulin light chain V gene segment L5 or A27.

9. The method of claim 1, wherein a V region DNA encoding a heavy chain variable region of the human monoclonal antibody or portion thereof is from human immunoglobulin heavy chain V gene segment 1-02 or 3-13, and a V region DNA encoding a light chain variable region of the human monoclonal antibody or portion thereof is from human immunoglobulin light chain V gene segment L5 or A27.

10. The method of claim 9, wherein the V region DNA encoding the heavy chain variable region of the human monoclonal antibody or portion thereof is from human immunoglobulin heavy chain V gene segment 1-02, and the V region DNA encoding the light chain variable region of the human monoclonal antibody or portion thereof is from human immunoglobulin light chain V gene segment L5.

11. The method of claim 9, wherein the V region DNA encoding the heavy chain variable region of the human monoclonal antibody or portion thereof is from human immunoglobulin heavy chain V gene segment 3-13, and the V region DNA encoding the light chain variable region of the human monoclonal antibody or portion thereof is from human immunoglobulin light chain V gene segment A27.

12. The method of claim 2, wherein a heavy chain polypeptide of the human monoclonal antibody or portion thereof comprises an amino acid sequence selected from the group consisting of:
  (a) amino acids from position 20 through 470 of SEQ ID NO:28,
  (b) amino acids from position 20 through 470 of SEQ ID NO:28 in which one to ten amino acid residues are deleted, substituted, or added,
  (c) amino acids from position 20 through 470 of SEQ ID NO:32,
  (d) amino acids from position 20 through 470 of SEQ ID NO:32 in which one to ten amino acid residues are deleted, substituted, or added,
  (e) amino acids from position 20 through 470 of SEQ ID NO:36, and
  (f) amino acids from position 20 through 470 of SEQ ID NO:36 in which one to ten amino acid residues are deleted, substituted, or added.

13. The method of claim 3, wherein a light chain polypeptide of the human monoclonal antibody or portion thereof comprises an amino acid sequence selected from the group consisting of:
  (a) amino acids from position 23 through 236 of SEQ ID NO:30,
  (b) amino acids from position 23 through 236 of SEQ ID NO:30 in which one to ten amino acid residues are deleted, substituted, or added,
  (c) amino acids from position 21 through 236 of SEQ ID NO:34,
  (d) amino acids from position 21 through 236 of SEQ ID NO:34 in which one to ten amino acid residues are deleted, substituted, or added,
  (e) amino acids from position 21 through 236 of SEQ ID NO:38, and
  (f) amino acids from position 21 through 236 of SEQ ID NO:38 in which one to ten amino acid residues are deleted, substituted, or added.

14. The method of claim 2, wherein the human monoclonal antibody or portion thereof comprises:
  a heavy chain variable region comprising amino acid 20 through 117 according to SEQ ID NO:28, and
  a light chain variable region comprising amino acid 23 through 116 according to SEQ ID NO:30.

15. The method of claim 12, wherein the human monoclonal antibody or portion thereof comprises:
  a heavy chain polypeptide comprising amino acid 20 through 470 according to SEQ ID NO:28, and
  a light chain polypeptide comprising amino acid 23 through 236 according to SEQ ID NO:30.

16. The method of claim 2, wherein the human monoclonal antibody or portion thereof comprises:
  a heavy chain variable region comprising amino acid 20 through 116 according to SEQ ID NO:32, and
  a light chain variable region comprising amino acid 21 through 116 according to SEQ ID NO:34.

17. The method of claim 12, wherein the human monoclonal antibody or portion thereof comprises:
  a heavy chain polypeptide comprising amino acid 20 through 470 according to SEQ ID NO:32, and a light chain polypeptide comprising amino acid 21 through 236 according to SEQ ID NO:34.

18. The method of claim 2, wherein the human monoclonal antibody or portion thereof comprises:
a heavy chain variable region comprising amino acid 20 through 116 according to SEQ ID NO:36, and
a light chain variable region comprising amino acid 21 through 116 according to SEQ ID NO:38.

19. The method of claim 12, wherein the human monoclonal antibody or portion thereof comprises:
a heavy chain polypeptide comprising amino acid 20 through 470 according to SEQ ID NO:36, and
a light chain polypeptide comprising amino acid 21 through 236 according to SEQ ID NO:38.

20. The method of claim 1, wherein the V region DNA encoding the heavy chain variable region of the human monoclonal antibody or portion thereof is from human immunoglobulin heavy chain V gene segment 1-02.

21. The method of claim 1, wherein the V region DNA encoding the heavy chain variable region of the human monoclonal antibody or portion thereof is from human immunoglobulin heavy chain V gene segment 3-13.

22. The method of claim 1, wherein the V region DNA encoding the light chain variable region of the human monoclonal antibody or portion thereof is from human immunoglobulin light chain V gene segment L5.

23. The method of claim 1, wherein the V region DNA encoding the light chain variable region of the human monoclonal antibody or portion thereof is from human immunoglobulin light chain V gene segment A27.

24. The method of claim 7, wherein the V region DNA encoding the light chain variable region of the human monoclonal antibody or portion thereof is from human immunoglobulin light chain V gene segment L5.

25. The method of claim 7, wherein the V region DNA encoding the light chain variable region of the human monoclonal antibody or portion thereof is from human immunoglobulin light chain V gene segment A27.

26. The method of claim 2, wherein the heavy chain variable region of the human monoclonal antibody or portion thereof comprises amino acids from position 20 through 117 of SEQ ID NO:28.

27. The method of claim 2, wherein the heavy chain variable region of the human monoclonal antibody or portion thereof comprises amino acids from position 20 through 116 of SEQ ID NO:32.

28. The method of claim 2, wherein the heavy chain variable region of the human monoclonal antibody or portion thereof comprises amino acids from position 20 through 116 of SEQ ID NO:36.

29. The method of claim 12, wherein the heavy chain polypeptide of the human monoclonal antibody or portion thereof comprises amino acids from position 20 through 470 of SEQ ID NO:28.

30. The method of claim 12, wherein the heavy chain polypeptide of the human monoclonal antibody or portion thereof comprises amino acids from position 20 through 470 of SEQ ID NO:32.

31. The method of claim 12, wherein the heavy chain polypeptide of the human monoclonal antibody or portion thereof comprises amino acids from position 20 through 470 of SEQ ID NO:36.

32. The method of claim 3, wherein the light chain variable region of the human monoclonal antibody or portion thereof comprises amino acids from position 23 through 116 of SEQ ID NO:30.

33. The method of claim 3, wherein the light chain variable region of the human monoclonal antibody or portion thereof comprises amino acids from position 21 through 116 of SEQ ID NO:34.

34. The method of claim 3, wherein the light chain variable region of the human monoclonal antibody or portion thereof comprises amino acids from position 21 through 116 of SEQ ID NO:38.

35. The method of claim 13, wherein the light chain polypeptide of the human monoclonal antibody or portion thereof comprises amino acids from position 23 through 236 of SEQ ID NO:30.

36. The method of claim 13, wherein the light chain polypeptide of the human monoclonal antibody or portion thereof comprises amino acids from position 21 through 236 of SEQ ID NO:34.

37. The method of claim 13, wherein the light chain polypeptide of the human monoclonal antibody or portion thereof comprises amino acids from position 21 through 236 of SEQ ID NO:38.

38. The method of claim 4, wherein a V region DNA encoding a heavy chain variable region of the human monoclonal antibody or portion thereof is from human immunoglobulin heavy chain V gene segment 1-02 or 3-13.

39. The method of claim 4, wherein a V region DNA encoding a light chain variable region of the human monoclonal antibody or portion thereof is from human immunoglobulin light chain V gene segment L5 or A27.

40. The method of claim 4, wherein a V region DNA encoding a heavy chain variable region of the human monoclonal antibody or portion thereof is from human immunoglobulin heavy chain V gene segment 1-02 or 3-13, and a V region DNA encoding a light chain variable region of the human monoclonal antibody or portion thereof is from human immunoglobulin light chain V gene segment L5 or A27.

41. The method of claim 40, wherein the V region DNA encoding the heavy chain variable region of the human monoclonal antibody or portion thereof is from human immunoglobulin heavy chain V gene segment 1-02, and the V region DNA encoding the light chain variable region of the human monoclonal antibody or portion thereof is from human immunoglobulin light chain V gene segment L5.

42. The method of claim 40, wherein the V region DNA encoding the heavy chain variable region of the human monoclonal antibody or portion thereof is from human immunoglobulin heavy chain V gene segment 3-13, and the V region DNA encoding the light chain variable region of the human monoclonal antibody or portion thereof is from human inimunoglobulin light chain V gene segment A27.

43. The method of claim 5, wherein a heavy chain polypeptide of the human monoclonal antibody or portion thereof comprises an amino acid sequence selected from the group consisting of:
(a) amino acids from position 20 through 470 of SEQ ID NO:28,
(b) amino acids from position 20 through 470 of SEQ ID NO:28 in which one to ten amino acid residues are deleted, substituted, or added,
(c) amino acids from position 20 through 470 of SEQ ID NO:32,
(d) amino acids from position 20 through 470 of SEQ ID NO:32 in which one to ten amino acid residues are deleted, substituted, or added,
(e) amino acids from position 20 through 470 of SEQ ID NO:36, and (f) amino acids from position 20 through 470 of SEQ ID NO:36 in which one to ten amino acid residues are deleted, substituted, or added.

44. The method of claim 6, wherein a light chain polypeptide of the human monoclonal antibody or portion thereof comprises an amino acid sequence selected from the group consisting of:
(a) amino acids from position 23 through 236 of SEQ ID NO:30,
(b) amino acids from position 23 through 236 of SEQ ID NO:30 in which one to ten amino acid residues are deleted, substituted, or added,
(c) amino acids from position 21 through 236 of SEQ ID NO:34,
(d) amino acids from position 21 through 236 of SEQ ID NO:34 in which one to ten amino acid residues are deleted, substituted, or added,
(e) amino acids from position 21 through 236 of SEQ ID NO:38, and
(f) amino acids from position 21 through 236 of SEQ ID NO:38 in which one to ten amino acid residues are deleted, substituted, or added.

45. The method of claim 5, wherein the human monoclonal antibody or portion thereof comprises:
a heavy chain variable region comprising amino acid 20 through 117 according to SEQ ID NO:28, and
a light chain variable region comprising amino acid 23 through 116 according to SEQ ID NO:30.

46. The method of claim 43, wherein the human monoclonal antibody or portion thereof comprises:
a heavy chain polypeptide comprising amino acid 20 through 470 according to SEQ ID NO:28, and
a light chain polypeptide comprising amino acid 23 through 236 according to SEQ ID NO:30.

47. The method of claim 5, wherein the human monoclonal antibody or portion thereof comprises:
a heavy chain variable region comprising amino acid 20 through 116 according to SEQ ID NO:32, and
a light chain variable region comprising amino acid 21 through 116 according to SEQ ID NO:34.

48. The method of claim 43, wherein the human monoclonal antibody or portion thereof comprises:
a heavy chain polypeptide comprising amino acid 20 through 470 according to SEQ ID NO:32, and
a light chain polypeptide comprising amino acid 21 through 236 according to SEQ ID NO:34.

49. The method of claim 5, wherein the human monoclonal antibody or portion thereof comprises:
a heavy chain variable region comprising amino acid 20 through 116 according to SEQ ID NO:36, and
a light chain variable region comprising amino acid 21 through 116 according to SEQ ID NO:38.

50. The method of claim 43, wherein the human monoclonal antibody or portion thereof comprises:
a heavy chain polypeptide comprising amino acid 20 through 470 according to SEQ ID NO:36, and
a light chain polypeptide comprising amino acid 21 through 236 according to SEQ ID NO:38.

51. The method of claim 4, wherein the V region DNA encoding the heavy chain variable region of the human monoclonal antibody or portion thereof is from human immunoglobulin heavy chain V gene segment 1-02.

52. The method of claim 4, wherein the V region DNA encoding the heavy chain variable region of the human monoclonal antibody or portion thereof is from human immunoglobulin heavy chain V gene segment 3-13.

53. The method of claim 4, wherein the V region DNA encoding the light chain variable region of the human monoclonal antibody or portion thereof is from human immunoglobulin light chain V gene segment L5.

54. The method of claim 4, wherein the V region DNA encoding the light chain variable region of the human monoclonal antibody or portion thereof is from human immunoglobulin light chain V gene segment A27.

55. The method of claim 38, wherein the V region DNA encoding the light chain variable region of the human monoclonal antibody or portion thereof is from human immunoglobulin light chain V gene segment L5.

56. The method of claim 38, wherein the V region DNA encoding the light chain variable region of the human monoclonal antibody or portion thereof is from human immunoglobulin light chain V gene segment A27.

57. The method of claim 5, wherein the heavy chain variable region of the human monoclonal antibody or portion thereof comprises amino acids from position 20 through 117 of SEQ ID NO:28.

58. The method of claim 5, wherein the heavy chain variable region of the human monoclonal antibody or portion thereof comprises amino acids from position 20 through 116 of SEQ ID NO:32.

59. The method of claim 5, wherein the heavy chain variable region of the human monoclonal antibody or portion thereof comprises amino acids from position 20 through 116 of SEQ ID NO:36.

60. The method of claim 43, wherein the heavy chain polypeptide of the human monoclonal antibody or portion thereof comprises amino acids from position 20 through 470 of SEQ ID NO:28.

61. The method of claim 43, wherein the heavy chain polypeptide of the human monoclonal antibody or portion thereof comprises amino acids from position 20 through 470 of SEQ ID NO:32.

62. The method of claim 43, wherein the heavy chain polypeptide of the human monoclonal antibody or portion thereof comprises amino acids from position 20 through 470 of SEQ ID NO:36.

63. The method of claim 6, wherein the light chain variable region of the human monoclonal antibody or portion thereof comprises amino acids from position 23 through 116 of SEQ ID NO:30.

64. The method of claim 6, wherein the light chain variable region of the human monoclonal antibody or portion thereof comprises amino acids from position 21 through 116 of SEQ ID NO:34.

65. The method of claim 6, wherein the light chain variable region of the human monoclonal antibody or portion thereof comprises amino acids from position 21 through 116 of SEQ ID NO:38.

66. The method of claim 44, wherein the light chain polypeptide of the human monoclonal antibody or portion thereof comprises amino acids from position 23 through 236 of SEQ ID NO:30.

67. The method of claim 44, wherein the light chain polypeptide of the human monoclonal antibody or portion thereof comprises amino acids from position 21 through 236 of SEQ ID NO:34.

68. The method of claim 44, wherein the light chain polypeptide of the human monoclonal antibody or portion thereof comprises amino acids from position 21 through 236 of SEQ ID NO:38.

69. The method of claim 1, wherein the inflammatory disorder is inflammation accompanying arthritis.

70. The method of claim 2, wherein the inflammatory disorder is inflanunation accompanying arthritis.
71. The method of claim 3, wherein the inflammatory disorder is inflammation accompanying arthritis.
72. The method of claim 7, wherein the inflammatory disorder is inflammation accompanying arthritis.
73. The method of claim 8, wherein the inflammatory disorder is inflammation accompanying arthritis.
74. The method of claim 9, wherein the inflammatory disorder is inflammation accompanying arthritis.
75. The method of claim 10, wherein the inflammatory disorder is inflammation accompanying arthritis.
76. The method of claim 11, wherein the inflammatory disorder is inflammation accompanying arthritis.
77. The method of claim 12, wherein the inflammatory disorder is inflammation accompanying arthritis.
78. The method of claim 13, wherein the inflammatory disorder is inflammation accompanying arthritis.
79. The method of claim 14, wherein the inflammatory disorder is inflammation accompanying arthritis.
80. The method of claim 15, wherein the inflammatory disorder is inflammation accompanying arthritis.
81. The method of claim 16, wherein the inflammatory disorder is inflammation accompanying arthritis.
82. The method of claim 17, wherein the inflammatory disorder is inflammation accompanying arthritis.
83. The method of claim 18, wherein the inflammatory disorder is inflammation accompanying arthritis.
84. The method of claim 19, wherein the inflammatory disorder is inflammation accompanying arthritis.
85. The method of claim 20, wherein the inflammatory disorder is inflammation accompanying arthritis.
86. The method of claim 21, wherein the inflammatory disorder is inflammation accompanying arthritis.
87. The method of claim 22, wherein the inflammatory disorder is inflammation accompanying arthritis.
88. The method of claim 23, wherein the inflammatory disorder is inflammation accompanying arthritis.
89. The method of claim 24, wherein the inflammatory disorder is inflammation accompanying arthritis.
90. The method of claim 25, wherein the inflammatory disorder is inflammation accompanying arthritis.
91. The method of claim 26, wherein the inflammatory disorder is inflammation accompanying arthritis.
92. The method of claim 27, wherein the inflammatory disorder is inflammation accompanying arthritis.
93. The method of claim 28, wherein the inflammatory disorder is inflammation accompanying arthritis.
94. The method of claim 29, wherein the inflammatory disorder is inflammation accompanying arthritis.
95. The method of claim 30, wherein the inflammatory disorder is inflammation accompanying arthritis.
96. The method of claim 31, wherein the inflammatory disorder is inflammation accompanying arthritis.
97. The method of claim 32, wherein the inflammatory disorder is inflammation accompanying arthritis.
98. The method of claim 33, wherein the inflammatory disorder is inflammation accompanying arthritis.
99. The method of claim 34, wherein the inflammatory disorder is inflammation accompanying arthritis.
100. The method of claim 35, wherein the inflammatory disorder is inflammation accompanying arthritis.
101. The method of claim 36, wherein the inflammatory disorder is inflammation accompanying arthritis.
102. The method of claim 37, wherein the inflammatory disorder is inflammation accompanying arthritis.

\* \* \* \* \*